United States Patent [19]

Sugiura et al.

[11] Patent Number: 5,338,844
[45] Date of Patent: Aug. 16, 1994

[54] 2-SUBSTITUTED-2-CYCLOPENTENONE COMPOUND AND ANTICANCER AGENT AND BONE FORMATION ACCELERATOR COMPRISING SAME AS ACTIVE INGREDIENT

[75] Inventors: Satoshi Sugiura; Toru Minoshima; Atsuo Hazato; Yoshinori Kato, all of Hino, Japan

[73] Assignee: Teijin Limited, Osaka, Japan

[21] Appl. No.: 104,393

[22] Filed: Jul. 16, 1993

Related U.S. Application Data

[63] Continuation of Ser. No. 690,889, Jun. 19, 1991, abandoned.

[30] Foreign Application Priority Data

Oct. 19, 1989 [JP] Japan .................. 1-272296

[51] Int. Cl.⁵ .................................. C07C 405/00
[52] U.S. Cl. ................................ 544/318; 546/301; 548/170; 548/221; 548/251; 548/324.1; 549/501
[58] Field of Search ............ 544/318; 546/301, 302; 548/170, 221, 259, 324.1

[56] References Cited

U.S. PATENT DOCUMENTS 5,116,869  5/1992  Sugiura .................. 514/456

FOREIGN PATENT DOCUMENTS 0131441  1/1985  European Pat. Off. .
2357542  2/1978  France .
58-109468  6/1983  Japan .................. C07C 149/26
2-22226  1/1990  Japan .
2-275849  11/1990  Japan .................. C07C 317/24

OTHER PUBLICATIONS

Chemical and Pharmaceutical Bulletin, vol. 33, NO. 7, 1985, Katsuhide Motoba et al. [Reduction of Vinylogous Thioesters with Lithium Aluminum Hydride. II] pp. 3001-3005 Particularly, refer to compound Vb on p. 3002.

*Primary Examiner*—Robert Gerstl
*Attorney, Agent, or Firm*—Sughrue, Mion, Zinn, Macpeak & Seas

[57] ABSTRACT

A 2-substituted-2-cyclopentenone compound represented by the following formula (I) and an anticancer agent and a bone formation accelerator comprising the same as an effective active ingredient:

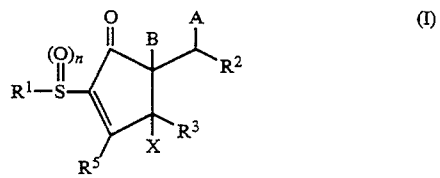

(I)

9 Claims, No Drawings

2-SUBSTITUTED-2-CYCLOPENTENONE COMPOUND AND ANTICANCER AGENT AND BONE FORMATION ACCELERATOR COMPRISING SAME AS ACTIVE INGREDIENT

This is a continuation of application Ser. No. 07/690,889, filed Jun. 19, 1991, now abandoned.

TECHNICAL FIELD

The present invention relates to a 2-substituted-2-cyclopentenone compound, and more particularly, to a 2-substituted-2-cyclopentenone compound having superior pharmacological activities, such as an anticancer activity and bone formation activity, and an anticancer agent and a bone formation accelerator comprising the same as an active ingredient.

BACKGROUND ART

A prostaglandin is a compound having specific biological activities, such as a platelet agglutination inhibitory activity and a vasodepressor activity, and is a useful naturally occurring substance which is now used in the medical field as a therapeutic agent for diseases of the peripheral cardiovascular system. Among the prostaglandins, prostaglandin A compounds are known as a prostaglandin having a double bond in its cyclopentane ring. For example, European Unexamined Patent Publication No. 0106576 (publication date: Apr. 25, 1984) discloses 4,5-substituted-2-cyclopentenone compounds embracing the prostaglandin A compounds, which include 5-alkylidene-4-substituted-2-cyclopentene compounds represented by the following formula:

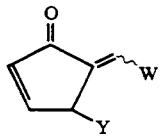

wherein W stands for a substituted or unsubstituted hydrocarbon group having 1 to 12 carbon atoms; and Y stands for a substituted or unsubstituted hydrocarbon group having 1 to 12 carbon atoms, and 5-(1-hydroxyhydrocarbon)-4-substituted-2-cyclopentenone compounds represented by the following formula:

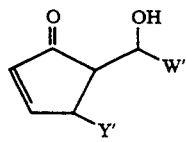

wherein W' and Y' are the same as W and Y, respectively.

Further, the above publication also states that the above-described compounds are useful for treating a malignant tumor.

European Unexamined Patent Publication No. 0131441 (publication date: Jan. 16, 1985) discloses 5-alkylidene-2-halo-4-substituted-2-cyclopentenone compounds represented by the following formula:

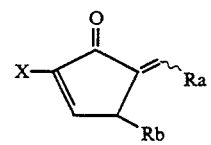

wherein Ra stands for a substituted or unsubstituted hydrocarbon having 1 to 12 carbon atoms or a substituted or unsubstituted phenyl group; Rb stands for a substituted or unsubstituted hydrocarbon having 1 to 12 carbon atoms; and X stands for a halogen atom, and further discloses that the above-described compounds are similarly useful for treating a malignant tumor.

Further, it is also known that prostaglandin D compounds and prostaglandin J compounds, although different from the prostaglandin A compounds, are useful as an antitumor agent [see Japanese Unexamined Patent Publication (Kokai) No. 58-216155 and Proc. Natl. Acad. Sci., U.S.A., 81, 1317–1321 (1984)].

Japanese Unexamined Patent Publication (Kokai) No. 62-96438 discloses 4-hydroxy-2-cyclopentenone compounds represented by the general formula:

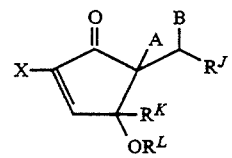

wherein X stands for a hydrogen atom or a halogen atom; A and B stand for a hydrogen atom and a hydroxyl group, respectively, or are combined with each other to form a single bond; $R^J$ stands for a substituted or unsubstituted alkyl, alkenyl or alkynyl group having 1 to 10 carbon atoms; $R^K$ stands for a substituted or unsubstituted alkyl, alkenyl or alkynyl group having 1 to 10 carbon atoms; and $R^L$ stands for a hydrogen atom or a protecting group for a hydroxyl group, provided that $R^K$ is not 2-octenyl, 8-acetoxy-2-octenyl or 2,5-octadienyl, and states that the above-described compounds are useful for the treatment of a malignant tumor.

The present inventors have reported, in The 109th Annual Meeting of the Pharmaceutical Society of Japan (Preprints on page 117), that 2-methylthio-2-cyclopentenone compounds represented by the following formulae have an anticancer activity:

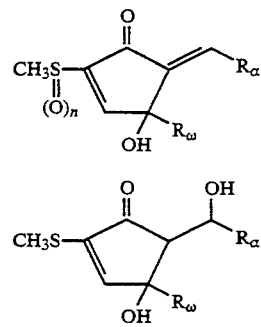

It is commonly recognized that the metabolism of the bone of healthy persons is established by a good balance of the repetition of the absorption of bone by osteoclasts and the formation of bone by osteoblasts, and it is considered that the breaking of the balance between the absorption of bone and the formation of bone leads to diseases such as osteoporosis and osteomalalacia. Active vitamin preparations, calcitonin preparations, diphosphonic acid preparations, estrogen preparations, calcium preparations, etc. are used as a therapeutic agent for these diseases of bone. Nevertheless, although it has been reported that many of these preparations have a bone absorption inhibitory activity, there is no report clearly showing that they exhibit a bone formation accelerative activity. Further, since the effect of these preparations is not clear, the development of a preparation capable of more surely attaining the effect and having an activity through which the formation of bone by the osteoblasts is accelerated has been desired in the art.

Koshihara et al. reported in Biochemical Society of Japan (Preprints, 1988, p.767) that prostaglandin $D_2$ has an activity through which the calcification by human osteoblasts is accelerated, and suggested that this activity is derived from the action of $^{12}\Delta$-prostaglandin $J_2$, which is a decomposition product of the prostaglandin $D_2$.

Problem to be Solved by the Invention

As described in European Unexamined Patent Publication No. 338796, the present inventors found that 2-cyclopentenone compounds having in their 2-position a group bonded to the skeleton through a sulfur atom represented by the following formula have an antitumor activity and a bone formation accelerative activity:

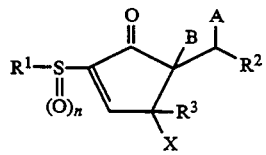

wherein A and B stand for a hydroxyl group or

and a hydrogen atom, respectively, or are combined with each other to form a bond line;

$R_1$ stands for a substituted or unsubstituted hydrocarbon group having 1 to 10 carbon atoms;

$R_2$ stands for a substituted or unsubstituted aliphatic hydrocarbon group having 1 to 10 carbon atoms;

$R_3$ stands for a substituted or unsubstituted aliphatic hydrocarbon group having 1 to 10 carbon atoms, provided that when $R_3$ is bonded to the cyclopentene skeleton through a single bond, X stands for a hydrogen atom, a hydroxyl group or a protected hydroxyl group, and when $R_3$ is bonded to the cyclopentene skeleton through a double bond, X stands for a bond constituting part of the double bond; and m and n, which may be the same or different from each other, stand for 0, 1 or 2.

Further, the present inventors have made extensive and intensive studies, and as a result, have found that not only the above-described compounds but also a wider range of 2-cyclopentenone compounds having in their 2-position a group attached to the skeleton through a sulfur atom have a similar activity.

Disclosure of the Invention

An object of the present invention is to provide a novel 2-substituted-2-cyclopentenone compound, that is, a 2-cyclopentenone compound having in its 2-position a group bonded to the skeleton through a sulfur atom.

Another object of the present invention is to provide a bone formation accelerator comprising a 2-substituted-2-cyclopentenone compound as an active ingredient.

A further object of the present invention is to provide a 2,3-epoxycyclopentanone compound or a 2-substituted-2-cyclopentenone compound useful as a starting compound for producing the 2-substituted-2-cyclopentenone compound of the present invention.

Other objects and advantages of the present invention will be apparent from the following description.

According to the present invention, there is provided a 2-substituted-2-cyclopentenone compound represented by the following formula (I):

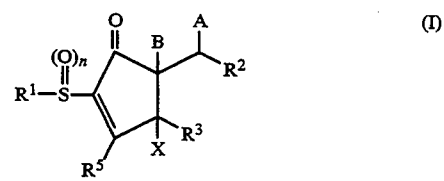

wherein $R^1$ stands for a substituted or unsubstituted (i) aliphatic hydrocarbon group having 1 to 10 carbon atoms, (ii) alicyclic hydrocarbon group having 4 to 10 carbon atoms, (iii) aromatic hydrocarbon group having 6 to 10 carbon atoms or (iv) heterocyclic group having 1 to 9 carbon atoms;

$R^2$ stands for a substituted or unsubstituted (i) aliphatic hydrocarbon group having 1 to 10 carbon atoms, (ii) alicyclic hydrocarbon group having 4 to 10 carbon atoms, (iii) aromatic hydrocarbon group having 6 to 10 carbon atoms or (iv) heterocyclic group having 1 to 9 carbon atoms;

$R^3$ stands for a hydrogen atom or a substituted or unsubstituted (i) aliphatic hydrocarbon group having 1 to 10 carbon atoms, (ii) alicyclic hydrocarbon group having 4 to 10 carbon atoms or (iii) aromatic hydrocarbon group having 6 to 10 carbon atoms;

X stands for a hydrogen atom, or —$OR^4$ (wherein $R^4$ stands for a hydrogen atom, an alkyl group having 1 to 4 carbon atoms, an acyl group having 2 to 7 carbon atoms, an alkoxycarbonyl group having 2 to 5 carbon atoms, a tri($C_1$–$C_7$) hydrocarbon silyl group or a group capable of forming an acetal bond together with the oxygen atom attached to the R4), provided that X is absent when $R^3$ is bonded to the carbon atom bonding thereto through a double bond;

$R^5$ stands for a hydrogen atom, or a substituted or unsubstituted (i) aliphatic hydrocarbon group having 1 to 10 carbon atoms or (ii) an alicyclic hydrocarbon group having 4 to 10 carbon atoms;

B stands for a hydrogen atom when A stands for a hydrogen atom, a hydroxyl group, an acyloxy group having 2 to 7 carbon atoms, an alkoxycarbonyloxy group having 2 to 5 carbon atoms, a sulfonyloxy group having 1 to 7 carbon atoms or

or A and B are combined with each other to form a bond line;

m and n, which may be the same or different from each other, stand for 0, 1 or 2, exclusive of the cases where $R^1$ stands for a substituted or unsubstituted aliphatic hydrocarbon group or aromatic hydrocarbon group or an aliphatic hydrocarbon group substituted with an aromatic hydrocarbon group, and $R^2$ stands for an aliphatic hydrocarbon group which may be substituted with an aromatic hydrocarbon group or an aliphatic hydrocarbon group, and $R^3$ does not stand for a hydrogen atom, and $R^5$ stands for a hydrogen atom, and A and B stand for any of i) A stands for a hydroxyl group, a sulfonyloxy group or

and B is a hydrogen atom and ii) A and B are combined with each other to form a bond line.

In the above-described formula (I), regarding A and B, when A stands for a hydrogen atom, a hydroxyl group, an acyloxy group having 2 to 7 carbon atoms, an alkoxycarbonyloxy group having 2 to 5 carbon atoms, a sulfonyloxy group having 1 to 7 carbon atoms or

and B stands for a hydrogen atom, the above-described formula (I) represents 2-substituted-2-cyclopentenone compounds represented by the following formula (I-B'):

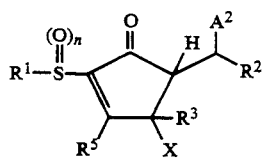

wherein $R^1$, $R^2$, $R^3$, $R^5$, X and n are as defined above, and $A^2$ stands for a hydrogen atom, a hydroxyl group, an acyloxy group having 2 to 7 carbon atoms, an alkoxycarbonyloxy group having 2 to 5 carbon atoms or a sulfonyloxy group having 1 to 7 carbon atoms;

When A stands for

and B stands for a hydrogen atom, the above-described formula (I) represents 2-substituted-2-cyclopentenone compounds represented by the following formula (I-B'')

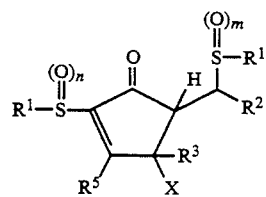

wherein $R^1$, $R^2$, $R^3$, $R^5$, X, m and n are as defined above; and

When A and B are combined with each other to form a bond line, the above-described formula (I) represents 2-substituted-2-cyclopentenone compounds represented by the following formula (I-A):

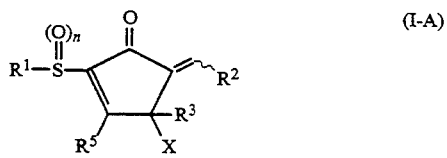

wherein $R^1$, $R^2$, $R^3$, $R^5$, X and n are as defined above and represents that the substituent attached to the double bond is in an E-configuration or a Z-configuration or a mixture thereof in any proportion, and further there are provided anticancer agents and bone formation accelerators comprising the above compounds as an active ingredient.

In the above-described formula (I), when A stands for an acyloxy group having 2 to 7 carbon atoms, examples of the acyloxy group having 2 to 7 carbon atoms include acetoxy, propionyloxy, isopropionyloxy, butyryloxy, isobutyryloxy, s-butyryloxy, valeryloxy, isovaleryloxy, hexanoyloxy, heptanoyloxy and benzoyloxy.

In the above-described formula (I), when A stands for an alkoxycarbonyloxy group having 2 to 5 carbon atoms, examples of the alkoxycarbonyloxy group having 2 to 5 carbon atoms include methoxycarbonyloxy, ethoxycarbonyloxy, propoxycarbonyloxy, isopropoxycarbonyloxy, butoxycarbonyloxy, isobutoxycarbonyloxy, s-butoxycarbonyloxy and t-butoxycarbonyloxy.

In the above-described formula (I), when A stands for a sulfonyloxy group having 1 to 7 carbon atoms, examples of the sulfonyloxy group having 1 to 7 carbon atoms include an alkylsulfonyloxy group having 1 to 4 carbon atoms which may be substituted with a halogen atom, a substituted or unsubstituted phenylsulfonyloxy group and a substituted or unsubstituted phenyl ($C_1$-$C_2$) alkylsulfonyloxy group.

Examples of the alkylsulfonyloxy group having 1 to 4 carbon atoms which may be substituted with a halogen atom include methanesulfonyloxy, ethanesulfonyloxy, butanesulfonyloxy, t-butanesulfonyloxy, chloromethanesulfonyloxy, dichloromethanesulfonyloxy, trifluoromethanesulfonyloxy and nonafluorobutanesulfonyloxy groups. Examples of the substituted or unsubstituted phenylsulfonyloxy group include benzenesulfonyloxy, p-bromobenzenesulfonyloxy and toluenesulfonyloxy groups. Examples of the substituted or unsubstituted phenyl ($C_1$ -$C_2$) alkylsulfonyloxy group include benzylsulfonyloxy, α-phenetylsulfonyloxy and α-phenetylsulfonyloxy groups.

In the above-described formula (I), $R^1$ stands for a substituted or unsubstituted aliphatic hydrocarbon group having 1 to 10 carbon atoms. an alicyclic hydrocarbon group having 4 to 10 carbon atoms, an aromatic hydrocarbon group having 6 to 10 carbon atoms or a heterocyclic group having 1 to 9 carbon atoms.

Examples of the unsubstituted aliphatic hydrocarbon group having 1 to 10 carbon atoms in the $R^1$ include alkyl groups such as methyl, ethyl, propyl, isopropyl, butyl, isobutyl, s-butyl, t-butyl. pentyl, isopentyl, neopentyl, t-pentyl, hexyl, heptyl, octyl, 3,7-dimethyloctyl, nonyl and decyl groups; alkenyl groups such as 2-propenyl, 2-butenyl, 3-butenyl, 2-pentenyl, 4-pentenyl, 2-hexenyl, 3-hexenyl and 5-hexenyl; and alkynyl groups such as 2-propynyl, 2-butynyl, 2-pentynyl, 2-hexynyl and 3-hexynyl.

Examples of the unsubstituted alicyclic hydrocarbon groups having 4 to 10 carbon atoms in the $R^1$ include cyclobutyl, cyclopentyl, cyclohexyl, 3-cyclohexenyl, 4-cyclohexenyl, cycloheptyl, cyclooctyl and bicyclo[4.4.0]decan-2-yl groups.

Examples of the unsubstituted aromatic hydrocarbon group having 6 to 10 carbon groups in the $R^1$ include phenyl,1-naphthyl and 2-naphthyl groups.

Examples of the unsubstituted heterocyclic group having 1 to 9 carbon atoms in the $R^1$ include monocyclic or bicyclic groups having an oxygen, nitrogen or sulfur atom, such as furyl, thienyl, pyrrolyl, oxazolyl, isooxazolyl. thiazolyl, isothiazolyl, imidazolyl, pyrazolyl, triazolyl, tetrazolyl, pyranyl, pyridyl, pyrazinyl, pyrimidinyl, benzofuranyl, indolyl, benzimidazolyl, benzothiazolyl, benzoxazolyl, quinolyl, isoquinolyl, quinazolyl, purinyl, pteridinyl, morpholinyl and piperidinyl groups.

$R^1$ may be a group comprising attached to each other, any combination of the above-described aliphatic hydrocarbon group having 1 to 10 carbon atoms, alicyclic hydrocarbon group having 4 to 10 carbon atoms, aromatic hydrocarbon group having 6 to 10 carbon atoms and heterocyclic group having 1 to 9 carbon atoms. Among them, preferred examples of the $R^1$ include a substituted or unsubstituted ($r^1$-a) aliphatic hydrocarbon group having 1 to 10 carbon atoms which may be substituted with one or a plurality of alkoxy groups having 1 to 4 carbon atoms;

($r^1$-b) alicyclic hydrocarbon group having 4 to 10 carbon atoms which may be substituted with one or a plurality of alkyl groups having 1 to 4 carbon atoms or alkoxy groups having 1 to 4 carbon atoms;

($r^1$-c) aromatic hydrocarbon group having 6 to 10 carbon atoms which may be substituted with one or a plurality of alkyl groups having 1 to 4 carbon atoms or alkoxy groups having 1 to 4 carbon atoms;

($r^1$-d) heterocyclic group having 1 to 9 carbon atoms which may be substituted with one or a plurality of alkyl groups having 1 to 4 carbon atoms or alkoxy groups having 1 to 4 carbon atoms;

($r^1$-e) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms or alkoxy groups having 1 to 4 carbon atoms;

($r^1$-f) aliphatic hydrocarbon group having 1 to 10 carbon atoms substituted with an aromatic hydrocarbon group having 6 to 10 carbon atoms and which may be substituted with one or a plurality of alkyl groups having 1 to 4 carbon atoms or alkoxy groups having 1 to 4 carbon atoms; and ($r^1$-g) aliphatic hydrocarbon group having 1 to 10 carbon atoms substituted with a heterocyclic group having 1 to 9 carbon atoms and which may be substituted with one or a plurality of alkyl groups having 1 to 4 carbon atoms or alkoxy groups having 1 to 4 carbon atoms.

Preferred examples of the unsubstituted group ($r^1$-a) include methyl, ethyl, propyl, isopropyl, butyl, isobutyl, s-butyl, t-butyl, pentyl, hexyl, octyl, decyl, 2-propenyl and 4-pentenyl groups. Preferred examples of the unsubstituted group ($r^1$-b) include cyclopentyl, cyclohexyl, cyclooctyl, 3-methylcyclopentyl, 4-methylcyclohexyl, 4-butylcyclohexyl, 3,4-dimethylcyclohexyl and 4-methoxycyclohexyl groups. Preferred examples of the unsubstituted group ($r^1$-c) include phenyl, 1-naphthyl, 2-naphthyl, 2-methylphenyl, 3-methylphenyl, 4-methylphenyl, 2,4-dimethylphenyl, 3,5-dimethylphenyl, 4-ethylphenyl, 4-butylphenyl, 3-t-butylphenyl, 2-methoxyphenyl, 3-methoxyphenyl, 4-methoxyphenyl, 4-ethoxyphenyl, 6-methoxy-2-naphthyl, 7-methoxy-2naphthyl and 6,7-dimethoxy-2-naphthyl groups. Preferred examples of the unsubstituted group ($r^1$-d) include 2-oxazolyl, 2-thiazolyl, 2-imidazolyl, 2-pyridyl, 4-pyridyl, 2-pyrimidinyl, 2-benzimidazolyl, 2-benzoxazolyl, 2-benzothiazolyl, 6-purinyl, 1-methylimidazol-2-yl, 4-methyl-1,2,4-triazol-3-yl, 1-methyl-5-tetrazolyl, 5-methyl-2-benzimidazolyl, 6-ethoxy-2-benzothiazolyl, 4-methyl-2-pyrimidinyl, 4,6-dimethyl-2-pyrimidinyl and 6-propyl-2-pyrimidinyl groups.

Preferred examples of the unsubstituted group ($r^1$-e) include cyclopentylmethyl, cyclohexylmethyl, 2-cyclohexylethyl, 2-cyclohexylpropyl, 3-cyclohexylpropyl, 4-cyclohexylbutyl, 1-cyclohexyl-1-methylethyl, (4-t-butylcyclohexyl)methyl and (4-methoxycyclohexyl)methyl groups. Preferred examples of the unsubstituted group ($r^1$-f) include benzyl, 2-phenylethyl, 3-phenylpropyl, 4-phenylbutyl, (1-naphthyl)methyl, (2-naphthyl)methyl, 2-(2-naphthyl)ethyl, (4-methylphenyl)methyl, (3-methylphenyl)methyl, (4-ethylphenyl)methyl, (4-butylphenyl)methyl, (4-methoxyphenyl)methyl, 2-(3,4-dimethoxyphenyl)ethyl and (6-methoxynaphthyl)methyl groups. Preferred examples of the unsubstituted group ($r^1$-g) include furfuryl and 3-(4-morpholinyl)propyl groups.

The above-described groups ($r^1$-a) to ($r^1$-g) may be substituted with a plurality of different groups, and examples of the substituent include (i) a halogen atom; (ii) an oxo group; (iii) a cyano group; (iv) a nitro group; (v) —COOR$^{61}$ (wherein R$^{61}$ stands for a hydrogen atom; one equivalent of cation; a residue of a saccharide; or an aliphatic hydrocarbon group having 1 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms); (vi) —OR$^{71}$ (wherein R$^{71}$ stands for a hydrogen atom; an alkyl group having 1 to 4 carbon atoms; an acyl group having 2 to 7 carbon atoms; an alkoxycarbonyl group having 2 to 5 carbon atoms; a tri($C_1$–$C_7$) hydrocarbon silyl group; a group capable of forming an acetal bond together with the oxygen atom attached to the R$^{71}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, a hydroxyl group, a nitro group, a tri($C_1$–$C_7$) hydrocarbon silyloxy group, an alkoxy group having 1 to 4 carbon atoms, an acyloxy group having 2 to 7 carbon atoms, an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms); (vii) —$CONR^{81}R^{810}$ (wherein $R^{81}$ and $R^{810}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon si y oxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein $R^{81}$ and $R^{810}$ are combined with each other to form a five- or six-membered ring); and (viii) —$NR^{91}R^{910}$ (wherein $R^{91}$ and $R^{910}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an alkyl group having 1 to 4 carbon atoms; or a group wherein $R^{91}$ and $R^{910}$ are combined with each other to form a five- or six-membered ring).

Preferred examples of the halogen atom as the substituent (i) include fluorine, chlorine and bromine atoms.

Examples of the $R^{61}$ in the group represented by the formula —$COOR^{61}$ as the substituent (v) include a hydrogen atom; cations such as ammonium, tetramethyl ammonium, cyclohexylammonium, benzylanlmonium and phenetyl ammonium, a morpholinium cation, a piperidinium cation and one equivalent of cations such as $Na^+$, $K^+$, $1/2Ca^+$, $1/2Mg^{2+}$ and $1/3Al^{3+}$; residues of saccharides, for example, monosaccharides such as altrose, glucose, mannose, galactose, ribose, arabinose, xylose and fructose, or deoxy saccharides thereof; and aliphatic hydrocarbon groups having 1 to 10 carbon atoms, i.e., alkyl groups such as methyl, ethyl, propyl, isopropyl, butyl, isobutyl, s-butyl, t-butyl, pentyl, isopentyl, neopentyl, hexyl, octyl and decyl groups, alkenyl groups such as 2-propenyl, 2-butenyl, 2-pentenyl, 2-hexenyl and 5-hexenyl groups and alkynyl group such as 2-butynyl, 2-pentynyl and 3-hexynyl groups, which may be substituted with a halogen atom such as fluorine, chlorine or bromine, an oxy group, a hydroxyl group, a tri ($C_1$–$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, a butyryloxy, isobutyryloxy, valeryloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy or butoxycarbonyloxy group, an alkoxy group having 1 to 4 carbon atoms such as a methoxy, ethoxy, propoxy, isopropoxy, butoxy, isobutoxy, s-butoxy or t-butoxy group an alicyclic hydrocarbon group having 4 to 10 carbon atoms such as a cyclobutyl, cyclopentyl or cyclohexyl group, or an aromatic hydrocarbon group having 6 to 10 carbon atoms such as a phenyl, 1-naphthyl or 2-naphthyl group.

Examples of the $R^{71}$ in the group represented by the formula —$OR^{71}$ as the substituent (iv) include a hydrogen atom; alkyl groups having 1 to 4 carbon atoms such as methyl, ethyl, propyl, isopropyl, butyl, isobutyl, s-butyl and t-butyl groups; acyl groups having 2 to 7 carbon atoms such as acetyl, propionyl, butyryl, isobutyryl, valeryl, isovaleryl, hexanoyl, heptanoyl and benzoyl groups; alkoxycarbonyl groups having 2 to 5 carbon atoms such as methoxycarbonyl, ethoxycarbonyl, propoxycarbonyl, isopropoxycarbonyl, butoxycarbonyl, isobutoxycarbonyl and t-butoxycarbonyl groups; tri($C_1$–$C_7$) hydrocarbon silyl groups such as trimethylsilyl, triethylsilyl, t-butyldimethylsilyl, t-butyldiphenylsilyl and tribenzylsilyl groups; a group capable of forming acetal bond together with the oxygen atom attached to the $R^{71}$ such as a methoxymethyl, 1-ethoxyethyl, 1-methoxy-1-methylethyl, 2-ethoxy-1-methylethyl, 2-methoxyethoxymethyl, tetrahydropyran-2-yl or tetrahydrofuran-2-yl, is attached; aliphatic hydrocarbon groups having 1 to 10 carbon atoms, i.e., alkyl groups such as methyl, ethyl, propyl, isopropyl, butyl, s-butyl, t-butyl, pentyl, isopentyl, neopentyl, t-pentyl, hexyl, heptyl, octyl, nonyl and decyl groups, alkenyl groups such as 2-propenyl, 2-butenyl, 3-butenyl and 3-hexenyl groups and alkynyl groups such as 2-propynyl, 2-butynyl and 3-hexynyl groups, or alicyclic hydrocarbon groups having 4 to 10 carbon atoms such as cyclobutyl, cyclopentyl, cyclohexyl, 3-cyclohexenyl, 4-cyclohexenyl, cyclooctyl and bicyclo[4.4.0]decan-2-yl groups, which may be substituted with a halogen atom such as fluorine, chlorine or bromine, an oxo group, a hydroxyl group, a gcarboxyl group a tri($C_1$–$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, isovaleryloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy or butoxycarbonyloxy group, an alkoxy group having 1 to 4 carbon atoms such as a methoxy, ethoxy propoxy, isopropoxy, butoxy, isobutoxy or t-butoxy group, an alkoxycarbonyl group having 2 to 5 carbon atoms such as a methoxycarbonyl, ethoxycarbonyl, isobutoxycarbonyl or t-butoxycarbonyl group, or an aromatic hydrocarbon group having 6 to 10 carbon atoms such as a phenyl, 1-naphthyl or 2-naphthyl group; and aromatic hydrocarbon groups having 6 to 10 carbon atoms such as phenyl, 1-naphthyl and 2-naphthyl groups, which may be substituted with a halogen atom such as fluorine, chlorine or bromine, an oxo group, a hydroxyl group, a nitro group, a tri($C_1$-$C_7$) hydrocarbon silyloxy group such as a trimethylsilyloxy, triethylsilyloxy or t-butyldimethylsilyloxy group, an alkoxy group having 1 to 4 carbon atoms such as a methoxy, ethoxy, propoxy, isopropoxy, butoxy, isobutoxy, s-butoxy or t-butoxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy group or t-butoxycarbonyloxy group, an acyl group having 2 to 7 carbon atoms such as an acetyl, propionyl, butyryl, isobutyryl, valeryl, hexanoyl, heptanoyl or benzoyl group, a carboxyl group, an alkoxycarbonyl group having 2 to 5 carbon atoms such as a methoxycarbonyl, ethoxycarbonyl, propoxycarbonyl, isopropoxycarbonyl, butoxycarbonyl, isobutoxycarbonyl or t-butoxycarbonyl group, or an alkyl group such as a methyl, ethyl, propyl, isopropyl, butyl, isobutyl, s-butyl or t-butyl group.

Examples of the $R^{81}$ and $R^{810}$ in the group represented by the formula —$CONR^{81}R^{810}$ as the substituent (vii) include a hydrogen atom; aliphatic hydrocarbon groups having 1 to 10 carbon atoms, i.e., alkyl groups such as methyl, ethyl, propyl, isopropyl, butyl, isobutyl, s-butyl, t-butyl, pentyl, isopentyl, neopentyl, t-pentyl, hexyl, heptyl, octyl, nonyl and decyl groups, alkenyl groups such as 2-propenyl, 2-butenyl, 2-pentenyl and 3-hexenyl groups and alklynyl groups such as 2-propynyl, 2-butynyl, 2-pentynyl and 3-hexynyl groups, or alicyclic hydrocarbon groups having 4 to 10 carbon atoms such as cyclobutyl, cyclopentyl, cyclohexyl, cyclooctyl and bicyclo[4.4.0]decan-2-yl groups, which may be substituted with a halogen atom such as fluorine, chlorine or bromine, an oxo group, a hydroxyl group, a tri($C_1$-$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy group or t-butoxycarbonyloxy group, an alkoxy group having 1 to 4 carbon atoms such as a methoxy, ethoxy, propoxy, isopropoxy, butoxy, isobutoxy, s-butoxy or t-butoxy group, or an aromatic hydrocarbon group having 6 to 10 carbon atoms such as a phenyl, 1-naphthyl or 2-naphthyl group; aromatic hydrocarbon groups having 6 to 10 carbon atoms such as phenyl, 1-naphthyl and 2-naphthyl groups, which may be substituted with a halogen atom such as fluorine, chlorine or bromine, a hydroxyl group, a nitro group, a tri($C_1$-$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy group or t-butoxycarbonyloxy group, an alkoxy group having 1 to 4 carbon atoms such as a methoxy, ethoxy, propoxy, isopropoxy, butoxy, isobutoxy, s-butoxy or t-butoxy group, an acyl group having 2 to 7 carbon atoms such as an acetyl, propionyl, butyryl, isobutyryl, valeryl, hexanoyl or benzoyl group, a carboxyl group, an alkoxycarbonyl group having 2 to 5 carbon atoms such as a methoxycarbonyl, ethoxycarbonyl, propoxycarbonyl, isopropoxycarbonyl, butoxycarbonyl, isobutoxycarbonyl or t-butoxycarbonyl group, or an alkyl group having 1 to 4 carbon atoms such as a methyl, ethyl, propyl, isopropyl, butyl, isobutyl, s-butyl or t-butyl group; or a group wherein the $R^{81}$ and $R^{810}$ are combined with each other to form a five- or six-membered ring together with a nitrogen atom intervening between the $R^{81}$ and the $R^{810}$, for example, 1-pyrrolidinyl, 1-piperidinyl, 1-imidazolidinyl, 1-piperazinyl, 4-morpholinyl and 2-thioxo-3-thiazolidinyl groups, which may be substituted with an alkoxy group having 1 to 4 carbon atoms such as methoxy, ethoxy, propoxy, isopropoxy, butoxy, isobutoxy, s-butoxy or t-butoxy group, or an alkyl group having 1 to 4 carbon atoms such as a methyl, ethyl, propyl, isopropyl, butyl, isobutyl, s-butyl or t-butyl group.

Examples of the $R^{91}$ and $R^{910}$ in the group represented by the formula —$NR^{91}R^{910}$ as the substituent (viii) include a hydrogen atom; aliphatic hydrocarbon groups having 1 to 10 carbon atoms, i.e., alkyl groups such as methyl, ethyl, propyl, isopropyl, butyl, isobutyl, s-butyl, t-butyl, pentyl, isopentyl, neopentyl, hexyl, octyl and decyl groups, alkenyl groups such as 2-propenyl, 2-butenyl, 2-pentenyl, 2-hexenyl and 5-hexenyl groups and alkynyl groups such as 2-butynyl, 2-pentynyl and 3-hexynyl groups, or alicyclic hydrocarbon groups having 4 to 10 carbon atoms such as cyclobutyl, cyclopentyl, cyclohexyl, cycloheptyl, cyclooctyl and bicyclo[4.4.0]decan-2-yl groups, which may be substituted with a halogen atom such as fluorine, chlorine or bromine, an oxo group, a hydroxyl group, a tri($C_1$-$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy or t-butoxycarbonyloxy group, an alkoxy group having 1 to 4 carbon atoms such as a methoxy, ethoxy, propoxy, isopropoxy, butoxy, s-butoxy or t-butoxy group, or an aromatic hydrocarbon group having 6 to 10 carbon atoms such as a phenyl, 1-naphthyl or 2-naphthyl group; aromatic hydrocarbon groups having 6 to 10 carbon atoms such as phenyl, 1-naphthyl and 2-naphthyl groups, which may be substituted with a halogen atom such as fluorine, chlorine or bromine, a hydroxyl group, a nitro group, a tri($C_1$-$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy or butoxycarbonyloxy group, an alkoxy group having 1 to 4 carbon atoms such as a methoxy, ethoxy, propoxy, isopropoxy, butoxy, isobutoxy or t-butoxy group, or an alkyl group such as a methyl, ethyl, propyl, isopropyl, butyl, isobutyl, s-butyl or t-butyl group; or a group wherein the R and $R^{910}$ are combined with each other to foden a five- or six-membered ring together with a nitrogen atom intervening between the $R^{91}$ and the $R^{910}$ for example, 1-pyrrolidinyl, 1-piperidinyl, 1-imidazolidinyl, 1-piperazinyl, 4-morpholinyl and 2-thioxo-3-thiazolidinyl groups, which may be substituted with an alkoxy group having 1 to 4 carbon atoms, such as methoxy, ethoxy, propoxy, isopropoxy, butoxy, isobutoxy or t-butoxy group, or an alkyl group having 1 to 4 carbon atoms such as a methyl, ethyl, propyl, isopropyl, butyl, isobutyl or t-butyl group.

Preferred examples of the $R^1$ include methyl, ethyl, propyl, 2-propenyl, isopropyl, butyl, isobutyl, s-butyl, t-butyl, hexyl, octyl, 2,3-dihydroxypropyl, 2,3-diacetoxypropyl, 3,4-dimethoxyphenylpropyl, 4-phenoxybutyl, carboxymethyl, methoxycarbonylmethyl, ethoxycarbonylmethyl, 2-carboxyethyl, 5-carboxypentyl, 5-methoxycarbonylpentyl, 5-butoxycarbonylpentyl, 5-decyloxycarbonylpentyl, 5-carboxy-4-pentenyl, 5-methoxycarbonyl-4-pentenyl, 5-methoxycarbonyl-5,5-difluoropentyl, 5-(2-thioxo-3-thiazolidinylcarbonyl)-pentyl, 5-(6-D-glucosylcarbonyl)pentyl, 5-(1-D-xylosylcarbonyl)pentyl, 5-(5-D-ribosylcarbonyl)pentyl, 2-(butylamino)ethyl, 2-(4-fluorophenylamino)ethyl, 2-(2-phenylethylamino)ethyl, cyclohexyl, phenyl, 3-methylphenyl, 4-methylphenyl, 3-methoxyphenyl, 4-methoxyphenyl, 4-fluorophenyl, 4-chlorophenyl, 4-bromophenyl, 2,5-dichlorophenyl, 4-bromo-3-methylphenyl, 2,3,5,6-tetrafluorophenyl, 2,4,5-trichlorophenyl, 3-aminophenyl, 4-aminophenyl, 4-nitrophenyl, 2-pyridinyl, 4-pyridinyl, 3-hydroxy-2-pyridinyl, 4-hydroxy-2-pyrimidinyl, 4,6-dimethyl-2-pyrimidinyl, 4,6-dichloro-2-pyrimidinyl, 4-hydroxy-6-propyl-2-pyrimidinyl, 4,5-diamino-2-pyrimidinyl, 4,6-diamino-2-pyrimidinyl, 4-amino-6-hydroxy-2-pyrimidinyl, 1-methyl-2-imidazolyl, 4-methyl-1,2,4-triazole-3-yl, 1-methyl-5-tetrazolyl, 2-benzimidazolyl, 2-benzoxazolyl, 2-benzothiazolyl, 5-chloro-2-benzothiazolyl, 6-ethoxy-2-benzothiazolyl, 2-quinolinyl, 4-hydroxy-pteridinyl, 6-hydroxy-8-purinyl, 6-purinyl, 4-pyrazolo[3,4-d]pyrimidinyl, 2-amino-6-purinyl, 6-hydroxy-2-purinyl, 2-hydroxy-6-purinyl, 3-cyclohexylpropyl, benzyl, (2-chlorophenyl)methyl, (4-chlorophenyl)methyl, 2-(3,4-dichlorophenyl)ethyl, (3-fluorophenyl)methyl, (4-methoxyphenyl)methyl, (3-trifluoromethylphenyl)-methyl and 3-phenylpropyl, 2-furanylmethyl, 3-(4-morpholinyl)propyl.

In the above-described formula (I), the $R^2$ stands for a substituted or unsubstituted aliphatic hydrocarbon group having 1 to 10 carbon atoms, alicyclic hydrocarbon group having 4 to 10 carbon atoms, aromatic hydrocarbon having 6 to 10 carbon atoms or heterocyclic group having 1 to 9 carbon atoms. Examples of the unsubstituted aliphatic hydrocarbon group having 1 to 10 carbon atoms in the $R^2$ include alkyl groups such as methyl, ethyl, propyl, isopropyl, butyl, isobutyl, s-butyl, t-butyl, pentyl, isopentyl, neopentyl, 4-methylpentyl, hexyl, heptyl, octyl, 3,7-dimethyloctyl, nonyl and decyl groups; alkenyl groups such as vinyl, 1-methylvinyl, 1-ethylvinyl, 1-propenyl, 2-propenyl, 2-methyl-1-propenyl, 1-butenyl, 2-butenyl, 2-methyl-1-butenyl, 1,3-butadienyl, 1-pentenyl, 2-pentenyl, 4-methyl-1-pentenyl, 1-hexenyl, 2-hexenyl, 3-hexenyl, 5-hexenyl, 1,5-hexadienyl, 1-heptenyl, 1-octenyl, 6-methyl-1-heptenyl, 1-nonenyl and 1-decenyl groups; and alkynyl groups such as ethynyl, 1-propynyl, 2-propynyl, 1-butynyl, 3-methyl-1-butynyl, 3,3-dimethyl-1-butynyl, 1-pentynyl, 2-pentynyl, 1-hexynyl, 2-hexynyl, 5-hexen-1-yl, 1-heptynyl, 1-nonynyl and 1-decynyl groups.

Examples of the unsubstituted alicyclic hydrocarbon group having 4 to 10 carbon atoms in the $R^2$ include cyclobutyl, cyclopentyl, cyclohexyl, 1-cyclohexenyl, 3-cyclohexenyl, 4-cyclohexenyl, cycloheptyl, cyclooctyl and bicyclo[4.4.0]decan-2-yl. Examples of the unsubstituted aromatic hydrocarbon group having 6 to 10 carbon atoms in the $R^2$ include phenyl, 1-naphthyl and 2-naphthyl groups. Examples of the unsubstituted heterocyclic hydrocarbon group having 1 to 9 carbon atoms in the $R^2$ include monocyclic or bicyclic groups having an oxygen, nitrogen or sulfur atom, such as furyl, thienyl, pyrolyl, oxazolyl, isooxazolyl, thiazolyl, isothiazolyl, imidazolyl, pyrazolyl, triazolyl, tetrazolyl, pyranyl, pyridyl, pyrazinyl, pyrimidinyl, benzofuranyl, indolyl, benzimidazolyl, benzothiazolyl, benzoxazolyl, quinolyl, isoquinolyl, quinazolyl, purinyl, pteridinyl, morpholinyl and piperidinyl groups.

The $R^2$ may be a group comprising, attached to each other, any combination of the above-described aliphatic hydrocarbon group having 1 to 10 carbon atoms, alicyclic hydrocarbon group having 4 to 10 carbon atoms, aromatic hydrocarbon group having 6 to 10 carbon atoms and heterocyclic group having 1 to 9 carbon atoms. Among them, preferred examples of the $R^2$ include a substituted or unsubstituted ($r^2$-a) aliphatic hydrocarbon group having 1 to 10 carbon atoms which may be substituted with one or a plurality of alkoxy groups having 1 to 4 carbon atoms;

($r^2$-b) alicyclic hydrocarbon group having 4 to 10 carbon atoms which may be substituted with one or a plurality of alkyl groups having 1 to 4 carbon atoms or alkoxy groups having 1 to 4 carbon atoms;

($r^2$-c) aromatic hydrocarbon group having 6 to 10 carbon atoms which may be substituted with one or a plurality of alkyl groups having 1 to 4 carbon atoms or alkoxy groups having 1 to 4 carbon atoms;

($r^2$-d) heterocyclic group having 1 to 9 carbon atoms which may be substituted with one or a plurality of alkyl groups having 1 to 4 carbon atoms or alkoxy groups having 1 to 4 carbon atoms;

($r^2$-e) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms or alkoxy groups having 1 to 4 carbon atoms;

($r^2$-f) aliphatic hydrocarbon group having 1 to 10 carbon atoms substituted with an aromatic hydrocarbon group having 6 to 10 carbon atoms and which may be substituted with one or a plurality of alkyl groups having 1 to 4 carbon atoms or alkoxy groups having 1 to 4 carbon atoms; and ($r^2$-g) aliphatic hydrocarbon group having 1 to 10 carbon atoms substituted with a heterocyclic group having 1 to 9 carbon atoms and which may be substituted with one or a plurality of alkyl groups having 1 to 4 carbon atoms or alkoxy groups having 1 to 4 carbon atoms.

Preferred examples of the unsubstituted group ($r^2$-a) include methyl, ethyl, propyl, isopropyl, butyl, isobutyl, s-butyl, pentyl, hexyl, octyl, nonyl, decyl, vinyl, 1-propenyl, 1-pentenyl, 4-pentenyl, 6-methyl-1-heptenyl, ethynyl, 1-propynyl, 1-pentynyl, 3-methoxypropyl and 1-(2-methoxyethyl)vinyl groups. Preferred examples of the unsubstituted group ($r^2$-b) include cyclopentyl, cyclohexyl, cyclooctyl, 3-methylcyclopentyl, 4-methylcyclohexyl, 4-butylcyclohexyl, 3,4-dimethylcyclohexyl and 4-methoxycyclohexyl groups. Preferred examples of the unsubstituted group ($r^2$-c) include phenyl, 1-naphthyl, 2-methylphenyl, 3-methylphenyl, 4-methylphenyl, 2,4-dimethylphenyl, 3,5-dimethylphenyl, 4-ethylphenyl, 4-isobutylphenyl, 3-t-butylphenyl, 2-methoxyphenyl, 3-methoxyphenyl, 4-methoxyphenyl, 4-ethoxyphenyl, 6-methoxy-2-naphthyl, 7-methoxy-2-naphthyl and 6,7-dimethoxy-2-naphthyl groups.

Preferred examples of the unsubstituted group ($r^2$-d) include 2-oxazolyl, 2-thiazolyl, 2-imidazolyl, 2-pyridyl, 4-pyridyl, 2-pyrimidinyl, 2-benzimidazolyl, 2-benzoxazolyl, 2-benzothiazolyl, 6-purinyl, 1-methylimidazol-2-yl, 4-methyl-1,2,4-triazol-3-yl, 1-methyl-5-tetrazolyl, 5-methyl-2-benzimidazolyl, 4-methyl-2-pyrimidinyl and 6-propyl-2-pyrimidinyl groups.

Preferred examples of the unsubstituted group ($r^2$-e) include cyclopentylmethyl, cyclohexylmethyl, 2-cyclohexylmethyl, 2-cyclohexylpropyl, 3-cyclohexylpropyl, 4-cyclohexylbutyl, (4-t-butylcyclohexyl)methyl and (4-methoxycyclohexyl)methyl groups. Preferred examples of the unsubstituted group ($r^2$-f) include benzyl, 2-phenylethyl, 3-phenylpropyl, 4-phenylbutyl, (1-naphthyl)methyl, (2-naphthyl)methyl, 2-phenylvinyl, 2-phenyl-1-propenyl, (4-methylphenyl)methyl, (3-methylphenyl)methyl, (4-ethylphenyl)methyl, (4-butylphenyl)methyl, (4-methoxyphenyl)methyl and 2-(3,4-dimethoxyphenyl)ethyl groups. Preferred examples of the unsubstituted group ($r^2$-g) include furfuryl and 3-(4-morpholinyl)propyl groups.

The above-described groups ($r^2$-a) to ($r^2$-g) may be substituted with a plurality of different groups, and examples of the substituent include (i) a halogen atom; (ii) an oxo group; (iii) a cyano group; (iv) a nitro group; (v) —COOR$^{62}$ (wherein R$^{62}$ stands for a hydrogen atom; ohe equivalent of cation; a residue of a saccharide; or an aliphatic hydrocarbon group having 1 to 10 carbon atoms which may be substituted with a halogen atom, an oxo group, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms); (vi) —OR$^{72}$ (wherein R$^{72}$ stands for a hydrogen atom; an alkyl group having 1 to 4 carbon atoms; an acyl group having 2 to 7 carbon atoms; an alkoxycarbonyl group having 2 to 5 carbon atoms; a tri($C_1$–$C_7$) hydrocarbon silyl group; a group capable of forming an acetal bond together with the oxygen atom attached to the R$^{72}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, hydroxyl group, a nitro group, a tri($C_1$–$C_7$) hydrocarbon silyloxy group an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms); (vii) —CONR$^{82}$R$^{820}$ (wherein R$^{82}$ and R$^{820}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein the R$^{82}$ and R$^{820}$ are combined with each other to form a five- or six-membered ring); (viii) —NR$^{92}$R$^{920}$ (wherein R$^{92}$ and R$^{920}$ and R which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein the R$^{92}$ and R$^{920}$ are combined with each other to form a five- or six-membered ring); and (ix) —SR$^{76}$(wherein R$^{76}$ stands for an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkylcarbonyl group having 2 to 5 carbon atoms or an aromatic hydrocarbon group having 6 to 10 carbon atoms; an aromatic hydrocarbon group having 6 to 10 carbon atoms which may be substituted with a halogen atom, a hydroxyl group, a tri($C_1$–$C_7$) hydrocarbon silyloxy group, a nitro group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms.

Examples of the substituents (i) to (viii) of the groups ($r^2$-a) to ($r^2$-g) include the same substituents as those of the groups ($r^1$-a) to ($r^1$-g) described above in connection with the $R^1$. Examples of the —$SR^{76}$ in the substituent (ix) of the groups ($r^2$-a) to ($r^2$-g) include aliphatic hydrocarbon groups having 1 to 10 carbon atoms, i.e., alkyl groups such as methyl, ethyl, propyl, isopropyl, butyl, isobutyl, s-butyl, t-butyl, pentyl, isopentyl, neopentyl, t-pentyl, hexyl, heptyl, octyl and decyl groups, alkenyl groups such as 2-propenyl, 2-butenyl, 3-hexenyl and 5-hexenyl groups and alkynyl groups such as 2-propynyl, 2-butynyl and 3-hexynyl groups, or alicyclic hydrocarbon groups having 4 to 10 carbon atoms such as cyclobutyl, cyclopentyl, cyclohexyl and bicyclo[4.4.0]decan-2-yl groups, which may be substituted with a halogen atom such as fluorine, chlorine or bromine, an oxo group, a hydroxyl group, a carboxyl group, a tri($C_1$-$C_7$) hydrocarbon silyloxy group such as a trimethylsilyloxy, triethylsilyloxy, t-butyldimethylsilyloxy or t-butyldiphenylsilyloxy group, an acyloxy group having 2 to 7 carbon atoms such as an acetoxy, propionyloxy, butyryloxy, isobutyryloxy, valenloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy group or t-butoxycarbonyloxy group, an alkoxy group having 1 to 4 carbon atoms such as a methoxy, ethoxy, propoxy, isopropoxy, butoxy, isobutoxy, or t-butoxy group, an alkoxycarbonyl group having 2 to 5 carbon atoms such as a methoxycarbonyl, ethoxycarbonyl, propoxycarbonyl, isopropoxycarbonyl, butoxycarbonyl or t-butoxycarbonyl group, or an aromatic hydrocarbon group having 6 to 10 carbon atoms such as a phenyl, 1-naphthyl or 2-naphthyl group; and aromatic hydrocarbon groups having 6 to 10 carbon atoms such as phenyl, 1-naphthyl and 2-naphthyl groups, which may be substituted with a halogen atom such as fluorine, chlorine or bromine, a hydroxy group, a tri($C_1$-$C_7$) hydrocarbon silyloxy group such as a trimethylsilyloxy, triethylsilyloxy or t-butyldimethylsilyloxy group, a nitro group, an acyloxy group having 2 to 7 carbon atoms such as an acetoxy, propionyloxy, butyryloxy, isobutyryloxy, valeryloxy, hexanoyloxy, heptanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy or t-butoxycarbonyloxy group, an alkoxy group having 1 to 4 carbon atoms such as a methoxy, ethoxy, propoxy, isopropoxy, butoxy, isobutoxy, s-butoxy or-t-butoxy group, an acyl group having 2 to 7 carbon atoms such as an acetyl, propionyl, butyryl, isobutyryl, valeryl, hexanoyl or benzoyl group, an alkoxycarbonyl group having 2 to 5 carbon atoms such as a carboxyl, methoxycarbonyl, ethoxycarbonyl, propoxycarbonyl, isopropoxycarbonyl, butoxycarbonyl, isobutoxycarbonyl or t-butoxycarbonyl group, or an alkyl group such as a methyl, ethyl, propyl, isopropyl, butyl, isobutyl, s-butyl or t-butyl group.

Preferred exeunples of the $R^2$ include methyl, ethyl, propyl, nonyl, 3-carboxypropyl, 3-methoxycarbonylpropyl, 3-(2-thioxo-3-thiazolidinylcarbonyl)propyl, 3-(6-D-glucosylcarbonyl)propyl, 5-carboxypentyl, 5-methoxycarbonylpentyl, 5-ethoxycarbonylpentyl, 5-butoxycarbonylpentyl, 5-decyloxycarbonylpentyl, 5-(2-thioxo-3-thiazolidinylcarbonyl)pentyl, 5-(6-D-glucosylcarbonyl)pentyl, 5-(1-D-xylosylcarbonyl)pentyl, 5-(5-D-ribosylcarbonyl)pentyl, 5-cyanopentyl, 5-methoxycarbonyl-5,5-difluoropentyl, 5-methoxycarbonyl-4pentenyl, 3,6-dihydroxyhexyl, 3,6-dihydroxy-1-hexenyl, 3,6-diacetoxy-1-hexenyl, 3,6-bis-t-butyldimethylsilyloxy-1-hexenyl, 3,6-bismethoxycarbonyloxy-1-hexenyl, 3,5-diacetoxy-4-(1-methoxy-1-methylethoxy-1-pentenyl, 3,5-diacetoxy-4-hydroxy-1-hexenyl, 7-hydroxy-6-hydroxymethyl-1-heptenyl, 3,4,5-triacetoxy-1-pentenyl, 5-methoxycarbonyl-1-pentnyl, 3-methoxycarbonylpropylthiomethyl, cyclohexyl, phenyl, 4-dimethylaminophenyl, 4-methoxycarbonylphenyl, 4-(3-hydroxy-2-hydroxymethylpropyl)phenyl, 4-pyridinyl, 5-methyl-2-furanyl, 2-cyclohexylethyl, 4-oxo-4-phenylbutyl, 2-phenylvinyl, 2-(3,4-dimethoxyphenyl)ethyl, 2-(4-dimethylaminophenyl)vinyl, 2-(1-piperidinyl)ethyl, 2-(4-morpholinyl)ethyl and 2-(4-methyl-1-piperazinyl)ethyl.

In the above-described formula (I), the $R^5$ stands for a hydrogen atom or a substituted or unsubstituted aliphatic hydrocarbon group having 1 to 10 carbon atoms or alicyclic hydrocarbon group having 4 to 10 carbon atoms. Examples of the unsubstituted aliphatic hydrocarbon group having 1 to 10 carbon atoms in the $R^5$ include alkyl groups such as methyl, ethyl, propyl, isopropyl, butyl, isobutyl, s-butyl, t-butyl, pentyl, isopentyl, neopentyl, hexyl, heptyl, octyl, 3,7-dimethyloctyl, nonyl and decyl groups; alkenyl groups such as 2-propenyl, 2-butenyl, 3-butenyl and 3-hexenyl groups; and alkynyl groups such as 2-propynyl and 2-butynyl groups.

Examples of the unsubstituted alicyclic hydrocarbon group having 4 to 10 carbon atoms in the $R^5$ include cyclobutyl, cyclopentyl, cyclohexyl, 3-cyclohexenyl, cyclooctyl and bicyclo[4.4.0]decan-2-yl.

The $R^5$ may be a group comprising, attached to each other, any combination of the above-described aliphatic hydrocarbon group having 1 to 10 carbon atoms and alicyclic hydrocarbon group having 4 to 10 carbon atoms. Among them, preferred examples of the $R^5$ include a substituted or unsubstituted ($r^5$-a) aliphatic hydrol carbon group having 1 to 10 carbon atoms which may be substituted with one or a plurality of phenyl groups;

($r^5$-b) alicyclic hydrocarbon group having 4 to 10 carbon atoms which may be substituted with one or a plurality of alkyl groups having 1 to 4 carbon atoms, alkoxy groups having 1 to 4 carbon atoms or phenyl groups; and ($r^5$-c) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms, alkoxy groups having 1 to 4 carbon atoms or phenyl groups.

Preferred examples of the unsubstituted group ($r^5$-a) include methyl, ethyl, propyl, isopropyl, butyl, isobutyl, s-butyl, t-butyl, pentyl, hexyl, octyl, decyl, 3,7-dimethyloctyl, benzyl, 2-phenylethyl, 3-phenylpropyl, 4-phenylbutyl and 5-phenylpentyl groups. Preferred examples of the unsubstituted group ($r^5$-b) include cyclopentyl, cyclohexyl, cyclooctyl, 3-methylcyclopentyl, 4-methylcyclohexyl, 4-butylcyclohexyl, 3,4-dimethylcyclohexyl, 4-methoxycyclohexyl and 4-phenylcyclohexyl groups. Preferred examples of the unsubstituted group (r⁵-c) include 3-cyclopentylpropyl, 3-cyclohexylpropyl, 4-cyclopentylbutyl and 4-cyclohexylbutyl groups.

The above-described groups (r⁵-a) to (r⁵-c) may be substituted with a plurality of different groups, and examples of the substituent include (i) a halogen atom; (ii) an oxo group; (iii) a cyano group; (iv) a nitro group; (v) —COOR$^{65}$ wherein R$^{65}$ stands for a hydrogen atom; one equivalent of cation; a residue of a saccharide; or an aliphatic hydrocarbon group having 1 to 10 carbon atoms which may be substituted with a halogen atom, an oxo group, a hydroxyl group, a nitro group, a tri(C$_1$-C$_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms); (vi) —OR$^{75}$ (wherein R$^{75}$ stands for a hydrogen atom; an alkyl group having 1 to 4 carbon atoms; an acyl group having 2 to 7 carbon atoms; an alkoxycarbonyl group having 2 to 5 carbon atoms; a tri(C$_1$-C$_7$) hydrocarbon silyl group; a group capable of forming an acetal bond together with the oxygen atom attached to the R$^{75}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri(C$_1$-C$_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, hydroxyl group, a nitro group, a tri (C$_1$-C$_7$) hydrocarbon silyloxy group, an alkoxy group having 1 to 4 carbon atoms, an acyloxy group having 2 to 7 carbon atoms, an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms ); (vii) —CONR$^{85}$R$^{850}$ (wherein R$^{85}$ and R$^{850}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri(C$_1$-C$_7$) hydrocarbon sily oxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group a nitro group, a tri(C$_1$-C$_7$) hydrocarbon silyloxy group, an acryloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein the R$^{85}$ and R$^{850}$ are combined with each other to form a five- or six-membered ring); (viii) —NR$^{95}$R$^{950}$(wherein R$^{95}$ and R$^{950}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri(C$_1$-C$_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; and an aromatic hydrocarbon group having 6 to 10 carbon atoms which may be substituted with a halogen atom, a hydroxyl group, a nitro group, a tri(C$_1$-C$_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein the R$^{95}$ and R$^{950}$ are combined with each other to form a five- or six-membered ring).

Examples of the substituents (i) to (viii) of the groups (r⁵-a) to (r⁵-c) include the same substituents as those of the groups (r¹-a) to (r¹-g) described above in connection with the R¹.

Preferred examples of the R⁵ include methyl, ethyl, propyl, isopropyl, butyl, t-butyl, hexyl, octyl, 3,7-dimethyloctyl, 3,7-dimethyl-6-octenyl, benzyl, 3-(3,4-dimethoxyphenyl)propyl, 5-phenylpentyl, cyclohexyl, 3-cyclohexylpropyl, 4-cyclohexylbutyl, 6-hydroxyhexyl, 6-t-butyldimethylsilyloxyhexyl, 6-acetoxyhexyl, 6-(1-ethoxyethoxy)hexyl, 5-carboxypentyl, 5-methoxycarbonylpentyl, 5-(6-D-glucosylcarbonyl)pentyl and 4-phenoxybutyl.

In the above-described formula (I) the R³ stands for a hydrogen atom, a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms. When the R³ is attached to the carbon atom of the cyclopentene skeleton through a single bond, X stands for a hydrogen atom, —OR⁴ (wherein R⁴ stands for a hydrogen atom, an alkyl group having 1 to 4 carbon atoms, an acyl group having 2 to 7 carbon atoms, an alkoxycarbonyl group having 2 to 5 carbon atoms, a tri(C$_1$-C$_7$) hydrocarbon silyl group or a group capable of forming an acetal bond together with the oxygen atom attached to the R⁴) or is absent when the R³ is attached to the carbon atom through a double bond. Specifically, when the R³ is attached to the cyclopentene skeleton through a single bond, the above-described formula (I) represents 2-substituted-2-cyclopentenones represented by the following formula (I'):

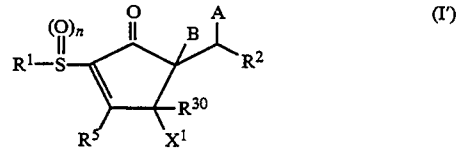

wherein A, B, R¹, R², R⁵ and n are as defined above;

R³⁰ stands for a hydrogen atom or a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms; and $X^1$ stands for a hydrogen atom or $OR^4$ (wherein $R^4$ is as defined above). When the $R^3$ is attached to the carbon atom of the cyclopentene skeleton through a double bond and X is absent, the above-described formula (I) represents 2-substituted-2-cyclopentenones represented by the following formula (I''):

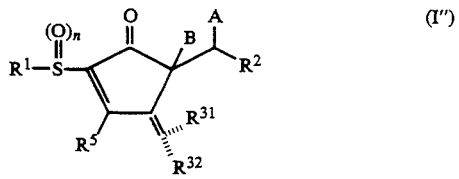

wherein A, B, $R^1$, $R^2$, $R^5$, n and are as defined above;

$R^{31}$ and $R^{32}$ which may be the same or different from each other stand for a hydrogen atom, a substituted or unsubstituted aliphatic hydrocarbon group having 1 to 9 carbon atoms, alicyclic hydrocarbon group having 4 to 10 carbon atoms or aromatic hydrocarbon group having 6 to 10 carbon atoms, or a group wherein the $R^{31}$ and $R^{32}$ are combined with each other to form an alicyclic hydrocarbon group having 4 to 10 carbon atoms.

The $R^{30}$ in the above-described formula (I') stands for a hydrogen atom, a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms. Examples of the unsubstituted aliphatic hydrocarbon group having 1 to 10 carbon atoms in the $R^{30}$ include alkyl groups such as methyl, ethyl, propyl, isopropyl, butyl, s-butyl, t-butyl, pentyl, isopentyl, neopentyl, hexyl, heptyl, octyl, 3,7-dimethyloctyl, nonyl and decyl groups; alkenyl groups such as vinyl, 1-methylvinyl, 1-propenyl, 2-propenyl, 2-methyl-ipropenyl, 1-butenyl, 2-butenyl, 2-methyl-1-butenyl, 1-pentenyl, 2-pentenyl, 1-hexenyl, 2-hexenyl, 3,3-dimethyl-1-butenyl, 5-hexenyl, 1,5-hexadienyl, 1-heptenyl, 1-octenyl, 3-methyl-1-octenyl, 4,4-dimethyl-1-octenyl, 1,7-octadienyl, 1-nonenyl, 5-methyl-1-nonenyl and 1-decenyl groups; and alkynyl groups such as ethynyl, 1-propynyl, 2-propynyl, 1-butynyl, 3-methyl-1-butynyl, 3,3-dimethyl-1-butynyl, 1-pentynyl, 2-pentynyl, 1-hexynyl, 2-hexynyl, 5-hexen-1-yl, 1-heptynyl, 1-nonynyl and 1-decynyl groups.

Examples of the unsubstituted alicyclic hydrocarbon groups having 4 to 10 carbon atoms in the $R^{30}$ include cyclobutyl, cyclopentyl, cyclohexyl, 1-cyclohexenyl, 3-cyclohexenyl, 4-cyclohexenyl, cycloheptyl, cyclooctyl and bicyclo[4.4.0]decan-2-yl groups.

Examples of the unsubstituted aromatic hydrocarbon group having 6 to 10 carbon groups in the $R^{30}$ include phenyl, 1-naphthyl and 2-naphthyl groups.

The $R^{30}$ may be a group comprising, attached to each other, any combination of the above-described aliphatic hydrocarbon group having 1 to 10 carbon atoms, alicyclic hydrocarbon group having 4 to 10 carbon atoms and aromatic hydrocarbon group having 6 to 10 carbon atoms. Among them, preferred examples of the $R^{30}$ include a substituted or unsubstituted ($r^{30}$-a) aliphatic hydrocarbon group having 1 to 10 carbon atoms which may be substituted with one or a plurality of alkoxy groups having 1 to 4 carbon atoms;

($r^{30}$-b) alicyclic hydrocarbon group having 4 to 10 carbon atoms which may be substituted with one or a plurality of alkyl groups having 1 to 4 carbon atoms and alkoxy groups having 1 to 4 carbon atoms;

($r^{30}$-c) aromatic hydrocarbon group having 6 to 10 carbon atoms which may be substituted with one or a plurality of alkyl groups having 1 to 4 carbon atoms and alkoxy groups having 1 to 4 carbon atoms;

($r^{30}$-d) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms and alkoxy groups having 1 to 4 carbon atoms; and ($r^{30}$-e) aliphatic hydrocarbon group having 1 to 10 carbon atoms substituted with an aromatic hydrocarbon group having 6 to 10 carbon atoms and which may be substituted with one or a plurality of alkyl groups having 1 to 4 carbon atoms and alkoxy groups having 1 to 4 carbon atoms.

Preferred examples of the unsubstituted group ($r^{30}$-a) include methyl, ethyl, propyl, isopropyl, butyl, isobutyl, t-butyl, pentyl, hexyl, octyl, decyl, 3,7-dimethyloctyl, vinyl, 1-propenyl, 1-methylvinyl, 1-butenyl, 1-octenyl, 3,3-dimethyl-1-butenyl, 3-methyl-1-octenyl, 4,4-dimethyl-1-octenyl, nona-7-yne-1-enyl, 5-methyl-1-nonenyl, 1-propynyl, 3,3-dimethyl-1-butynyl, 1-pentynyl, 3,3-dimethyl-1-hexynyl and 2-hexenyl. Preferred examples of the unsubstituted group ($r^{30}$-b) include cyclopentyl, cyclohexyl, cyclooctyl, 3-methylcyclopentyl, 4-methylcyclohexyl, 4-butylcyclohexyl, 3,4-dimethylcyclohexyl and 4-methoxycyclohexyl groups. Preferred examples of the unsubstituted group ($r^{30}$-c) include phenyl, 1-naphthyl, 4-methylphenyl, 3,5-dimethylphenyl, 4-ethylphenyl, 4-butylphenyl, 4-methoxyphenyl, 4-ethoxyphenyl, 6-methoxy-2-naphthyl and 6,7-dimethoxy-2-naphthyl groups. Preferred examples of the unsubstituted group ($r^{30}$-d) include 3-cyclopentyl-1-propenyl, 3-cyclohexylpropyl, 3-cyclopentyl-3,3-dimethyl-1-propenyl, 4-cyclohexyl-1-propenyl and 3-(3-methylcyclopentyl)-1-propenyl groups. Preferred examples of the unsubstituted group ($r^{30}$-e) include benzyl, 2-phenylethyl, 3-phenylpropyl, 4-phenylbutyl, 1-naphthylmethyl, 2-naphthylmethyl, 4-butylbenzyl, 4-methoxybenzyl, 3,4-dimethoxybenzyl and 3,3-dimethyl-4-phenyl-1-butenyl groups.

The $X^1$ in the above-described formula (I') stands for a hydrogen atom or $—OR^4$ wherein $R^4$ stands for a hydrogen atom, an alkyl group having 1 to 4 carbon atoms, an acyl group having 2 to 7 carbon atoms, an alkoxycarbonyl group having 2 to 5 carbon atoms, a tri($C_1$–$C_7$) hydrocarbon silyl group or a group combining with the oxygen atom attached to the $R^4$ to form an acetal bond. Examples of the alkyl group having 1 to 4 carbon atoms in the $R^4$ include methyl, ethyl, propyl, isopropyl, butyl, isobutyl and t-butyl groups. Examples of the acyl group having 2 to 7 carbon atoms include acetyl, propionyl, butyryl, isobutyryl, valeryl, hexanoyl and benzoyl groups. Examples of the alkoxycarbonyl group having 2 to 5 carbon atoms include methoxycarbonyl, ethoxycarbonyl, propoxycarbonyl, isopropoxycarbonyl, butoxycarbonyl and t-butoxycarbonyl groups. Examples of the tri($C_1$–$C_7$) hydrocarbon silyl group include trimethylsilyl, triethylsilyl, t-butyldimethylsilyl, t-butyldiphenylsilyl and tribenzylsilyl groups. Examples of the group combining with an oxygen atom attached to the $R^4$ to form an acetal bond include methoxymethyl, 1-ethoxyethyl, 1-methoxy-1-methylethyl, 2-ethoxy-1-methylethyl, 2-methoxyethoxymethyl, tetrahydropyran-2-yl, 6,6-dimethyl-3-oxa-2-oxobicyclo[3.1.0]hexane-4-yl groups.

Examples of the $X^1$ include a hydrogen atom and hydroxyl, methoxy, ethoxy, trimethylsilyloxy, acetoxy, methoxycarbonyloxy and isopropoxycarbonyloxy groups.

The $R^{31}$ and $R^{32}$ in the above-described formula (II') each stand for a hydrogen atom, a substituted or unsubstituted aliphatic hydrocarbon group having 1 to 9 carbon atoms, alicyclic hydrocarbon group having 4 to 10 carbon atoms or aromatic hydrocarbon group having 6 to 10 carbon atoms, or a group wherein the $R^{31}$ and $R^{32}$ are combined with each other to foden an alicyclic hydrocarbon group having a four to ten-membered ring. Examples of the unsubstituted aliphatic hydrocarbon group having 1 to 9 carbon atoms in the $R^{31}$ and $R^{32}$ include alkyl groups such as methyl, ethyl, isopropyl, butyl, pentyl, heptyl, octyl, nonyl and 2,6-dimethylheptyl groups; alkenyl groups such as vinyl, 1-propenyl, 1-pentenyl and 1-hexenyl groups; and alkynyl groups such as 1-propynyl and 1-pentynyl groups.

Examples of the unsubstituted alicyclic hydrocarbon group having 4 to 10 carbon atoms and aromatic hydrocarbon having 6 to 10 carbon atoms in the $R^{31}$ and $R^{32}$ include those described above in connection with the $R^{30}$. Examples of the unsubstituted group which is an alicyclic hydrocarbon group having a four to ten-membered ring formed by combining $R^{31}$ with $R^{32}$ to each other together with a carbon atom intervening between the $R^{31}$ and the $R^{32}$ include cyclobutylidene, cyclopentylidene, cyclohexylidene, 2-cyclohexenylidene and bicyclo[4.4.0]decan-2-ylidene groups. The $R^{31}$ and $R^{32}$ may also be one comprising, attached to each other, any combination of the above-described aliphatic hydrocarbon group having 1 to 9 carbon atoms, alicyclic hydrocarbon group having 4 to 10 carbon atoms and aromatic hydrocarbon group having 6 to 10 carbon atoms; or a group wherein the $R^{31}$ and $R^{32}$ are combined with each other to form an alicyclic hydrocarbon group having a four to ten-membered ring to which the above-described aliphatic hydrocarbon having 1 to 9 carbon atoms or aromatic hydrocarbon group having 6 to 10 carbon atoms is attached. Among them, preferred examples of the $R^{31}$ and $R^{32}$ include a substituted or unsubstituted ($r^{31}$-a) aliphatic hydrocarbon group having 1 to 10 carbon atoms which may be substituted with one or a plurality of alkoxy groups having 1 to 4 carbon atoms;

($r^{31}$-b) alicyclic hydrocarbon group having 4 to 10 carbon atoms which may be substituted with one or a plurality of alkyl groups having 1 to 4 carbon atoms and alkoxy groups having 1 to 4 carbon atoms;

($r^{31}$-c) aromatic hydrocarbon group having 6 to 10 carbon atoms which may be substituted with one or a plurality of alkyl groups having 1 to 4 carbon atoms and alkoxy groups having 1 to 4 carbon atoms;

($r^{31}$-d) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms and alkoxy groups having 1 to 4 carbon atoms;

($r^{31}$-e) aliphatic hydrocarbon group having 1 to 10 carbon atoms substituted with an aromatic hydrocarbon group having 6 to 10 carbon atoms and which may be substituted with one or a plurality of alkyl groups having 1 to 4 carbon atoms and alkoxy groups having 1 to 4 carbon atoms; and ($r^{31}$-f) group wherein $R^{31}$ and $R^{32}$ are combined with each other to forth an alicyclic hydrocarbon having a four to ten-membered ring, which may be substituted with one or a plurality of alkyl groups having 1 to 4 carbon atoms and alkoxy groups having 1 to 4 carbon atoms.

Preferred examples of the unsubstituted group ($r^{31}$-a) include methyl, ethyl, propyl, isopropyl, butyl, isobutyl, t-butyl, pentyl, heptyl, nonyl, 2,6-dimethylheptyl, vinyl, 1-propenyl and 1-pentenyl groups. Preferred examples of the unsubstituted groups ($r^{31}$-b) and ($r^{31}$-c) include respectively those of the ($r^{30}$-b) and ($r^{30}$-c) described above in connection with the $R^{30}$. Preferred examples of the unsubstituted group ($r^{31}$-f) include cyclopentylidene and cyclohexylidene.

The above-described groups ($r^{30}$-a) to ($r^{30}$-e) or ($r^{31}$-a) to ($r^{31}$-f) may be substituted with a plurality of different groups, and examples of the substituent include (i) a halogen atom; (ii) an oxo group; (iii) a cyano group; (iv) a nitro group; (v) —COOR$^{63}$ (wherein R$^{63}$ stands for a hydrogen atom; one equivalent of cation; a residue of a saccharide; or an aliphatic hydrocarbon group having 1 to 10 carbon atoms which may be substituted with a halogen atom, an oxo group, a hydroxyl group a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms); (vi) —OR$^{73}$ (wherein R$^{73}$ stands for a hydrogen atom; an alkyl group having 1 to 4 carbon atoms; an acyl group having 2 to 7 carbon atoms; an alkoxycarbonyl group having 2 to 5 carbon atoms; a tri($C_1$–$C_7$) hydrocarbon silyl group; a group capable of forming an acetal bond together with the oxygen atom attached to the R$^{73}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, hydroxyl group, a nitro group, a tri($C_1$–$C_7$) hydrocarbon silyloxy group, an alkoxy group having 1 to 4 carbon atoms, an acyloxy group having 2 to 7 carbon atoms, an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms); (vii) —CONR$^{83}$R$^{830}$ (wherein R$^{83}$ and R$^{830}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein $R^{83}$ and $R^{830}$ are combined with each other to form a five- or six-membered ring); and (viii) —$NR^{93}R^{930}$ (wherein $R^{93}$ and $R^{930}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; and an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein $R^{93}$ and $R^{930}$ are combined with each other to form a five- or six-membered ring).

Examples of the substituents (i) to (viii) of the groups ($r^{30}$-a) to ($r^{30}$-e) or ($r^{31}$-a) to ($r^{31}$-f) include the same substituents as those of the groups ($r^1$-a) to ($r^1$-g) described above in connection with the $R^1$.

Preferred examples of the $R^{30}$ include methyl, ethyl, propyl, isopropyl, butyl, isobutyl, butyl, t-butyl, octyl, 3,7-dimethyloctyl, 1-methylvinyl, 1-octenyl, 3,3-dimethyl-4-phenyl-1-butenyl, 3,3-dimethyl-1-butynyl, 1-pentynyl, 1-hexynyl, 3-t-butyldimethylsilyloxy-1-octenyl, 3-hydroxy-1-octenyl, 3-acetoxy-1-octenyl, 3-methoxycarbonyloxy-1-octenyl, 3-trimethylsilyloxy-3-methyl-1-octenyl, 3-hydroxy-3-methyl-1-octenyl, 3-t-butyldimethylsilyloxy-5-methyl-1-nonenyl, 3-hydroxy-5-methyl-1-nonenyl, 6-carboxyhexyl, 6-methoxycarbonylhexyl, 6-(2-thioxo-3-thiazolidinylcarbonyl)hexyl, 6-(6-D-glucosylcarbonyl)hexyl, 6-(1-D-xylosylcarbonyl)hexyl, 6-(5-D-ribosylcarbonyl)hexyl, 6-hydroxyhexyl, 6-t-butyldimethylsilyloxyhexyl, 6-acetoxyhexyl, 6-hydroxy-2-hexenyl, 6-carboxy-2-hexenyl, 6-methoxycarbonyl-2-hexenyl, 3-cyclohexylpropyl, 3-hydroxy-3-cyclopentyl-1-propenyl, 3-methoxycarbonyloxy-3-cyclopentyl-1-propenyl, 3-isopropoxycarbonyloxy-3-cyclopentyl-1-propenyl, 3-t-butyldimethylsilyloxy-3-cyclopentyl-1-propenyl, 3-hydroxy-3-cyclohexyl-1-propenyl, 3-t-butyldimethylsilyloxy-3-cyclohexyl-1-propenyl, 3-hydroxy-4-cyclohexyl-1-butenyl, 4-phenoxybutyl, 3-(3,4-dimethoxyphenyl) propyl, benzyl, 2-phenylethyl, 5-phenylpentyl, cyclohexyl and phenyl.

Preferred examples of the $R^{31}$ and $R^{310}$ include a hydrogen atom, methyl, ethyl, propyl, 1-heptenyl, 5-methoxycarbonylpentyl, 5-methoxycarbonyl-1-pentenyl and 3-phenoxypropyl.

Among the 2-substituted-2-cyclopentenone compounds represented by the above-described formula (I), a 2-substituted-2-cyclopentenone compound represented by the formula (I-b-1-1) can be produced through the following scheme 1 by subjecting a 2-cyclopentenone compound represented by the formula (III-b) to an epoxidation reaction to prepare a 2,3-epoxycyclopentanone compound represented by the formula (IV-b), reacting the 2,3-epoxycyclopentanone compound with a thiol compound represented by the formula (V) in the presence of a basic compound to prepare a 2-substituted-2-cyclopentenone compound represented by the formula (I-b-10) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 1:

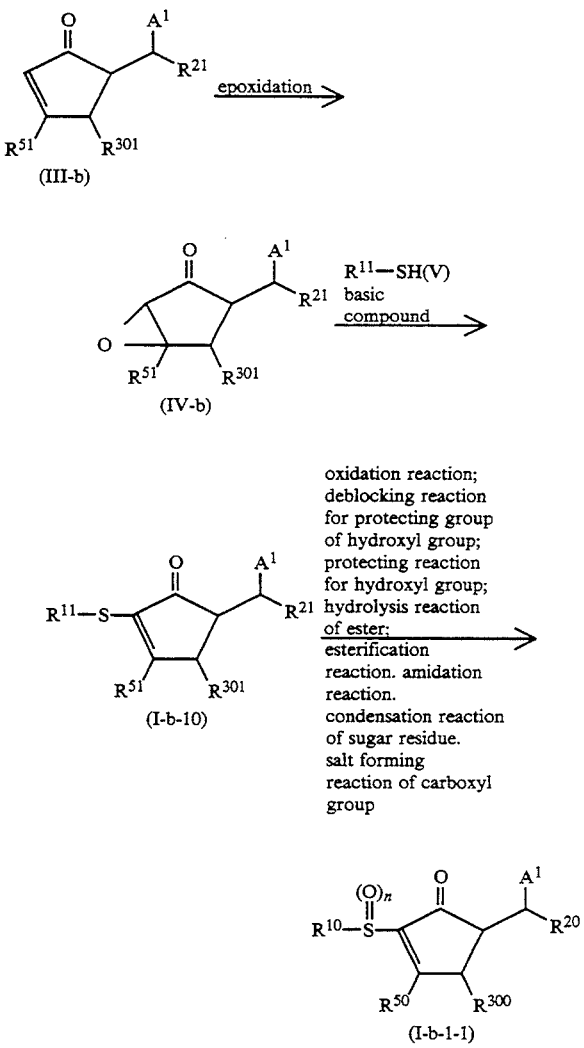

Scheme 1:

-continued

{
wherein $R^{10}$ and $R^{11}$ each stand for a substituted or unsubstituted aliphatic hydrocarbon group having 1 to 10 carbon atoms, alicyclic hydrocarbon group having 4 to 10 carbon atoms, aromatic hydrocarbon group having 6 to 10 carbon atoms or heterocyclic group having 1 to 9 carbon atoms;

$R^{20}$ and $R^{21}$ each stand for a substituted or unsubstituted aliphatic hydrocarbon group having 1 to 10 carbon atoms, alicyclic hydrocarbon group having 4 to 10 carbon atoms, aromatic hydrocarbon group having 6 to 10 carbon atoms or heterocyclic group having 1 to 9 carbon atoms;

$R^{300}$ and $R^{301}$ each stand for a hydrogen atom or a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms;

$R^{50}$ and $R^{51}$ each stand for a hydrogen atom or a substituted or unsubstituted aliphatic hydrocarbon group having 1 to 10 carbon atoms or alicyclic hydrocarbon group having 4 to 10 carbon atoms;

$A^1$ is a hydrogen atom or a hydroxyl group; and n is 0, 1 or 2.

Specific examples of the $R^{10}$ and $R^{11}$ include to groups referred to in the specific examples of the $R^1$ described above in connection with the above-described formula (I). Specific examples of the $R^{20}$ and $R^{21}$ include the groups referred to in the specific examples of the $R^2$ described above in connection with the above-described formula (I). Specific examples of the $R^{300}$ and $R^{301}$ include the groups referred to in the specific examples of the $R^3$ described above in connection with the above-described formula (I). Specific examples of the $R^{50}$ and $R^{51}$ include the groups referred to in the specific examples of the $R^5$ described above in connection with the above-described formula (I).

Preferred substituents of the $R^{10}$, $R^{20}$, $R^{300}$ and $R^{50}$ are respectively the same substituents as those of the $R^1$, $R^2$, $R^3$ and $R^5$, and preferred substituents of the $R^{11}$, $R^{21}$, $R^{301}$ and $R^{51}$ are respectively the same substituents as those of the $R^1$, $R^2$, $R^3$ and $R^5$, other than the salts of carboxylic acids.
}

The starting compound represented by the formula (III-b) can be prepared, for example, through the following scheme comprising a combination of processes described in Japanese Unexamined Patent Publication (Kokai) Nos. 59-164747 and 62-81344.

Scheme:

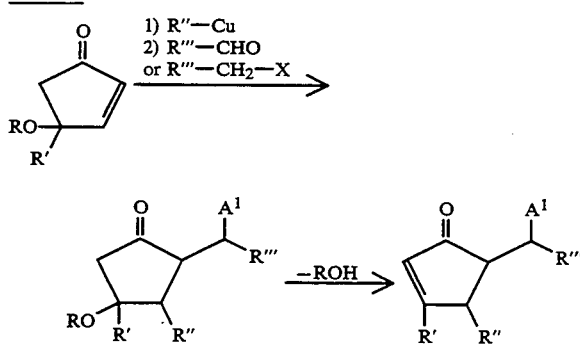

wherein $A^1$ is as defined above.

Among the 2-substituted-2-cyclopentenone compounds represented by the above-described formula (I), a 2-substituted-2-cyclopentenone compound represented by the formula (I-b-1-2) can be produced through the following scheme 2 by subjecting a 2-substituted-2-cyclopentenone compound represented by the formula (I-b-11) belonging to the 2-substituted-2-cyclopentenone compound represented by the above-described formula (I-b-10) to an acylation reaction or an alkoxycarbonylation reaction to prepare a 2-substituted-2-cyclopentenone compound represented by the formula (I-b-12) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 2:

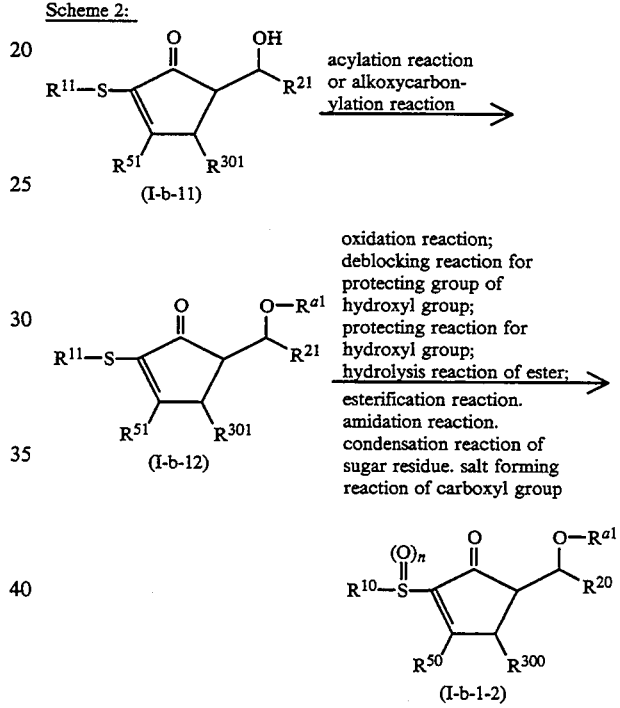

wherein $R^{10}$, $R^{11}$, $R^2$, $R^{21}$, $R^{300}$, $R^{301}$, $R^{50}$, $R^{51}$ and n are each as defined above; and $R^{a1}$ stands for an acyl group having 2 to 7 carbon atoms or an alkoxycarbonyl group having 2 to 5 carbon atoms.

Specific examples of the $R^{a1}$ in the —O—$R^{a1}$ include the groups referred to in the specific examples of the acyloxy group having 2 to 7 carbon atoms and alkoxycarbonyloxy group having 2 to 5 carbon atoms in the A described above in connection with the above-described formula (I).

Among the 2-substituted-2-cyclopentenone compounds represented by the above-described formula (I), a 2-substituted-2-cyclopentenone compound represented by the formula (I-a-1) can be produced through the following scheme 3 by subjecting a 2-substituted-2-cyclopentenone compound represented by the formula (I-b-11) to a sulfonylation reaction to prepare a 2-substituted-2-cyclopentenone compound represented by the formula (I-b-13), subjecting the 2-substituted-2-cyclopentenone compound to a desulfonation reaction to prepare a 2-substituted-2-cyclopentenone compound represented by the formula (I-a-10) and then subjecting the 2-substituted-2-cyclopentenone compound to the following optional reactions: an oxidation reaction; a deblocking reaction for a protecting group of a hydroxyl group; A protecting reaction for a hydroxyl group; a hydrolysis reaction of an ester; and an esterification reaction, an amidation reaction, a condensation reaction of a sugar residue and/or a salt forming reaction of a carboxyl group.

Scheme 3:

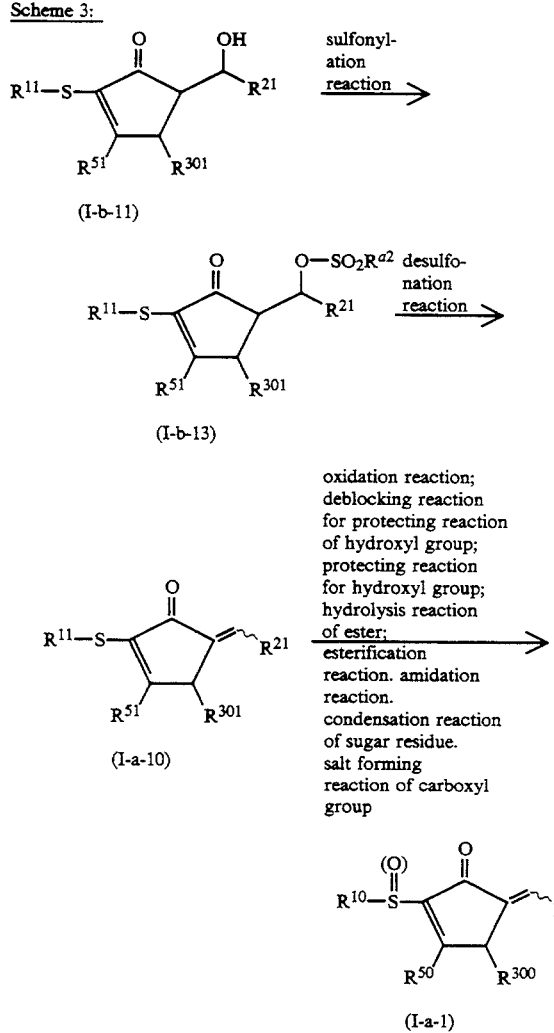

wherein $R^{10}$, $R^{11}$, $R^{20}$, $R^{21}$, $R^{300}$, $R^{301}$, $R^{50}$, $R^{51}$ and n are each as defined above; represents that the substituent attached to the double bond is in an E-configuration or a Z-configuration or a mixture thereof in any proportion; and $R^{a2}$ stands for an alkyl group which may be substituted with a halogen atom, a substituted or unsubstituted phenyl group or a substituted or unsubstituted phenyl ($C_1$-$C_2$) alkyl group.

Specific examples of the $R^{a2}$ in the form of —O—$SO_2R^{a2}$ include the groups referred to in the specific examples of the alkylsulfonyloxy group having 1 to 4 carbon atoms which may be substituted with a halogen atom, the substituted or unsubstituted phenylsulfonyloxy group or the substituted or unsubstituted phenyl ($C_1$-$C_2$) alkylsulfonyloxy group in the A described above in connection with the above-described formula (I).

Among the 2-substituted-2-cyclopentenone compounds represented by the above-described formula (I), a 2-substituted-2-cyclopentenone compound represented by the formula (I-b-1-3) and a 2-substituted-2-cyclopentenons compound represented by the formula (I-a-1) can be produced through the following scheme 4 by reacting a 2,3-epoxycyclopentanone compound represented by the formula (IV-a-1) with a thiol compound represented by the formula (V) in the presence of a basic compound to prepare 2-substituted-2-cyclopentenone compounds respectively represented by the formula (I-b-14) and (I-a-10) and then subjecting the 2-substituted-2-cyclopentenone compounds to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 4:

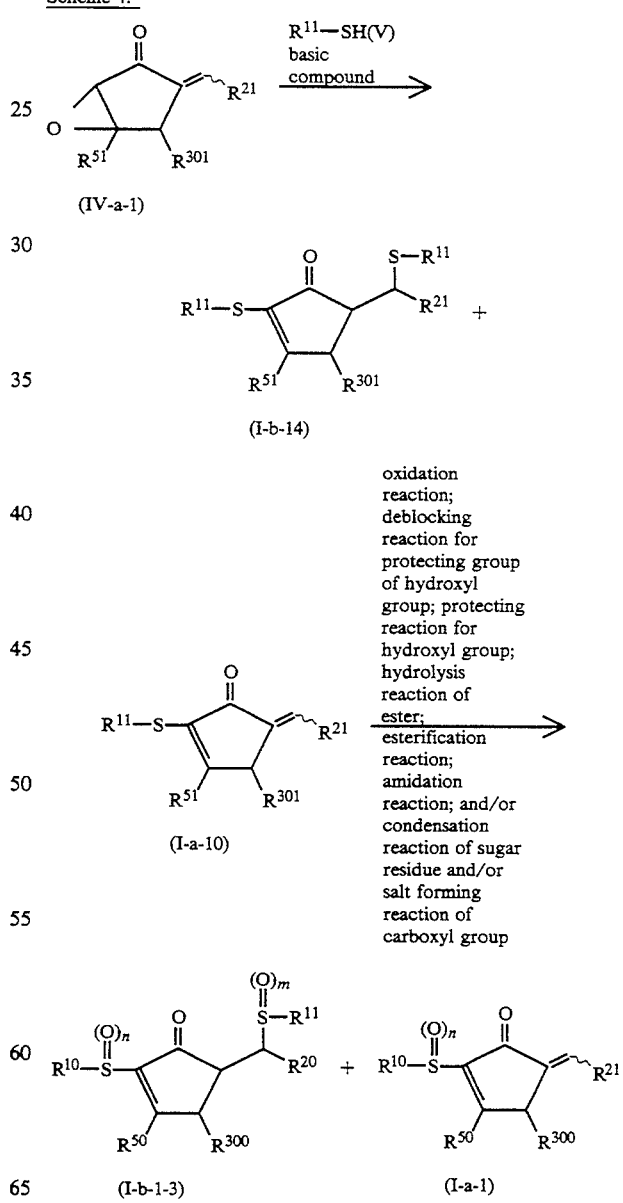

wherein $R^{10}$, $R^{11}$, $R^{20}$, $R^{21}$, $R^{300}$, $R^{301}$, $R^{50}$, $R^{51}$ and n are each as defined above; and m is 0, 1 or 2.

The starting compound represents by the formula (IV-a-1) can be prepared, for example, through the following scheme in the same manner as that described in japanese Unexamined Patent Publication (Kokai) Nos. 61-47437.

Scheme:

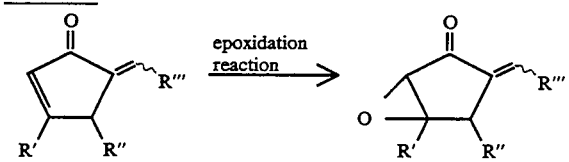

Among the 2-substituted-2-cyclopentenone compounds represented by the above-described formula (I), a 2-substituted-2-cyclopentenone compound represented by the formula (I-c-1) can be produced through the following scheme 5 by subjecting a 2-cyclopentenone compound represented by the formula (III-a) to an epoxidation reaction to prepare a 2,3-epoxycyclopentanone compound represented by the formula (IV-a-2), reacting the 2,3-epoxycyclopentanone compound with a thiol compound in the presence of a basic compound represented by the formula (V) to prepare a 2-substituted-2-cyclopentenone compound represented by the formula (I-c-2) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 5:

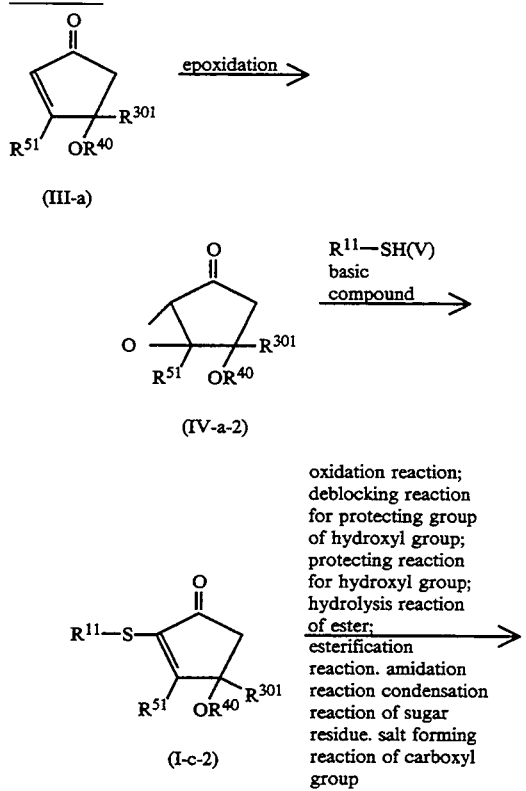

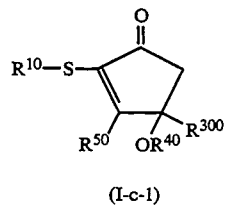

(I-c-1)

wherein $R^{10}$, $R^{11}$, $R^{300}$, $R^{301}$, $R^{50}$ and $R^{51}$ are each as defined above; and $R^{40}$ stands for a hydrogen atom, an alkyl group having 1 to 4 carbon atoms, an acyl group having 2 to 7 carbon atoms, an alkoxycarbonyl group having 2 to 5 carbon atoms, a tri($C_1$-$C_7$) hydrocarbon silyl group or a group capable of forming an acetal bond together with an oxygen atom attached to the $R^{40}$.

Specific examples of the $R^{40}$ include the groups referred to in the specific examples of the $R^4$ described above in connection with the above-described formula (I).

The starting compound represented by the formula (III-a) can be prepared, for example, by a process represented by the following scheme.

Scheme:

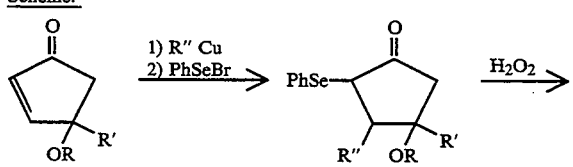

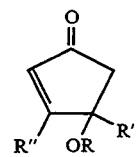

Among the 2-substituted-2-cyclopentenone compounds represented by the above-described formula (I), a 2-substituted-2-cyclopentenone compound represented by the formula (I-b-2-1) can be produced through the following scheme 6 by subjecting a 2-cyclopentenone compound represented by the formula (I-c-21) belonging to the 2-substituted-2-cyclopentenone compound represented by the above-described formula (I-c-2) to an aldol condensation reaction with an aldehyde compound represented by the formula (II-a) in the presence of a lithium amide compound or (a tertiary amine compound and a dialkylborontrifluoromethanesulfonic acid) to prepare a 2-substituted-2-cyclopentenone compound represented by the formula (I-b-21) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 6:

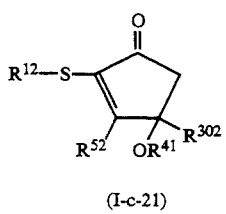

(I-c-21)

1) lithium amide compound or (tertiary amine compound and dialkylboron-trifluoromethane-sulfonic acid)
2) OHC—R22 (II-a)

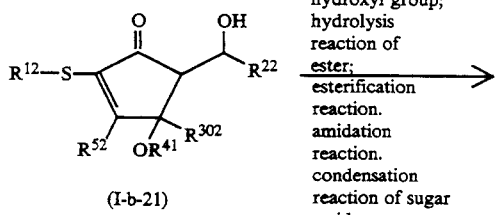

(I-b-21)

oxidation reaction;
deblocking reaction for protecting group of hydroxyl group; protecting reaction for hydroxyl group;
hydrolysis reaction of ester;
esterification reaction.
amidation reaction.
condensation reaction of sugar residue.
salt forming.
reaction of carboxyl group

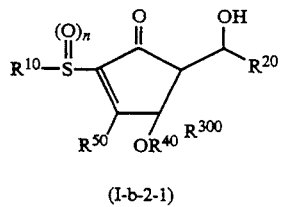

(I-b-2-1)

wherein $R^{10}$, $R^{20}$, $R^{300}$, $R^{40}$, $R^{50}$ and n are each as defined above;

$R^{12}$ stands for a substituted or unsubstituted aliphatic hydrocarbon group having 1 to 10 carbon atoms, alicyclic hydrocarbon group having 4 to 10 carbon atoms, aromatic hydrocarbon group having 6 to 10 carbon atoms or heterocyclic group having 1 to 9 carbon atoms;

$R^{22}$ stands for a substituted or unsubstituted aliphatic hydrocarbon group having 1 to 10 carbon atoms, allcyclic hydrocarbon group having 4 to 10 carbon atoms, aromatic hydrocarbon group having 6 to 10 carbon atoms or heterocyclic group having 1 to 9 carbon atoms;

$R^{302}$ stands for a hydrogen atom or a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms;

$R^{41}$ stands for an alkyl group having 1 to 4 carbon atoms, an acyl group having 2 to 7 carbon atoms, an alkoxycarbonyl group having 2 to 5 carbon atoms, a tri($C_1$-$C_7$) hydrocarbon silyl group or a group capable of forming an acetal bond together with an oxygen atom attached to the $R^{41}$; and $R^{52}$ stands for a hydrogen atom or a substituted or unsubstituted aliphatic hydrocarbon group having 1 to 10 carbon atoms or alicyclic hydrocarbon group having 4 to 10 carbon atoms.

Specific examples of the $R^{12}$ include the groups referred to in the specific examples of the $R^1$ described above in connection with the above-described formula (I).

Specific examples of the $R^{22}$ include the groups referred to in the specific examples of the $R^2$ described above in connection with the above-described formula (I).

Specific examples of the $R^{302}$ include the groups referred to in the specific examples of the $R^3$ described above in connection with the above-described formula (I).

Specific examples of the $R^{52}$ include the groups referred to in the specific examples of the $R^5$ described above in connection with the above-described formula (I).

Preferred substituents of the $R^{12}$, $R^{22}$, $R^{302}$ and $R^{52}$ are respectively the groups described as the substituents of the $R^1$, $R^2$, $R^3$ and $R^5$ exclusive of the groups having a carboxylic acid, a salt of a carboxylic acid and a hydroxyl group.

Among the 2-substituted-2-cyclopentenone compounds represented by the above-described formula (I), a 2-substituted-2-cyclopentenone compound represented by the formula (I-b-2-2) can be produced through the following scheme 7 by subjecting a 2-cyclopentenone compound represented by the formula (I-b-21) to an acylation reaction or an alkoxycarbonylation reaction to prepare a 2-substituted-2-cyclopentenone compound represented by the formula (I-b-22) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 7:

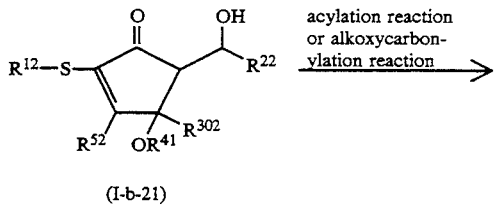

(I-b-21)

acylation reaction or alkoxycarbonylation reaction

Scheme 7:

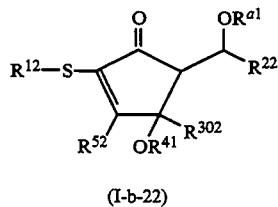
(I-b-22)

oxidation reaction; deblocking reaction for protecting group of hydroxyl group; protecting reaction for hydroxyl group; hydrolysis reaction of ester; esterification reaction. amidation reaction. condensation reaction of sugar residue. salt forming reaction of carboxyl group
$\longrightarrow$

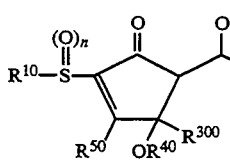
(I-b-2-2)

wherein $R^{10}$, $R^{12}$, $R^{20}$, $R^{22}$, $R^{300}$, $R^{302}$, $R^{40}$, $R^{41}$, $R^{50}$, $R^{52}$, $R^{a1}$ and n are each as defined above.

Among the 2-substituted-2-cyclopentenone compounds represented by the above-described formula (I), a 2-substituted-2-cyclopentenone compound represented by the formula (I-b-2-3) can be produced through the following scheme 8 by subjecting a 2-substituted-2-cyclopentenone compound represented by the formula (I-c-21) to an enolation with a lithium amide compound, reacting the enolation product with an organoiodide represented by the formula (II-b) in the presence of an organotin compound to prepare a 2-substituted-2-cyclopentenone compound represented by the formula (I-b-23) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 8:

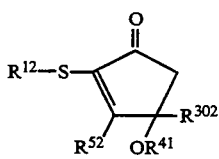
(I-c-21)

1) lithium amide compound
2) organotin compound
2) I—CH$_2$—R$^{22}$ (II-b)
$\longrightarrow$

Scheme 8:
-continued

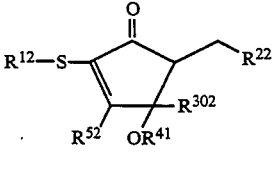
(I-b-23)

oxidation reaction; deblocking reaction for protecting group of hydroxyl group; protecting reaction for hydroxyl group; hydrolysis reaction of ester; esterification reaction. amidation reaction. condensation reaction of sugar residue. salt forming reaction of carboxyl group
$\longrightarrow$

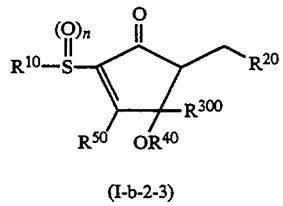
(I-b-2-3)

wherein $R^{10}$, $R^{12}$, $R^{20}$, $R^{22}$, $R^{300}$, $R^{302}$, $R^{40}$, $R^{41}$ $R^{50}$, $R^{52}$ and n are each as defined above.

Among the 2-substituted-2-cyclopentenone compounds represented by the above-described formula (I), a 2-substituted-2-cyclopentenone compound represented by the formula (I-a-2) can be produced through the following scheme 9 by subjecting a 2-substituted-2-cyclopentenone compound represented by the formula (I-b-21) to a sulfonylation reaction to prepare a 2-substituted-2-cyclopentenone compound represented by the formula (I-b-24), subjecting the 2-substituted-2-cyclopentenone compound to a desulfonation reaction to prepare a 2-substituted-2-cyclopentenone compound represented by the formula (I-a-20) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 9:

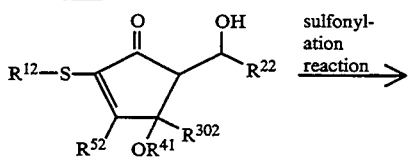
(I-b-21)

sulfonylation reaction $\longrightarrow$

Scheme 9:

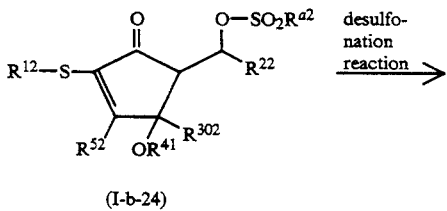

(I-b-24)

desulfonation reaction →

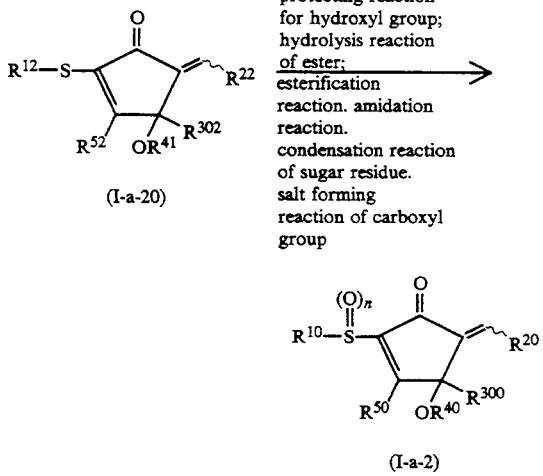

(I-a-20)

oxidation reaction; deblocking reaction for protecting group of hydroxyl group; protecting reaction for hydroxyl group; hydrolysis reaction of ester; esterification reaction. amidation reaction. condensation reaction of sugar residue. salt forming reaction of carboxyl group →

(I-a-2)

$$\left[\begin{array}{l}\text{wherein } R^{10}, R^{12}, R^{20}, R^{22}, R^{300}, R^{302}, R^{40}, R^{41},\\ R^{50}, R^{52}, n, R^{a2} \text{ and } \sim \text{are each as defined above.}\end{array}\right]$$

Among the 2-substituted-2-cyclopentenone compounds represented by the above-described formula (I), a 2-substituted-2-cyclopentenone compound represented by the formula (I-a-3) can be produced through the following scheme 10 by subjecting a 2-substituted-2-cyclopentenone compound represented by the formula (I-a-21) belonging to the 2-substituted-2-cyclopentenone compounds represented by the above-described formula (I-a-2) to an elimination reaction under an acidic condition to prepare a 2-substituted-2-cyclopentenone compound represented by the formula (I-a-22) and then subjecting the 2-substituted-2-cyclopentenone compound represented by the formula (I-a-22) and then subjecting the 2-substituted-2-cyclopentenone compound to the following optional reactions: an oxidation reaction; a deblocking reaction for a protecting group of a hydroxyl group; a protecting reaction for a hydroxyl group, a hydrolysis reaction of an ester; and an esterification reaction, an amidation reaction, a condensation reaction of a sugar residue and/or a salt forming reaction of a carboxyl group.

Scheme 10:

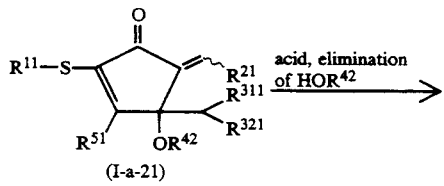

(I-a-21)

acid, elimination of HOR$^{42}$ →

Scheme 10: -continued

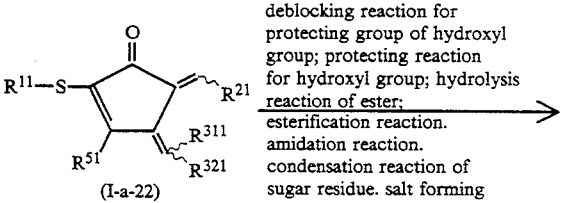

(I-a-22)

oxidation reaction; deblocking reaction for protecting group of hydroxyl group; protecting reaction for hydroxyl group; hydrolysis reaction of ester; esterification reaction. amidation reaction. condensation reaction of sugar residue. salt forming reaction of carboxyl group →

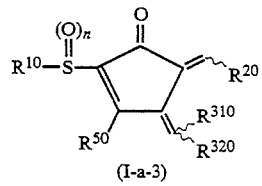

(I-a-3)

wherein $R^{10}$, $R^{11}$, $R^{20}$, $R^{21}$, $R^{50}$, $R^{51}$, and $\sim$ are each as defined above;

$R^{310}$ and $R^{320}$, or $R^{311}$ and $R^{321}$ which may be the same of different from each other stand for a hydrogen atom, a substituted or unsubstituted aliphatic hydrocarbon group having 1 to 9 carbon atoms, alicyclic hydrocarbon group having 4 to 10 carbon atoms or aromatic hydrocarbon group having 6 to 10 carbon atoms or a group wherein $R^{310}$ and $R^{320}$, $R^{311}$ and $R^{321}$ are combined with each other to form an alicyclic hydrocarbon group having a four to ten-membered ring; and $R^{42}$ stands for a hydrogen atom or a tri($C_1$-$C_7$) hydrocarbon silyloxy group.

Specific examples of the $R^{310}$ and $R^{320}$, or $R^{311}$ and $R^{321}$ include the groups referred to in the specific examples of the $R^{31}$ and $R^{32}$ described above in connection with the above-described formula (I).

Specific examples of the $R^{42}$ include the groups referred to in the specific examples of the $R^4$ described above in connection with the above-described formula (I).

Preferred substituents of the $R^{310}$ and $R^{320}$ are respectively the same substituents as those of the $R^{31}$ and $R^{32}$, and preferred substituents of the $R^{311}$ and $R^{321}$ are respectively the groups described as the substituents of the $R^{31}$ and $R^{32}$ exclusive of the salt of a carboxylic acid.

The compounds of the present invention are administered to patients by methods such as oral administration, suppository administration, dermal administration, nasal administration, subcutaneous administration, intramuscular administration, intravenous injection and intra-arterial injection.

In the case of the oral administration, the compounds of the present invention may be in the form of a solid preparation or a liquid preparation. Examples of the dosage form include tablets, pills, powders, granules, solutions, suspensions and capsules.

Pharmaceutical preparations in the forth of a tablet are prepared by a conventional procedure through the use of additives, for example, excipients such as lactose, starch, calcium carbonate, crystalline cellulose and silicic acid; binders such as carboxymethyl cellulose, methyl cellulose, calcium phosphate and polyvinyl pyrrolidone; disintegrators such as sodium alginate, sodium bicarbonate, sodium laurylsulfate and monoglyceride stearate; lubricants such as glycerin; absorbers such as kaolin and colloidal silica; and lubricants such as talc and granular boric acid.

Pharmaceutical preparations in the form of a pill, powder or granule also may be prepared by a conventional procedure through the use of the same additives as those described above.

Liquid preparations, such as a solution and a suspension, also may be prepared by a conventional procedure. Examples of the carrier used include glycerol esters such as tricaprylin, triacetin and iodided poppy seed oil fatty acid esters; water; alcohols such as ethanol; and oleaginous bases such as liquid paraffin, coconut oil, soybean oil, sesame oil and corn oil.

The above-described powders, granules and liquid preparations may be encapsulated in a gelatin or the like.

In the present invention, the pharmaceutically acceptable carrier includes, besides the above-described carriers, auxiliary substances, perfuming agents, stabilizers and preservatures commonly used in the art, according to need.

Examples of the dosage form in the case of the dermal administration include ointments, creams, lotions and solutions.

Examples of the base for the ointment include fatty oils such as castor oil, oliver oil, sesame oil and safflower oil, lanolin; white, yellow or hydrophilic petrolatum; wax; higher alcohols such as oleyl alcohol, isostearyl alcohol, octyldodecanol and hexyldecanol; and glycols such as glycerin, diglycerin, ethylene glycol, propylene glycol, sorbitol and 1,3-butanediol. Ethanol, dimethylsulfoxide, polyethylene glycol, etc. may be used as a solubilizing agent for the compound of the present invention. If necessary, it is also possible to use preservatives such as p-oxybenzoates, sodium benzoate, salicylic acid, sorbic acid and boric acid; and antioxidants such as butylhydroxyanisole and dibutylhydroxytoluene.

Absorbefacients, such as diisopropyl adipate, diethyl sebacate, ethyl caproate and ethyl laurate, may be added to thereby promote the percutaneous absorption. Further, to enhance the stabilization, the compounds of the present invention can be used in the form of a compound included in an $\alpha$, $\beta$ or $\gamma$-cyclodextrin.

The ointment can be prepared by a conventional procedure. The cream is preferably in an oil-in-water cream foden from the viewpoint of stabilizing the compounds of the present invention. The above-described fatty oils, higher alcohols and glycols are used as the base, and use is made of emulsifiers such as diethylene glycol, propylene glycol, sorbitan monofatty acid ester, polysorbate 80 and sodium laurylsulfate. Further, if necessary, the above-described preservatives, antioxidants, etc. may be added. As with the ointment, in the case of the cream, the compound of the present invention may be used in the form of a compound included in a cyclodextrin or a methylated cyclodextrin. The cream can be prepared by a conventional procedure.

Examples of the lotion include lotions in the form of a suspension, an emulsion and a solution. The lotion in the form of a suspension is prepared through the use of a suspending agent, such as sodium alginate, tragacanth or sodium carboxymethylcellulose, and antioxidants, preservatives, etc. are added thereto according to need.

The lotion in the form of an emulsion is prepared through the use of an emulsifier, such as sorbitan monofatty acid ester, polysorbate 80 or sodium laurylsulfate, by a conventional procedure.

The lotion in the form of a solution is preferably an alcoholic lotion, and the alcoholic lotion is prepared through the use of an alcohol, such as ethanol, by a conventional procedure. Examples of the preparation in the form of a solution include that prepared by dissolving the compound of the present invention in ethanol, and optionally, adding an antioxidantor or a preservative, etc. to the solution.

Examples of other dosage forms include dermatologic pastes, cataplasms and aerosols. These preparations can be prepared by a conventional procedure.

The preparation for nasal administration is provided in the form of a liquid or powdery composition. Water, a saline solution, a phosphate buffer and an acetate buffer are used as a base for the liquid formulation, and the liquid formulation may contain surfactants, antioxidants, stabilizers, preservatives and tackifiers. Water absorbing bases are preferred as a base for the powder formulation, and examples thereof include bases easily soluble in water, for example, polyacrylates such as sodium polyacrylate, potassium polyacrylate and ammonium polyacrylate, cellulose lower alkyl ethers, such as methyl cellulose, hydroxyethyl cellulose, hydroxypropyl cellulose and sodium carboxymethyl cellulose, polyethylene glycol polyvinyl pyrrolidone, amylose and pullulan, and bases hardly soluble in water, for example, celluloses such as crystalline cellulose, $\alpha$-cellulose and crosslinked carboxymethyl cellulose, starches such as hydroxypropyl starch, carboxymethyl starch, crosslinked starch, amylose, amylopectin and pectin, proteins Such as gelatin, casein, sodium casein, gums such as gum arabic, tragacanth gum and glucomannan, and crosslinked vinyl polymers such as polyvinyl polypyrrolidone, crosslinked polyacrylic acid and its salts, crosslinked polyvinyl alcohol and polyhydroxyethyl methacrylate, which may be used in the form of a mixture thereof. Further, the powder formulation may contain antioxidants, colorants, preservatives, antiseptics, and corrigents, etc. The above-described liquid and powder formulations may be administered by, for example, a spray.

The preparation for injection administration is provided in the foden of an aseptic aqueous or non-aqueous solution, suspension or emulsion. In the non-aqueous solution or suspension, propylene glycol, polyethylene glycol, vegetable oils such as olive oil and injectable organic esters such as ethyl oleate and iodided poppy seed oil fatty acid ester are used as a pharmaceutically acceptable carrier. These preparations may contain auxiliary agents such as antiseptics, wetting agents, emulsifiers, dispersants and stabilizers, and may be in a sustained release forth. The above-described solutions, suspensions and emulsions can be made aseptic through a proper filtration whereby they are passed through a bacteria retaining filter, incorporation of a germicide, or treatments such as irradiation. Further, an aseptic solid preparation may be prepared and dissolved in an aseptic water or an aseptic solvent for injection immediately before use.

Further, it is also possible to use the compound of the present invention in the forth of a compound included in an $\alpha$, $\beta$ or $\gamma$-cyclodextrin or a methylated cyclodextrin. Further, the compound of the present invention may be used in the form of an injection wherein a fat is bonded to the compound.

Although the effective dose of the compound of the present invention varies depending upon the administration method, age, sex and condition of patients, it is generally 1 to $10^5$ $\mu$g/kg/day, preferably about 10 to $10^4$ $\mu$g/kg/day.

Industrial Applicability

The 2-substituted-2-cyclopentenone compound of the present invention exhibits, at a low concentration thereof, a strong effect of inhibiting the growth of L1210 leukemia cells and therefore, can be considered for use as an anticancer agent. Moreover, this compound enhances the alkaline phosphatase activity of human osteoblasts, and further, enhances the content of calcium and phosphorus in the human osteoblasts. Therefore, the compound of the present invention is useful as a bone formation accelerator and is effective for the treatment or prevention of osteoporosis and osteomalalacia. Further, the compound of the present invention can be expected to have an antiviral activity and an antimicrobial activity, which renders the compound of the present invention very useful as a pharmaceutical.

EXAMPLES

The present invention will now be described in more detail by way of the following Examples, but is not limited to these Examples.

Reference Example 1

First, 10 g of a starting 2-cyclopentenone compound as given in the following Table 1 was dissolved in 10 ml of dichloromethane, 5.71 ml of pyridine was added to the solution and 10.8 g of phenylselenenyl chloride was then added and the mixture stirred for 5 hr. The stirred mixture was poured in an aqueous potassium hydrogen sulfate solution and extracted with ethyl acetate, and the resultant organic phase was washed with an aqueous sodium bicarbonate and a saline solution, and then dried over magnesium sulfate. The dried organic phase was filtered, concentrated, and then subjected to silica gel chromatography to obtain a 2-cyclopentenone compound as given in Table 1. Spectral data ($^1$H-NMR ($\delta$, CDCl$_3$)) are also given in Table 1.

Reference Example 2

First, 1.56 g of 1-pentynyl copper was weighed and purged with nitrogen, 5.4 ml of hexamethylphosphoric triamide was added thereto, the mixture was stirred for 20 min, 15 ml of tetrahydrofuran and 40 ml of an ether were added thereto, and the mixture was cooled to −70° C. Then, 7.86 ml of a 1.52 M pentane solution of a starting organolithium reagent as given in the following Table 2 was added thereto, the mixture was stirred for 20 min, a solution of 4.0 g of a starting 2-cyclopentenone compound as given in Table 2 in 20 ml of tetrahydrofuran was added thereto, and the mixture was again stirred at −70° to −50° C. for 2 hr. The stirred mixture was poured in an acetate buffer having a pH value of 4, and hexane was added thereto for extraction. The resultant organic phase was washed with a saline solution, dried over magnesium sulfate, and filtered and concentrated to obtain an oily residue. The oily residue was dissolved in 50 ml of dichloromethane, 1 ml of pyridine was added to the solution, then 5 ml of a 30% aqueous hydrogen peroxide was added thereto with stirring and cooling on ice, and the mixture was stirred for 30 min. The stirred mixture was poured in an aqueous potassium hydrogensulfate and extracted with hexane. The resultant organic phase was washed with a saline solution, dried over magnesium sulfate, filtered, concentrated, and then subjected to silica gel chromatography to obtain a 2-cyclopentenone compound (an intended product) as given in the following Table 2.

Reference Example 3

First, 157 mg of 1-pentynyl copper was weighed and purged with nitrogen, 545 µl of hexamethylphosphoric triamide was added thereto, and the mixture was stirred for 20 min. Then 5 ml of tetrahydrofuran was added thereto, and the mixture was cooled to −70° C. and added to 1.2 mmol of a starting organolithium compound as given in the following Table 2. The mixture was stirred at −70° C. for 20 min, a solution of 318 mg of a starting 2-cyclopentenone compound given in Table 2 in 10 ml of tetrahydrofuran was added thereto, and the mixture was again stirred for 2 hr. A solution of 283 mg of phenylselenenyl bromide in 10 ml of tetrahydrofuran was added thereto, and the mixture was stirred for 1 hr, and the stirred mixture was poured in an aqueous ammonium chloride and extracted with ethyl acetate. The resultant organic phases were combined with each other, washed with a saline solution, and dried over magnesium sulfate. The dried organic phase was filtered, concentrated, and then subjected to silica gel chromatography to obtain an intermediate. The intermediate was dissolved in 20 ml of dichloromethane, 500 µl of pyridine was added thereto, 2 ml of a 30% aqueous hydrogen peroxide was added thereto, and the mixture was stirred for 1.5 hr. The stirred mixture was poured in potassium hydrogensulfate and extracted with ethyl acetate. The resultant organic phases were combined with each other, washed with an aqueous sodium carbonate solution and a saline solution, in that order, and then dried over magnesium sulfate. The dried organic phase was filtered, concentrated, and then subjected to silica gel chromatography to obtain a 2-cyclopentenone compound as given in Table 2.

Reference Examples 4 and 5

The 2-cyclopentenone compounds (intended products) as given in the following Table 2 were prepared in the same manner as that of Reference Example 3.

Reference Example 6

First, 61 mg of copper (II) chloride dihydrate and 30 mg of lithium chloride were weighed and heat-dried under a reduced pressure, 5 ml of tetrahydrofuran was added thereto, and the mixture was cooled to −70° C. Then a solution of 955 mg of a starting 2-cyclopentenone as given in the following Table 3 in 10 ml of tetrahydrofuran was added thereto, 3.6 mmol of a Grignard's reagent as given in Table 3 was added thereto, and the mixture was stirred at −70° to −30° C. for 2.5 hr. Then a solution of 944 mg of phenylselenenyl bromide in 10 ml of tetrahydrofuran was added thereto, the mixture was stirred at −30° C. for 1 hr, an aqueous ammonium chloride solution was added thereto, and the mixture was extracted with ethyl acetate. The resultant organic phase was washed with a saline solution, the washed organic layer was concentrated, the resultant oil residue containing an intermediate was dissolved in 40 ml of dichloromethane, 1 ml of pyridine was added thereto, and then 4 ml of a 30% aqueous hydrogen peroxide was added thereto with stirring and cooling on ice, and the mixture was stirred for 1 hr. An aqueous potassium hydrogensulfate solution was added thereto, and the mixture was extracted with ethyl acetate. The resultant organic layer was washed with an aqueous sodium bicarbonate solution and a saline solution and dried over magnesium sulfate. The dried organic phase was filtered, concentrated and then subjected to silica gel chromatography to obtain a 2-cyclopentenone compound (an intended product) given in Table 3.

Reference Examples 7 to 13

The 2-cyclopentenone compounds as given in the following Table 3 were prepared in the same manner as that of Reference Example 6.

Reference Example 14

First, 1.3 ml of hexamethylphosphorous triamide was added to 313 mg of 1-pentynyl copper, the mixture was stirred for 20 min, 5 ml of an ether was added thereto, and the mixture was cooled to −70° C. and added to 2.5 mmol of a starting organolithium compound as given in the following Table 4. Then the mixture was stirred at −70° C. for 15 min, a solution of 453 mg of a starting 2-cyclopentenone compound given in Table 4 in 10 ml of an ether was added thereto, 300 μl of a boron trifluoride-ether complex was further added thereto, and the mixture was stirred at −70° to −30° C. for 1 hr. Then a solution of 375 mg of an aldehyde compound given in Table 1 in 10 ml of an ether was added thereto, the mixture was stirred at −30° C. for 1 hr, an aqueous ammonium chloride was added thereto, and the mixture was extracted with ethyl acetate. The resultant organic phase was washed with a saline solution and dried over magnesium sulfate, the dried organic phase was filtered and concentrated, the resultant oily residue was dissolved in 40 ml of dichloromethane, 400 μl of 1,8-diazabicyclo[5.4.0.]-7-undecene was added thereto, and the mixture was stirred for 5 hr. Then an aqueous potassium hydrogensulfate solution was added thereto, and the mixture was extracted with ethyl acetate. The resultant organic phase was washed with a saline solution and then dried over magnesium sulfate. The dried organic phase was filtered, concentrated and then subjected to silica gel chromatography to obtain a 2-cyclopentenone compound as given in Table 4.

Reference Examples 15 to 17

The 2-cyclopentenone compounds as given in the following Table 4 were prepared in the same manner as that of Reference Example 14.

Example 1

First, 3.3 g of a starting 2-cyclopentenone compound as given in the following Table 5 was dissolved in 50 ml of methanol, 5.0 ml of a 30% aqueous hydrogen peroxide was added thereto with stirring and cooling on ice, and 500 μl of a 1 N aqueous sodium hydroxide solution was added thereto. Then the mixture was stirred for 3.5 hr, an aqueous ammonium chloride solution was added thereto, and the mixture was extracted with ethyl acetate. The resultant organic phase was washed with a saline solution and dried over magnesium sulfate, and the dried organic phase was filtered, concentrated and then subjected to silica gel chromatography to obtain a 2,3-epoxycyclopentanone compound as given in Table 5.

Examples 2 to 39

The 2,3-cyclopentanone compounds as given in the following Table 5 were prepared in the same manner as that of Example 1.

Example 40

First, 9.2 mg of sodium thiomethoxide was dissolved 2 ml of methanol, 11.2 μl of acetic acid was added thereto with stirring and cooling on ice, 36.4 μl of triethylamine was added thereto, 19 mg of a 2,3-epoxycyclopentanone compound as given in the following Table 6 was added, and the mixture was stirred for 5 hr. Then an aqueous ammonium chloride solution was added thereto, and the mixture was extracted with ethyl acetate, and the resultant organic phase was washed with a saline solution and dried over magnesium sulfate, and the dried organic phase was filtered, concentrated and then subjected to silica gel chromatography to obtain a 2-substituted-2-cyclopentenone compound as given in Table 6.

Example 41

A 2-substituted-2-cyclopentenone compound as given in the following Table 6 was prepared in the same manner as that of Example 40.

Reference Examples 18 to 20

The 2-Substituted-2-cyclopentenone compounds as given in the following Table 7 were prepared in the same manner as that of Example 40.

Example 42

First, 1.5 g of sodium thiomethoxide was dissolved in 80 ml of methanol, 1.8 ml of acetic acid was added thereto with cooling on ice, the mixture was stirred for 5 min, 4.8 ml of triethylamine was added thereto, and a solution of 1.38 g of a starting 2,3-epoxycyclopentanone compound as given in the following Table 6 in 20 ml of methanol was added thereto. Then the mixture was stirred for 4 hr, water was added thereto, and the mixture was extracted with ethyl acetate. The resultant organic phases were combined with each other, washed with a saline solution and dried over magnesium sulfate. The dried organic phase was filtered and concentrated, the resultant oily residue was dissolved in 15 ml of dimethylformamide, 1.15 g of imidazole and 1.04 ml of chlorotrimethylsilane were added thereto with stirring and cooling on ice, and the mixture was stirred at 0° C. for 3 hr. Water and hexane were added thereto for extraction, and the resultant organic phase was washed with a saline solution. The organic phase was dried over sodium sulfate, filtered, concentrated and then subjected to a silica gel chromatography to obtain a 2-substituted-2-cyclopentenone compound as given in Table 6.

Examples 43 to 45

The 2-Substituted-2-cyclopentenone compounds as given in the following Table 6 were prepared in the same manner as that of Example 42.

Reference Examples 21 to 23

The 2-Substituted-2-cyclopentenone compounds as given in the following Table 7 were prepared in the same manner as that of Example 42.

Example 46

First, 5 g of a starting 2,3-epoxycyclopentanone compound as given in the following Table 8 was dissolved in 100 ml of methanol, 10 ml of triethylamine was added thereto, 1.2 g of a thiol compound was added thereto, and the mixture was stirred for 2 hr. The reaction mixture was poured in an aqueous potassium hydrogensulfate solution and extracted with ethyl acetate, and the extract was washed with a saline solution and dried over magnesium sulfate, and the dried extract was filtered, concentrated and then subjected to silica gel chromatography to obtain a 2-substituted-2-cyclopentenone compound as given in Table 8.

Examples 47 to 76

The 2-Substituted-2-cyclopentenone compounds as given in the following Table 8 were prepared in the same manner as that of Example 46.

Reference Examples 24 to 32

The 2-Substituted-2-cyclopentenone compounds as given in the following Table 9 were prepared in the same manner as that of Example 46.

Reference Examples 33 to 40

The 2-Substituted-2-cyclopentenone compounds as given in the following Table 11 were prepared in the same manner as that of Example 77.

Example 77

First, 1.8 g of a starting 2,3-epoxycyclopentanone compound as given in the following Table 10 was dissolved in 15 ml of methanol, 1.0 ml of triethylamine was added thereto, 790 mg of a thiol compound was added thereto, and the mixture was stirred for 1.5 hr. The reaction mixture was poured in an aqueous potassium hydrogensulfate solution and extracted with ethyl acetate, and the resultant organic phase was washed with a saline solution and dried over magnesium sulfate. The dried organic phase was filtered and concentrated, the resultant crude oily residue was dissolved in 20 ml of dimethylformamide, and 1.5 g of imidazole was added thereto with stirring and cooling on ice. Then 1.4 g of chlorotrimethylsilane was added thereto, the mixture was stirred at 0° C. for 5 hr, and water and hexane were added thereto for extraction. The resultant organic phase was washed with a saline solution, dried over sodium sulfate, filtered, concentrated and then subjected to silica gel chromatography to obtain a 2-substituted-2-cyclopentenone compound as given in Table 10.

Examples 78 to 113

The 2-Substituted-2-cyclopentenone compounds as given in the following Table 10 were prepared in the same manner as that of Example 77.

Example 114

First, 65 mg of a starting 2,3-epoxycyclopentanone compound as given in the following Table 12 was dissolved in 2 ml of methanol, 150 μl of triethylamine and 25 mg of cyclohexanethiol were added thereto, the mixture was stirred for 4 hr, an aqueous ammonium chloride solution was added thereto, and the mixture was extracted with ethyl acetate. The resultant organic phase was washed with a saline solution and dried over magnesium sulfate, and the dried organic phase was filtered, concentrated and then subjected to silica gel chromatography to obtain two 2-substituted-2-cyclopentenone compounds as given in Table 12.

Example 115

First, 216 mg of a starting 2-substituted-2-cyclopentenone compound as given in the following Table 13 was weighed, 2.5 ml of an ether and 2.5 ml of hexane were added thereto, 157 μl of diisopropylethylamine was added thereto, and the mixture was cooled to −70° C. Then, 750 μl of a 1 M dichloromethane solution of dibutylboron trifluoromethanesulfonate was added thereto, the mixture was stirred for 1 hr, a solution of 373 mg of a starting aldehyde compound in 10 ml of an ether was cooled to −70° C. and added thereto, and the mixture was stirred at −70 to −25° C. for 4 hr. Then the stirred mixture was dried over magnesium sulfate, filtered, concentrated and then subjected to silica gel chromatography to obtain a 2-substituted-2-cyclopentenone compound (an intended product) as given in Table 13.

Examples 116 to 202

The 2-Substituted-2-cyclopentenone compounds (intended products) as given in the following Table 13 were prepared in the same manner as that of Example 115.

Reference Examples 41 to 45

The 2-Substituted-2-cyclopentenone compounds (intended products) as given in the following Table 14 were prepared in the same manner as that of Example 115.

Example 203

First, 861 mg of a starting 2-substituted-2-cyclopentenone compound as given in the following Table 15 was dissolved in 5 ml of tetrahydrofuran, the solution was cooled to −70° C., 1.67 ml of a 1.5 M tetrahydrofuran solution of lithium diisopropylamide was added thereto, and the mixture was stirred for 30 min. Then a solution of 526 mg of a starting aldehyde compound in 5 ml of tetrahydrofuran was added thereto, the mixture was stirred at −70° to −40° C. for 3 hr, the reaction mixture was poured in an aqueous ammonium chloride solution, and the mixture was extracted with ethyl acetate. The resultant organic phase was washed with a saline solution and dried over magnesium sulfate, and the dried organic phase was filtered, concentrated and then subjected to silica gel chromatography to obtain a 2-substituted-2-cyclopentenone compound (an intended product) as given in Table 15.

Examples 204 to 207

The 2-Substituted-2-cyclopentenone compounds as given in the following Table 15 were prepared in the same manner as that of Example 203.

Example 208

First, 60 mg of a starting 2-substituted-2-cyclopentenone compound as given in the following Table 16 was dissolved in 3 ml of dichloromethane, 200 μl of pyridine was added thereto, 100 μl of acetyl chloride was added thereto, and the mixture was stirred for 16 hr. Then the mixture was poured in an aqueous potassium hydrogensulfate solution, the mixture was extracted with ethyl acetate, and the resultant organic phase was washed with an aqueous sodium bicarbonate solution and a saline solution and then dried over magnesium sulfate. The dried organic phase was filtered, concentrated and then subjected to silica gel chromatography to obtain a 2-substituted-2-cyclopentenone compound (an intended product) as given in Table 16.

Examples 209 to 219

The 2-Substituted-2-cyclopentenone compounds as given in the following Table 16 were prepared in the same manner as that of Example 208.

Example 220

First, 60 mg of a starting 2-substituted-2-cyclopentenone compound as given in the following Table 16 was dissolved in 3 ml of dichloromethane, 500 µl of pyridine was added thereto, 300 µl of methoxycarbonyl chloride was added thereto, and the mixture was stirred for 16 hr. Then the mixture was poured in an aqueous potassium hydrogensulfate solution, the mixture was extracted with ethyl acetate, and the resultant organic phases were combined with each other, washed with an aqueous sodium bicarbonate solution and a saline solution and then dried over magnesium sulfate. The dried organic phase was filtered, concentrated and then subjected to silica gel chromatography to obtain a 2-substituted-2-cyclopentenone compound (an intended product) as given in Table 16.

Examples 221 to 222

The 2-Substituted-2-cyclopentenone compounds as given in the following Table 16 were prepared in the same manner as that of Example 220.

Example 223

First, 60 mg of a starting 2-substituted-2-cyclopentenone compound as given in the following Table 16 was dissolved in 3 ml of dichloromethane, 200 µl of pyridine was added thereto, 300 µl of isopropoxycarbonyl chloride was added thereto, and the mixture was stirred for 16 hr. Then the mixture was poured in an aqueous potassium hydrogensulfate solution, the mixture was extracted with ethyl acetate and the resultant organic phases were combined with each other, Washed with an aqueous sodium bicarbonate solution and a saline solution and then dried over magnesium sulfate. The dried organic phase was filtered, concentrated and then subjected to silica gel chromatography to obtain a 2-substituted-2-cyclopentenone compound (an intended product) as given in Table 16.

Examples 224 to 231

The 2-Substituted-2-cyclopentenone compounds as given in the following Table 16 were prepared in the same manner as that of Example 223.

Example 232

First, 182 mg of a starting 2-substituted-2-cyclopentenone compound as given in the following Table 17 was weighed and purged with nitrogen, 15 ml of tetrahydrofuran was added thereto, the mixture was cooled to −70° C., 600 µl of a 1.5 M cyclohexane solution of lithium diisopropylamide was added thereto, and the mixture was stirred at −70° C. for 40 min. Then 1 ml of N-methyl pyrrolidone was added thereto, a solution of 251 mg of triphenyltin chloride in 10 ml of tetrahydrofuran was added thereto, the mixture was stirred at −70° C. for 1 hr, a solution of 400 mg of a starting organoiodide in 10 ml of tetrahydrofuran was added thereto, the mixture was stirred at −40° to −10° C. for 19 hr and poured in an aqueous potassium hydrogensulfate solution, and the mixture was extracted with ethyl acetate. The resultant organic phases were combined with each other, washed with an aqueous sodium bicarbonate solution and a saline solution and then dried over magnesium sulfate, and the dried organic phase was filtered, concentrated and then subjected to silica gel chromatography to obtain a 2-substituted-2-cyclopentenone compound (an intended product) as given in Table 17.

Examples 233 to 237

The 2-Substituted-2-cyclopentenone compounds as given in the following Table 17 were prepared in the same manner as that of Example 232.

Example 238

First, Dimethylaminopyridine (1.5 g) was added to a solution of 3.5 g of a starting 2-substituted-2-cyclopentenone compound as given in the following Table 18 in dichloromethane (30 ml), the mixture was cooled to 0° C., 0.6 ml of methanesulfonyl chloride was dropwise added thereto, and the mixture was stirred at room temperature for 13 hr. Then ethyl acetate and an aqueous potassium hydrogensulfate were added to the reaction mixture to extract the product into an organic phase, the extract was washed with an aqueous sodium bicarbonate solution and a saline solution, dried over magnesium sulfate, filtered and concentrated, and the concentrate was subjected to silica gel chromatography to obtain a 2-substituted-2-cyclopentenone compound (an intended product) as given in Table 18.

Examples 239 to 348

The 2-Substituted-2-cyclopentenone compounds as given in the following Table 18 were prepared in the same manner as that of Example 238.

Example 349

First, 300 mg of a starting 2-substituted-2-cyclopentenone compound as given in the following Table 19 was dissolved in 15 ml of acetonitrile, 2 ml of pyridine was added thereto, 1 ml of a hydrogen fluoride-pyridine solution was added thereto with stirring and cooling on ice, and the mixture was stirred at 0° C. to room temperature for 16 hr. Then the stirred mixture was poured in an aqueous potassium hydrogensulfate solution, the mixture was extracted with ethyl acetate, and the resultant organic phases were combined with each other, washed with a saline solution and then dried over magnesium sulfate. The dried organic phase was filtered, concentrated and then subjected to silica gel chromatography to obtain a 2-substituted-2-cyclopentenone compound (an intended product) as given in Table 19.

Examples 350 to 511

The 2-Substituted-2-cyclopentenone compounds as given in the following Table 19 were prepared in the same manner as that of Example 349.

Examples 512 and 513

The Two 2-substituted-2-cyclopentenone compounds as given in the following Table 20 were prepared in the same manner as that of Example 349.

Example 514

First, 50 mg of a starting 2-substituted-2-cyclopentenone compound as given in the following Table 20 was dissolved in 5 ml of a mixed solvent comprising acetic acid, tetrahydrofuran and water in a ratio of 2:1:1, and the mixture was stirred for 5 hr. Then the the solution was neutralized with sodium bicarbonate and extracted with ethyl acetate, and the resultant organic phases were combined with each other, washed with a saline solution, dried over magnesium sulfate, filtered, concentrated, and then subjected to silica gel chromatography to obtain a 2-substituted-2-cyclopentenone compound (an intended product) as given in Table 20.

Examples 515

A 2-substituted-2-cyclopentenone compound as given in the following Table 20 was prepared in the same manner as that of Example 514.

Example 516

First, 5 mg of a starting 2-substituted-2-cyclopentenone compound as given in the following Table 20 was dissolved in 1 ml of methanol, 0.5 $\mu$l of acetic acid was added thereto, and the mixture was stirred for 24 hr. Then an aqueous sodium bicarbonate solution was added thereto, and the mixture was extracted with ethyl acetate. The extract was dried over magnesium sulfate, filtered, concentrated and then subjected to a silica gel chromatography to obtain a 2-substituted-2-cyclopentenone compound (an intended product) as given in Table 20.

Example 517

First, 30 mg of a starting 2-substituted-2-cyclopentenone compound as given in the following Table 20 was dissolved in 5 ml of ethanol, 5 $\mu$l of acetic acid was added thereto, and the mixture was stirred for 40 hr. Then an aqueous sodium bicarbonate solution was added thereto, the mixture was extracted with ethyl acetate, and the extract was dried over magnesium sulfate, filtered, concentrated and then subjected to silica gel chromatography to obtain a 2-substituted-2-cyclopentenone compound (an intended product) as given in Table 20.

Example 518

First, 36 mg of the 2-substituted-2-cyclopentenone compound as given in the following Table 20 was dissolved in 2 ml of dichloromethane, 200 $\mu$l of triethylamine was added thereto, 20 $\mu$l of acetyl chloride was added while stirring and cooling on ice, and the mixture was stirred at 0° C. for 2 hr. Then a saline solution was added thereto, the mixture was extracted with ethyl acetate, and the extract was dried over magnesium sulfate, filtered, concentrated and then subjected to silica gel chromatography to obtain two 2-substituted-2-cyclopentenone compounds (intended products) as given in Table 20.

Example 519

First, 500 mg of a starting 2-substituted-2-cyclopentenone compound as given in the following Table 20 was dissolved in 20 ml of acetone, 220 ml of a 0.1 M phosphate buffer having a pH value of 8 was added to the solution, 24 mg of pig liver esterase was added thereto with stirring, and the mixture was stirred at 30° to 35° C. for 6 days. Then a 0.1 N hydrochloric acid was added to adjust the pH value to 4, ammonium sulfate was added to saturate the solution, ethyl acetate was added thereto, and the mixture was filtered. The filtrate was extracted with ethyl acetate and the resultant organic phases were combined with each other and then washed with a saline solution, and the washed organic phase was dried over magnesium sulfate, filtered, concentrated and then subjected to silica gel chromatography to obtain an 2-substituted-2-cyclopentenone compound (an intended product) as given in Table 20.

Example 520

A 2-substituted-2-cyclopentenone compound as given in the following Table 20 was prepared in the same manner as that of Example 519.

Example 521

First, 70 mg of a starting 2-substituted-2-cyclopentenone compound as given in the following Table 20 was dissolved in 5 ml of dichloromethane, and the solution was cooled to $-70°$ C., 15 $\mu$l of triethylamine was added, and 10 $\mu$l of isobutoxycarbonyl chloride was then added thereto. Then the mixture was stirred at room temperature for 10 min, the temperature of the mixture was returned to room temperature, 500 $\mu$l of an aqueous ammonia was added thereto, the mixture was stirred for 30 min, an aqueous ammonium chloride solution was added thereto, and the mixture was extracted with dichloromethane. The organic phase was dried over magnesium sulfate, filtered and concentrated, the resultant oily residue was dissolved in a mixed solvent comprising 3 ml of acetic acid, 2 ml of tetrahydrofuran and 2 ml of water, and the mixture was stirred for 24 hr. The mixture was concentrated and extracted with an aqueous sodium hydrogencarbonate solution and ethyl acetate, and the resultant organic phases were combined with each other and washed with a saline solution. The washed organic phase was dried over magnesium sulfate, filtered, concentrated and then subjected to silica gel chromatography to obtain a 2-substituted-2-cyclopentenone compound (an intended product) as given in Table 20.

Example 522

First, 90 mg of a starting 2-substituted-2-cyclopentenone compound as given in the following Table 20 was dissolved in 3 ml of dichloromethane, 45 mg of 1-methyl-2-fluoropyridinium methylsulfate, 15 mg of cyclohexylmethylamine and 20 mg of triethylamine were added to the solution, and the mixture was stirred for 18 hr. Then water was added, the mixture was extracted with dichloromethane and dried over magnesium sulfate, the dried extract was filtered and concentrated, the resultant oily residue was dissolved in 2 ml of acetonitrile, 200 $\mu$l of pyridine was added thereto, 200 $\mu$l of a hydrogen fluoride-pyridine solution was added thereto, and the mixture was stirred for 16 hr. An aqueous potassium hydrogensulfate solution was added thereto, the mixture was extracted with ethyl acetate, and the resultant organic phase was washed with an aqueous sodium hydrogencarbonate and a saline solution, dried over magnesium sulfate, filtered, concentrated and then subjected to silica gel chromatography to obtain a 2-substituted-2-cyclopentenone compound (an intended product) as given in Table 20.

Example 523

A solution of 30 mg of a starting 2-substituted-2-cyclopentenone compound as given in the following Table 20 in dichloromethane (4 ml) was cooled to 0° C., a solution of 3-chloroperbenzoic acid (13 mg) in dichloromethane (3 ml) was dropwise added thereto, the mixture was stirred at 0° C. for 1 hr, and ethyl acetate and an aqueous sodium hydrogen carbonate solution were added thereto to extract the product into an organic phase. The extract was successively washed with a saline solution, an aqueous ammonium chloride and a saline solution, dried over magnesium sulfate, filtered and then concentrated, and the concentrate was subjected to silica gel chromatography to obtain a 2-substituted-2-cyclopentenone compound (an intended product) as given in Table 20.

Example 524

A 2-substituted-2-cyclopentenone compound as given in the following Table 20 was prepared in the same manner as that of Example 523.

Example 525

A solution of 20 mg of a starting 2-substituted-2-cyclopentenone compound as given in the following Table 20 in dichloromethane (1.5 ml) was cooled to 0° C., a solution of 3-chloroperbenzoic acid (15.7 mg) in dichloromethane (1 ml) was dropwise added thereto, the mixture was stirred at 0° C. for 2 hr, and ethyl acetate and an aqueous sodium hydrogen carbonate solution were added thereto to extract the product into an organic phase. The extract was successively washed with an aqueous ammonium chloride and a saline solution, dried over magnesium sulfate, filtered and then concentrated, and the concentrate was subjected to silica gel chromatography to obtain a 2-substituted-2-cyclopentenone compound (an intended product) as given in Table 20.

Example 526

A 2-substituted-2-cyclopentenone compound as given in the following Table 20 was prepared in the same manner as that of Example 525.

Example 527

First, 320 mg of a starting 2-substituted-2-cyclopentenone compound as given in the following Table 20 was dissolved in 25 ml of dichloromethane, 120 µl of triethylamine was added to the solution, the mixture was cooled to −20° C., 110 µl of pivaloyl chloride was added thereto, the mixture was stirred for 2 hr, 95 mg of 2-mercaptothiazoline and 9 mg of 4-dimethylaminopyridine were added thereto, and the mixture was again stirred for 2 hr. Then an aqueous sodium hydrogen carbonate solution was added thereto, the mixture was extracted with ethyl acetate, the resultant organic phase was washed with an aqueous potassium hydrogensulfate solution, an aqueous sodium hydrogen carbonate solution, and a saline solution, and dried over magnesium sulfate. The dried organic phase was filtered, concentrated and then subjected to silica gel chromatography to obtain a 2-substituted-2-cyclopentenone compound (an intended product) as given in Table 20.

Example 528

First, 85 mg of a starting 2-substituted-2-cyclopentenone compound as given in the following Table 20 was dissolved in 4 ml of pyridine, 85 mg of D-glucose was added thereto. 3 mg of sodium hydride (60% in oil) and 3 mg of 4-dimethylaminopyridine was added thereto, and the mixture was stirred for 16 hr. Then 5 ml of a 0.1 M phosphate buffer having a pH value of 7 was added thereto, and mixture was extracted with butanol, and the organic layer was washed with a saline solution, concentrated and then subjected to silica gel chromatography to obtain a 2-substituted-2-cyclopentenone compound (an intended product) as given in Table 20.

Example 529

First, 63 mg of a starting 2-substituted-2-cyclopentenone compound as given in the following Table 20 was dissolved in 4 ml of pyridine, and 70 mg of D-xylose was added thereto, 2.5 mg sodium hydride (60% in oil) was added thereto, and the mixture was stirred for 16 hr. Then 5 ml Of a 0.1 M phosphate buffer having a pH value of 7 was added thereto, the mixture was extracted with butanol, and the organic layer was washed with a saline solution, concentrated and then subjected to silica gel chromatography to obtain a 2-substituted-2-cyclopentenone compound (an intended product) as given in Table 20.

Example 530

Measurement of anticancer activity

Tumor cells were grown in an RPMI 1640 medium containing of 10% fetal calf serum.

The compound was dissolved in 99.5% ethanol, adjusted before use so that the final concentration of ethanol was 0.1% or less, and added to the medium.

The control was 0.1% ethanol, and L1210 tumor cells were inoculated in the medium in a concentration of 2.5 ×10⁴ cells/ml and grown for 2 days. The number of surviving cells were measured by trypan blue staining.

The results are given in the following Table 21.

Example 531

Measurement of bone formation activity

Human osteoblasts (KK-3, 18PDL) were cultured in an α-MEM containing 10% fetal calf serum. After the growth became stationary, the compound was added in a given concentration in the presence of 2 mM α-glycerophosphate and treated for 14 days. The cell phase was washed with physiological saline, and the alkaline phosphatase activity (ALP) was measured through the absorption of $OD_{415}$. Then, calcium (Ca) and phosphorus (P) were extracted with a 2 N hydrochloric acid and quantitatively determined. The results are given in Tables 22 to 32.

TABLE 1

| Ref. Ex. No. | Starting Compd. (2-Cyclopentenones) | 2-Cyclopentenones | Yield (%) | NMR (δ, CDCl₃) |
|---|---|---|---|---|
| 1 | [structure] | [structure] | 100 | 0.04(s, 3H), 0.05(s, 3H), 2.40(dd, 1H, J=18.3, 2.2Hz), 2.84(dd, 1H, J=18.3, 5.9Hz), 4.86(dt, 1H, J=5.7, 2.4Hz), 6.73(d, 1H, J=2.4Hz), 7.1–7.8(m, 6H) |

TABLE 2

| Ref. Ex. No. | Starting Compd. 2-Cyclopentenones | Organolithium reagent | 2-Cyclopentenones | Yield (%) | NMR ($\delta$, $CDCl_3$) |
|---|---|---|---|---|---|
| 2 | (PhSe-substituted cyclopentenone with OSi group) | t-BuLi | (cyclopentenone with OSi group) | 81 | 0.12(s, 3H), 0.16(s, 3H), 0.91(s, 9H), 1.26(s, 9H), 2.31(dd, 1H, J=7.9, 2.6Hz), 2.70(dd, 1H, J=7.9, 5.8 Hz), 5.04(ddd, 1H, J=5.8, 2.6, 1.0 Hz), 5.96(d, 1H, J=1.0Hz) |
| 3 | (cyclopentenone with OSi and OPh chain) | n-BuLi | (cyclopentenone with butyl, OSi and OPh chain) | 53 | 0.10(s, 9H), 0.7–1.05(m, 3H), 1.05–2.8(m, 12H), 2.56(s, 2H), 3.93(t, 2H, J=5.8Hz), 5.90(t, 1H, J=1.5Hz), 6.7–7.05(m, 3H), 7.1–7.5(m, 2H) |
| 4 | (cyclopentenone with OSi and dimethoxyphenyl chain) | MeLi | (cyclopentenone with Me, OSi and dimethoxyphenyl chain) | 68 | 0.08(s, 9H), 1.5–2.0(m, 4H), 2.19 (d, 3H, J=13Hz), 2.3–2.8(m, 4H), 3.80(s, 6H), 5.93(brs, 1H), 6.4–6.9(m, 3H) |
| 5 | (cyclopentenone with Me and OSi) | t-BuLi | (cyclopentenone with Me and OSi) | 33 | 0.07(s, 9H), 1.26(s, 12H), 2.57(s, 2H), 5.94(d, 1H, J=1.0Hz) |

TABLE 3

| Ref. Ex. No. | Starting Compd. 2-Cyclopentenones | Grignard's reagent | 2-Cyclopentenones | Yield (%) | NMR (δ, CDCl₃) |
|---|---|---|---|---|---|
| 6 | (cyclopentenone with OPh side chain, OSi) | EtMgBr | (cyclopentenone product with Et, OPh, OSi) | 31 | 0.10(s, 9H), 1.17(t, 3H, J=7.5Hz), 2.57(s, 2H), 3.93(t, 2H, J=5.8Hz), 5.90(brs, 1H), 6.7-7.1(m, 3H), 7.1-7.5(m, 2H) |
| 7 | Same as above | Ph(CH₂)₅MgBr | (product with Ph(CH₂)₅, OPh, OSi) | 47 | 0.08(s, 9H), 1.1-3.1(m, 19H), 2.55(s, 2H), 3.93(t, 2H, J=5.8Hz), 5.92 (brs, 1H), 6.7-7.5(m, 10H) |
| 8 | Same as above | (citronellyl MgBr) | (product with citronellyl group, OPh, OSi) | 38 | 0.08(s, 9H), 0.85(brd, 3H, J=4.3 Hz), 1.0-2.7(m, 21H), 2.55(s, 2H), 3.91(t, 2H, J=6.0Hz), 4.8-5.2(m, 1H), 5.90(brs, 1H), 6.7-7.1(m, 3H), 7.1-7.5(m, 2H) |
| 9 | (cyclopentenone with propyl, OSi) | EtMgBr | (product with propyl, Et, OSi) | 61 | 0.09(s, 9H), 0.7-1.0(m, 3H), 1.18 (t, 3H, J=7.6Hz), 1.2-1.9(m, 6H), 2.57(s, 2H), 2.4-2.7(m, 2H), 5.91 (brs, 1H) |
| 10 | Same as above | cyclohexyl-MgBr | (product with propyl, cyclohexyl, OSi) | 32 | 0.09(s, 9H), 0.7-1.0(m, 3H), 1.1-1.9(m, 16H), 2.55(s, 2H), 2.4-2.7 (m, 1H), 5.90(brs, 1H) |
| 11 | (cyclopentenone with pentynyl, OSi) | PrMgBr | (product with pentyl, Pr, OSi) | 42 | 0.07(s, 9H), 0.7-1.0(m, 6H), 1.1-2.0(m, 6H), 2.2-2.8(m, 6H), 5.90 (brs, 1H) |

TABLE 3-continued

| Ref. Ex. No. | Starting Compd. 2-Cyclopentenones | Grignard's reagent | 2-Cyclopentenones | Yield (%) | NMR (δ, CDCl₃) |
|---|---|---|---|---|---|
| 12 | (cyclopentenone with OSi and cyclohexyl-vinyl substituents) | (cyclohexyl-butyl)MgBr | (cyclopentenone product with cyclohexylpropyl and cyclohexyl-vinyl-OSi groups) | 39 | 0.0–0.1(m, 15H), 0.89(s, 9H), 1.0–2.0(m, 26H), 2.4–2.8(m, 4H), 5.4–6.1(m, 3H) |
| 13 | (cyclopentenone with isooctyl-OSi group) | i-PrMgBr | (cyclopentenone product with i-Pr and OSi groups) | 27 | 0.09(s, 9H), 0.7–1.2(m, 15H), 1.2–2.1(m, 12H), 2.53(s, 2H), 2.4–2.7(m, 1H), 5.88(s, 1H) |

TABLE 4

| Ref. Ex. No. | Starting Compd. 2-Cyclopentenones | Organolithium reagent | Aldehydes | 2-Cyclopentenones | Yield (%) | NMR (δ, CDCl₃) |
|---|---|---|---|---|---|---|
| 14 | | | | | 35 | 0–0.1(m, 6H), 0.89(s, 9H), 0.7–1.1(m, 6H), 1.1–2.7(m, 26H), 3.0–3.3(m, 1H), 3.60(s, 3H), 3.6–4.1(m, 2H), 5.4–5.8(m, 2H), 5.92(brs, 1H) |
| 15 | Same as above | | | | 28 | 0.0–0.1(m, 6H), 0.88(s, 9H), 0.7–1.0(m, 3H), 1.0–2.9(m, 23H), 3.1–3.3(m, 1H), 3.69(s, 3H), 3.5–3.8(m, 1H), 4.6–5.0(m, 1H), 5.4–5.9(m, 3H) |
| 16 | | MeLi | | | 26 | 0.86(d, 1H, J=6.5Hz), 1.3–2.1(m, 6H), 2.5–3.0(m, 7H), 3.5–4.1(m, 3H), 5.9(brs, 1H), 6.7–7.5(m, 10H) |
| 17 | | t-BuLi | | | 16 | 0.7–1.1(m, 3H), 0.88(s, 9H), 1.1–1.9(m, 16H), 2.18(d, 3H, J=1.5Hz), 2.6–2.9(m, 3H), 3.5–3.8(m, 1H), 5.9(m, 1H) |

TABLE 5
| Ex. No. | Starting Compd. (2-Cyclopentenones) | 2,3-Epoxycyclopentanones | Yield (%) | NMR (δ, CDCl₃) |
|---|---|---|---|---|
| 1 | 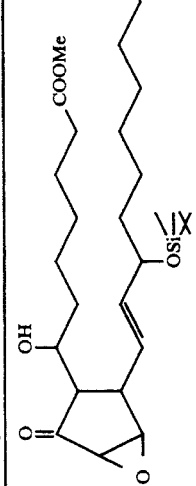 | 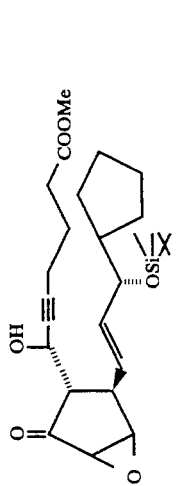 | 74 | −0.03(3H, s), 0.00(3H, s), 0.84 (9H, s), 0.7−1.1(3H, brt), 1.1−2.3 (20H, m), 3.4−3.5(1H, m), 3.61(3H, s), 3.68(1H, brs), 3.6−4.1(2H, m), 5.5−5.7(2H, m) |
| 2 | 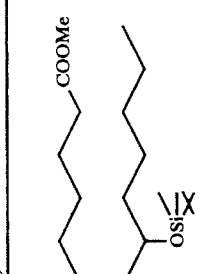 | 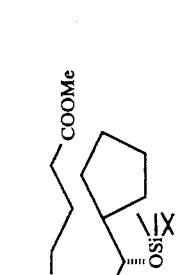 | 51 | 0.00(3H, s), 0.05(3H, s), 0.89(9H, s), 1.2−2.0(11H, m), 2.0−2.6(5H, m), 3.1−3.3(1H, m), 3.50(1H, d, J=2.5Hz), 3.69(3H, s), 3.77(1H, d, J=2.5Hz), 3.8−4.05(1H, m), 4.6−4.9 (1H, m), 5.3−5.9(2H, m) |
| 3 | 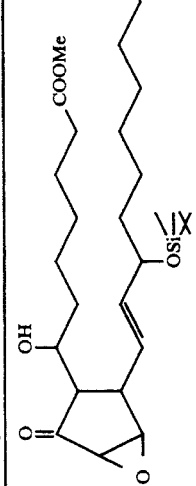 | 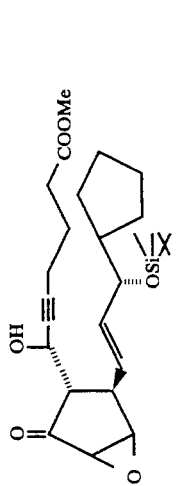 | 63 | 0.01(3H, s), 0.06(3H, s), 0.89(9H, s), 0.7−1.1(6H, m), 1.1−2.7(17H, m), 3.0−3.3(1H, m), 3.49(1H, d, J=2.5Hz), 3.68(3H, s), 3.79(1H, d, J=2.5Hz), 3.6−4.6(2H, m), 5.4−5.9 (2H, m), 5.87(1H, d, J=16.0Hz), 7.03(1H, dt, J=16.0, 7.2Hz) |
| 4 | 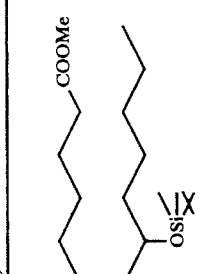 | 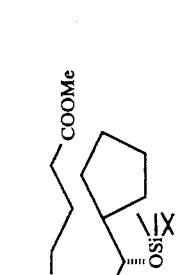 | 43 | 1.1−2.7(29H, m), 2.9−3.3(1H, m), 3.3−4.4(5H, m), 3.69(3H, s), 4.5−5.0(2H, m), 5.3−5.8(2H, m) |
| 5 | 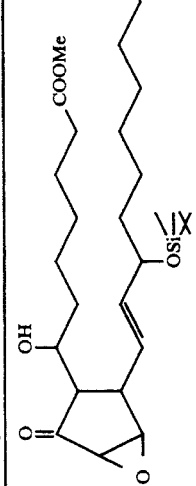 | 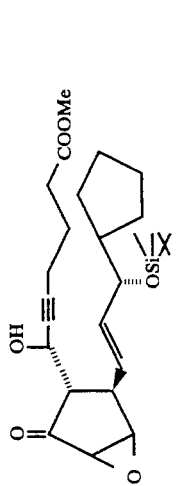 | 69 | 0.7−1.1(3H, m), 1.1−3.1(9H, m), 3.3−3.6(1H, m), 3.49(1H, d, J=2.6 Hz), 3.76(1H, d, J=2.6Hz), 4.3−4.7 (1H, m), 6.4−6.8(1H, m), 7.0−8.0 (5H, m) |

TABLE 5-continued

| Ex. No. | Starting Compd. (2-Cyclopentenones) | 2,3-Epoxycyclopentanones | Yield (%) | NMR (δ, CDCl₃) |
|---|---|---|---|---|
| 6 | | | 36 | 0.03(s, 12H), 0.88(s, 18H), 1.1–2.9(m, 13H), 3.2–3.5(m, 1H), 3.4–3.7(m, 2H), 3.6–3.8(m, 1H), 3.8–4.1(m, 2H), 4.0–4.3(m, 2H), 4.3–4.6(m, 1H), 5.3–5.9(m, 2H), 6.7–7.1(m, 3H), 7.1–7.6(m, 2H) |
| 7 | | | 53 | 0–0.15(12H, m), 0.84(9H, s), 0.86 (9H, s), 1.3–1.7(4H, m), 2.4–2.7 (1H, m), 3.5–3.7(2H, m), 3.7–3.9 (1H, m), 3.78(1H, d, J=2.4Hz), 3.90 (1H, t, J=2.2Hz), 4.0–4.3(1H, m), 4.3–4.7(1H, m), 5.4–5.9(2H, m), 7.0–7.4(5H, m) |
| 8 | | | 48 | 0.08(s, 12H), 0.89(s, 19H), 1.1–2.9(m, 17H), 3.2–3.5(m, 1H), 3.4–3.7(m, 3H), 3.6–3.8(m, 1H), 4.0–4.3(m, 1H), 4.3–4.6(m, 1H), 5.3–5.9 (m, 2H) |
| 9 | | | 27 | 0.0–0.1(m, 6H), 0.90(s, 9H), 0.7–1.0(m, 3H), 1.2–2.0(m, 17H), 2.0–2.6(m, 5H), 3.1–3.3(m, 1H), 3.40 (s, 1H), 3.69(s, 3H), 3.8–4.1(m, 1H), 4.4–4.9(m, 2H), 5.3–5.9(m, 2H) |
| 10 | | | 33 | 0–0.1(s, 6H), 0.86(s, 9H), 0.7–1.1 (m, 6H), 1.1–2.7(m, 26H), 3.0–3.3 (m, 1H), 3.60(s, 3H), 3.5–4.1(m, 3H), 5.4–5.8(m, 2H) |

TABLE 5-continued

| Ex. No. | Starting Compd. (2-Cyclopentenones) | 2,3-Epoxycyclopentanones | Yield (%) | NMR (δ, CDCl₃) |
|---|---|---|---|---|
| 11 | (structure) | (structure) | 28 | 0.86(d, 1H, J=6.6Hz), 1.3–2.1(m, 8H), 2.3–3.0(m, 4H), 3.41(s, 1H), 3.5–4.1(m, 3H), 6.7–7.5(m, 10H) |
| 12 | (structure) | (structure) | 39 | 0.7–1.1(m, 3H), 0.88(s, 9H), 1.30 (s, 3H), 1.1–1.9(m, 16H), 2.3–2.8 (m, 3H), 3.35(s, 1H), 3.5–3.8(m, 1H) |
| 13 | (structure) | (structure) | 57 | 0–0.1(m, 6H), 0.89(s, 9H), 0.7–1.1 (m, 6H), 1.27(s, 3H), 1.1–2.8(m, 21H), 3.41(s, 1H), 3.6–4.6(m, 4H), 5.4–6.1(m, 3H), 7.0(dt, 1H, J=16.0, 7.4Hz) |
| 14 | (structure) | (structure) | 69 | 0–0.2(m, 6H), 0.89(s, 9H), 0.7–1.0 (m, 3H), 1.1–2.4(m, 22H), 3.45(d, 1H, J=2.1Hz), 3.69(s, 3H), 3.73(d, 1H, J=2.1Hz), 4.0–4.1(m, 1H), 5.5–5.8(m, 2H) |
| 15 | (structure) | (structure) | 46 | 0.0(s, 3H), 0.03(s, 3H), 0.87(s, 9H), 0.7–1.0(m, 3H), 1.2–2.6(m, 19H), 2.9–3.2(m, 1H), 3.50(d, 1H, J=2.3Hz), 3.73(s, 3H), 3.79(d, 1H, J=2.3Hz), 4.0–4.3(m, 1H), 4.7–5.0 (m, 2H), 5.5–5.8(m, 2H) |

TABLE 5-continued

| Ex. No. | Starting Compd. (2-Cyclopentenones) | 2,3-Epoxycyclopentanones | Yield (%) | NMR (δ, CDCl₃) |
|---|---|---|---|---|
| 16 | (cyclopentenone with OH and n-octyl chain) | (2,3-epoxycyclopentanone with OH and n-octyl chain) | 58 | 0.7–1.0(m, 3H), 1.2–2.0(m, 14H), 2.33(d, 1H, J=16.0Hz), 2.42(d, 1H, J=16.0Hz), 2.4–2.8(m, 1H), 3.3–3.6(m, 1H), 3.7–3.9(m, 1H) |
| 17 | (cyclopentenone with OH and isoalkyl chain) | (2,3-epoxycyclopentanone with OH and isoalkyl chain) | 49 | 0.7–1.2(m, 9H), 1.2–2.0(m, 12H), 2.35(d, 1H, J=16.2Hz), 2.43(d, 1H, J=16.2Hz), 2.4–2.8(m, 1H), 3.3–3.5(m, 1H), 3.6–3.9(m, 1H) |
| 18 | (cyclopentenone with OH and chain terminating in COOMe) | (2,3-epoxycyclopentanone with OH and chain terminating in COOMe) | 53 | 1.1–2.0(m, 10H), 2.1–2.9(m, 5H), 3.3–3.5(m, 1H), 3.68(s, 3H), 3.6–3.8(m, 1H) |
| 19 | (cyclopentenone with OH and chain terminating in OPh) | (2,3-epoxycyclopentanone with OH and chain terminating in OPh) | 79 | 1.4–2.1(6H, m), 2.31(1H, d, J=16.3 Hz), 2.4(1H, d, J=16.3Hz), 2.4–2.8 (1H, m), 3.35–3.6(1H, m), 3.65–4.2 (3H, m), 6.7–7.05(3H, m), 7.1–7.45 (2H, m) |
| 20 | (cyclopentenone with OH and 3,4-dimethoxyphenyl chain) | (2,3-epoxycyclopentanone with OH and 3,4-dimethoxyphenyl chain) | 63 | 1.4–1.9(m, 4H), 2.3–2.9(m, 5H), 3.3–3.5(m, 1H), 3.6–3.8(m, 1H), 3.80(s, 6H), 6.4–6.9(m, 3H) |
| 21 | (cyclopentenone with OH and alkyne chain) | (2,3-epoxycyclopentanone with OH and alkyne chain) | 42 | 0.7–1.0(m, 3H), 1.1–2.8(m, 9H), 3.3–3.5(m, 1H), 3.7–3.9(m, 1H) |

TABLE 5-continued

| Ex. No. | Starting Compd. (2-Cyclopentenones) | 2,3-Epoxycyclopentanones | Yield (%) | NMR (δ, CDCl₃) |
|---|---|---|---|---|
| 22 | (cyclohexyl-substituted allylic OSi alcohol cyclopentenone) | (2,3-epoxy analog) | 47 | 0-0.1(m, 6H), 0.89(s, 9H), 1.0-2.0 (m, 11H), 2.3-2.8(m, 3H), 3.3-3.6 (m, 1H), 3.6-3.8((m, 1H), 4.6-4.9 (m, 1H), 5.4-5.9(m, 2H) |
| 23 | 4-methyl-4-hydroxy-2-cyclopentenone | 4-methyl-4-hydroxy-2,3-epoxycyclopentanone | 63 | 1.24(s, 3H), 2.44(s, 2H), 2.5-2.8 (m, 1H), 3.3-3.6(m, 1H), 3.7-3.9 (m, 1H) |
| 24 | 4-(3,3-dimethyl-1-butynyl)-4-hydroxy-2-cyclopentenone | 2,3-epoxy analog | 49 | 1.08(s, 9H), 2.51(s, 2H), 2.5-2.8 (m, 1H), 3.3-3.6(m, 1H), 3.7-3.9 (m, 1H) |
| 25 | 4-(3-methyl-3-phenyl-1-butenyl)-4-hydroxy-2-cyclopentenone | 2,3-epoxy analog | 54 | 1.68(m, 6H), 2.49(s, 2H), 2.5-2.8 (m, 1H), 3.3-3.6(m, 1H), 3.6-3.8 (m, 1H), 5.4-5.9(m, 2H), 7.0-7.5 (m, 5H) |
| 26 | 4-butyl-4-OSi-2-ethyl-2-cyclopentenone | 4-butyl-4-hydroxy-2-ethyl-cyclopentanone | 47 | 0.7-1.1(m, 6H), 1.1-2.0(m, 8H), 2.45(s, 2H), 2.5-2.8(m, 1H), 3.40 (s, 1H) |

TABLE 5-continued

| Ex. No. | Starting Compd. (2-Cyclopentenones) | 2,3-Epoxycyclopentanones | Yield (%) | NMR (δ, CDCl₃) |
|---|---|---|---|---|
| 27 | (structure) | (structure) | 16 | 0.7–1.0(m, 3H), 1.1–2.0(m, 17H), 2.44(s, 2H), 2.5–2.8(m, 1H), 3.37(s, 1H) |
| 28 | (structure) | (structure) | 39 | 0.7–1.0(m, 6H), 1.1–2.7(m, 13H), 3.39(s, 1H) |
| 29 | (structure) | (structure) | 21 | 0–0.1(m, 6H), 0.88(s, 9H), 1.0–2.0 (m, 28H), 2.3–2.8(m, 3H), 3.38(s, 1H), 4.6–4.9(m, 1H), 5.4–5.8(m, 2H) |
| 30 | (structure) | (structure) | 30 | 0.7–1.2(m, 15H), 1.2–2.0(m, 13H), 2.1–2.6(m, 3H), 3.35(s, 1H) |

TABLE 5-continued

| Ex. No. | Starting Compd. (2-Cyclopentenones) | 2,3-Epoxycyclopentanones | Yield (%) | NMR (δ, CDCl₃) |
|---|---|---|---|---|
| 31 | [structure: cyclopentenone with Me, OSi, t-Bu] | [structure: epoxycyclopentanone with Me, OH, t-Bu] | 13 | 1.18(s, 9H), 1.22(s, 3H), 2.42(s, 2H), 2.5–2.8(m, 1H), 3.36(s, 1H) |
| 32 | [structure: cyclopentenone with Me, OSi, 3,4-dimethoxyphenylpropyl] | [structure: epoxycyclopentanone with Me, OH, 3,4-dimethoxyphenylpropyl] | 42 | 1.28(s, 3H), 1.4–1.9(m, 4H), 2.3–2.8(m, 5H), 3.38(s, 1H), 3.80(s, 6H), 6.4–6.9(m, 3H) |
| 33 | [structure: cyclopentenone with isopropyl, OSi, PhO-butyl] | [structure: epoxycyclopentanone with isopropyl, OH, PhO-butyl] | 33 | 0.7–1.2(m, 6H), 1.3–1.9(m, 7H), 2.39(s, 2H), 2.4–2.8(m, 1H), 6.7–7.1(m, 3H), 7.1–7.5(m, 2H) |
| 34 | [structure: cyclopentenone with butyl, OSi, PhO-butyl] | [structure: epoxycyclopentanone with butyl, OH, PhO-butyl] | 55 | 0.7–1.05(m, 3H), 1.05–2.7(m, 13H) 2.42(s, 2H), 3.38(s, 1H), 3.97(t, 2H, J=6.0Hz), 6.7–7.1(m, 3H), 7.1–7.4(m, 2H) |

TABLE 5-continued

| Ex. No. | Starting Compd. (2-Cyclopentenones) | 2,3-Epoxycyclopentanones | Yield (%) | NMR (δ, CDCl₃) |
|---|---|---|---|---|
| 35 | [structure: cyclopentenone with OPh-alkyl chain, OSi group, and ethyl] | [structure: epoxycyclopentanone with OPh-alkyl chain, OH, and ethyl] | 43 | 0.7–1.1(m, 3H), 1.1–2.7(m, 9H) 2.43(s, 2H), 3.39(s, 1H), 3.98(t, 2H, J=6.0Hz), 6.7–7.1(m, 3H), 7.1–7.4(m, 2H) |
| 36 | [structure: cyclopentenone with OPh chain, OSi, and Ph-alkyl chain] | [structure: epoxycyclopentanone with OPh chain, OH, and Ph-alkyl chain] | 29 | 1.0–3.0(m, 17H), 2.41(s, 2H), 3.40 (s, 1H), 3.96(t, 2H, J=6.0Hz), 6.7–7.4(m, 10H) |
| 37 | [structure: cyclopentenone with OPh chain, OSi, and methylated alkenyl chain] | [structure: epoxycyclopentanone with OPh chain, OH, and methylated alkenyl chain] | 31 | 0.85(brd, 3H, J=4.3Hz), 1.0–2.7(m, 24H), 3.37(s, 1H), 3.93(t, 2H, J=5.8Hz), 4.8–5.2(m, 1H), 6.7–7.1 (m, 3H), 7.1–7.4(m, 2H) |
| 38 | [structure: cyclopentenone with OSiX] | [structure: epoxycyclopentanone with OSiX] | 89 | 0.12(s, 6H), 0.88(s, 9H), 1.93(d, 1H, J=18.0Hz), 2.53(dd, 1H, J=18.0, 6.0Hz), 3.36(d, 1H, J=2.4Hz), 3.75 (d, 1H, J=2.4Hz), 4.57(d, 1H, J=6.0Hz) |

TABLE 5-continued
| Ex. No. | Starting Compd. (2-Cyclopentenones) | 2,3-Epoxycyclopentanones | Yield (%) | NMR (δ, CDCl₃) |
|---|---|---|---|---|
| 39 | 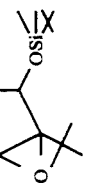 | | 67 | 0.09(s, 3H), 0.14(s, 3H), 0.92(s, 9H), 1.10(s, 9H), 1.93(d, 1H, J=17.6Hz), 2.70(dd, 1H, J=17.6, 5.9 Hz), 3.30(d, 1H, J=0.7Hz), 4.72(d, 1H, J=5.9Hz) |

TABLE 6

| Ex. No. | Starting Compd. (2,3-Epoxycyclopentanones) | 2-substituted-2-cyclopentenones | Yield (%) | NMR(δ, CDCl₃) |
|---|---|---|---|---|
| 40 | | | 74 | 0-0.1(m, 6H), 0.89(s, 9H), 0.7-1.1(m, 6H), 1.1-2.77(m, 26H), 2.34(s, 3H), 3.1-3.3(m, 1H), 3.61(s, 3H), 3.6-4.1(m, 2H), 5.4-5.7(m, 2H) |
| 41 | | | 63 | 0-0.2(m, 6H), 0.90(s, 9H), 0.7-1.0(m, 3H), 1.1-2.3(m, 21H), 2.35(s, 3H), 3.0-3.4(m, 1H), 3.68(s, 3H), 3.8-4.1(m, 1H), 5.5-5.8(m, 2H), 7.18(d, 1H, J=2.7Hz) |
| 42 | | | 67 | 0.11(s, 9H), 0.7-1.1(m, 3H), 1.1-2.0(m, 10H), 2.36(s, 3H), 2.56(s, 2H), 2.3-2.9(m, 2H), 3.93(t, 3H, J=6.2Hz), 6.8-7.1(m, 5H), 7.1-7.4(m, 2H) |
| 43 | | | 48 | 0.08(s, 9H), 0.7-1.0(m, 3H), 1.1-1.9(m, 16H), 2.53(s, 2H), 2.4-2.8(m, 1H) |
| 44 | | | 59 | 0.07(s, 9H), 1.26(s, 3H), 1.33(s, 9H), 2.34(s, 3H), 2.53(s, 2H) |

TABLE 6-continued

| Ex. No. | Starting Compd. (2,3-Epoxycyclopentanones) | 2-substituted-2-cyclopentenones | Yield (%) | NMR(δ, CDCl₃) |
|---|---|---|---|---|
| 45 | (structure: cyclopentanone with OH, alkyne, epoxide, pentyl chain) | (structure: cyclopentenone with MeS, OSi, alkyne, propyl chain) | 47 | 0.06(s, 9H), 0.7-1.1(m, 6H), 1.1-2.0(m, 6H), 2.2-2.8(m, 6H), 2.36 (s, 3H) |

TABLE 7

| Ex. No. | Starting Compd. (2,3-Epoxycyclopentanones) | 2-substituted-2-cyclopentenones | yield (%) | NMR(δ, CDCl₃) |
|---|---|---|---|---|
| 18 | | | 70 | 0.03(s, 12H), 0.88(s, 18H), 1.1–2.0(m, 10H), 2.32(s, 3H), 2.2–3.0(m, 3H), 3.4–3.7(m, 2H), 3.8–4.1(m, 2H), 4.0–4.7(m, 2H), 5.5–5.8(m, 2H), 6.7–7.1(m, 4H), 7.1–7.5(m, 2H) |
| 19 | | | 27 | 0–0.1(12H, m), 0.85(9H, s), 0.88(9H, s), 1.3–1.6(4H, m), 2.35(3H, s), 2.6–2.8(1H, m), 3.4–3.7(2H, m), 3.9–4.2(2H, m), 4.6–4.8(1H, m), 5.6–5.8(2H, m), 6.95(1H, d, J=3.1, Hz), 7.1–7.5(5H, m) |
| 20 | | | 89 | 0.12(s, 6H), 0.91(s, 9H), 2.34(s, 3H), 2.38(dd, 1H, J=18.3, 2.2Hz), 2.83(dd, 1H, J=18.3, 5.7Hz), 4.95(dt, 1H, J=5.7, 2.5Hz), 6.73(d, 1H, J=2.6Hz) |
| 21 | | | 72 | 0.11(s, 9H), 1.3–1.9(m, 6H), 2.35(s, 3H), 2.66(s, 2H), 3.95(t, 2H, J=5.9Hz), 6.80(s, 1H), 6.8–7.45(m, 5H) |
| 22 | | | 67 | 0.09(s, 9H), 1.4–1.9(m, 4H), 2.3–2.9(m, 4H), 2.35(s, 3H), 3.82(s, 6H), 6.6–7.1(m, 4H) |
| 23 | | | 49 | 0.01–0.08(m, 15H), 0.89(s, 9H), 1.0–2.0(m, 11H), 2.39(s, 3H), 2.68(s, 2H), 4.6–4.85(m, 1H), 5.4–5.8(m, 2H), 6.85(s, 1H) |

TABLE 8

| Ex. No. | Starting Material 2,3-Epoxycyclopentanones | Starting Material Thiols | 2-Substituted-2-cyclopentenones | Yield (%) | NMR (δ, CDCl₃) |
|---|---|---|---|---|---|
| 46 | (epoxycyclopentanone with OH, COOMe chain, OSi group) | cyclohexyl-SH | (cyclopentenone with S-cyclohexyl, OH, COOMe chain, OSi) | 75 | −0.03–0.06(6H, m), 0.85(9H, s), 0.7–1.1(3H, brt), 1.1–2.6(31H, m), 3.1–3.3(1H, m), 3.64(3H, s), 3.69(1H, brs), 3.9–4.2(1H, m), 5.5–5.7(2H, m), 6.80(1H, d, J=3Hz) |
| 47 | Same as above | pyridyl-SH | (cyclopentenone with S-pyridyl) | 53 | 0–0.1(6H, m), 0.89(9H, s), 0.7–1.1(3H, brt), 1.1–2.4(20H, m), 3.1–3.3(1H, m), 3.67(3H, s), 3.6–3.8(1H, m), 3.9–4.2(1H, m), 5.5–5.7(2H, m), 6.7(1H, d, J=2.8Hz), 7.2–8.1(4H, m) |
| 48 | Same as above | N-methyltetrazole-SH | (cyclopentenone with S-tetrazolyl) | 29 | 0–0.1(6H, s), 0.90(9H, s), 0.7–1.1(3H, brt), 1.1–2.4(20H, m), 3.1–3.3(1H, m), 3.68(3H, s), 3.6–3.8(1H, m), 3.9–4.2(1H, m), 4.1(3H, s), 5.5–5.8(2H, m), 6.8(1H, d, J=2.8Hz) |
| 49 | (epoxycyclopentanone variant) | benzoxazole-2-thiol | (cyclopentenone with S-benzoxazolyl) | 68 | 0–0.1(6H, m), 0.89(9H, s), 0.7–1.1(6H, m), 1.1–2.7(17H, m), 3.1–3.3(1H, m), 3.68(3H, s), 3.6–3.9(1H, m), 3.8–4.3(1H, m), 5.4–5.8(2H, m), 5.89(1H, d, J=16Hz), 6.8–7.2(2H, m), 7.2–7.8(4H, m) |
| 50 | (epoxycyclopentanone with OSi, OPh chain) | N-methylimidazole-2-thiol | (cyclopentenone with S-imidazolyl, OSi, OPh) | 57 | 0.02(s, 12H), 0.89(s, 18H), 1.1–2.0(m, 10H), 2.2–3.0(m, 3H), 3.4–3.7(m, 2H), 3.66(s, 3H), 3.8–4.1(m, 2H), 4.0–4.7(m, 2H), 5.5–5.8(m, 2H), 6.7–7.1(m, 5H), 7.1–7.5(m, 2H) |

TABLE 8-continued

| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 51 | [structure] | [structure with NH₂, SH on phenyl] | [structure with S-phenyl-NH₂] | 31 | 0–0.2(m, 6H), 0.89(s, 9H), 1.1–2.1 (m, 11H), 2.1–3.2(m, 6H), 3.4–4.0 (m, 4H), 3.67(s, 3H), 4.6–4.9(m, 1H), 5.4–5.8(m, 2H), 6.5–7.6(m, 5H) |
| 52 | Same as above | [pyrimidine-SH structure] | [structure with S-pyrimidine] | 29 | 0–0.2(m, 6H), 0.88(s, 9H), 1.1–2.1 (m, 11H), 2.1–3.2(m, 6H), 3.4–3.6 (m, 1H), 3.68(s, 3H), 3.9–4.3(m, 1H), 4.6–5.0(m, 1H), 5.4–5.8(m, 1H), 6.9–7.2(m, 1H), 8.21(s, 1H), 8.55(s, 1H) |
| 53 | Same as above | [furan-CH₂SH] | [structure with S-CH₂-furan] | 65 | 0–0.1(6H, m), 0.89(9H, s), 1.0–2.1 (11H, m), 2.1–3.2(6H, m), 3.4–3.7 (1H, m), 3.67(3H, s), 3.7–4.3(3H, m), 4.6–4.9(1H, m), 5.4–5.8(2H, m), 6.0–6.5(2H, m), 7.12(1H, d, J=3Hz), 7.25–7.4(1H, m) |
| 54 | [structure] | [N-methylimidazole-SH] | [structure with S-N-methylimidazole] | 47 | 0.09(s, 12H), 0.89(s, 18H), 1.1–2.0 (m, 16H), 2.2–3.0(m, 3H), 3.4–3.7 (m, 2H), 3.67(s, 3H), 3.8–4.1(m, 2H), 4.0–4.7(m, 2H), 5.5–5.8(m, 2H), 6.7–7.2(m, 3H) |

TABLE 8-continued

| Ex. No. | Starting Material | | Yield (%) | NMR (δ, CDCl₃) |
|---|---|---|---|---|
| | 2,3-Epoxycyclopentanones | Thiols | | |
| 55 | (structure) | i-PrSH | 37 | 0–0.1(m, 6H), 0.87(s, 9H), 0.7–1.1 (m, 6H), 1.1–3.0(m, 33H), 3.3–3.6 (m, 1H), 3.68(s, 3H), 3.6–4.2(m, 2H), 5.4–5.7(m, 2H) |
| 56 | Same as above | EtSH | 41 | 0–0.1(m, 6H), 0.85(s, 9H), 0.7–1.0 (m, 6H), 1.0–3.0(m, 31H), 3.3–3.6 (m, 1H), 3.67(s, 3H), 3.6–4.1(m, 2H), 5.4–5.7(m, 2H) |
| 57 | Same as above | t-BuSH | 23 | 0–0.1(m, 6H), 0.87(s, 9H), 0.7–1.0 (m, 6H), 1.38(s, 9H), 1.0–2.0(m, 26H), 3.3–3.7(m, 1H), 3.68(s, 3H), 3.6–4.2(m, 2H), 5.4–5.7(m, 2H) |
| 58 | Same as above | (cyclohexyl-SH) | 38 | 0–0.1(m, 6H), 0.90(s, 9H), 0.7–1.1 (m, 6H), 1.1–2.7(m, 37H), 3.1–3.3 (m, 1H), 3.62(s, 3H), 3.6–4.1(m, 2H), 5.4–5.8(m, 2H) |
| 59 | Same as above | (pyridyl-SH) | 27 | 0–0.1(m, 6H), 0.89(s, 9H), 0.7–1.1 (m, 6H), 1.1–3.0(m, 26H), 3.1–3.3 (m, 1H), 3.68(s, 3H), 3.6–3.8(m, 1H), 3.9–4.2(m, 1H), 5.5–5.7(m, 2H), 7.2–8.1(m, 4H) |

TABLE 8-continued
| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 60 | Same as above | 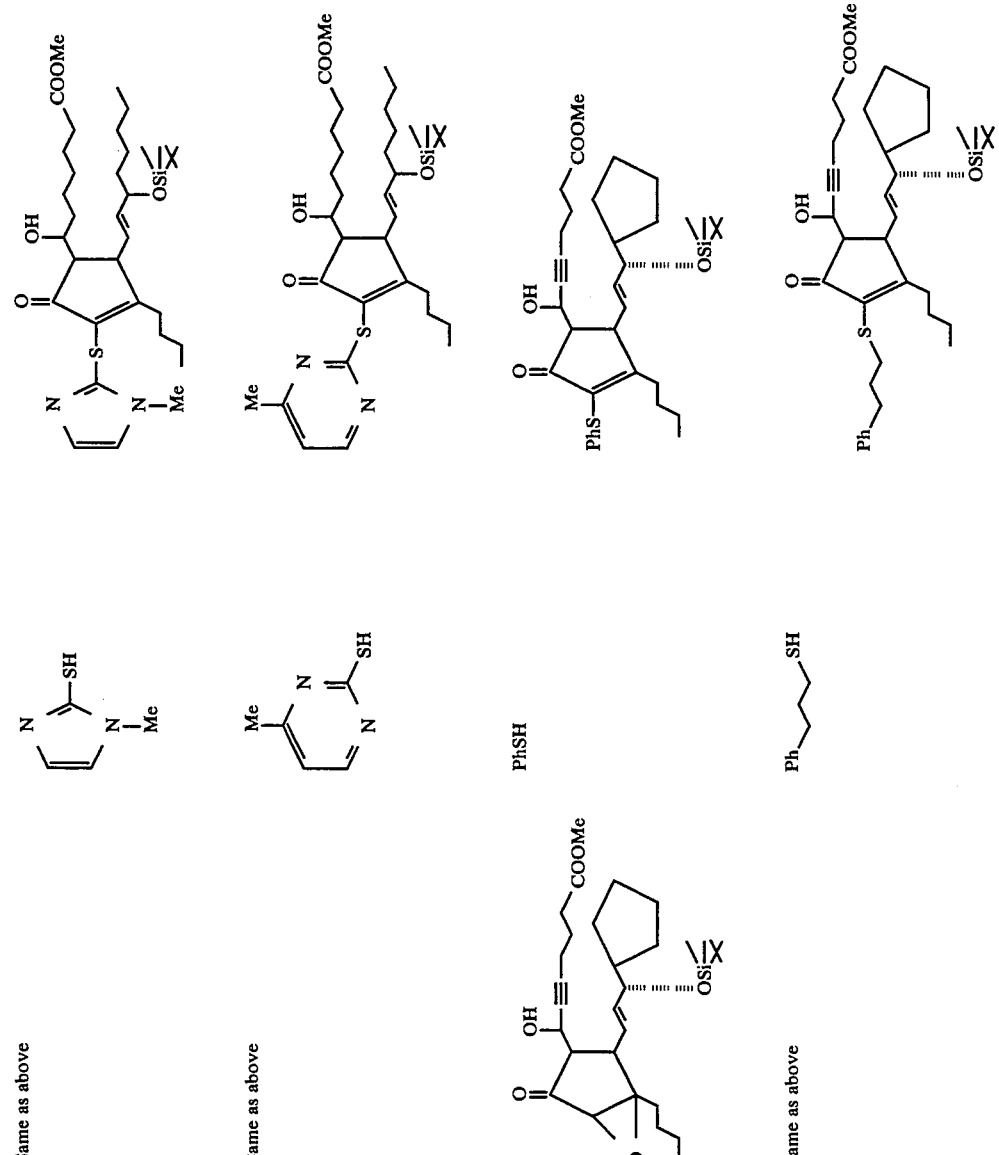 | | 31 | 0–0.1(m, 6H), 0.87(s, 9H), 0.7–1.1 (m, 6H), 1.1–3.0(m, 26H), 3.1–3.3 (m, 1H), 3.66(s, 3H), 3.68(s, 3H), 3.6–3.8(m, 1H), 3.9–4.2(m, 1H), 5.5–5.7(m, 2H), 7.0–7.3(m, 2H) |
| 61 | Same as above | | | 28 | 0–0.1(m, 6H), 0.89(s, 9H), 0.7–1.1 (m, 6H), 1.1–3.0(m, 26H), 2.43(s, 3H), 3.1–3.3(m, 1H), 3.67(s, 3H), 3.6–3.8(m, 1H), 3.9–4.2(m, 1H), 5.4–5.8(m, 2H), 6.87(d, 1H, J=5.1Hz), 8.32(d, 1H, J=5.1Hz) |
| 62 | | PhSH | | 55 | 0.06(s, 6H), 0.89(s, 9H), 0.7–1.0 (m, 3H), 1.1–2.9(m, 22H), 3.0–3.3 (m, 1H), 3.4–3.6(m, 1H), 3.69(s, 3H), 3.8–4.0(m, 1H), 4.7–4.9(m, 1H), 5.4–5.8(m, 2H), 7.2–7.7(m, 5H) |
| 63 | Same as above | Ph~~SH | | 49 | 0.07(s, 6H), 0.90(s, 9H), 0.7–1.0 (m, 3H), 1.0–3.1(m, 29H), 3.3–3.7 (m, 1H), 3.69(s, 3H), 3.8–4.0(m, 1H), 4.6–4.9(m, 1H), 5.4–5.7(m, 2H), 7.0–7.4(m, 5H) |

TABLE 8-continued

| Ex. No. | Starting Material | | Yield (%) | NMR (δ, CDCl₃) |
|---|---|---|---|---|
| | 2,3-Epoxycyclopentanones | Thiols | | |
| 64 | Same as above | MeOOC〜〜〜SH | 26 | 0.05(s, 6H), 0.89(s, 9H), 0.7–1.0 (m, 3H), 1.1–3.1(m, 33H), 3.4–3.8 (m, 1H), 3.68(s, 6H), 3.8–4.0(m, 1H), 4.6–4.9(m, 1H), 5.4–5.8(m, 2H) |
| 65 | Same as above | [6-methoxy-2-naphthalenethiol] | 43 | 0.08(s, 6H), 0.88(s, 9H), 0.7–1.0 (m, 3H), 1.1–2.9(m, 23H), 3.3–3.5 (m, 1H), 3.69(s, 3H), 3.8–4.1(m, 1H), 3.97(s, 3H), 4.6–4.8(m, 1H), 5.4–5.9(m, 2H), 7.0–8.1(m, 5H) |
| 66 | Same as above | [4-methylbenzenethiol] | 29 | 0.08(s, 6H), 0.89(s, 9H), 0.7–1.0 (m, 3H), 1.1–2.9(m, 23H), 2.3(s, 3H), 3.3–3.5(m, 1H), 3.68(s, 3H), 3.8–4.1(m, 1H), 4.6–4.8(m, 1H), 5.4–5.9(m, 2H), 6.9–7.5(m, 4H) |
| 67 | Same as above | [furfuryl mercaptan] | 26 | 0.0–0.1(m, 6H), 0.89(s, 9H), 0.7–1.0 (m, 3H), 1.0–3.2(m, 23H), 3.4–3.7 (m, 1H), 3.68(s, 3H), 3.7–4.3 (m, 3H), 4.6–4.9(m, 1H), 5.4–5.8 (m, 2H), 6.0–6.5(m, 2H), 7.3–7.6 (m, 1H) |

TABLE 8-continued

| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 68 | Same as above | HO—[CH(OH)—CH₂SH] | (structure with COOMe, cyclopentyl, OSiX, OH, S-CH₂-CH(OH)-CH₂OH, butyl on cyclopentenone) | 35 | 0–0.1(m, 6H), 0.89(s, 9H), 0.7–1.0 (m, 3H), 1.1–2.8(m, 23H), 2.8–3.4 (m, 5H), 3.68(s, 3H), 3.4–4.0(m, 4H), 4.5–4.9(m, 1H), 5.4–5.8(m, 2H) |
| 69 | (cyclopentanone with OH, Ph, Me, epoxide, CH₂CH₂CH₂OPh) | cyclopentyl-SH | (cyclopentenone with OH, Ph, Me, S-cyclopentyl, CH₂CH₂CH₂OPh) | 44 | 0.86(d, 3H, J=6.5Hz), 1.3–2.1(m, 14H), 2.2–3.0(m, 8H), 3.5–4.1(m, 3H), 6.7–7.5(m, 10H) |
| 70 | (cyclopentanone with OH, hexyl, epoxide, Me) | F₃C—C₆H₄—CH₂SH | (cyclopentenone with OH, hexyl, S-CH₂-C₆H₄-CF₃, Me) | 51 | 0.7–1.1(m, 3H), 0.89(s, 9H), 1.0–2.0 (m, 13H), 2.27(s, 3H), 2.4–2.8 (m, 2H), 4.12(d, 2H, J=3.0Hz), 4.20(s, 2H), 6.9–7.1(m, 1H), 7.3–7.7(m, 3H) |
| 71 | (cyclopentanone with OH, COOEt chain, OSi, epoxide, Me) | Cl—C₆H₄—CH₂SH | (cyclopentenone with OH, COOEt chain, OSi, S-CH₂-C₆H₄-Cl, Me) | 59 | 0.7–1.1(m, 6H), 1.1–2.8(m, 21H), 2.25(s, 3H), 3.1–3.3(m, 1H), 3.6–4.0 (m, 4H), 4.05(s, 2H), 5.4–5.8 (m, 2H), 5.89(d, 1H, J=16.0Hz), 6.92(dt, 1H, J=16.0, 6.8Hz), 7.1–7.4(m, 4H) |
| 72 | (cyclopentanone with COOMe chain, OSi, epoxide) | PhSH | (cyclopentenone with COOMe chain, OSi, SPh) | 82 | 0–0.2(m, 6H), 0.89(s, 9H), 0.7–1.0 (m, 3H), 1.1–2.3(m, 21H), 3.0–3.4 (m, 1H), 3.70(s, 3H), 3.9–4.1 (m, 1H), 5.4–5.8(m, 2H), 7.1–7.4(m, 6H) |

TABLE 8-continued

| Ex. No. | Starting Material | | Yield (%) | NMR (δ, CDCl₃) |
|---|---|---|---|---|
| | 2,3-Epoxycyclopentanones | Thiols | | 2-Substituted-2-cyclopentenones |
| 73 | Same as above | cyclohexyl-SH | 70 | 0–0.2(m, 6H), 0.89(s, 9H), 0.7–1.0 (m, 3H), 1.1–2.5(m, 32H), 3.0–3.4 (m, 1H), 3.69(s, 3H), 3.9–4.1(m, 1H), 5.4–5.7(m, 2H), 7.18(d, 1H, J=2.3Hz) |
| 74 | Same as above | N-methylimidazole-2-thiol | 76 | 0–0.2(m, 6H), 0.88(s, 9H), 0.7–1.0 (m, 3H), 1.1–2.2(m, 21H), 3.0–3.4 (m, 1H), 3.66(s, 3H), 3.70(s, 3H), 3.9–4.2(m, 1H), 5.4–5.8(m, 2H), 6.7–7.2(m, 3H) |
| 75 | | HOCH₂CH(OH)CH₂SH | 68 | 0.0(s, 6H), 0.88(s, 9H), 0.7–1.0 (m, 3H), 1.1–2.8(m, 21H), 2.8–3.3 (m, 3H), 3.67(s, 3H), 3.6–4.2(m, 4H), 4.80(brs, 2H), 5.4–5.7(m, 2H), 7.16(d, 1H, J=2.9Hz) |
| 76 | | PhSH | 72 | 0.13(s, 3H), 0.17(s, 3H), 0.92(s, 9H), 1.46(s, 9H), 2.33(dd, 1H, J=18.2, 1.5Hz), 2.69(dd, 1H, J=18.2, 5.7Hz), 5.11(dd, 1H, J=5.5, 1.5Hz), 7.2(s, 5H) |

TABLE 9

| Ex. No. | Starting Material 2,3-Epoxycyclopentanones | Thiols | 2-Substituted-2-cyclopentenones | Yield (%) | NMR (δ, CDCl₃) |
|---|---|---|---|---|---|
| 24 | (structure: epoxycyclopentanone with OH, alkyne, alkene, OSi, cyclopentyl, COOMe chain) | HO-CH(OH)-CH₂-SH (with OH) | (cyclopentenone with S-CH₂-CH(OH)-CH₂OH substituent, OH, alkyne, alkene, OSi, cyclopentyl, COOMe) | 62 | 0.05(3H, s), 0.09(3H, s), 0.89(9H, s), 1.1–2.0(11H, m), 2.0–2.7(6H, m), 2.7–3.4(6H, m), 3.67(3H, s), 3.4–4.0(3H, m), 4.5–4.9(1H, m), 5.4–5.8(2H, m), 7.1–7.3(1H, m) |
| 25 | Same as above | Ph-CH₂CH₂CH₂-SH | (cyclopentenone with S-CH₂CH₂CH₂Ph substituent, OH, alkyne, alkene, OSi, cyclopentyl, COOMe) | 74 | 0.04(6H, s), 0.90(9H, s), 1.0–3.0 (23H, m), 3.35–3.7(1H, m), 3.68 (3H, s), 3.8–4.0(1H, m), 4.6–4.8 (1H, m), 5.4–5.7(2H, m), 6.89(1H, d, J=2.8Hz), 7.0–7.4(5H, m) |
| 26 | Same as above | PhSH | (cyclopentenone with PhS substituent, OH, alkyne, alkene, OSi, cyclopentyl, COOMe) | 91 | 0.07(6H, s), 0.89(9H, s), 1.1–2.0 (11H, m), 2.0–2.7(5H, m), 3.0–3.3 (1H, m), 3.4–3.6(1H, m), 3.7(3H, s), 3.8–4.0(1H, m), 4.7–4.9(1H, m), 5.4–5.8(2H, m), 6.85(1H, d, J=2.7Hz), 7.2–7.7(5H, m) |
| 27 | (2,3-epoxycyclopentanone) | PhSH | (2-PhS-cyclopentenone) | 52 | 2.5–2.7(m, 4H), 6.95(t, 1H, J=2.6 Hz), 7.2–7.6(m, 5H) |
| 28 | (epoxycyclopentanone with OSi group) | benzoxazole-2-thiol | (cyclopentenone with benzoxazolyl-S substituent, OSi) | 21 | 0.16(s, 3H), 0.17(s, 3H), 0.93(s, 9H), 2.44(dd, 1H, J=18.2, 2.4Hz), 2.95(dd, 1H, J=18.2, 5.8Hz), 5.0–5.2(m, 1H), 7.2–7.8(m, 4H), 8.03 (d, 1H, J=2.6Hz) |
| 29 | Same as above | 4-methylpyrimidine-2-thiol | (cyclopentenone with methylpyrimidinyl-S substituent, OSi) | 77 | 0.15(s, 6H), 0.93(s, 9H), 2.43(dd, 1H, J=18.0, 2.4Hz), 2.44(s, 3H), 2.93(dd, 1H, J=18.0, 5.9Hz) 5.0–5.1(m, 1H), 6.88(d, 1H, J=5.1Hz), 7.89(d, 1H, J=2.6Hz), 8.33(d, 1H, J=5.1Hz) |

TABLE 9-continued

| Ex. No. | Starting Material 2,3-Epoxycyclopentanones | Thiols | 2-Subsituted-2-cyclopentenones | Yield (%) | NMR(δ, CDCl₃) |
|---|---|---|---|---|---|
| 30 | Same as above | ![thiol structure with tetrazole N-Me, SH] | ![cyclopentenone with S-tetrazole(N-Me) and OSi≡X] | 79 | 0.13(s, 6H), 0.90(s, 9H), 2.38(dd, 1H, J=18.5, 2.2Hz), 2.90(dd, 1H, J=18.5, 5.8Hz), 4.10(s, 3H), 4.9–5.1(m, 1H), 7.73(d, 1H, J=2.6Hz) |
| 31 | Same as above | PhSH | ![cyclopentenone with SPh and OSi≡X] | 63 | 0.14(s, 6H), 0.92(s, 9H), 2.45(dd, 1H, J=18.0, 2.1Hz), 2.94(dd, 1H, J=18.0, 5.7Hz), 5.0–5.2(m, 1H), 7.2–7.7(m, 6H) |
| 32 | Same as above | ![cyclohexyl-SH] | ![cyclopentenone with S-cyclohexyl and OSi≡X] | 68 | 0.11(s, 6H), 0.90(s, 9H), 1.1–2.0(m, 10H), 2.44(dd, 1H, J=18.3, 2.2Hz), 2.3–2.8(m, 1H), 2.91(dd, 1H, J=18.3, 6.0Hz), 5.0–5.2(m, 1H), 7.19(d, 1H, J=2.1Hz) |

TABLE 10

| Ex. No. | Starting Material 2,3-Epoxycyclopentanones | Thiols | 2-Substituted-2-cyclopentenones | Yield (%) | NMR (δ, CDCl₃) |
|---|---|---|---|---|---|
| 77 | cyclopentanone with OH, OPh side chain, epoxide | cyclohexanethiol | cyclopentenone with S-cyclohexyl, OSi, propyl-OPh | 84 | 0.11(s, 9H), 1.3–2.0(16H, m), 2.3–2.7(3H, m), 3.95(t, 2H, J=5.9Hz), 6.80–7.6(m, 6H) |
| 78 | Same as above | cyclopentanethiol | cyclopentenone with S-cyclopentyl, OSi, propyl-OPh | 77 | 0.09(s, 9H), 1.3–2.0(m, 14H), 2.3–2.7(m, 3H), 3.96(t, 2H, J=6.0Hz), 6.8–7.6(m, 6H) |
| 79 | Same as above | 2-cyclohexylethanethiol | cyclopentenone with S-CH₂CH₂-cyclohexyl, OSi, propyl-OPh | 83 | 0.10(s, 9H), 1.2–2.1(m, 21H), 2.3–2.7(m, 4H), 3.94(t, 2H, J=6.2Hz), 6.8–7.6(m, 6H) |
| 80 | Same as above | 2-mercaptopyridine | cyclopentenone with S-(2-pyridyl), OSi, propyl-OPh | 77 | 0.08(s, 9H), 1.1–1.9(m, 6H), 2.56(s, 2H), 3.84(t, 2H, J=5.9Hz), 6.6–7.5(m, 8H), 7.55(s, 1H), 8.1–8.4(m, 1H) |
| 81 | Same as above | 2-mercapto-6-ethoxybenzothiazole | cyclopentenone with S-(6-ethoxybenzothiazol-2-yl), OSi, propyl-OPh | 72 | 0.06(s, 9H), 1.37(t, 3H, J=7.0Hz), 1.2–1.9(m, 6H), 2.62(s, 2H), 3.88(t, 2H, J=6.9Hz), 3.99(q, 2H, J=7.0Hz), 6.6–7.4(m, 7H), 7.68(s, 1H), 7.75(d, 1H, J=9.0Hz) |

TABLE 10-continued
| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 82 | Same as above |  |  | 62 | 0.0(s, 9H), 1.1–2.2(m, 6H), 2.58(s, 2H), 3.67(s, 3H), 3.90(t, 2H, J=5.9Hz), 6.83(s, 1H), 6.6–7.4(m, 7H) |
| 83 | Same as above | 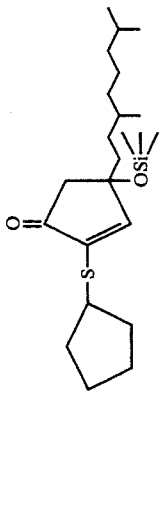 | 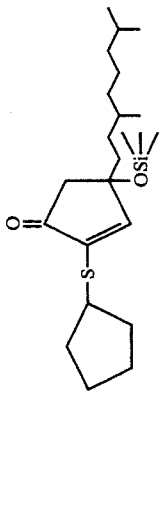 | 6 | 0.08(s, 9H), 1.3–2.1(m, 7H), 2.6–2.7(m, 2H), 3.2–3.8(m, 2H), 3.8–4.4(m, 4H), 6.7–7.0(m, 3H), 7.1–7.4(m, 2H), 7.84(s, 1H) |
| 84 | 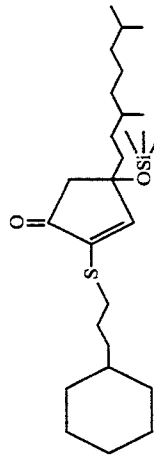 | 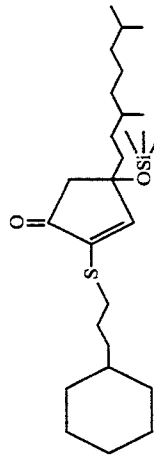 | 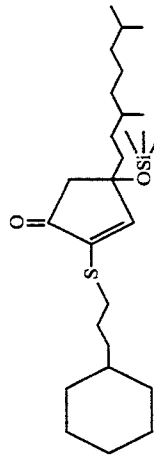 | 61 | 0.08(9H, s), 0.83(9H, d, J=4.4Hz), 0.9–2.1(20H, m), 2.3–2.7(3H, m), 6.85(1H, s) |
| 85 | Same as above | 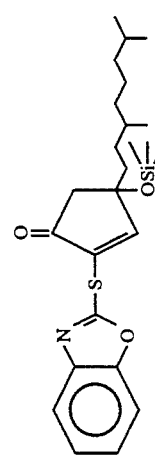 | 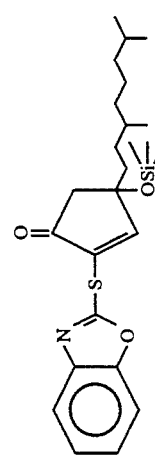 | 59 | 0.10(9H, s), 0.84(9H, d, J=4.6Hz), 0.9–2.8(31H, m), 6.80(1H, s) |
| 86 | Same as above | 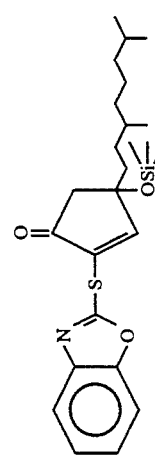 | 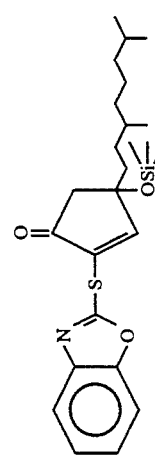 | 46 | 0.09(s, 9H), 0.84(d, 9H, J=4.6Hz), 0.9–2.1(m, 12H), 2.60(s, 2H), 6.84(s, 1H), 7.2–7.8(m, 4H) |
| 87 | 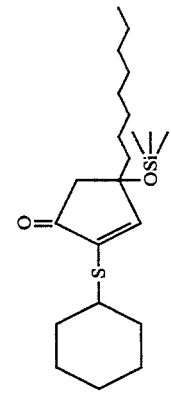 | 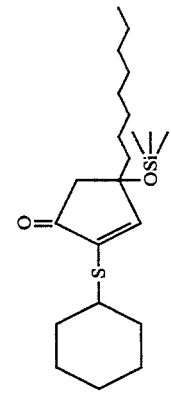 | 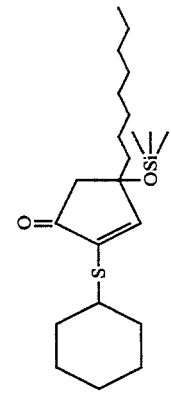 | 54 | 0.09(s, 9H), 0.7–1.0(m, 3H), 1.1–2.0(m, 24H), 2.3–2.9(m, 3H), 6.75(s, 1H) |

TABLE 10-continued

| Ex. No. | Starting Material 2,3-Epoxycyclopentanones | Thiols | 2-Substituted-2-cyclopentenones | Yield (%) | NMR (δ, CDCl₃) |
|---|---|---|---|---|---|
| 88 | Same as above | N=\<SH, N—Me (methylimidazole-2-thiol) | cyclopentenone with OSi, hexyl, and S-(N-methylimidazolyl) substituent | 49 | 0.06(9H, s), 0.89(3H, brt), 1.1–1.9(14H, m), 2.59(2H, s), 3.69(3H, s), 6.6–6.9(3H, m) |
| 89 | cyclopentanone with 3,4-dimethoxyphenethyl, OH, and epoxide | cyclohexanethiol | cyclopentenone with OSi, 3,4-dimethoxyphenethyl, and S-cyclohexyl | 69 | 0.10(s, 9H), 1.2–2.1(m, 14H), 2.3–2.9(m, 5H), 3.79(s, 6H), 6.4–6.9(m, 4H) |
| 90 | Same as above | N=\<SH, N—Me | cyclopentenone with OSi, 3,4-dimethoxyphenethyl, and S-(N-methylimidazolyl) | 44 | 0.09(s, 9H), 1.3–2.1(m, 4H), 2.2–2.6(m, 2H), 2.60(s, 2H), 3.66(s, 3H), 3.78(s, 6H), 6.4–7.2(m, 6H) |
| 91 | Same as above | 3-mercaptopyridine | cyclopentenone with OSi, 3,4-dimethoxyphenethyl, and S-(3-pyridyl) | 53 | 0.08(s, 9H), 1.3–2.1(m, 4H), 2.2–2.6(m, 2H), 2.58(s, 2H), 3.80(s, 6H), 6.4–6.9(m, 4H), 7.2–8.1(m, 4H) |
| 92 | Same as above | 2-mercaptobenzoxazole | cyclopentenone with OSi, 3,4-dimethoxyphenethyl, and S-(benzoxazol-2-yl) | 51 | 0.09(s, 9H), 1.4–1.9(m, 4H), 2.3–2.9(m, 4H), 3.84(s, 6H), 6.4–6.9(m, 3H), 7.2–7.8(m, 4H) |

TABLE 10-continued

| Ex. No. | Starting Material 2,3-Epoxycyclopentanones | Starting Material Thioles | 2-Substituted-2-cyclopentenones | Yield (%) | NMR (δ, CDCl₃) |
|---|---|---|---|---|---|
| 93 | same as above | (furan-CH₂-SH) | (cyclopentenone with S-CH₂-furan and OSi(Me)₃ with CH₂CH₂-3,4-dimethoxyphenyl) | 47 | 0.08(s, 9H), 1.4–1.9(m, 4H), 2.3–2.9(m, 4H), 3.85(s, 6H), 4.03(s, 2H), 6.0–6.5(m, 2H), 6.84(s, 1H), 7.3–7.6(m, 1H) |
| 94 | (epoxycyclopentanone with Me, OH) | (benzothiazole-2-SH) | (cyclopentenone with S-benzothiazole, Me, OSi) | 58 | 0.09(s, 9H), 1.25(s, 3H), 2.57(s, 2H), 7.2–7.9(m, 5H) |
| 95 | Same as above | (furan-CH₂-SH) | (cyclopentenone with S-CH₂-furan, Me, OSi) | 49 | 0.08(s, 3H), 1.27(s, 3H), 2.56(s, 2H), 4.03(s, 2H), 6.0–6.5(m, 2H), 6.85(s, 1H), 7.2–7.4(m, 1H) |
| 96 | (epoxycyclopentanone with (CH₂)₅COOMe, OH) | (N-methylimidazole-2-thiol) | (cyclopentenone with S-(N-Me-imidazole), (CH₂)₅COOMe, OSi) | 73 | 0.04(s, 9H), 1.0–2.0(m, 10H), 2.1–2.4(m, 2H), 2.56(s, 2H), 3.68(s, 3H), 6.6–6.9(m, 3H) |
| 97 | (epoxycyclopentanone with CH=CH-CH(OSi)-cyclohexyl, OH) | (4-methylpyrimidine-2-thiol) | (cyclopentenone with S-(4-Me-pyrimidine), CH=CH-CH(OSi)-cyclohexyl, OSi) | 42 | 0–0.15(m, 15H), 0.89(s, 9H), 1.1–2.1(m, 11H), 2.45(s, 3H), 2.60(s, 2H), 4.6–4.9(m, 1H), 5.4–5.8(m, 2H), 6.6–7.0(m, 2H), 8.32(d, 1H, J=5.1Hz) |

TABLE 10-continued

| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thioles | | | |
| 98 | Same as above | (6-chlorobenzothiazole-2-thiol) | (cyclohexyl vinyl TMS-O cyclopentenone with 6-chlorobenzothiazol-2-ylthio) | 32 | 0–0.2(m, 15H), 0.90(s, 9H), 1.1–2.1(m, 11H), 2.59(s, 2H), 4.6–4.9(m, 1H), 5.4–5.8(m, 2H), 7.0–7.8(m, 4H) |
| 99 | (hydroxy phenyl-dimethyl-vinyl epoxycyclopentanone) | (1-methylimidazole-2-thiol) | (TMS-O phenyl-dimethyl-vinyl cyclopentenone with 1-methylimidazol-2-ylthio) | 52 | 0.08(s, 9H), 1.66(s, 6H), 2.60(s, 2H), 3.66(s, 3H), 5.4–5.9(m, 2H), 6.6–7.5(m, 8H) |
| 100 | (hydroxy pentynyl epoxycyclopentanone) | (pyridine-3-thiol) | (TMS-O pentynyl cyclopentenone with pyridin-3-ylthio) | 51 | 0.08(s, 9H), 0.7–1.0(m, 3H), 1.2–1.9(m, 4H), 2.2–2.6(m, 2H), 2.61(s, 2H), 7.10(s, 3H), 7.4–7.9(m, 4H) |
| 101 | Same as above | (6-ethoxybenzothiazole-2-thiol) | (TMS-O pentynyl cyclopentenone with 6-ethoxybenzothiazol-2-ylthio) | 41 | 0.04(s, 9H), 0.7–1.0(m, 3H), 1.40(t, 3H, J=7.0Hz), 1.3–2.1(m, 4H), 2.2–2.8(m, 4H), 4.01(q, 2H, J=7.0Hz), 6.8–7.4(m, 3H), 7.63(s, 1H) |
| 102 | (hydroxy cyano epoxycyclopentanone) | (1-methylimidazole-2-thiol) | (TMS-O cyano cyclopentenone with 1-methylimidazol-2-ylthio) | 40 | 0.09(s, 9H), 1.05(s, 9H), 2.58(s, 2H), 3.67(s, 3H), 6.6–7.1(m, 3H) |

TABLE 10-continued

| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 103 | [structure] | PhSH | [structure with PhS] | 63 | 0.04(s, 9H), 0.7-1.0(m, 3H), 1.1-1.9(m, 13H), 2.63(s, 2H), 2.4-2.8(m, 2H), 3.95(t, 2H, J=6.0Hz), 6.8-7.7(m, 11H) |
| 104 | Same as above | t-BuSH | [structure with t-BuS] | 39 | 0.07(s, 9H), 0.7-1.0(m, 3H), 1.1-2.0(m, 10H), 1.36(s, 9H), 2.4-2.9(m, 4H), 3.95(t, 2H, J=5.8Hz), 6.8-7.1(m, 3H), 7.1-7.5(m, 2H) |
| 105 | Same as above | [cyclohexyl-SH] | [structure with cyclohexyl-S] | 53 | 0.10(s, 9H), 0.7-1.0(m, 3H), 1.3-2.0(m, 20H), 2.3-2.8(m, 5H), 3.93(t, 2H, J=5.9Hz), 6.7-7.5(m, 5H) |
| 106 | Same as above | [N-methylimidazole-SH] | [structure with N-methylimidazole-S] | 68 | 0.08(s, 9H), 0.8-1.1(m, 3H), 1.1-2.3(m, 10H), 2.56(s, 2H), 2.3-2.9(m, 2H), 3.81(s, 3H), 3.92(t, 2H, J=6.2Hz), 6.8-7.1(m, 5H), 7.1-7.4(m, 2H) |
| 107 | [structure] | [pyridyl-SH] | [structure with pyridyl-S] | 49 | 0.10(s, 9H), 0.8-1.1(m, 3H), 1.1-2.3(m, 6H), 2.60(s, 2H), 2.3-2.8(m, 2H), 3.93(t, 2H, J=6.2Hz), 7.2-8.1(m, 4H) |

TABLE 10-continued
| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 108 | 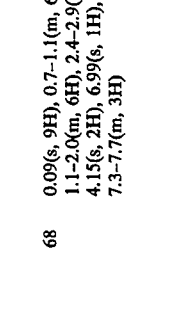 | 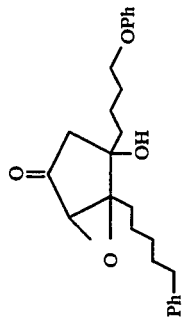 | 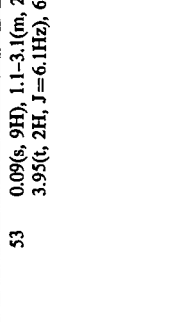 | 53 | 0.09(s, 9H), 1.1–3.1(m, 27H), 3.95(t, 2H, J=6.1Hz), 6.7–7.5(m, 10H) |
| 109 | 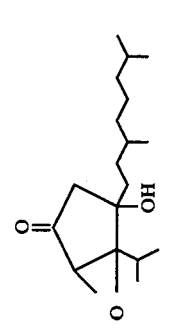 | 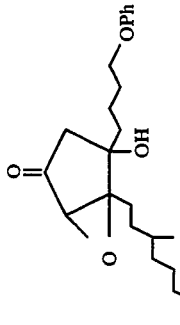 | 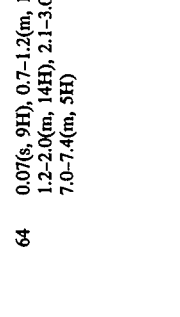 | 47 | 0.07(s, 9H), 0.85(brd, 3H, J=4.5Hz), 1.0–2.7(m, 33H), 3.67(s, 3H), 3.95(t, 2H, J=5.9Hz), 4.8–5.2(m, 1H), 6.7–7.1(m, 3H), 7.1–7.4(m, 2H) |
| 110 | 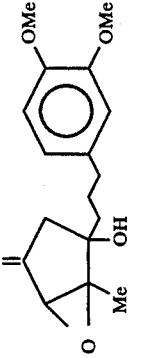 | 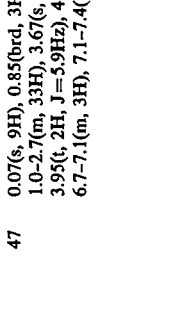 | 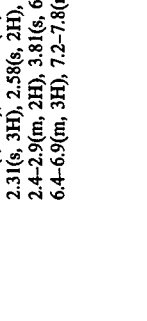 | 68 | 0.09(s, 9H), 0.7–1.1(m, 6H), 1.1–2.0(m, 6H), 2.4–2.9(m, 4H), 4.15(s, 2H), 6.99(s, 1H), 7.3–7.7(m, 3H) |
| 111 | 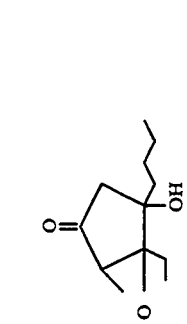 | | | 64 | 0.07(s, 9H), 0.7–1.2(m, 15H), 1.2–2.0(m, 14H), 2.1–3.0(m, 7H), 7.0–7.4(m, 5H) |
| 112 | | | | 68 | 0.08(s, 9H), 1.5–2.0(m, 4H), 2.31(s, 3H), 2.58(s, 2H), 2.4–2.9(m, 2H), 3.81(s, 6H), 6.4–6.9(m, 3H), 7.2–7.8(m, 4H) |

TABLE 10-continued
| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thioles | | | |
| 113 |  | MeO—⟨⟩—SH | (structure with MeO-phenyl-S, OSi(Me)₃, t-Bu, PhO side chain on cyclopentenone) | 33 | 0.08(s, 9H), 0.7–1.2(m, 6H), 1.3–1.8(m, 5H), 2.3–2.8(m, 4H), 3.77(s, 3H), 3.95(t, 2H, J=6.1Hz), 6.6–7.5(m, 9H) |

TABLE 11

| Ex. No. | Starting Material 2,3-Epoxycyclopentanones | Thiols | 2-substituted-2-cyclopentenones | Yield (%) | NMR (δ, CDCl₃) |
|---|---|---|---|---|---|
| 33 | (3-hydroxy-3-heptyl-2,3-epoxycyclopentanone structure) | EtSH | (2-ethylthio-4-heptyl-4-OSi cyclopentenone) | 41 | 0.09(s, 9H), 0.7–1.0 (m, 6H), 1.1–2.1(m, 14H), 2.2–2.8(m, 4H), 6.84(s, 1H) |
| 34 | (3-hydroxy-3-(5-methylhexyl)-2,3-epoxycyclopentanone) | i-PrSH | (2-isopropylthio-4-(5-methylhexyl)-4-OSi cyclopentenone) | 44 | 0.08(s, 9H), 0.7–1.3 (m, 15H), 1.2–2.8(m, 15H), 6.73(s, 1H) |
| 35 | (3-hydroxy-3-[(E)-3-cyclohexyl-3-OSiX-1-propenyl]-2,3-epoxycyclopentanone) | MeOOC~~~SH | (2-(5-methoxycarbonylpentylthio)-4-[(E)-3-cyclohexyl-3-OSiX-1-propenyl]-4-OSi cyclopentenone) | 28 | 0–0.1(m, 15H), 0.90(s, 9H), 1.0–2.0(m, 17H), 2.1–2.9(m, 6H), 3.69(s, 3H), 4.6–4.8(m, 1H), 5.4–5.8(m, 2H), 6.90(s, 1H) |
| 36 | (3-hydroxy-3-(4-phenoxybutyl)-2,3-epoxycyclopentanone) | PhSH | (2-phenylthio-4-(4-phenoxybutyl)-4-OSi cyclopentenone) | 37 | 0.05(s, 9H), 1.1–1.9(m, 6H), 2.63(s, 2H), 3.95(t, 2H, J=6.0Hz), 6.8–7.8(m, 11H) |
| 37 | Same as above | (4-chlorobenzyl mercaptan) | (2-(4-chlorobenzylthio)-4-(4-phenoxybutyl)-4-OSi cyclopentenone) | 32 | 0.08(s, 9H), 1.1–2.0(m, 6H), 2.59(s, 2H), 3.92(t, 2H, J=6.1Hz), 4.04(s, 2H), 6.8–7.7(m, 10H) |

TABLE 11-continued

| Ex. No. | Starting Material | | 2-substituted-2-cyclopentenones | Yield (%) | NMR (δ, CDCl₃) |
|---|---|---|---|---|---|
| | 2,3-Epoxycyclopentanones | Thiols | | | |
| 38 | (cyclopentanone with OH, epoxide, and 3,4-dimethoxyphenyl propyl chain) | 4-MeO-C₆H₄-SH | (2-cyclopentenone with OSi, 3,4-dimethoxyphenyl propyl, and S-(4-MeO-C₆H₄)) | 61 | 0.09(s, 9H), 1.5–2.0(m, 4H), 2.4–2.9(m, 4H), 3.76(s, 3H), 3.80(s, 6H), 6.6–7.5(m, 8H) |
| 39 | Same as above | Ph(CH₂)₃SH | (2-cyclopentenone with OSi, 3,4-dimethoxyphenyl propyl, S-(CH₂)₃Ph) | 63 | 0.09(s, 9H), 1.2–2.0(m, 6H), 2.3–2.9(m, 8H), 3.82(s, 6H), 6.6–7.4(m, 9H) |
| 40 | Same as above | 3-CF₃-C₆H₄-CH₂SH | (2-cyclopentenone with OSi, 3,4-dimethoxyphenyl propyl, S-CH₂-(3-CF₃-C₆H₄)) | 57 | 0.08(s, 9H), 1.5–2.0(m, 4H), 2.4–2.9(m, 4H), 3.80(s, 6H), 4.20(s, 2H), 6.6–7.7(m, 8H) |

TABLE 12

| Ex. No. | Starting compd. (2,3-Epoxycyclopentanones) | 2-Substituted-2-cyclopentenones | Yield (%) | NMR(δ, CDCl$_3$) |
|---|---|---|---|---|
| 114 | (structure with O, COOMe) | (structure with S-cyclohexyl, COOMe) | 20 | 0.89(3H, brt, J=5.5Hz), 1.0–2.6(31H, m), 3.68(3H, s), 3.7–4.1(1H, m), 5.20(1H, dd, J=15.0, 8.Hz), 5.67(1H, dt, J=15.0, 6.4Hz), 6.5–6.8(2H, m) |
| | | (structure with two S-cyclohexyl groups, COOMe) | 14 | 0.89(3H, brt, J=5.0Hz), 1.1–2.7(43H, m), 3.0–3.3(1H, s), 5.36(1H, dd, J=15.5, 7.8 Hz), 5.61(1H, dt, J=15.5, 7.8 Hz), 6.87  6.90(1H, d, J=3.0Hz) |

TABLE 13

| Ex. No. | Starting Material 2-Substituted-2-cyclopentenones | Aldehydes | 2-Substituted-2-cyclopentenones | Yield (%) | NMR (δ, CDCl₃) |
|---|---|---|---|---|---|
| 115 | [structure with OPh, OSi, S-cyclohexyl] | OHC—CH=CH—C(OSiX₃)—CH₂CH₂—OSiX₃ | [product structure] | 82 | 0–0.2(21H, m), 0.85(18H, s), 1.0–2.9(20H, m), 3.0–3.4(1H, m), 3.4–3.7(2H, m), 3.7–4.3(3H, m), 4.3–4.8(1H, m), 5.4–6.0(2H, m), 6.6–7.6(6H, m) |
| 116 | Same as above | OHC—(CH₂)₄—COOMe | [product structure] | 72 | 0.03(9H, s), 1.1–2.5(30H, m), 2.6–2.9(1H, m), 3.68(3H, s), 3.6–4.1(3H, m), 6.7–7.4(6H, m) |
| 117 | Same as above | OHC—CH₂—S—(CH₂)₃—COOMe | [product structure] | 14 | 0.09(s, 9H), 1.2–2.0(m, 19H), 2.0–2.7(m, 7H), 2.8–3.0(m, 1H), 3.5–4.0(m, 3H), 3.76(s, 3H), 6.7–7.1(m, 4H), 7.1–7.5(m, 2H) |
| 118 | Same as above | OHC—CH₂—O—(CH₂)₃—COOMe | [product structure] | 61 | 0.08(s, 9H), 1.2–2.0(m, 21H), 2.2–2.4(m, 1H), 2.8–3.0(m, 1H), 3.4–4.0(m, 5H), 3.73(s, 3H), 4.09(s, 2H), 6.8–7.1(m, 4H), 7.1–7.5(m, 2H) |
| 119 | Same as above | OHC—CH₂—[cyclohexyl]—COOMe | [product structure] | 70 | 0.07(s, 9H), 1.1–2.9(m, 33H), 3.67(s, 3H), 3.5–4.1(m, 3H), 6.7–7.4(m, 6H) |
| 120 | Same as above | OHC—[phenyl]—O—CH₂—COOMe | [product structure] | 83 | 0.03(s, 9H), 1.0–2.4(m, 17H), 3.0–3.3(m, 1H), 3.75(s, 3H), 3.94(t, 2H, J=5.4Hz), 4.3–4.5 (m, 1H), 4.57(s, 2H), 4.9–5.1 (m, 1H), 6.5–7.4(m, 10H) |

TABLE 13-continued

| Ex. No. | Starting Material | | 2-Substituted-2-cyclopentenones | Yield (%) | NMR (δ, CDCl₃) |
|---|---|---|---|---|---|
| | 2-Substituted-2-cyclopentenones | Aldehydes | | | |
| 121 | [structure] | [structure] | [structure] | 83 | 0.10(s, 9H), 0.7–1.0(m, 6H), 1.1–2.0(m, 41H), 2.3–2.6(m, 1H), 2.9–3.1(m, 1H), 3.5–3.9(m, 1H), 6.77(s, 1H) |
| 122 | [structure] | [structure] | [structure] | 39 | 0.10(s, 9H), 1.2–2.1(m, 21H), 2.1–3.0(m, 8H), 3.83(s, 6H), 3.9–4.2(m, 1H), 5.2–5.5(m, 1H), 6.4–6.9(m, 4H) |
| 123 | [structure] | [structure] | [structure] | 75 | 0.09(s, 9H), 0.7–1.0(m, 3H), 1.1–2.5(m, 20H), 2.8–3.0(m, 1H), 3.5–4.0(m, 3H), 6.7–7.4(m, 6H) |
| 124 | Same as above | [structure] | [structure] | 49 | 0.06(s, 9H), 1.1–2.9(m, 22H), 3.74(s, 3H), 3.5–4.1(m, 3H), 6.6–7.5(m, 10H) |
| 125 | [structure] | [structure] | [structure] | 50 | 0.09(s, 9H), 0.83(d, 9H, J=4.7 Hz), 0.9–2.1(m, 21H), 2.3–2.9 (m, 2H), 4.9–5.1(m, 1H), 6.7–7.4 (m, 5H) |
| 126 | [structure] | [structure] | [structure] | 40 | 0.13(s, 9H), 1.2–2.6(m, 30H), 2.8–3.0(m, 1H), 3.67(s, 3H), 3.8–4.1(m, 2H), 4.6–4.9(m, 1H), 6.8–7.1(m, 4H), 7.1–7.5(m, 2H) |

TABLE 13-continued

| Ex. No. | Starting Material — 2-Substituted-2-cyclopentenones | Aldehydes | 2-Substituted-2-cyclopentenones (product) | Yield (%) | NMR (δ, CDCl₃) |
|---|---|---|---|---|---|
| 127 | (structure) | OHC-CH₂-Ph | (structure) | 61 | 0.10(s, 9H), 0.85(d, 9H, J=4.7 Hz), 0.9-3.0(m, 36H), 3.5-3.8 (m, 1H), 6.80(s, 1H), 7.1-7.5 (m, 5H) |
| 128 | (structure) | OHC-(CH₂)₅-CH₃ | (structure) | 39 | 0.07(s, 9H), 0.7-1.0(m, 3H), 1.1-1.9(m, 19H), 2.9-3.1(m, 1H), 3.5-4.0(m, 3H), 6.6-7.8(m, 8H), 7.80(s, 1H), 8.2-8.4(m, 1H) |
| 129 | Same as above | (structure) | (structure) | 54 | 0.08(s, 21H), 0.85(s, 18H), 1.1-2.9(m, 12H), 3.4-3.7(m, 2H), 3.8-4.3(m, 3H), 4.4-4.6(m, 1H), 5.5-6.1(m, 2H), 6.7-7.9(m, 8H), 7.79(s, 1H), 8.2-8.5(m, 1H) |
| 130 | (structure) | (structure) | (structure) | 60 | 0.08(s, 18H), 0.88(s, 18H), 1.3-2.1(m, 6H), 2.4-2.7(m, 4H), 3.0-3.3(m, 1H), 3.56(d, 4H, J=5.5Hz), 3.75(s, 6H), 5.0-5.1(m, 1H), 6.4-7.0(m, 4H), 7.2-8.1(m, 8H) |
| 131 | (structure) | EtCHO | (structure) | 43 | 0.09(s, 9H), 0.7-1.0(m, 6H), 1.2-1.9(m, 7H), 2.2-2.6(m, 2H), 2.9-3.1(m, 1H), 3.5-3.7(m, 1H), 7.02(s, 1H), 7.4-7.9(m, 4H) |
| 132 | (structure) | (structure) | (structure) | 60 | 0-0.2(m, 9H), 0.7-1.1(m, 3H), 1.1-2.2(m, 13H), 2.6-2.8(m, 1H), 3.68(s, 3H), 3.8-4.1(m, 2H), 4.3-4.6(m, 1H), 5.5-5.8(m, 2H), 6.7-7.45(m, 8H) |

TABLE 13-continued

| Ex. No. | Starting Material | | Yield (%) | NMR (δ, CDCl₃) |
|---|---|---|---|---|
| | 2-Substituted-2-cyclopentenones | Aldehydes | | |
| | | | | 2-Substituted-2-cyclopentenones |
| 133 | Same as above | (structure: OHC-CH=CH-CH(OSi≡X)-CH₂-OSi≡X type aldehyde) | 22 | 0–0.2(m, 15H), 0.89(s, 9H), 1.1–2.0(m, 7H), 2.7–2.9(m, 1H), 3.65(s, 3H), 3.7–4.3(m, 3H), 4.5–4.7(m, 1H), 5.6–5.9(m, 2H), 6.8–7.5(m, 8H) |
| 134 | Same as above | (aldehyde with two OSi≡X groups) | 48 | 0.03(s, 12H), 0.07(s, 9H), 0.88(s, 18H), 1.1–2.0(m, 14H), 2.3–2.6(m, 1H), 3.54(d, 4H, J=5Hz), 3.69(s, 3H), 3.6–3.8(m, 1H), 3.8–4.0(m, 2H), 6.8–7.4(m, 8H) |
| 135 | Same as above | (aldehyde structure) | 46 | 0–0.15(21H, m), 0.85(18H, s), 1.1–2.1(10H, m), 2.3–2.9(1H, m), 3.3–3.8(2H, m), 3.66(3H, s), 3.75–4.1(2H, m), 4.0–4.3(1H, m), 4.3–4.6(1H, m), 5.5–6.1(2H, m), 6.7–7.4(8H, m) |
| 136 | Same as above | (aldehyde structure) | 42 | 0.03(s, 12H), 0.06(s, 9H), 0.88(s, 18H), 1.1–2.5(m, 14H), 2.5–2.8(m, 1H), 3.54(d, 4H, J=5Hz), 3.68(s, 3H), 3.8–4.0(m, 2H), 4.2–4.4(m, 1H), 5.6–5.8(m, 2H), 6.8–7.4(m, 8H) |
| 137 | Same as above | (OHC-...-COOMe aldehyde) | 69 | 0.13(s, 9H), 1.1–2.0(m, 14H), 2.1–2.7(m, 4H), 3.2–3.5(m, 1H), 3.65(s, 3H), 3.71(s, 3H), 3.8–4.1(m, 2H), 6.7–7.5(m, 8H) |
| 138 | Same as above | (OHC-C≡C-...-COOMe aldehyde) | 70 | 0.12(s, 9H), 1.3–2.1(m, 8H), 2.1–2.6(m, 5H), 2.8–3.0(m, 1H), 3.67(s, 3H), 3.70(s, 3H), 3.8–4.1(m, 2H), 4.6–4.9(m, 1H), 6.8–7.5(m, 6H) |

TABLE 13-continued

| Ex. No. | Starting Material | | 2-Substituted-2-cyclopentenones | Yield (%) | NMR (δ, CDCl₃) |
|---|---|---|---|---|---|
| | 2-Substituted-2-cyclopentenones | Aldehydes | | | |
| 139 | Same as above | OHC~~O~~COOMe | [structure with imidazole-S, OSi, OH, O, OPh, COOMe] | 63 | 0.09(s, 9H), 1.2–2.0(m, 11H), 2.8–3.1(m, 1H), 3.4–4.1(m, 5H), 3.65(s, 3H), 3.70(s, 3H), 4.10 (s, 2H), 6.7–7.5(m, 8H) |
| 140 | Same as above | OHC~~O~~COOMe (branched) | [structure] | 36 | 0.07(s, 9H), 1.0–2.2(m, 7H), 2.2–3.1(m, 3H), 3.3–4.6(m, 5H), 3.70(s, 3H), 3.74(s, 3H), 4.10(s, 2H), 5.0–5.3(m, 2H), 6.7–7.5(m, 8H) |
| 141 | Same as above | OHC~~O~~OMe (branched) | [structure] | 23 | 0.07(s, 9H), 1.0–2.2(m, 7H), 2.2–3.0(m, 3H), 3.49(s, 3H), 3.74(s, 3H), 3.7–4.1(m, 2H), 4.07(s, 2H), 4.1–4.6(m, 3H), 5.0–5.1(m, 1H), 5.1–5.3(m, 1H), 6.7–7.5(m, 8H) |
| 142 | Same as above | OHC~~NSO₂~~–C₆H₄–Cl (H on N) | [structure with NHSO₂-aryl-Cl] | 10 | 0.08(s, 9H), 1.1–2.0(m, 8H), 2.0–3.3(m, 4H), 3.4–3.7(m, 1H), 3.67(s, 3H), 3.8–4.1(m, 2H), 5.2–5.7(m, 1H), 6.7–7.6(m, 10H), 7.7–7.9(m, 2H) |
| 143 | Same as above | OHC~~C₆H₃(OMe)₂~~ | [structure with dimethoxyphenyl] | 35 | 0.06(s, 9H), 1.0–2.1(m, 10H), 2.2–2.9(m, 2H), 3.74(s, 3H), 3.89(s, 3H), 3.91(s, 3H), 3.7–4.1(m, 3H), 6.7–7.4(m, 11H) |
| 144 | Same as above | OHC=cyclohexylidene | [structure with cyclohexylidene] | 37 | –0.04(s, 9H), 1.2–2.0(m, 13H), 2.1–2.5(m, 4H), 2.7–3.0(m, 1H), 3.69(s, 3H), 3.7–4.2(m, 3H), 5.2–5.5(m, 1H), 6.8–7.4(m, 8H) |

TABLE 13-continued

| Ex. No. | Starting Material 2-Substituted-2-cyclopentenones | Aldehydes | 2-Substituted-2-cyclopentenones | Yield (%) | NMR (δ, CDCl₃) |
|---|---|---|---|---|---|
| 145 | Same as above | 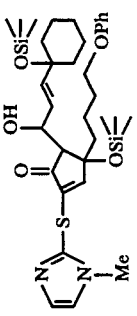 | 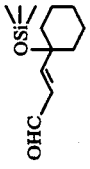 | 33 | 0.11(s, 9H), 0.15(s, 9H), 1.2–2.0(m, 16H), 2.77(d, 1H, J=7.0Hz), 3.71(s, 3H), 3.99(t, 2H, J=7.0Hz), 4.56(d, 1H, J=7.0 Hz), 5.7–6.1(m, 2H), 6.8–7.5 (m, 18H) |
| 146 | Same as above | 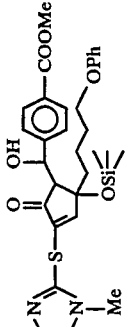 | 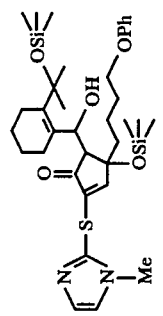 | 9 | 0.04(s, 18H), 1.07(s, 3H), 1.12(s, 3H), 1.0–2.1(m, 15H), 2.58(d, 1H, J=1.8Hz), 3.71(s, 3H), 3.97(t, 2H, J=5.9Hz), 4.8–5.0(m, 1H), 6.7–7.4(m, 8H) |
| 147 | Same as above | 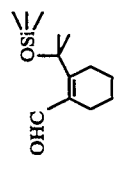 | 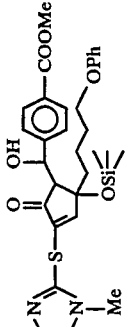 | 76 | −0.02(s, 9H), 1.4–2.0(m, 7H), 3.17(d, 1H, J=7.3Hz), 3.70(s, 3H), 3.7–4.1(m, 2H), 3.91(s, 3H), 5.11(d, 1H, J=7.2Hz), 6.75–7.4(m, 8H), 7.45(d, 2H, J=8.6Hz), 8.01(d, 2H, J=8.1Hz) |
| 148 | Same as above | 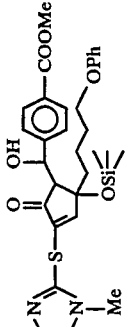 | 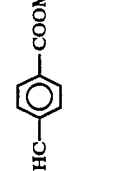 | 42 | −0.05(s, 9H), 0.0(s, 12H), 0.88(s, 18H), 1.1–2.1(m, 7H), 2.64(d, 2H, J=2.0Hz), 3.22(d, 1H, J=7.8Hz), 3.56(d, 4H, J=5.3Hz), 3.73(s, 3H), 3.92(t, 2H, J=5.8Hz), 5.01(d, 1H, J=7.8Hz), 6.8–7.5(m, 12H) |
| 149 | 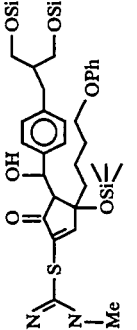 | 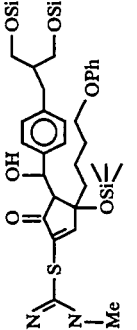 | 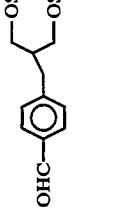 | 69 | 0.06(s, 9H), 0.7–1.0(m, 3H), 1.1–2.4(m, 29H), 2.8–3.0(m, 1H), 3.4–3.8(m, 1H), 3.69(s, 3H), 3.76(s, 3H), 6.6–6.9(m, 3H) |
| 150 | 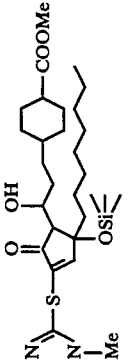 | 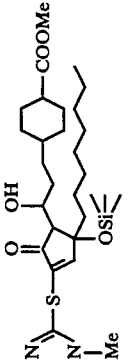 | 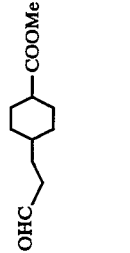 | 40 | 0.05(s, 9H), 1.1–2.1(m, 12H), 2.3–2.6(m, 2H), 2.9–3.1(m, 1H), 3.65(s, 3H), 3.80(s, 6H), 3.5–3.9(m, 1H), 6.4–7.2(m, 6H) |

TABLE 13-continued

| Ex. No. | Starting Material | | 2-Substituted-2-cyclopentenones | Yield (%) | NMR (δ, CDCl₃) |
|---|---|---|---|---|---|
| | 2-Substituted-2-cyclopentenones | Aldehydes | | | |
| 151 | [structure: cyclopentenone with N-methylimidazole-S, OSi, and alkyne-t-Bu substituents] | OHC-CH=CH-CH₂-CH₂-CH₃ | [structure: product with OH, hexenyl chain] | 37 | 0.08(s, 9H), 0.7–1.0(m, 3H), 1.05(s, 9H), 1.2–2.0(m, 5H), 2.2–2.5(m, 2H), 3.0–3.2(m, 1H), 3.67(s, 3H), 3.8–4.1(m, 1H), 6.6–7.1(m, 3H) |
| 152 | [structure: cyclopentenone with N-methylimidazole-S, OSi, and Ph-CMe₂-vinyl substituents] | OHC-CH₂-CH₂-O-CH₂-COOMe | [structure: product with OH, COOMe chain] | 50 | 0.10(s, 9H), 1.68(s, 6H), 1.5–1.9(m, 5H), 2.8–3.0(m, 1H), 3.4–4.0(m, 3H), 3.66(s, 3H), 3.71(s, 3H), 4.10(s, 2H), 5.4–5.9(m, 2H), 6.6–7.5(m, 8H) |
| 153 | [structure: cyclopentenone with N-methylpyrimidine-S, OSi, and COOMe-hexyl chain] | OHC-CH=CH-CH₂-CH₂-CH₂-CH₃ | [structure: product] | 68 | 0.08(s, 9H), 0.7–1.0(m, 3H), 1.0–2.1(m, 17H), 2.2–2.5(m, 4H), 2.8–3.0(m, 1H), 3.68(s, 3H), 3.70(s, 3H), 3.7–4.0(m, 1H), 5.4–5.9(m, 2H), 6.7–7.3(m, 3H) |
| 154 | [structure: cyclopentenone with Me-pyrimidine-S, OSi, cyclohexyl-OSi-vinyl chain] | OHC-CH₂-CH(OSi)-CH₂-CN | [structure: product] | 54 | 0–0.2(m, 21H), 0.88(s, 9H), 0.90(s, 9H), 1.1–2.1(m, 18H), 2.40(t, 2H, J=7.5Hz), 2.47(s, 3H), 2.9–3.1(m, 1H), 3.5–4.0(m, 2H), 4.6–4.9(m, 1H), 5.4–5.8(m, 2H), 6.6–7.0(m, 2H), 8.33(d, 1H, J=5.0Hz) |
| 155 | [structure: cyclopentenone with benzoxazole-S, OSi, isoprenyl chain] | OHC-CH₂-CH₂-CH(CH₃)-CH₂-CH(CH₃)₂ | [structure: product] | 75 | 0.09(s, 9H), 0.7–1.1(m, 18H), 1.1–2.0(m, 23H), 2.8–3.0(m, 1H), 3.5–3.9(m, 1H), 6.86(s, 1H), 7.2–7.8(m, 4H) |
| 156 | [structure: cyclopentenone with benzoxazole-S, OSi, dimethoxyphenyl-ethyl chain] | OHC-CH₂-CH₂-CH₂-CH₃ | [structure: product] | 59 | 0.09(s, 9H), 0.7–1.0(m, 3H), 1.2–1.9(m, 13H), 2.3–3.0(m, 3H), 3.5–3.9(m, 1H), 3.85(s, 6H), 6.4–6.9(m, 4H), 7.2–7.8(m, 4H) |

TABLE 13-continued

| Ex. No. | Starting Material 2-Substituted-2-cyclopentenones | Aldehydes | Yield (%) | 2-Substituted-2-cyclopentenones | NMR (δ, CDCl₃) |
|---|---|---|---|---|---|
| 154 | [structure: 6-methylpyrimidinyl-S-cyclopentenone with cyclohexyl-CH=CH-OSi side chain] | [structure: OHC-CH₂-CH(OSiX)-CH₂-CH₂-CN] | 54 | [structure: product] | 0–0.2(m, 21H), 0.88(s, 9H), 0.90(s, 9H), 1.1–2.1(m, 18H), 2.40(t, 2H, J=7.5Hz), 2.47(s, 3H), 2.9–3.1(m, 1H), 3.5–4.0(m, 2H), 4.6–4.9(m, 1H), 5.4–5.8(m, 2H), 6.6–7.0(m, 2H), 8.33(d, 1H, J=5.0Hz) |
| 155 | [structure: benzothiazolyl-S-cyclopentenone with OMe-Mme-substituted alkyl chain] | [structure: isoprenyl aldehyde] | 75 | [structure: product] | 0.09(s, 9H), 0.7–1.1(m, 18H), 1.1–2.0(m, 23H), 2.8–3.0(m, 1H), 3.5–3.9(m, 1H), 6.86(s, 1H), 7.2–7.8(m, 4H) |
| 156 | [structure: benzoxazolyl-S-cyclopentenone with dimethoxyphenylethyl side chain] | [structure: OHC-hexyl] | 59 | [structure: product] | 0.09(s, 9H), 0.7–1.0(m, 3H), 1.2–1.9(m, 13H), 2.3–3.0(m, 3H), 3.5–3.9(m, 1H), 3.85(s, 6H), 6.4–6.9(m, 4H), 7.2–7.8(m, 4H) |
| 157 | [structure: benzothiazolyl-S-cyclopentenone with Me-OSi] | [structure: OHC-isobutyl] | 38 | [structure: product] | 0.07(s, 9H), 0.95(d, 6H, J=6.4Hz), 1.23(s, 3H), 1.2–1.8(m, 3H), 2.0–2.3(m, 1H), 2.8–3.1(m, 1H), 3.4–3.9(m, 1H), 7.2–7.9(m, 5H) |
| 158 | [structure: 5-chlorobenzothiazolyl-S-cyclopentenone with cyclohexyl-CH=CH-OSi side chain] | [structure: OHC-butyl] | 54 | [structure: product] | 0–0.2(m, 15H), 0.90(s, 9H), 0.7–1.0(m, 3H), 1.1–2.1(m, 16H), 2.8–3.0(m, 1H), 3.5–3.9(m, 1H), 4.6–4.9(m, 1H), 5.4–5.8(m, 2H), 7.0–7.8(m, 4H) |
| 159 | [structure: 6-ethoxybenzothiazolyl-S-cyclopentenone with OPh-butyl side chain] | [structure: OHC-CH=CH-CH(OSiX)-CH₂-CH₂-OPh] | 60 | [structure: product] | 0.10(s, 21H), 0.85(s, 18H), 1.40(t, 3H, J=6.9Hz), 1.1–2.9(m, 11H), 3.4–3.7(m, 2H), 3.7–4.3(m, 5H), 4.53(t, 1H, J=5.4Hz), 5.5–6.1(m, 2H), 6.7–7.4(m, 7H), 7.6–7.9(m, 1H), 7.90(s, 1H) |

TABLE 13-continued

| Ex. No. | Starting Material | | Yield (%) | NMR (δ, CDCl₃) |
|---|---|---|---|---|
| | 2-Substituted-2-cyclopentenones | Aldehydes · 2-Substituted-2-cyclopentenones (product) | | |
| 160 | (structure) | OHC–CH=CH–COOEt | 70 | 0.08(s, 9H), 0.7–1.1(m, 6H), 1.1–2.9(m, 14H), 3.5–4.3(m, 7H), 5.88(d, 1H, J=16.0Hz), 6.7–7.9 (m, 10H) |
| 161 | (structure) | (structure with OMe) | 71 | 0.05(s, 9H), 0.7–1.0(m, 3H), 1.40(t, 3H, J=7.0Hz), 1.1–2.1 (m, 9H), 2.2–3.0(m, 5H), 3.74 (s, 3H), 3.6–3.9(m, 1H), 4.01 (q, 2H, J=7.0Hz), 6.6–7.4(m, 7H), 7.60(s, 1H) |
| 162 | (structure) | OHC–C≡C–(CH₂)ₙ–COOMe | 44 | 0.08(s, 9H), 1.3–1.9(m, 9H), 2.0–3.0(m, 7H), 3.74(s, 3H), 3.84(s, 6H), 3.8–4.2(m, 3H), 6.0–6.5(m, 2H), 6.85(s, 1H), 7.3–7.6(m, 1H) |
| 163 | (structure) | (structure with OMe, OMe) | 70 | 0.09(s, 9H), 1.07(s, 3H), 1.3–1.7(m, 3H), 2.3–2.6(m, 2H), 2.9–3.1(m, 1H), 3.7–3.9(m, 1H), 3.90(s, 6H), 4.07(s, 2H), 6.0–6.9(m, 6H), 7.2–7.4(m, 1H) |
| 164 | (structure) | (structure with OPh, COOMe) | 87 | 0.03(9H, s), 1.0–2.0(6H, m), 2.31(3H, s), 3.18(1H, d, J=7.5 Hz), 3.75(3H, s), 3.92(2H, t, J=5.0Hz), 4.3–4.5(1H, m), 4.58(2H, s), 4.9–5.1(1H, m), 6.5–7.4(10H, m) |
| 165 | Same as above | OHC–cyclohexyl | 70 | 0.08(s, 9H), 1.1–2.0(m, 18H), 2.34(s, 3H), 2.8–3.1(m, 1H), 3.4–3.7(m, 1H), 3.94(t, 2H, J=6.0Hz), 6.7–7.1(m, 4H), 7.1–7.4(m, 2H) |

TABLE 13-continued

| Ex. No. | Starting Material | | Yield (%) | NMR (δ, CDCl₃) |
|---|---|---|---|---|
| | 2-Substituted-2-cyclopentenones | Aldehydes | | |
| 166 | [structure: 2-cyclopentenone with EtS, OSi group, and alkyl chain] | [structure: furan aldehyde with Me] | 18 | 0.08(s, 9H), 0.7–1.0(m, 6H), 1.1–2.1(m, 14H), 2.2–2.6(m, 2H), 2.35(s, 3H), 6.14(d, 1H, J=3.4 Hz), 6.63(d, 1H, J=3.4Hz), 6.85 (s, 1H), 7.35(s, 1H) |
| 167 | [structure: 2-cyclopentenone with iPrS, OSi, and branched alkyl chain] | [structure: 3,5-dimethylbenzaldehyde] | 72 | 0.08(s, 9H), 0.7–1.3(m, 15H), 1.2–2.8(m, 14H), 2.25(s, 6H), 3.0–3.3(m, 1H), 4.9–5.1(m, 2H), 6.6–7.1(m, 4H) |
| 168 | [structure: 2-cyclopentenone with thioester chain, MeOOC, OSi, cyclohexyl vinyl] | [structure: cyclohexanecarbaldehyde] | 44 | 0–0.1(m, 15H), 0.90(s, 9H), 1.0–2.0(m, 29H), 2.1–3.0(m, 5H), 3.4–3.7(m, 1H), 3.69(s, 3H), 4.6–4.8(m, 1H), 5.4–5.8(m, 2H), 6.90(s, 1H) |
| 169 | [structure: 2-cyclopentenone with PhS, OSi, OPh chain] | Same as above | 42 | 0.08(s, 9H), 1.1–2.0(m, 18H), 2.8–3.1(m, 1H), 3.4–3.7(m, 1H), 3.95(t, 2H, J=6.0Hz), 6.8–7.7 (m, 11H) |
| 170 | Same as above | [structure: aryl aldehyde with two OSi-bearing chains] | 65 | 0–0.2(m, 21H), 0.89(s, 18H), 1.1–2.1(m, 7H), 2.66(d, 2H, J=2.2Hz), 3.24(d, 1H, J=7.6Hz), 3.55(d, 4H, J=5.0Hz), 3.94(t, 2H, J=6.0Hz), 5.03(d, 1H, J=7.6Hz), 6.8–7.5(m, 15H) |
| 171 | [structure: 2-cyclopentenone with 4-MeO-phenylthio, OSi, and 3,4-dimethoxyphenethyl] | [structure: cyclopentanecarbaldehyde] | 63 | 0.08(s, 9H), 1.1–2.0(m, 14H), 2.4–3.0(m, 3H), 3.4–3.7(m, 1H), 3.76(s, 3H), 3.79(s, 6H), 6.6–7.5(m, 8H) |

TABLE 13-continued
| Ex. No. | Starting Material 2-Substituted-2-cyclopentenones | Aldehydes | 2-Substituted-2-cyclopentenones | Yield (%) | NMR (δ, CDCl₃) |
|---|---|---|---|---|---|
| 172 | 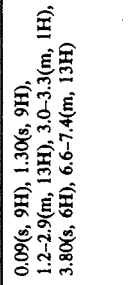 | 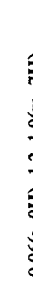 | 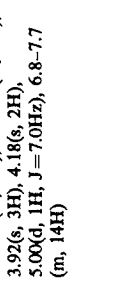 | 69 | 0.09(s, 9H), 1.30(s, 9H), 1.2–2.9(m, 13H), 3.0–3.3(m, 1H), 3.80(s, 6H), 6.6–7.4(m, 13H) |
| 173 | 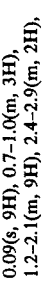 |  |  | 49 | 0.06(s, 9H), 1.2–1.9(m, 7H), 3.1–3.4(m, 1H), 3.7–4.1(m, 2H), 3.92(s, 3H), 4.18(s, 2H), 5.00(d, 1H, J=7.0Hz), 6.8–7.7 (m, 14H) |
| 174 |  |  |  | 50 | 0.09(s, 9H), 0.7–1.0(m, 3H), 1.2–2.1(m, 9H), 2.4–2.9(m, 2H), 3.0–3.3(m, 1H), 3.80(s, 6H), 3.75–4.20(m, 3H), 6.6–7.7 (m, 12H) |
| 175 | 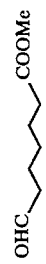 | | | 56 | 0–0.2(m, 21H), 0.90(s, 18H), 0.7–1.0(m, 3H), 1.0–2.1(m, 14H), 2.35(s, 3H), 2.2–2.9(m, 4H), 3.4–3.7(m, 2H), 3.98(t, 2H, J=5.4 Hz), 4.0–4.3(m, 1H), 4.3–4.8 (m, 1H), 5.5–6.2(m, 2H), 6.7–7.1 (m, 3H), 7.1–7.5(m, 2H) |
| 176 | Same as above | | | 41 | 0.04(s, 9H), 0.7–1.0(m, 3H), 1.1–2.1(m, 14H), 2.1–2.9(m, 6H), 2.34(s, 3H), 3.67(s, 3H), 3.6–4.1(m, 3H), 6.7–7.1(m, 3H), 7.1–7.5(m, 2H) |
| 177 | | | | 46 | 0.06(s, 9H), 1.29(s, 3H), 1.34(s, 9H), 1.1–2.3(m, 9H), 2.34(s, 3H), 2.6–3.0(m, 2H), 3.67(s, 3H), 3.7–4.0(m, 1H) |

TABLE 13-continued

| Ex. No. | Starting Material | | Yield (%) | NMR (δ, CDCl₃) |
|---|---|---|---|---|
| | 2-Substituted-2-cyclopentenones | Aldehydes | | |
| 178 | [structure] | Same as above | 37 | 0.07(s, 9H), 0.7–1.1(m, 6H), 1.1–2.0(m, 14H), 2.34(s, 3H), 2.1–2.9(m, 8H), 3.68(s, 3H), 3.7–4.0(m, 1H) |
| 179 | [structure] | [structure] | 40 | 0.07(s, 9H), 0.7–1.0(m, 6H), 1.1–1.9(m, 32H), 2.36(s, 3H), 2.4–2.9(m, 3H), 3.7–4.0(m, 1H) |
| 180 | [structure] | [structure] | 26 | 0–0.1(m, 15H), 0.89(s, 9H), 1.0–2.0(m, 31H), 2.1–3.0(m, 10H), 3.67(s, 3H), 3.8–4.0(m, 1H), 4.6–4.8(m, 1H), 5.3–5.9(m, 2H) |
| 181 | [structure] | PhCHO | 38 | 0.05(s, 9H), 0.7–1.0(m, 3H), 1.1–2.0(m, 10H), 1.31(s, 9H), 2.4–2.8(m, 2H), 3.0–3.3(m, 1H), 3.86(t, 2H, J=5.7Hz), 4.0–4.4 (m, 1H), 4.6–5.0(m, 1H), 6.7–7.6 (m, 10H) |
| 182 | [structure] | [structure] | 21 | 0.06(s, 9H), 0.7–1.0(m, 3H), 1.1–2.1(m, 36H), 2.1–2.8(m, 11H), 3.67(s, 3H), 3.69(s, 3H), 3.8–4.3(m, 3H), 4.8–5.2(m, 1H), 6.7–7.1(m, 3H), 7.1–7.4(m, 2H) |
| 183 | [structure] | [structure] | 52 | 0.07(s, 9H), 0.7–1.0(m, 3H), 1.1–2.0(m, 23H), 2.1–2.9(m, 4H), 3.6–4.2(m, 3H), 6.7–7.5(m, 10H) |

TABLE 13-continued

| Ex. No. | Starting Material | | Yield (%) | NMR (δ, CDCl₃) |
|---|---|---|---|---|
| | 2-Substituted-2-cyclopentenones | Aldehydes | 2-Substituted-2-cyclopentenones | |
| 184 | [structure: 2-(4-MeO-phenylthio) cyclopentenone with OSi group and PhO-butyl chain] | EtCHO | [structure: product with OH and Et] | 29 | 0.07(s, 9H), 0.7–1.2(m, 9H), 1.3–1.9(m, 7H), 2.3–2.8(m, 4H), 3.78(s, 3H), 3.6–4.1(m, 3H), 6.6–7.5(m, 9H) |
| 185 | [structure with S-phenethyl, isopropyl, isohexyl, OSi] | OHC—(CH₂)₄—CH(Me)—COOMe | [product with OH, COOMe] | 40 | 0.08(s, 9H), 0.7–1.2(m, 15H), 1.2–2.0(m, 22H), 2.1–3.0(m, 9H), 3.67(s, 3H), 3.7–4.00(m, 1H), 7.0–7.4(m, 5H) |
| 186 | [structure with CF₃-benzyl-S, Et, iPr, OSi] | OHC—CH₂—CH(Me)—iBu | [product with OH] | 34 | 0.06(s, 9H), 0.7–1.1(m, 15H), 1.1–2.0(m, 16H), 2.4–2.9(m, 4H), 3.6–3.9(m, 1H), 4.16(s, 2H), 6.69(s, 1H), 7.3–7.7(m, 3H) |
| 187 | [structure with S-cyclohexyl, propyl, OPh-butyl, OSi] | OHC—(CH₂)₄—CH(Me)—COOMe | [product with OH, COOMe] | 42 | 0.07(s, 9H), 0.7–1.0(m, 3H), 1.1–2.0(m, 28H), 2.1–2.9(m, 7H), 3.68(s, 3H), 3.6–4.1(m, 3H), 6.7–7.0(m, 3H), 7.1–7.4(m, 2H) |
| 188 | [structure with S-cyclopentyl, phenethyl-butyl, OSi] | OHC—CH₂—C₆H₄—OMe | [product with OH, p-MeO-phenyl] | 20 | 0.07(s, 9H), 1.1–2.0(m, 24H), 2.1–2.9(m, 9H), 3.72(s, 3H), 3.7–4.3(m, 3H), 6.6–7.5(m, 14H) |
| 189 | [structure with S-pyridyl, Et, OPh-butyl, OSi] | OHC—cyclohexyl | [product with OH, cyclohexyl] | 39 | 0.09(s, 9H), 0.7–1.0(m, 3H), 1.1–2.2(m, 18H), 2.3–2.9(m, 3H), 3.3–3.7(m, 1H), 3.93(t, 2H, J=6.1Hz), 6.7–7.1(m, 3H), 7.1–8.1(m, 6H) |

TABLE 13-continued

| Ex. No. | Starting Material: 2-Substituted-2-cyclopentenones | Starting Material: Aldehydes | 2-Substituted-2-cyclopentenones | Yield (%) | NMR (δ, CDCl₃) |
|---|---|---|---|---|---|
| 190 | [structure with imidazolyl-S, OPh side chain, OSi≡X] | OHC-CH=CH-CH(OSi≡X)-CH₂-CH₂-OSi≡X | [product structure] | 11 | 0–0.1(m, 21H), 0.91(s, 18H), 0.8–1.1(m, 3H), 1.1–2.3(m, 15H), 2.4–2.8(m, 3H), 3.4–4.3(m, 5H), 3.70(s, 3H), 4.3–4.6(m, 1H), 5.6–5.8(m, 2H), 6.7–7.1(m, 5H), 7.1–7.4(m, 2H) |
| 191 | [structure with benzoxazolyl-S, dimethoxyphenyl, Me, OSi≡X] | OHC-CH=CH-CH₂-CH(COOEt) | [product structure] | 33 | 0.06(s, 9H), 1.2–2.1(m, 11H), 2.40(s, 3H), 2.2–3.0(m, 6H), 3.80(s, 6H), 3.6–4.0(m, 3H), 5.89(d, 1H, J=16Hz), 6.4–7.1 (m, 4H), 7.2–7.8(m, 4H) |
| 192 | [MeS-cyclopentenone, OSi≡X] | OHC-CH=CH-CH₂-CH₂-CH(OSi≡X)-CH₂-CH₂-OSi≡X | [product structure] | 24 | 0.04(s, 12H), 0.15(s, 6H), 0.89(s, 18H), 0.91(s, 9H), 1.4–1.8(m, 4H), 2.32(s, 3H), 2.6–2.8(m, 1H), 3.5–3.8(m, 2H), 4.0–4.2(m, 1H), 4.4–4.7(m, 1H), 4.8–4.95(m, 1H), 5.6–5.8(m, 2H), 6.69(d, 1H, J=2.6Hz) |
| 193 | Same as above | OHC-(CH₂)₄-COOMe | [product structure] | 27 | 0.08(s, 6H), 0.88(s, 9H), 1.1–2.2(m, 11H), 2.34(s, 3H), 2.5–2.8(m, 1H), 3.68(s, 3H), 3.7–4.0(m, 1H), 4.7–5.0(m, 1H), 6.79(d, 1H, J=2.4Hz) |
| 194 | [cyclohexyl-S cyclopentenone, OSi≡X] | OHC-CH=CH-CH(OSi≡X)-CH₂-CH₂-OSi≡X | [product structure] | 26 | 0–0.2(m, 18H), 0.89(s, 18H), 0.92(s, 9H), 1.1–2.0(m, 15H), 2.2–2.8(m, 2H), 3.5–3.8(m, 2H), 4.0–4.2(m, 1H), 4.4–4.7(m, 1H), 4.8–4.95(m, 1H), 5.6–5.8(m, 2H), 6.70(d, 1H, J=2.3Hz) |
| 195 | [PhS-cyclopentenone, OSi≡X] | Same as above | [product structure] | 18 | 0–0.2(m, 18H), 0.89(s, 18H), 0.90(s, 9H), 1.1–1.8(m, 5H), 2.4–2.7(m, 1H), 3.5–3.8(m, 2H), 4.0–4.7(m, 2H), 4.8–5.0(m, 1H), 5.6–5.9(m, 2H), 6.75(d, 1H, J=1.4Hz) |

TABLE 13-continued

| Ex. No. | Starting Material 2-Substituted-2-cyclopentenones | Aldehydes | 2-Substituted-2-cyclopentenones | Yield (%) | NMR (δ, CDCl₃) |
|---|---|---|---|---|---|
| 196 | [Me-pyrimidinyl-S-cyclopentenone-OSiX] | Same as above | [Me-pyrimidinyl-S-cyclopentenone with OH, CH=CH-CH(OSiX)-CH₂-OSiX side chain] | 20 | 0–0.2(m, 18H), 0.88(s, 18H), 0.90(s, 9H), 1.1–1.9(m, 5H), 2.46(s, 3H), 2.5–2.8(m, 1H), 3.5–3.8(m, 2H), 4.0–4.7(m, 2H), 4.8–5.0(m, 1H), 5.6–5.8(m, 2H), 6.88(d, 1H, J=5.1Hz), 7.89(d, 1H, J=2.6Hz), 8.32(d, 1H, J=5.1Hz) |
| 197 | [benzoxazolyl-S-cyclopentenone-OSiX] | OHC-(CH₂)₅-COOMe | [benzoxazolyl-S-cyclopentenone with OH, (CH₂)₅COOMe side chain] | 21 | 0.08(s, 6H), 0.87(s, 9H), 1.1–2.2(m, 11H), 2.5–2.8(m, 1H), 3.69(s, 3H), 3.7–4.0(m, 1H), 5.0–5.2(m, 1H), 7.2–7.8(m, 4H), 8.03(d, 1H, J=2.6Hz) |
| 198 | [triazolyl-S-cyclopentenone-OSiX] | Same as above | [triazolyl-S-cyclopentenone with OH, (CH₂)₅COOMe side chain] | 6 | 0.09(s, 6H), 0.89(s, 9H), 1.0–2.2(m, 11H), 2.5–2.9(m, 1H), 3.68(s, 3H), 3.7–4.0(m, 1H), 4.10(s, 3H), 4.9–5.1(m, 1H), 7.73(d, 1H, J=2.6Hz) |
| 199 | [PhS-dimethyl-cyclopentenone-OSiX] | OHC-CH=CH-CH(OSiX)-CH₂-OSiX | [PhS-dimethyl-cyclopentenone with OH-CH=CH side chain OSiX] | 85 | 0–0.25(m, 18H), 0.89(s, 18H), 0.90(s, 9H), 1.44(s, 9H), 1.3–1.8(m, 5H), 2.4–2.7(m, 1H), 3.5–3.8(m, 2H), 4.0–4.7(m, 2H), 4.99(s, 1H), 5.6–5.9(m, 2H), 7.0(s, 5H) |
| 200 | [PhS-cyclopentenone] | OHC-cyclohexyl | [PhS-cyclopentenone with OH-cyclohexyl] | 20 | 1.0–1.9(m, 11H), 2.1–2.9(m, 3H), 3.4–3.7(m, 1H), 6.99(t, 1H, J=2.9Hz), 7.2–7.7(m, 5H) |
| 201 | Same as above | OHC-CH₂-cyclohexyl | [PhS-cyclopentenone with OH-CH₂-cyclohexyl] | 9 | 0.9–1.9(m, 15H), 2.1–2.9(m, 3H), 3.5–3.9(m, 1H), 6.98(t, 1H, J=2.9Hz), 7.2–7.7(m, 5H) |
| 202 | Same as above | OHC-(Me-furyl) | [PhS-cyclopentenone with =CH-(Me-furyl)] | 23 | 2.35(s, 3H), 3.4–3.6(m, 2H), 6.12(d, 1H, J=3.3Hz), 6.61(d, 1H, J=3.5Hz), 6.86(t, 1H, J=2.8Hz), 7.2–7.6(m, 6H) |

TABLE 14

| Ref. Ex. No. | Starting Material | | Yield (%) | NMR(δ, CDCl₃) |
|---|---|---|---|---|
| | 2-Substituted-2-cyclopentenones | Aldehydes | 2-Substituted-2-cyclopentenones | |
| 41 | [structure: cyclopentenone with MeS, OSi, and (CH₂)-OPh chain] | [structure: OHC-CH=CH-pentyl] | [structure: product with OH, MeS, OSi, OPh] 50 | 0.10(s, 9H), 0.7–1.0(m, 3H), 1.1–2.1(m, 14H), 2.33(s, 3H), 2.5–2.8 (m, 1H), 3.8–4.1(m, 3H), 5.6–5.9 (m, 2H), 6.7–7.1(m, 4H), 7.1–7.5 (m, 2H) |
| 42 | Same as above | [structure: OHC-C≡C-CH₂CH₂-COOMe] | [structure: product with OH, alkyne, MeS, COOMe, OPh] 59 | 0.14(s, 9H), 1.3–2.1(m, 8H), 2.1–2.6(m, 5H), 2.34(s, 3H), 2.8–3.0 (m, 1H), 3.66(s, 3H), 3.8–4.1(m, 2H), 4.6–4.9(m, 1H), 6.8–7.1(m, 4H), 7.1–7.45(m, 2H) |
| 43 | Same as above | [structure: OHC-CH=CH-CH₂CH₂-CH(OSiX)-alkyl] | [structure: product with OH, OSiX, MeS, OPh] 75 | 0–0.2(m, 21H), 0.90(s, 18H), 1.0–2.1(m, 10H), 2.34(s, 3H), 2.74(d, 1H, J=7.0Hz), 3.5–3.7(m, 2H), 3.98 (t, 2H, J=5.4Hz), 4.05–4.35(m, 1H), 4.35–4.7(m, 1H), 5.5–6.2(m, 2H), 6.7–7.1(m, 4H), 7.1–7.5(m, 2H) |
| 44 | [structure: cyclopentenone with iPrS, OSi, OPh chain] | Same as above | [structure: product with OH, OSiX, iPrS, OPh] 82 | 0–0.2(m, 21H), 0.85(s, 18H), 1.1–2.2(m, 12H), 2.3–2.9(m, 1H), 3.1–3.7(m, 3H), 3.8–4.3(m, 3H), 4.4–4.8(m, 1H), 5.5–6.1(m, 2H), 6.7–7.6(m, 6H) |
| 45 | [structure: cyclopentenone with PhS, OSi, OPh chain] | Same as above | [structure: product with OH, OSiX, PhS, OPh] 66 | 0–0.1(m, 21H), 0.87(s, 18H), 1.1–2.1(m, 10H), 2.6–2.8(m, 1H), 3.3–3.7(m, 2H), 3.7–4.0(m, 3H), 4.0–4.3(m, 1H), 4.4–4.7(m, 1H), 5.5–6.1(m, 2H), 6.3–6.7(m, 1H), 6.7–7.05(m, 3H), 7.05–7.8(m, 7H) |

TABLE 15

| Ex. No. | Starting Material 2-Substituted-2-cyclopentenones | Aldehydes | 2-Substituted-2-cyclopentenones | Yield (%) | NMR(δ, CDCl₃) |
|---|---|---|---|---|---|
| 203 | [structure] | [structure] | [structure] | 42 | 0.09(s, 9H), 1.2–2.0(m, 6H), 2.3–2.8(m, 2H), 2.95(s, 6H), 3.68(s, 3H), 3.90(t, 2H, J=6.1Hz), 4.7–5.0(m, 1H), 5.98(dd, 1H, J=15.4, 6.3 Hz), 6.4–7.4(m, 13H) |
| 204 | [structure] | [structure] | [structure] | 24 | 0.09(s, 9H), 1.2–1.9(m, 7H), 2.9–3.2(m, 1H), 3.90(s, 2H, J=5.9Hz), 5.0–5.2(m, 1H), 6.7–7.4(m, 11H), 8.2–8.4(m, 2H) |
| 205 | [structure] | [structure] | [structure] | 36 | 0.09(s, 9H), 1.2–2.0(m, 6H), 2.3–3.0(m, 10H), 3.55(s, 2H), 3.68(s, 3H), 3.9–4.2(m, 3H), 5.2–5.5(m, 1H), 6.7–7.1(m, 6H), 7.1–7.5(m, 7H) |
| 206 | [structure] | [structure] | [structure] | 32 | 0.07(s, 9H), 0.7–1.0(m, 3H), 1.1–2.0(m, 10H), 2.34(s, 3H), 2.2–2.8(m, 4H), 2.95(s, 6H), 3.95(t, 2H, J=5.8Hz), 4.7–5.0(m, 1H), 6.00(dd, 1H, J=15.7, 6.7Hz), 6.4–6.8(m, 3H), 6.8–7.5(m, 7H) |
| 207 | [structure] | Same as above | [structure] | 32 | 0.08(s, 3H), 0.12(s, 3H), 0.87(s, 9H), 2.34(s, 3H), 2.6–2.8(m, 2H), 2.95(s, 6H), 4.7–5.0(m, 2H), 6.00 (dd, 1H, J=15.7, 6.7Hz), 6.4–6.8(m, 4H), 7.2–7.3(m, 2H) |

TABLE 16

| Ex. No. | Starting compd. (2-Substituted-2-cyclopentenones) | 2-Substituted-2-cyclopentenones | Yield (%) | NMR (δ, CDCl₃) |
|---|---|---|---|---|
| 208 | | | 47 | 0.03(s, 12H), 0.89(s, 18H), 1.1–2.3(m, 11H), 1.94(s, 3H), 2.33(s, 3H), 2.5–2.8(m, 1H), 3.5–3.8(m, 2H), 3.8–4.2(m, 3H), 5.5–6.0(m, 3H), 6.7–7.1(m, 4H), 7.1–7.4(m, 2H) |
| 209 | | | 37 | 0–0.15(s, 12H), 0.87(s, 18H), 1.2–1.7(m, 4H), 1.93(s, 3H), 2.36(s, 3H), 2.6–2.9(m, 1H), 3.4–3.7(m, 2H), 4.0–4.2(m, 2H), 4.6–4.8(m, 1H), 5.5–6.0(m, 3H), 6.97(d, 1H, J=2.7Hz), 7.1–7.5(m, 5H) |
| 210 | | | 24 | 0–0.1(m, 6H), 0.98(s, 9H), 1.0–2.8(m, 18H), 2.07(s, 9H), 3.10(d, 1H, J=6.5Hz), 3.67(s, 3H), 3.8–4.0(m, 1H), 4.1–4.5(m, 2H), 5.0–5.3(m, 1H), 5.4–5.9(m, 3H), 7.26(d, 1H, J=7.0 Hz) |
| 211 | | | 43 | 0.0–0.1(m, 12H), 0.87(s, 18H), 1.1–2.3(m, 11H), 1.96(s, 3H), 2.5–2.8(m, 1H), 3.5–3.8(m, 2H), 3.72(s, 3H), 3.8–4.2(m, 3H), 5.5–6.0(m, 3H), 6.7–7.5(m, 8H) |
| 212 | | | 44 | 0.09(s, 9H), 0.7–1.0(m, 3H), 1.2–2.1(m, 12H), 1.95(s, 3H), 2.35(s, 3H), 2.6–2.9(m, 1H), 3.7–4.0(m, 2H), 5.5–6.0(m, 3H), 6.7–7.1(m, 4H), 7.1–7.4(m, 2H) |

TABLE 16-continued

| Ex. No. | Starting compd. (2-Substituted-2-cyclopentenones) | 2-Substituted-2-cyclopentenones | Yield (%) | NMR(δ, CDCl₃) |
|---|---|---|---|---|
| 213 | | | 48 | 0–0.15(m, 21H), 0.88(s, 18H), 1.0–2.4(m, 10H), 1.93(s, 3H), 2.32(s, 3H), 2.8–2.9(m, 1H), 3.4–3.7(m, 2H), 3.8–4.3(m, 3H), 5.4–6.1(m, 3H), 6.7–7.1 (m, 4H), 7.1–7.4(m, 2H) |
| 214 | | | 40 | 0.09(s, 9H), 1.1–2.3(m, 12H), 1.98(s, 3H), 2.34(s, 3H), 2.6–2.8(m, 1H), 3.69(s, 3H), 5.4–5.8(m, 1H), 6.7–7.1(m, 4H), 7.1–7.4(m, 2H) |
| 215 | | | 52 | 0–0.2(m, 21H), 0.89(s, 18H), 1.1–2.2(m, 11H), 1.97(s, 3H), 2.3–2.9(m, 1H), 3.1–3.7(m, 3H), 3.8–4.3(m, 3H), 5.4–6.1(m, 3H), 6.7–7.1(m, 4H), 7.1–7.4(m, 2H) |
| 216 | | | 52 | 0–0.2(m, 21H), 0.89(s, 18H), 1.1–2.3(m, 10H), 1.95(s, 3H), 2.8–3.0(m, 1H), 3.5–3.7(m, 2H), 3.8–4.2(m, 3H), 5.4–6.1(m, 3H), 6.7–7.1(m, 4H), 7.1–7.5(m, 7H) |

TABLE 16-continued
| Ex. No. | Starting compd. (2-Substituted-2-cyclopentenones) | 2-Substituted-2-cyclopentenones | Yield (%) | NMR(δ, CDCl₃) |
|---|---|---|---|---|
| 217 | 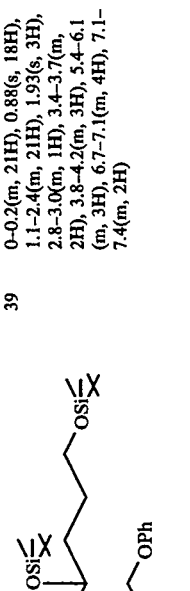 | 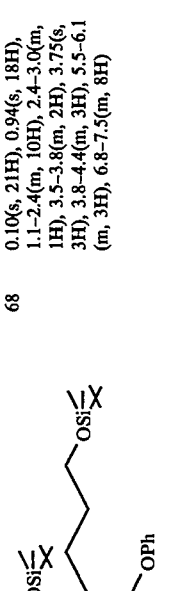 | 39 | 0–0.2(m, 21H), 0.88(s, 18H), 1.1–2.4(m, 21H), 1.93(s, 3H), 2.8–3.0(m, 1H), 3.4–3.7(m, 2H), 3.8–4.2(m, 3H), 5.4–6.1 (m, 3H), 6.7–7.1(m, 4H), 7.1–7.4(m, 2H) |
| 218 | 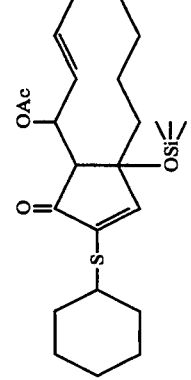 | 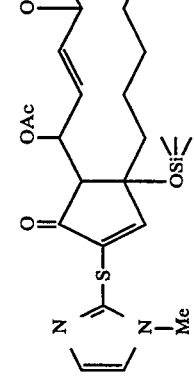 | 68 | 0.10(s, 21H), 0.94(s, 18H), 1.1–2.4(m, 10H), 2.4–3.0(m, 1H), 3.5–3.8(m, 2H), 3.75(s, 3H), 3.8–4.4(m, 3H), 5.5–6.1 (m, 3H), 6.8–7.5(m, 8H) |
| 219 | 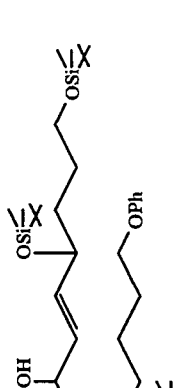 | 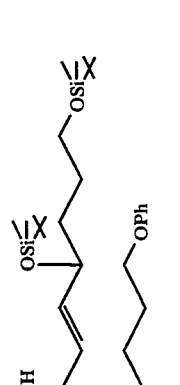 | 55 | 0–0.2(m, 21H), 0.90(s, 18H), 0.7–1.0(m, 3H), 1.1–2.4(m, 16H), 2.4–3.0(m, 1H), 3.5–3.8 (m, 2H), 3.77(s, 3H), 3.8–4.4 (m, 3H), 5.5–6.0(m, 3H), 6.8–7.5(m, 7H) |
| 220 | 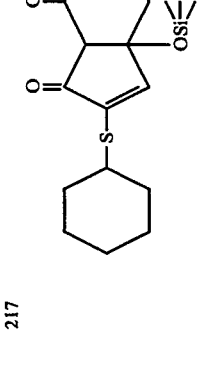 | 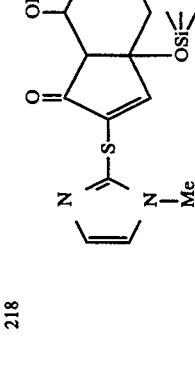 | 31 | 0–0.1(m, 6H), 0.86(s, 9H), 1.0–2.0(m, 11H), 2.0–2.9(m, 6H), 3.66(s, 3H), 3.77(s, 3H), 3.6–4.0(m, 1H), 5.4–5.8(m, 3H), 6.83(d, 1H, J=2.8Hz), 7.1–7.7(m, 5H) |

TABLE 16-continued

| Ex. No. | Starting compd. (2-Substituted-2-cyclopentenones) | 2-Substituted-2-cyclopentenones | Yield (%) | NMR(δ, CDCl₃) |
|---|---|---|---|---|
| 221 | | | 28 | 0–0.2(m, 21H), 0.89(s, 18H), 1.0–2.0(m, 10H), 2.37(s, 3H), 2.5–3.0(m, 1H), 3.5–3.7(m, 2H), 3.78(s, 3H), 3.8–4.2(m, 3H), 5.3–6.1(m, 3H), 6.6–7.1(m, 4H), 7.1–7.4(m, 2H) |
| 222 | | | 25 | 0–0.2(m, 21H), 1.0–2.0(m, 10H), 2.5–3.0(m, 1H), 3.5–3.7(m, 2H), 3.74(s, 3H), 3.77(s, 3H), 3.8–4.3(m, 3H), 5.3–6.2(m, 3H), 6.7–8.5(m, 8H), 0.88 (s, 18H) |
| 223 | | | 76 | 0–0.1(m, 6H), 0.89(s, 9H), 1.0–3.0(m, 29H), 3.64(s, 3H), 3.7–4.0(m, 1H), 4.6–5.1(m, 1H), 5.3–5.9(m, 3H), 6.94(d, 1H, J=2.8Hz), 7.1–7.5(m, 5H) |
| 224 | | | 53 | 0–0.2(m, 12H), 0.88(s, 18H), 1.22(d, 1H, J=5.9Hz), 1.1–2.3(m, 12H), 2.33(s, 3H), 2.5–3.0(m, 1H), 3.4–3.7(m, 2H), 3.8–4.2(m, 3H), 4.4–5.0(m, 1H), 5.3–6.0(m, 3H), 6.7–7.1(m, 4H), 7.1–7.4(m, 2H) |
| 225 | | | 59 | 0–0.2(m, 12H), 0.89(s, 18H), 1.23(d, 1H, J=6.1Hz), 1.1–2.3(m, 12H), 2.5–3.0(m, 1H), 3.4–3.7(m, 2H), 3.76(s, 3H), 3.8–4.2(m, 3H), 4.5–5.0(m, 1H), 5.4–6.1(m, 3H), 6.7–7.4(m, 8H) |

TABLE 16-continued

| Ex. No. | Starting compd. (2-Substituted-2-cyclopentenones) | 2-Substituted-2-cyclopentenones | Yield (%) | NMR(δ, CDCl₃) |
|---|---|---|---|---|
| 226 | | | 43 | 0–0.2(m, 12H), 0.87(s, 9H), 0.90(s, 9H), 1.23(d, 1H, J=6.0 Hz), 1.3–1.6(m, 4H), 2.35(s, 3H), 2.6–3.0(m, 1H), 3.4–3.7 (m, 2H), 4.0–4.2(m, 1H), 4.4–4.9(m, 1H), 5.4–5.9(m, 3H), 6.97(d, 1H, J=3.3Hz), 7.1–7.5 (m, 5H) |
| 227 | | | 80 | 0–0.15(m, 21H), 0.89(s, 18H), 1.21(d, 1H, J=6.4Hz), 1.1–2.1 (m, 10H), 2.29(s, 3H), 2.5–3.0 (m, 1H), 3.4–3.7(m, 2H), 3.8–4.2(m, 3H), 4.4–5.0(m, 1H), 5.3–6.1(m, 3H), 6.7–7.1(m, 4H), 7.1–7.4(m, 2H) |
| 228 | | | 77 | 0–0.2(m, 21H), 0.90(s, 18H), 1.24(d, 1H, J=6.1Hz), 1.1–2.3 (m, 10H), 2.5–3.0(m, 1H), 3.4–3.7(m, 2H), 3.8–4.2(m, 3H), 4.5–5.0(m, 1H), 5.4–6.0(m, 3H), 6.7–7.1(m, 4H), 7.1–7.4 (m, 7H) |
| 229 | | | 63 | 0–0.2(m, 21H), 0.89(s, 18H), 1.25(d, 6H, J=6.4Hz), 1.1–2.4 (m, 21H), 2.5–3.0(m, 1H), 3.4–3.7(m, 2H), 3.8–4.2(m, 3H), 4.5–5.0(m, 1H), 5.3–6.0(m, 3H), 6.7–7.1(m, 4H), 7.1–7.4 (m, 2H) |

TABLE 16-continued

| Ex. No. | Starting compd. (2-Substituted-2-cyclopentenones) | 2-Substituted-2-cyclopentenones | Yield (%) | NMR(δ, CDCl$_3$) |
|---|---|---|---|---|
| 230 | | | 90 | 0.–0.2(m, 21H), 0.91(s, 18H), 1.28(d, 6H, J=6.2Hz), 1.0–2.4 (m, 10H), 2.5–3.0(m, 1H), 3.5–3.8(m, 2H), 3.73(s, 3H), 3.74 (s, 3H), 3.8–4.3(m, 3H), 4.4–5.1(m, 1H), 5.3–6.2(m, 3H), 6.8–7.5(m, 8H) |
| 231 | | | 69 | 0–0.2(m, 21H), 0.90(s, 18H), 0.7–1.0(m, 3H), 1.25(d, 6H, J= 6.0Hz), 1.0–2.3(m, 16H), 2.5–3.0(m, 1H), 3.5–3.8(m, 2H), 3.75(s, 3H), 3.77(s, 3H), 3.8–4.3(m, 3H), 4.5–5.1(m, 1H), 5.3–6.1(m, 3H), 6.8–7.5(m, 7H) |

TABLE 17

| Ex. No. | Starting Material 2-Substituted-2-cyclopentenones | organic iodides | 2-Substituted-2-cyclopentenones | Yield (%) | NMR (δ, CDCl₃) |
|---|---|---|---|---|---|
| 232 | (MeS-substituted cyclopentenone with OPh and OSi side chains) | (iodide with OSi groups) | (product with MeS, OSi, OPh chains) | 31 | 0-0.15(m, 21H), 0.89(s, 18H), 1.1-2.0(m, 10H), 2.0-2.8(m, 3H), 2.33(s, 3H), 3.4-3.7(m, 2H), 3.8-4.2(m, 3H), 5.4-5.8(m, 2H), 6.7-7.1(m, 4H), 7.1-7.4(m, 2H) |
| 233 | Same as above | (iodide with COOMe, alkyne) | (product with MeS, COOMe) | 56 | 0.12(s, 9H), 1.3-2.9(m, 15H), 2.33(s, 3H), 3.66(s, 3H), 3.97 (t, 2H, J=5.8Hz), 6.7-7.1(m, 4H), 7.1-7.4(m, 2H) |
| 234 | (PhS-substituted cyclopentenone) | Same as above | (product with PhS, COOMe) | 49 | 0.10(s, 9H), 1.3-2.9(m, 15H), 3.69(s, 3H), 3.95(t, 2H, J=6.0 Hz), 6.7-7.1(m, 4H), 7.1-7.6(m, 7H) |
| 235 | (cyclohexyl-S substituted cyclopentenone) | Same as above | (product with cyclohexyl-S, COOMe) | 53 | 0.11(s, 9H), 1.3-2.9(m, 26H), 3.68(s, 3H), 3.96(t, 2H, J=6.1 Hz), 6.7-7.1(m, 4H), 7.1-7.4(m, 2H) |
| 236 | (N-methylimidazole-S substituted cyclopentenone) | Same as above | (product with imidazole-S, COOMe) | 36 | 0.10(s, 9H), 1.3-2.9(m, 15H), 3.65(s, 3H), 3.69(s, 3H), 3.95 (t, 2H, J=6.2Hz), 6.7-7.4(m, 8H) |
| 237 | (N-methylimidazole-S substituted cyclopentenone with propyl) | Same as above | (product) | 33 | 0.10(s, 9H), 0.7-1.0(m, 3H), 1.3-2.9(m, 21H), 3.66(s, 3H), 3.70(s, 3H), 3.96(t, 2H, J=6.1 Hz), 6.7-7.4(m, 7H) |

TABLE 18

| Ex. No. | Starting compd. (2-Substituted-2-cyclopentenones) | 2-Substituted-2-cyclopentenones | Yield (%) | NMR (δ, CDCl₃) |
|---|---|---|---|---|
| 238 | (structure) | (structure) | 78 | 0(3H, s), 0.02(3H, s), 0.87 (9H, s), 0.7–1.1(3H, brt), 1.1–2.5(29H, m), 3.65(3H, s), 3.9–4.1(2H, m), 5.38(1H, dd, J=7.5 Hz), 5.65(1H, dd, J=15.6Hz), 6.5–6.8(2H, m) |
| 239 | (structure) | (structure) | 75 | 0–0.1(6H, m), 0.89(9H, s), 0.7–1.1(3H, brt), 1.1–2.6(18H, m), 3.68(3H, s), 3.9–4.1(2H, m), 5.3–5.8(2H, m), 6.5–6.9 (2H, m), 7.2–8.1(4H, m) |
| 240 | (structure) | (structure) | 52 | 0–0.1(6H, m), 0.90(9H, s), 0.7–1.1(3H, brt), 1.1–2.5(18H, m), 3.69(3H, s), 3.9–4.1(2H, m), 4.1(3H, s), 5.5–5.9(2H, m), 6.5–7.0(2H, m) |
| 241 | (structure) | (structure) | 67 | 0–0.3(m, 12H), 0.90(s, 18H), 1.1–2.0(m, 10H), 3.4–3.8(m, 3H), 3.70(s, 3H), 3.8–4.1(m, 2H), 4.1–4.5(m, 1H), 6.0–6.8 (m, 2H), 6.8–7.5(m, 9H) |
| 242 | (structure) | (structure) | 71 | 0–0.1(6H, m), 0.88(9H, s), 1.0–2.0(11H, m), 2.0–3.0(4H, m), 3.67(3H, s), 3.8–4.3(3H, m), 4.6–4.9(1H, m), 5.3–5.8(2H, m), 6.0–6.5(2H, m), 6.6–7.1 (2H, m), 7.2–7.4(1H, m) |

| | | |
|---|---|---|
| 243 | 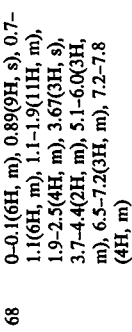 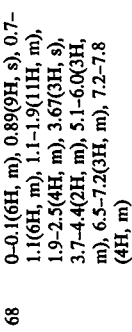 | 0-0.1(6H, m), 0.89(9H, s), 0.7-1.1(6H, m), 1.1-1.9(11H, m), 1.9-2.5(4H, m), 3.67(3H, s), 3.7-4.4(2H, m), 5.1-6.0(3H, m), 6.5-7.2(3H, m), 7.2-7.8 (4H, m) | 68 |
| 244 | 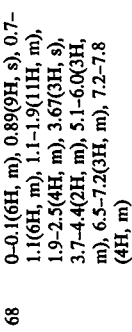 | 0-0.2(m, 12H), 0.89(s, 18H), 1.0-2.1(m, 15H), 3.4-3.8(m, 3H), 3.68(s, 3H), 4.1-4.5(m, 1H), 6.0-6.8(m, 2H), 6.8-7.4 (m, 4H) | 52 |
| 245 | 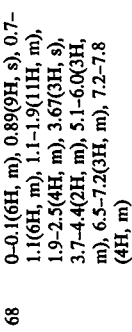 | 0-0.1(m, 6H), 0.90(s, 9H), 0.7-1.1(m, 6H), 1.1-2.8(m, 24H), 2.33(s, 3H), 3.63(s, 3H), 3.8-4.1(m, 2H), 5.3-5.9(m, 2H), 6.6-6.8(m, 1H) | 89 |
| 246 | 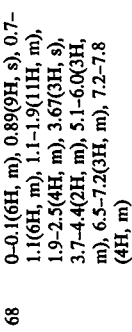 | 0-0.1(m, 6H), 0.89(s, 9H), 0.7-1.1(m, 6H), 1.1-2.9(m, 29H), 3.67(s, 3H), 3.7-4.1(m, 2H), 5.4-5.7(m, 2H), 6.6-6.9(m, 1H) | 75 |
| 247 | 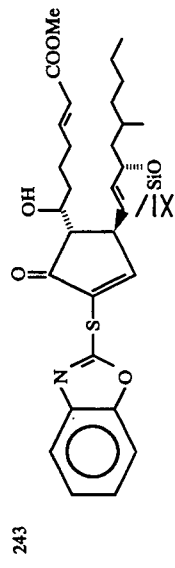 | 0-0.1(m, 6H), 0.88(s, 9H), 0.7-1.1(m, 6H), 1.1-3.0(m, 31H), 3.67(s, 3H), 3.7-4.1(m, 2H), 5.4-5.8(m, 2H), 6.6-6.9(m, 1H) | 78 |
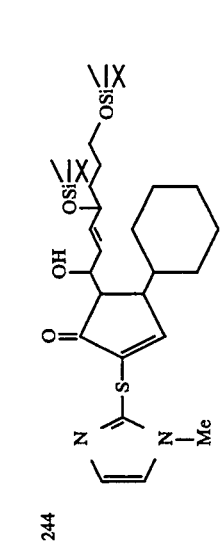
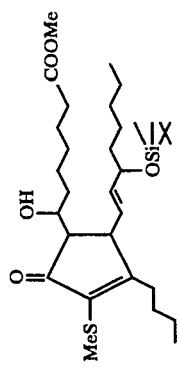
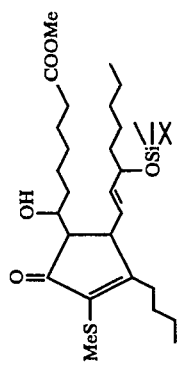
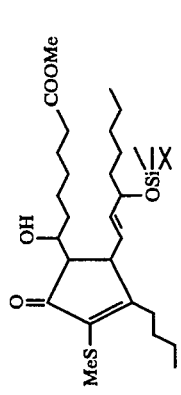

| | | | |
|---|---|---|---|
| 248 | 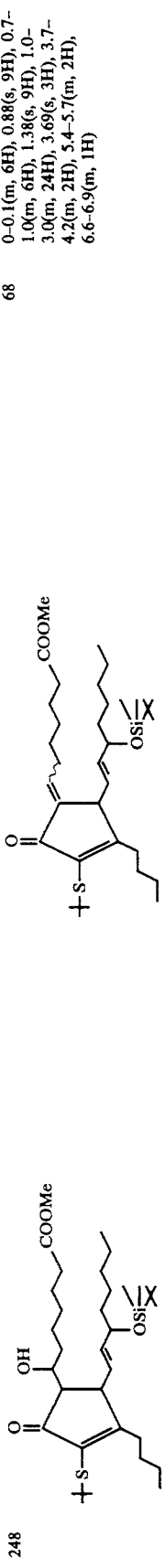 | 68 | 0-0.1(m, 6H), 0.88(s, 9H), 0.7-1.0(m, 6H), 1.38(s, 9H), 1.0-3.0(m, 24H), 3.69(s, 3H), 3.7-4.2(m, 2H), 5.4-5.7(m, 2H), 6.6-6.9(m, 1H) |
| 249 | 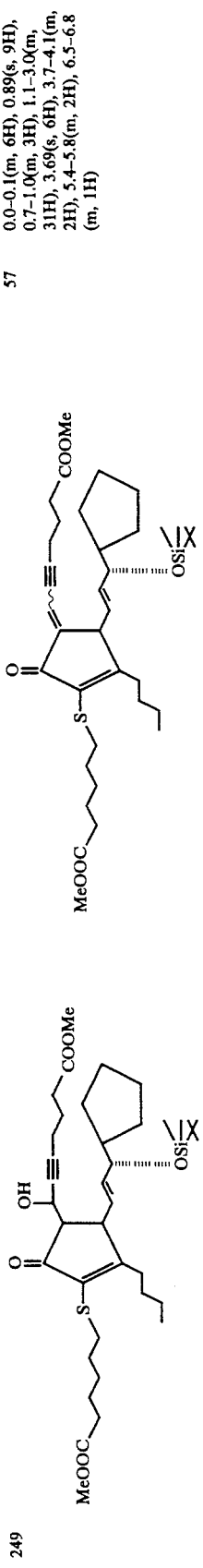 | 57 | 0.0-0.1(m, 6H), 0.89(s, 9H), 0.7-1.0(m, 3H), 1.1-3.0(m, 31H), 3.69(s, 6H), 3.7-4.1(m, 2H), 5.4-5.8(m, 2H), 6.5-6.8 (m, 1H) |
| 250 | 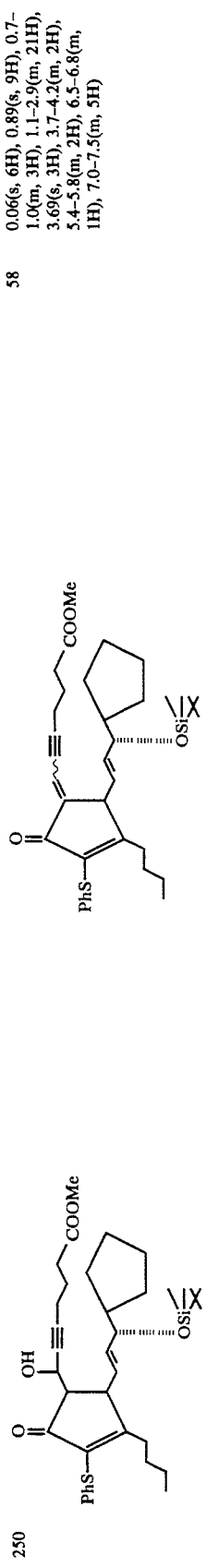 | 58 | 0.06(s, 6H), 0.89(s, 9H), 0.7-1.0(m, 3H), 1.1-2.9(m, 21H), 3.69(s, 3H), 3.7-4.2(m, 2H), 5.4-5.8(m, 2H), 6.5-6.8(m, 1H), 7.0-7.5(m, 5H) |
| 251 | 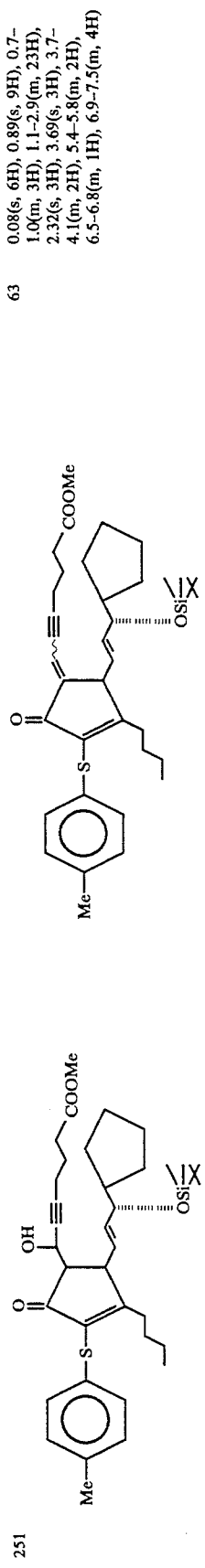 | 63 | 0.08(s, 6H), 0.89(s, 9H), 0.7-1.0(m, 3H), 1.1-2.9(m, 23H), 2.32(s, 3H), 3.69(s, 3H), 3.7-4.1(m, 2H), 5.4-5.8(m, 2H), 6.5-6.8(m, 1H), 6.9-7.5(m, 4H) |
| 252 | 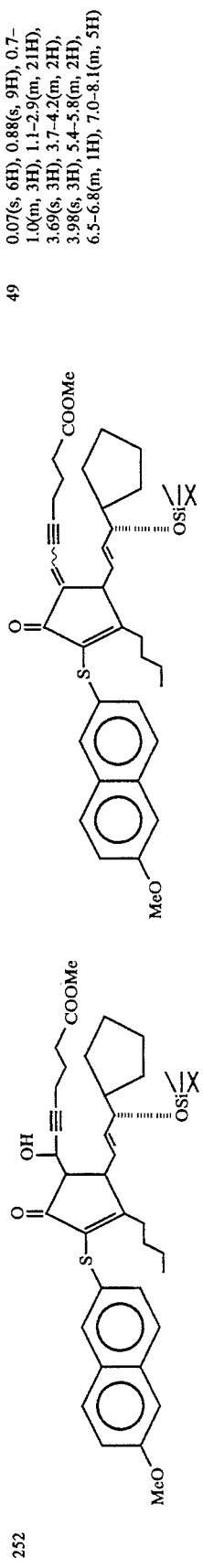 | 49 | 0.07(s, 6H), 0.88(s, 9H), 0.7-1.0(m, 3H), 1.1-2.9(m, 21H), 3.69(s, 3H), 3.7-4.2(m, 2H), 3.98(s, 3H), 5.4-5.8(m, 2H), 6.5-6.8(m, 1H), 7.0-8.1(m, 5H) |

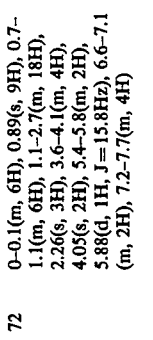
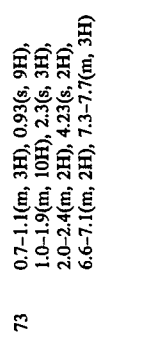
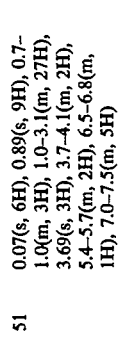
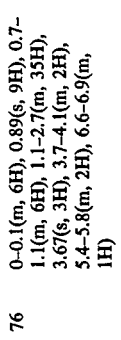
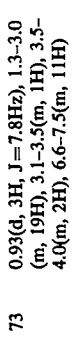
| | | |
|---|---|---|
| 253 | 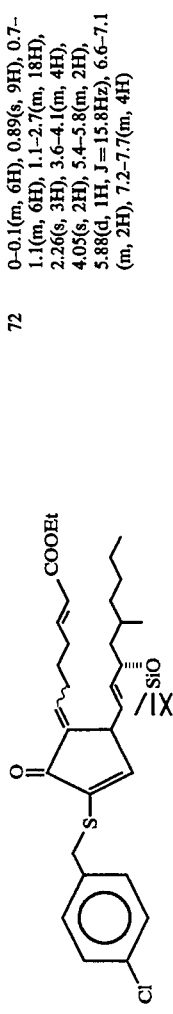 | 72 | 0-0.1(m, 6H), 0.89(s, 9H), 0.7-1.1(m, 6H), 1.1-2.7(m, 18H), 2.26(s, 3H), 3.6-4.1(m, 4H), 4.05(s, 2H), 5.4-5.8(m, 2H), 5.88(d, 1H, J=15.8Hz), 6.6-7.1(m, 2H), 7.2-7.7(m, 4H) |
| 254 | | 73 | 0.7-1.1(m, 3H), 0.93(s, 9H), 1.0-1.9(m, 10H), 2.3(s, 3H), 2.0-2.4(m, 2H), 4.23(s, 2H), 6.6-7.1(m, 2H), 7.3-7.7(m, 3H) |
| 255 | 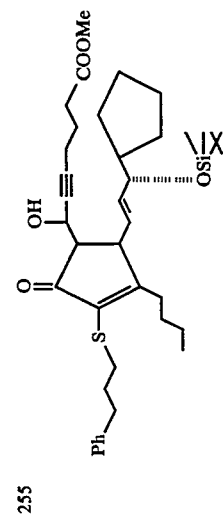 | 51 | 0.07(s, 6H), 0.89(s, 9H), 0.7-1.0(m, 3H), 1.0-3.1(m, 27H), 3.69(s, 3H), 3.7-4.1(m, 2H), 5.4-5.7(m, 2H), 6.5-6.8(m, 1H), 7.0-7.5(m, 5H) |
| 256 | 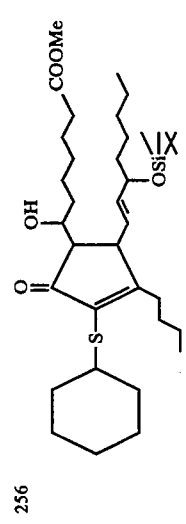 | 76 | 0-0.1(m, 6H), 0.89(s, 9H), 0.7-1.1(m, 6H), 1.1-2.7(m, 35H), 3.67(s, 3H), 3.7-4.1(m, 2H), 5.4-5.8(m, 2H), 6.6-6.9(m, 1H) |
| 257 | 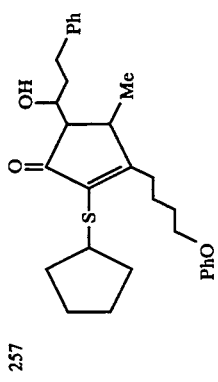 | 73 | 0.93(d, 3H, J=7.8Hz), 1.3-3.0(m, 19H), 3.1-3.5(m, 1H), 3.5-4.0(m, 2H), 6.6-7.5(m, 11H) |
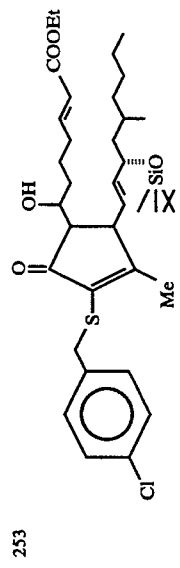

| | |
|---|---|
| 59 | 0-0.1(m, 6H), 0.88(s, 9H), 0.7-1.0(m, 6H), 1.0-3.0(m, 24H), 3.68(s, 3H), 3.7-4.2(m, 2H), 5.4-5.8(m, 2H), 6.6-6.9(m, 1H), 7.2-8.1(m, 4H) |
| 72 | 0-0.1(m, 6H), 0.87(s, 9H), 0.7-1.0(m, 6H), 1.0-3.0(m, 24H), 3.67(s, 3H), 3.68(s, 3H), 3.6-4.2(m, 2H), 5.4-5.8(m, 2H), 6.6-6.9(m, 1H), 7.0-7.3(m, 2H) |
| 71 | 0-0.1(m, 6H), 0.88(s, 9H), 0.7-1.1(m, 6H), 1.1-2.9(m, 24H), 2.45(s, 3H), 3.68(s, 3H), 3.6-4.2(m, 2H), 5.4-5.8(m, 2H), 6.6-7.1(m, 2H), 8.30(d, 1H, J=5.0Hz) |
| 65 | 0-0.1(m, 6H), 0.88(s, 9H), 0.7-1.0(m, 3H), 1.0-3.1(m, 21H), 3.69(s, 3H), 3.7-4.3(m, 4H), 5.4-5.8(m, 2H), 6.0-6.5(m, 1H), 6.5-6.8(m, 1H), 7.3-7.6 (m, 1H) |
| 76 | 0.04(9H, s), 1.1-2.2(6H, m), 2.3(3H, s), 3.6-4.1(2H, m), 3.77(3H, s), 4.61(2H, s), 6.6-7.1(5H, m), 7.1-7.7(5H, m), 8.0(1H, m) |

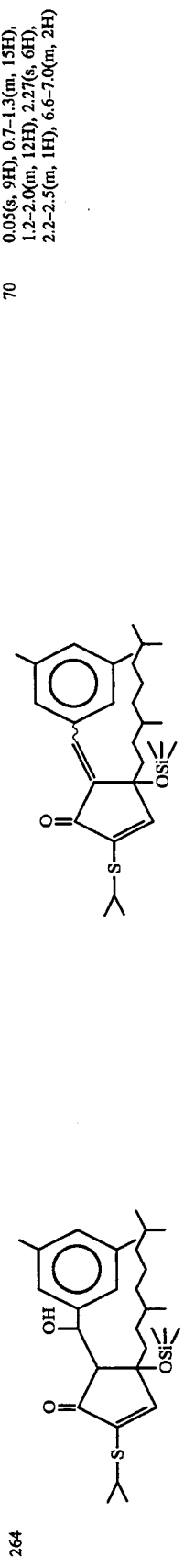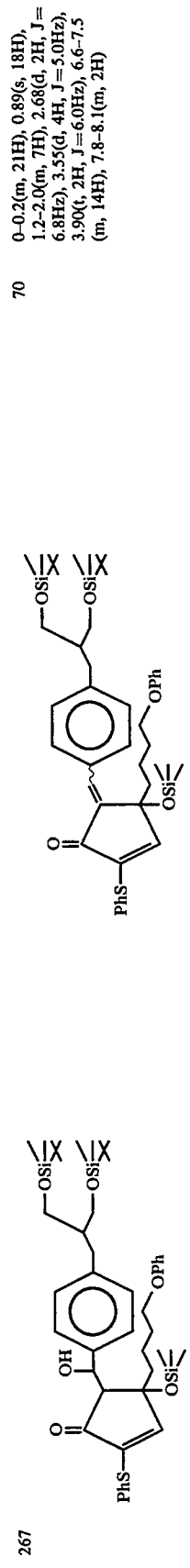

| | | |
|---|---|---|
| 63 | 0.09(s, 9H), 1.1–1.8(m, 6H), 3.90(s, 3H), 3.7–4.1(m, 4H), 6.6–7.7(m, 14H), 7.9–8.1(m, 1H) | |
| 68 | 0.09(s, 9H), 0.7–1.0(m, 3H), 1.1–2.1(m, 8H), 2.4–2.9(m, 2H), 3.79(s, 6H), 3.7–4.25(m, 4H), 6.5–7.8(m, 13H) | |
| 51 | 0.09(s, 9H), 1.37(s, 9H), 1.2–2.0(m, 6H), 2.2–2.7(m, 6H), 3.80(s, 6H), 6.5–7.5(m, 14H) | |
| 95 | 0–0.2(21H, m), 0.89(18H, s), 1.0–2.3(20H, m), 2.3–2.8(1H, m), 3.4–3.7(2H, m), 3.7–4.1 (2H, m), 4.1–4.5(1H, m), 5.6–6.2(2H, m), 6.3–7.1(4H, m), 7.1–8.0(3H, m) | |
| 74 | 0.03(9H, s), 1.1–2.5(27H, m), 3.68(3H, s), 3.9(2H, t, J=6.0 Hz), 6.4–6.7(2H, m), 6.7–7.0 (3H, m), 7.1–7.4(2H, m) | |

268, 269, 270, 271, 272

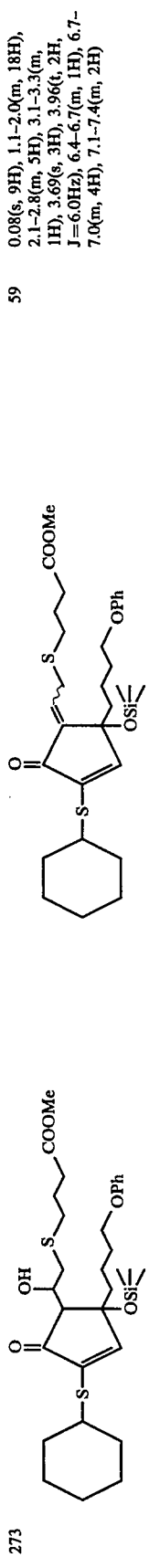

| | | |
|---|---|---|
| 278 | [structure] | 73 | 0.04(s, 9H), 1.2-2.0(m, 20H), 2.1-2.5(m, 5H), 3.83(s, 6H), 6.3-7.3(m, 6H) |
| 279 | [structure] | 89 | 0.05(s, 9H), 0.7-1.0(m, 3H), 1.1-2.0(m, 16H), 2.1-2.5(m, 3H), 3.95(t, 2H, J=6.0Hz), 6.4-7.1(m, 5H), 7.4-7.4(m, 2H) |
| 280 | [structure] | 60 | 0.10(s, 9H), 1.1-2.0(m, 16H), 2.1-2.6(m, 5H), 3.75(s, 3H), 3.93(t, 2H, J=6.2Hz), 6.3-7.5 (m, 11H) |
| 281 | [structure] | 63 | 0.09(s, 9H), 0.83(d, 9H, J=4.7 Hz), 0.9-2.1(m, 20H), 2.1-2.5 (m, 1H), 6.6-7.5(m, 5H), 8.0-8.1(m, 1H) |
| 282 | [structure] | 70 | 0.09(s, 9H), 1.2-2.5(m, 29H), 3.68(s, 3H), 3.8-4.1(m, 2H), 6.10(t, 1H, J=2.0Hz), 6.69(s, 1H), 6.8-7.1(m, 3H), 7.1-7.4 (m, 2H) |

| | | |
|---|---|---|
| 283 | 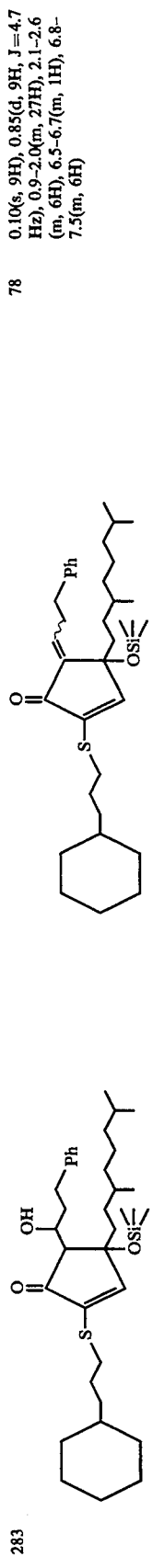 | 78 | 0.10(s, 9H), 0.85(d, 9H, J=4.7 Hz), 0.9–2.0(m, 27H), 2.1–2.6 (m, 6H), 6.5–6.7(m, 1H), 6.8–7.5(m, 6H) |
| 284 | 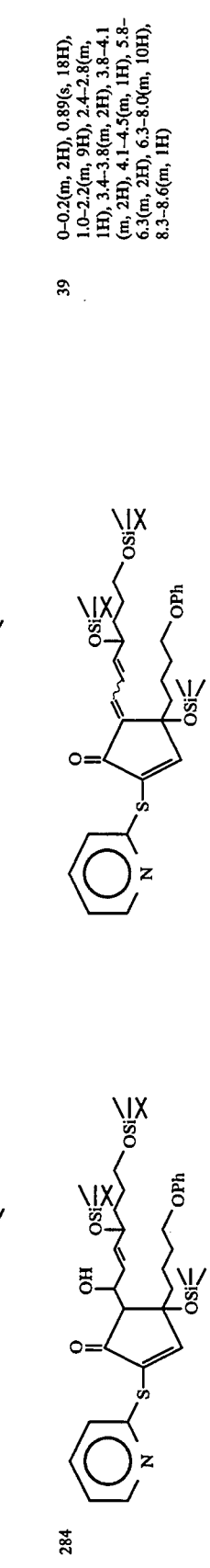 | 39 | 0–0.2(m, 2H), 0.89(s, 18H), 1.0–2.2(m, 9H), 2.4–2.8(m, 1H), 3.4–3.8(m, 2H), 3.8–4.1 (m, 2H), 4.1–4.5(m, 1H), 5.8–6.3(m, 2H), 6.3–8.0(m, 10H), 8.3–8.6(m, 1H) |
| 285 | 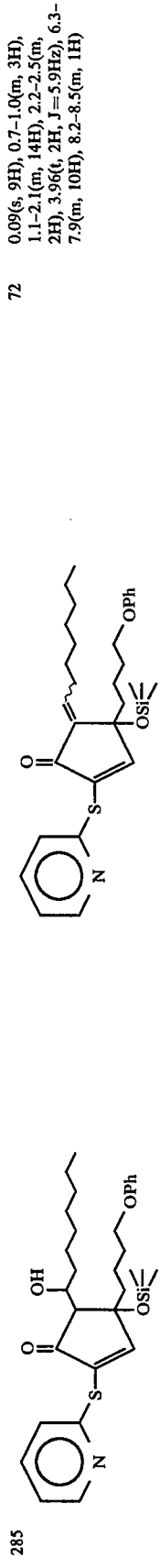 | 72 | 0.09(s, 9H), 0.7–1.0(m, 3H), 1.1–2.1(m, 14H), 2.2–2.5(m, 2H), 3.96(t, 2H, J=5.9Hz), 6.3–7.9(m, 10H), 8.2–8.5(m, 1H) |
| 286 | 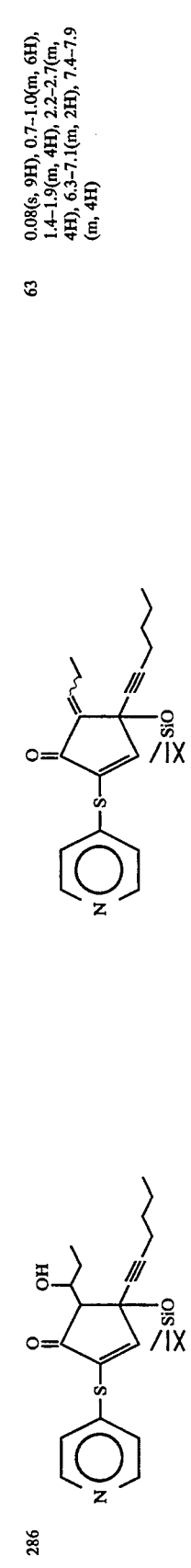 | 63 | 0.08(s, 9H), 0.7–1.0(m, 6H), 1.4–1.9(m, 4H), 2.2–2.7(m, 4H), 6.3–7.1(m, 2H), 7.4–7.9 (m, 4H) |
| 287 | 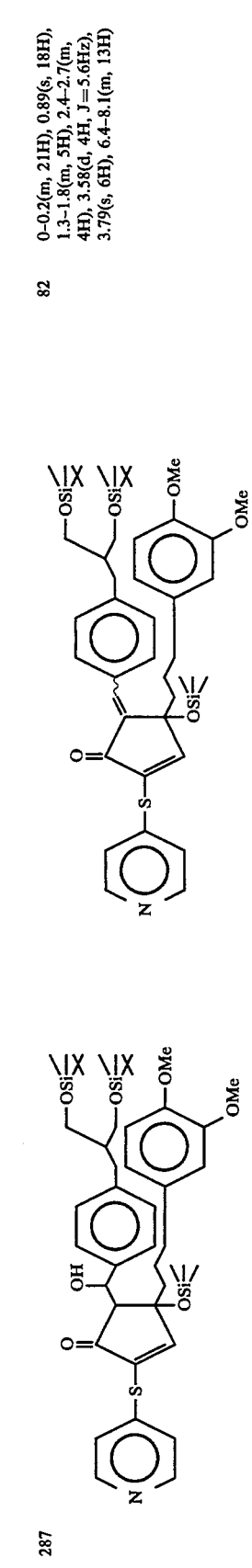 | 82 | 0–0.2(m, 21H), 0.89(s, 18H), 1.3–1.8(m, 5H), 2.4–2.7(m, 4H), 3.58(d, 4H, J=5.6Hz), 3.79(s, 6H), 6.4–8.1(m, 13H) |

| | |
|---|---|
| 83 | 0–0.2(m, 21H), 0.88(s, 9H), 0.90(s, 9H), 1.1–2.0(m, 15H), 2.2–2.6(m, 4H), 2.50(s, 3H), 3.5–3.9(m, 1H), 4.6–4.9(m, 1H), 5.4–5.8(m, 2H), 6.3–7.0(m, 3H), 8.28(d, 1H, J=5.0Hz) |
| 35 | −0.06(s, 9H), 0.7–1.0(m, 3H), 1.0–2.4(m, 12H), 3.63(s, 3H), 3.82(t, 2H, J=6.2Hz), 5.9–8.1(m, 11H) |
| 43 | −0.1–0.1(m, 15H), 0.86(s, 9H), 3.76(s, 3H), 3.7–4.0(m, 2H), 4.2–4.4(m, 2H), 6.5–7.4(m, 11H) |
| 65 | −0.05–0.15(m, 21H), 0.89(s, 18H), 1.0–2.1(m, 9H), 2.1–2.5(m, 1H), 3.4–3.8(m, 2H), 3.70(s, 3H), 3.8–4.1(m, 2H), 4.2–4.5(m, 1H), 5.9–6.3(m, 1H), 6.4–7.9(m, 10H) |
| 68 | −0.04(s, 9H), 0.03(s, 12H), 0.88(s, 18H), 1.1–2.0(m, 11H), 2.0–2.4(m, 2H), 3.54(d, 4H, J=5 Hz), 3.69(s, 3H), 3.90(t, 2H, J=6Hz), 6.5–7.4(m, 9H) |
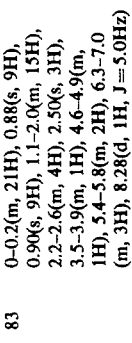
288
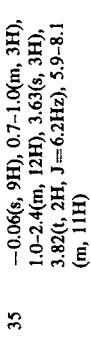
289
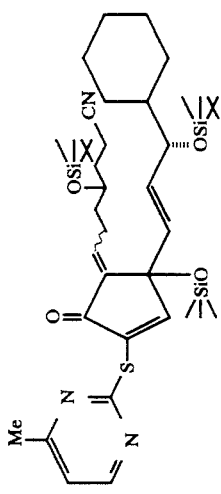
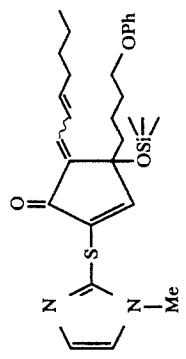
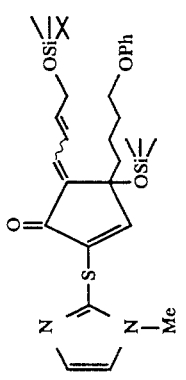
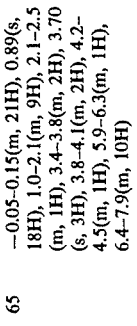
290
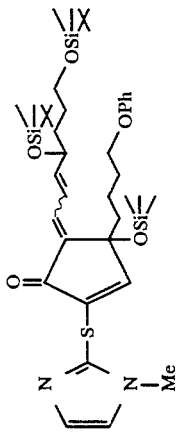
291
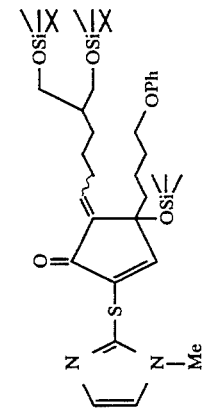
292
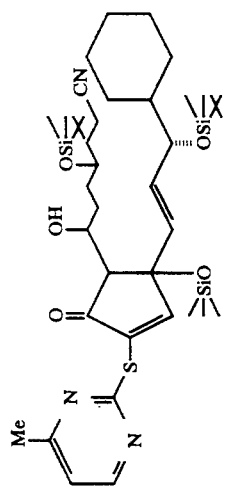
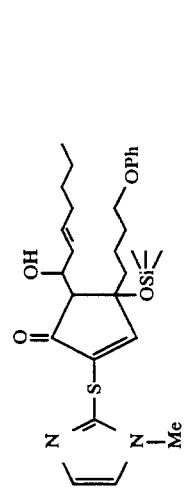
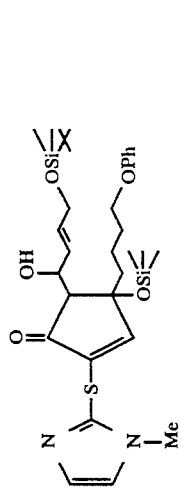
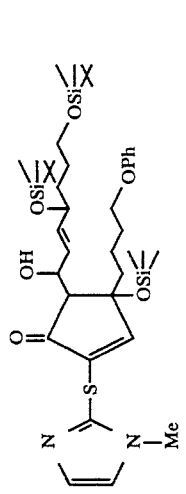
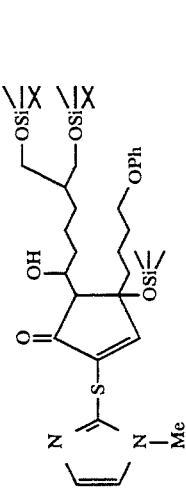

-continued
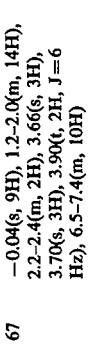
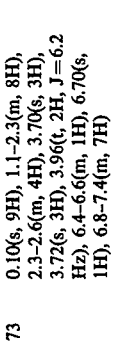
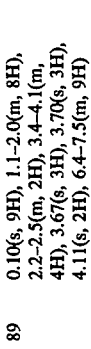
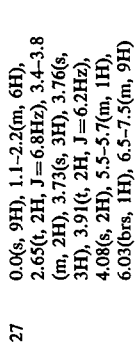
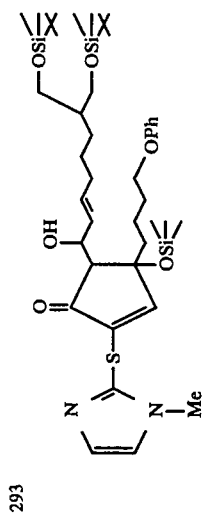
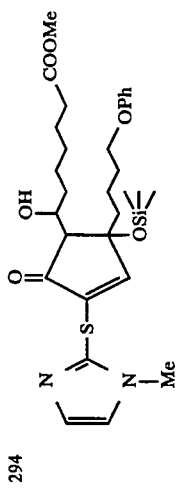
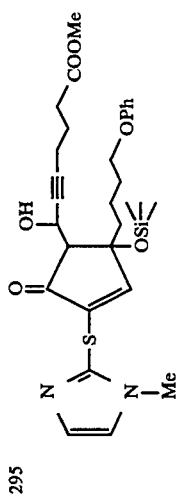
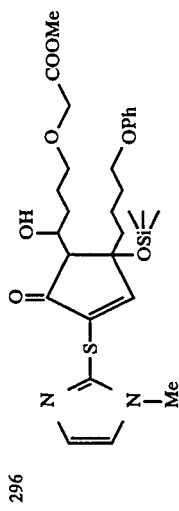
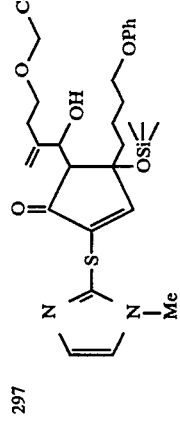
| | | |
|---|---|---|
| 293 | 68 | −0.04(s, 9H), 0.03(s, 12H), 0.88(s, 18H), 1.1–2.0(m, 11H), 2.0–2.4(m, 2H), 3.54(d, 4H, J=5 Hz), 3.69(s, 3H), 3.90(t, 2H, J=6Hz), 6.5–7.4(m, 9H) |
| 294 | 67 | −0.04(s, 9H), 1.2–2.0(m, 14H), 2.2–2.4(m, 2H), 3.66(s, 3H), 3.70(s, 3H), 3.90(t, 2H, J=6 Hz), 6.5–7.4(m, 10H) |
| 295 | 73 | 0.10(s, 9H), 1.1–2.3(m, 8H), 2.3–2.6(m, 4H), 3.70(s, 3H), 3.72(s, 3H), 3.96(t, 2H, J=6.2 Hz), 6.4–6.6(m, 1H), 6.70(s, 1H), 6.8–7.4(m, 7H) |
| 296 | 89 | 0.10(s, 9H), 1.1–2.0(m, 8H), 2.2–2.5(m, 2H), 3.4–4.1(m, 4H), 3.67(s, 3H), 3.70(s, 3H), 4.11(s, 2H), 6.4–7.5(m, 7H) |
| 297 | 27 | 0.0(s, 9H), 1.1–2.2(m, 6H), 2.65(t, 2H, J=6.8Hz), 3.4–3.8 (m, 2H), 3.73(s, 3H), 3.76(s, 3H), 3.91(t, 2H, J=6.2Hz), 4.08(s, 2H), 5.5–5.7(m, 1H), 6.03(brs, 1H), 6.5–7.5(m, 9H) |

| | | |
|---|---|---|
| 46 | 0.0(s, 9H), 1.0–2.2(m, 6H), 2.68(t, 2H, J=6.6Hz), 3.45(s, 3H), 3.73(s, 3H), 3.91(t, 2H, J=6.2Hz), 4.28(t, 2H, J=6.7Hz), 5.4–5.7(m, 1H), 6.05(brs, 1H), 6.4–7.5(m, 9H) | 298 |
| 61 | 0.04(s, 9H), 1.2–2.1(m, 6H), 2.6–2.9(m, 4H), 3.80(s, 3H), 3.95(s, 3H), 3.7–4.1(m, 2H), 6.2–7.5(m, 12H) | 299 |
| 61 | 0.10(s, 9H), 1.2–1.9(m, 6H), 2.97(s, 6H), 3.68(s, 3H), 3.94(t, 2H, J=5.9Hz), 6.0–7.7(m, 15H) | 300 |
| 81 | −0.05(s, 9H), 1.1–2.0(m, 16H), 3.74(s, 3H), 3.8–4.0(m, 2H), 6.1–7.8(m, 11H) | 301 |
| 48 | −0.04(s, 9H), 1.2–2.0(m, 12H), 2.1–2.5(m, 4H), 3.72(s, 3H), 3.8–4.0(m, 2H), 6.3–7.4(m, 10H) | 302 |

| | NMR data | Structure (top) | Structure (bottom, #) |
|---|---|---|---|
| 48 | 0.09(s, 9H), 1.2–2.0(m, 6H), 2.2–2.6(m, 8H), 3.56(s, 2H), 3.69(s, 3H), 3.96(t, 2H, J=5.9 Hz), 6.4–7.4(m, 14H), 7.5–7.8 (m, 1H) | | 303 |
| 59 | 0.0(s, 9H), 1.4–1.8(m, 6H), 3.73(s, 3H), 3.94(s, 3H), 3.6–3.8(m, 2H), 6.6–7.0(m, 4H), 7.0–7.5(m, 5H), 8.03(s, 4H) | | 304 |
| 82 | 0.04(s, 12H), 0.01(s, 9H), 0.89(s, 18H), 1.2–2.2(m, 7H), 2.64(d, 2H, J=7.3Hz), 3.53(d, 4H, J=5.3Hz), 3.71(s, 3H), 3.7–4.0(m, 2H), 6.6–7.5(m, 11H), 7.8–8.1(m, 2H) | | 305 |
| 73 | 0.09(s, 9H), 0.7–1.0(m, 3H), 1.2–2.0(m, 16H), 2.1–2.5(m, 4H), 3.67(s, 3H), 3.68(s, 3H), 5.9–8.0(m, 6H) | | 306 |
| 83 | 0.04(s, 9H), 0.7–1.0(m, 3H), 1.1–2.0(m, 25H), 2.2–2.5(m, 3H), 3.69(s, 3H), 3.72(s, 3H), 6.4–6.9(m, 4H) | | 307 |

| # | Structure | Product | Yield (%) | NMR |
|---|---|---|---|---|
| 308 | 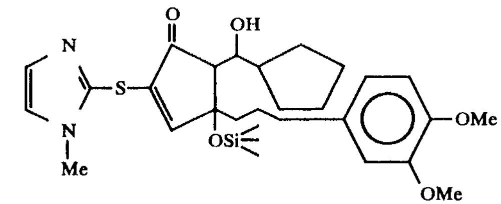 | | 71 | 0.08(s, 9H), 1.2–2.1(m, 12H), 2.2–2.5(m, 3H), 3.67(s, 3H), 3.79(s, 6H), 6.4–7.2(m, 7H) |
| 309 | 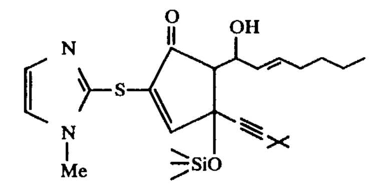 | | 59 | 0.09(s, 9H), 0.7–1.0(m, 3H), 1.06(s, 9H), 1.2–1.8(m, 4H), 2.1–2.3(m, 2H), 3.69(s, 3H), 6.0–7.4(m, 6H) |
| 310 | 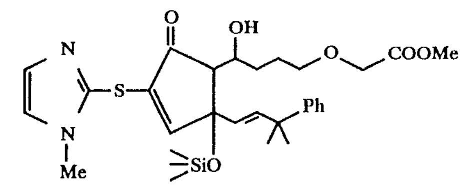 | | 72 | 0.10(s, 9H), 1.69(s, 6H), 1.5–1.9(m, 2H), 2.1–2.4(m, 2H), 3.4–3.9(m, 2H), 3.68(s, 3H), 3.73(s, 3H), 4.10(s, 2H), 5.4–5.9(m, 2H), 6.4–7.5(m, 9H) |
| 311 | 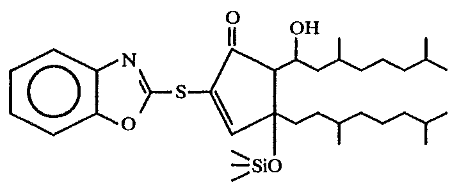 | | 72 | 0.10(s, 9H), 0.7–1.1(m, 18H), 1.1–2.0(m, 20H), 2.1–2.4(m, 2H), 6.4–6.7(m, 1H), 6.7–7.1(m, 9H), 7.2–7.8(m, 4H) |
| 312 | 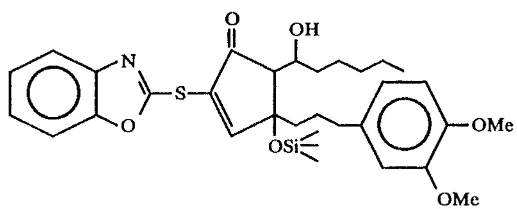 | | 58 | 0.10(s, 9H), 0.7–1.0(m, 3H), 1.2–2.0(m, 10H), 2.1–2.5(m, 4H), 3.84(s, 6H), 6.3–7.0(m, 5H), 7.2–7.8(m, 4H) |

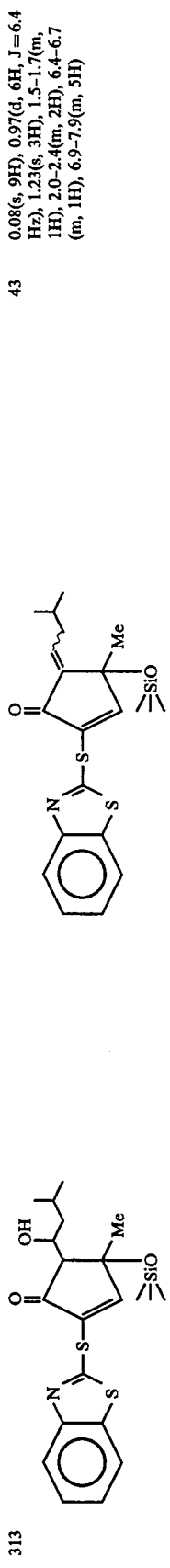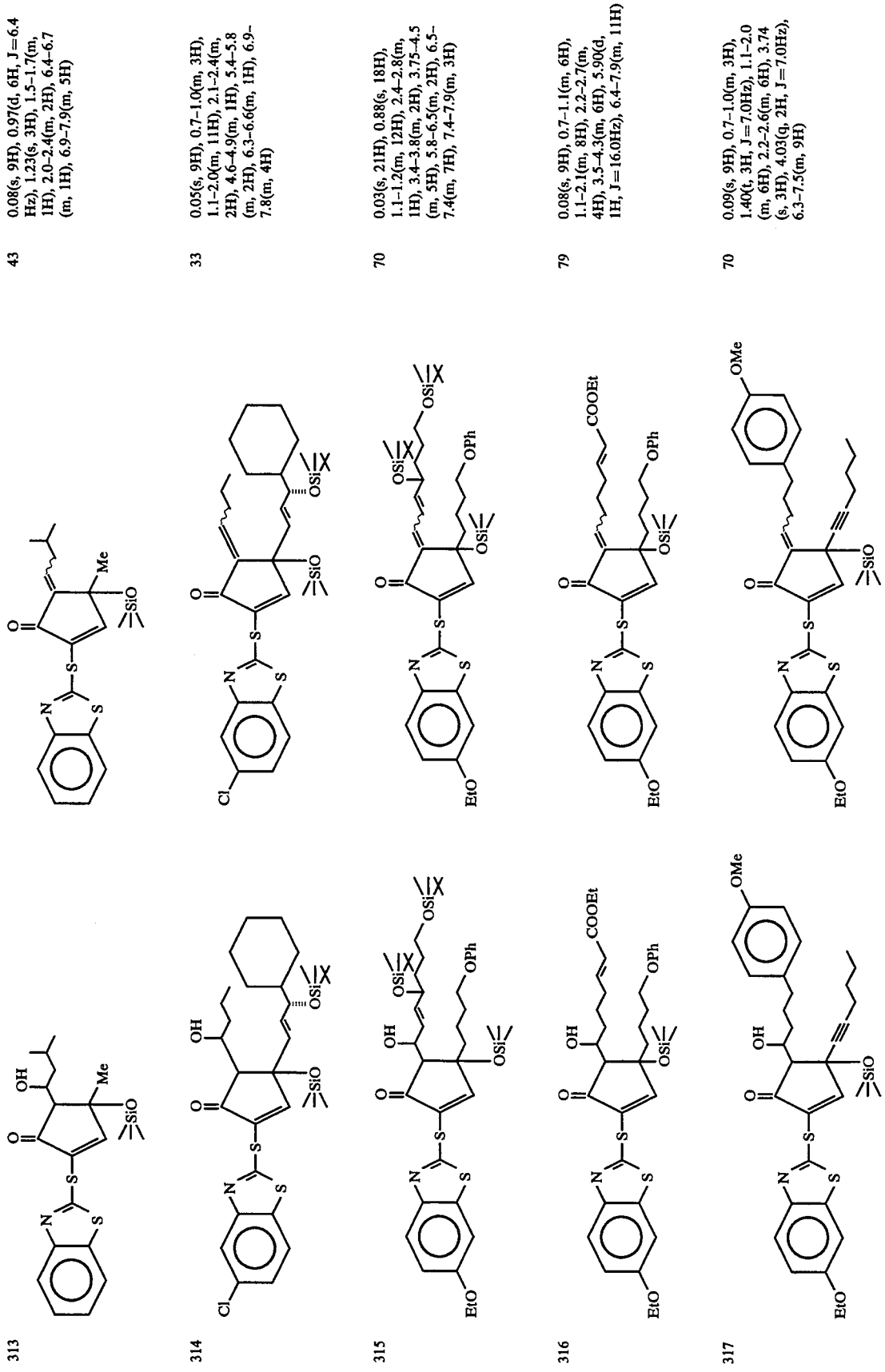

| | |
|---|---|
| 63 | 0.08(s, 9H), 1.3–2.0(m, 6H), 2.2–2.6(m, 6H), 3.69(s, 3H), 3.80(s, 6H), 4.03(s, 2H), 6.0–6.6(m, 3H), 6.70(s, 1H), 7.3–7.6(m, 1H) |
| 81 | 0.10(s, 9H), 1.09(s, 3H), 2.1–2.5(m, 4H), 3.89(s, 6H), 4.10(s, 2H), 6.0–7.1(m, 7H), 7.2–7.4(m, 1H) |
| 62 | 0–0.1(m, 21H), 0.90(s, 18H), 0.7–1.0(m, 3H), 1.1–2.1(m, 14H), 2.35(s, 3H), 2.3–2.9(m, 2H), 3.4–3.7(m, 2H), 3.97(t, 2H, J=6.2Hz), 4.1–4.4(m, 1H), 5.9–6.2(m, 1H), 6.2–6.5(m, 1H), 6.7–7.8(m, 8H) |
| 67 | 0.04(s, 9H), 0.7–1.0(m, 3H), 1.1–2.1(m, 12H), 2.36(s, 3H), 2.2–2.9(m, 6H), 3.68(s, 3H), 3.93(t, 2H, J=5.8Hz), 6.5–7.0(m, 4H), 7.1–7.4(m, 2H) |
| 42 | 0.08(s, 9H), 0.7–1.0(m, 3H), 1.2–2.1(m, 10H), 2.36(s, 3H), 2.4–2.9(m, 2H), 2.98(s, 6H), 3.96(t, 2H, J=6.0Hz), 6.0–7.7(m, 12H) |
-continued
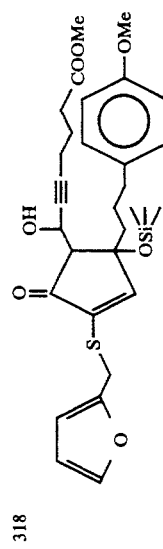
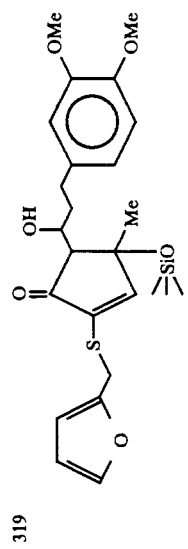
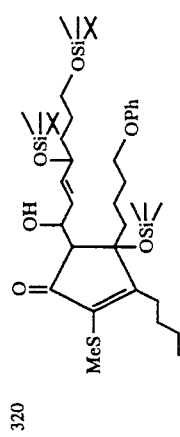
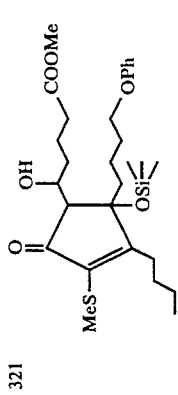
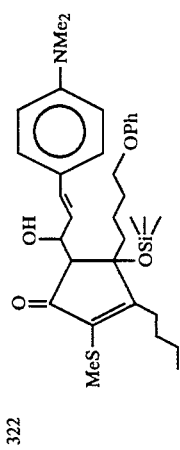

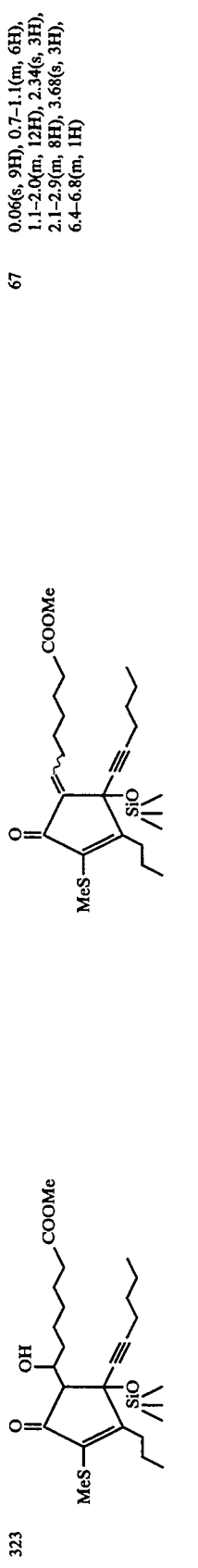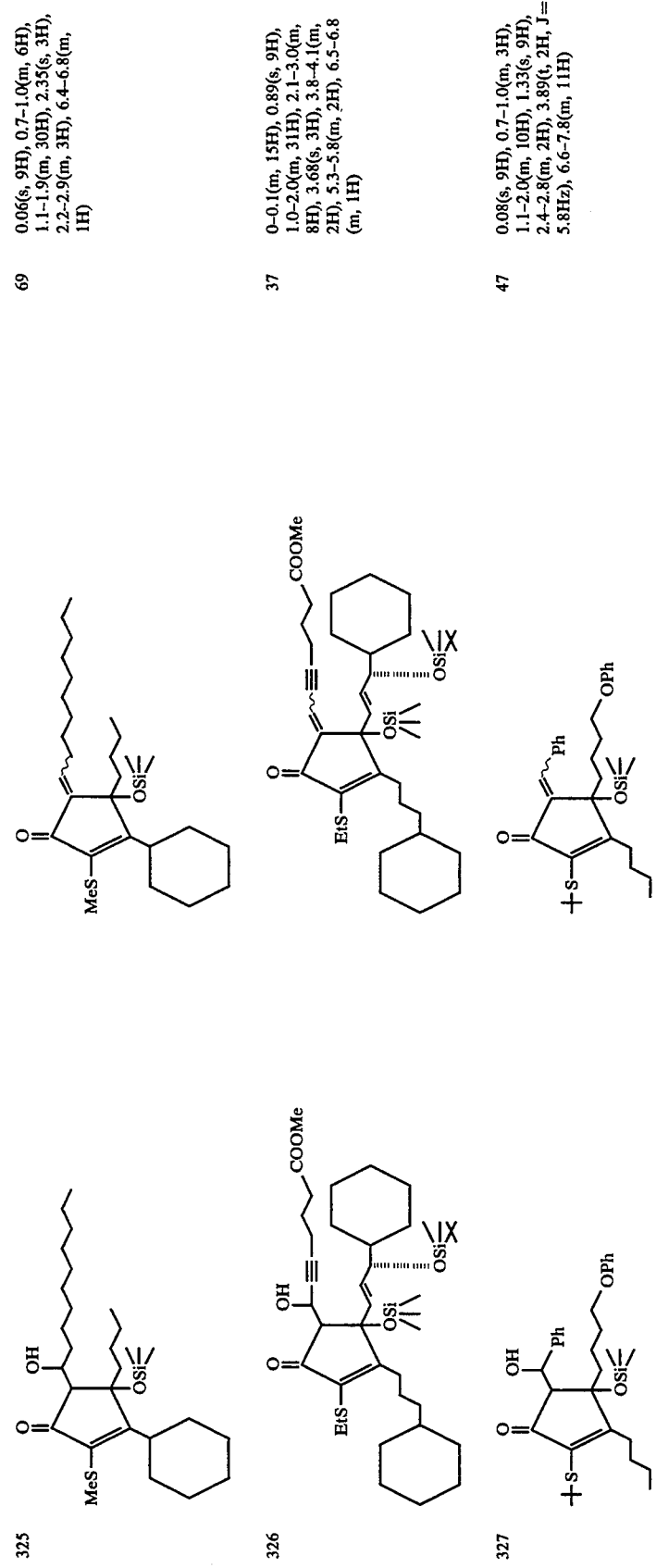

| | | |
|---|---|---|
| 328 | 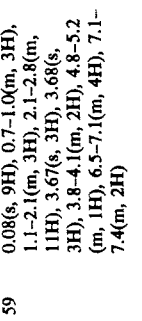 | 59 | 0.08(s, 9H), 0.7-1.0(m, 3H), 1.1-2.1(m, 3H), 2.1-2.8(m, 11H), 3.67(s, 3H), 3.68(s, 3H), 3.8-4.1(m, 2H), 4.8-5.2(m, 1H), 6.5-7.1(m, 4H), 7.1-7.4(m, 2H) |
| 329 | 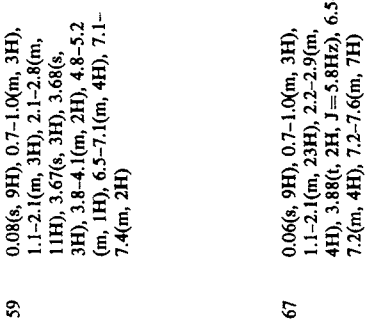 | 67 | 0.06(s, 9H), 0.7-1.0(m, 3H), 1.1-2.1(m, 23H), 2.2-2.9(m, 4H), 3.88(t, 2H, J=5.8Hz), 6.5-7.2(m, 4H), 7.2-7.6(m, 7H) |
| 330 | 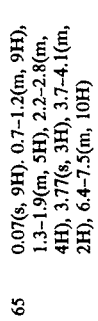 | 65 | 0.07(s, 9H), 0.7-1.2(m, 9H), 1.3-1.9(m, 5H), 2.2-2.8(m, 4H), 3.77(s, 3H), 3.7-4.1(m, 2H), 6.4-7.5(m, 10H) |
| 331 | 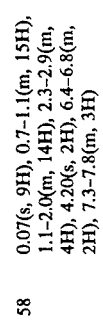 | 58 | 0.07(s, 9H), 0.7-1.1(m, 15H), 1.1-2.0(m, 14H), 2.3-2.9(m, 4H), 4.20(s, 2H), 6.4-6.8(m, 2H), 7.3-7.8(m, 3H) |
| 332 | 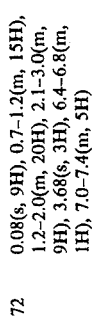 | 72 | 0.08(s, 9H), 0.7-1.2(m, 15H), 1.2-2.0(m, 20H), 2.1-3.0(m, 9H), 3.68(s, 3H), 6.4-6.8(m, 1H), 7.0-7.4(m, 5H) |
-continued
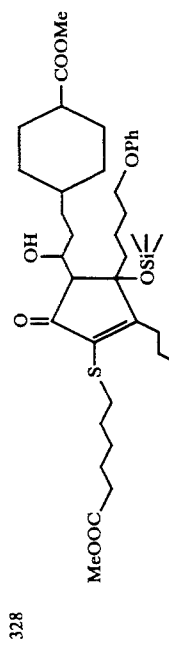
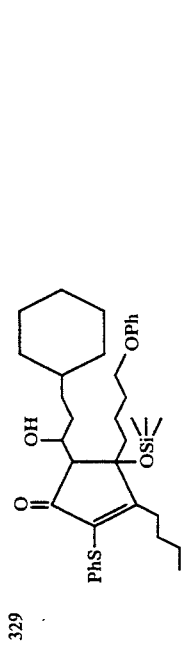
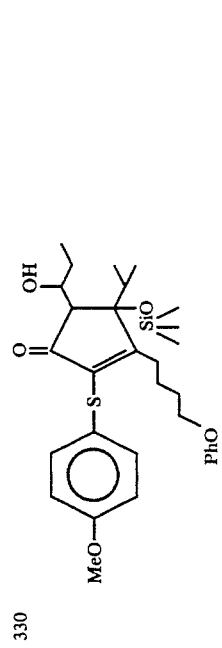
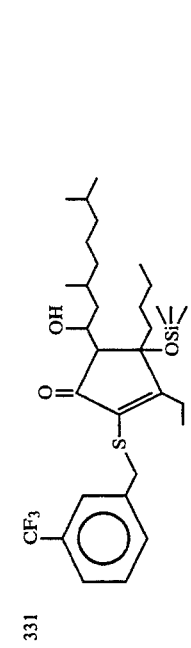
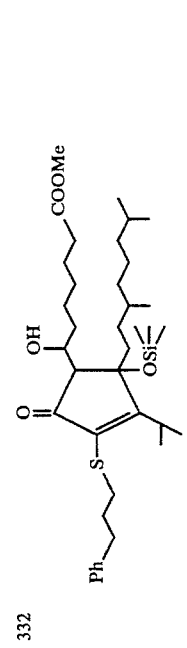

| | | |
|---|---|---|
| 333 |  |  | 68 | 0.08(s, 9H), 0.7–1.0(m, 3H), 1.1–2.0(m, 26H), 2.1–2.9(m, 7H), 3.67(s, 3H), 3.88(t, 2H, J=5.8Hz), 6.5–7.5(m, 6H) |
| 334 | 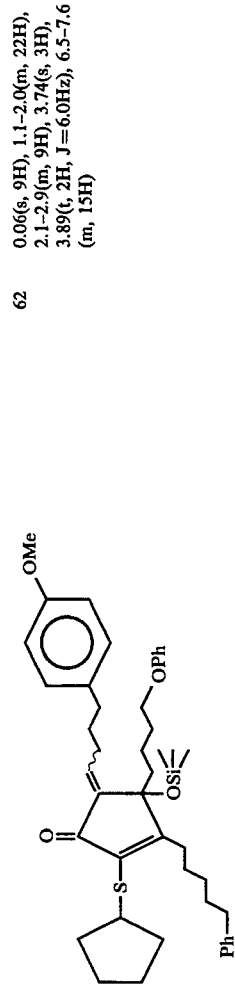 | 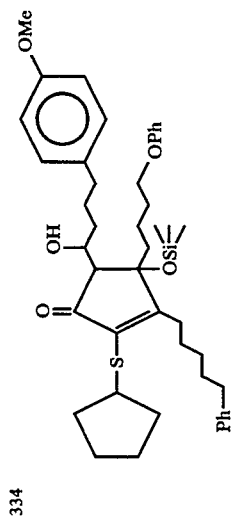 | 62 | 0.06(s, 9H), 1.1–2.0(m, 22H), 2.1–2.9(m, 9H), 3.74(s, 3H), 3.89(t, 2H, J=6.0Hz), 6.5–7.6(m, 15H) |
| 335 |  | 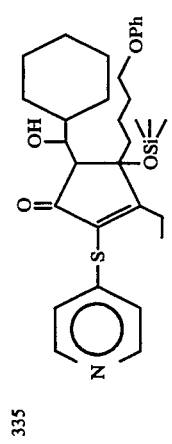 | 49 | 0.08(s, 9H), 0.7–1.0(m, 3H), 1.1–2.0(m, 16H), 2.1–2.7(m, 3H), 3.91(t, 2H, J=6.5Hz), 6.7–7.1(m, 4H), 7.1–8.1(m, 6H) |
| 336 |  | 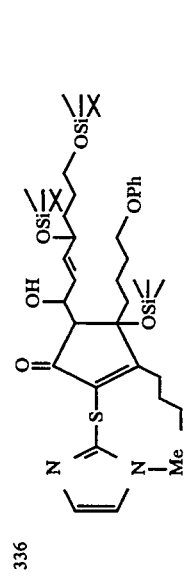 | 59 | 0–0.1(m, 21H), 0.92(s, 18H), 0.8–1.1(m, 3H), 1.3–2.2(m, 14H), 2.3–2.8(m, 2H), 3.4–3.7(m, H), 3.88(s, 3H), 3.7–4.0(m, 2H), 4.1–4.4(m, 1H), 5.9–6.2(m, 1H), 6.2–6.5(m, 1H), 6.7–7.8(m, 8H) |
| 337 | 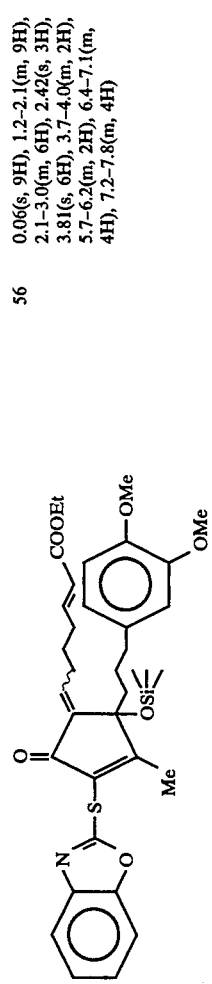 | 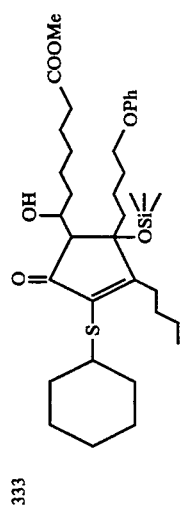 | 56 | 0.06(s, 9H), 1.2–2.1(m, 9H), 2.1–3.0(m, 6H), 2.42(s, 3H), 3.81(s, 6H), 3.7–4.0(m, 2H), 5.7–6.2(m, 2H), 6.4–7.1(m, 4H), 7.2–7.8(m, 4H) |

| | | |
|---|---|---|
| 338 | [structure: cyclopentenone with MeS, OH, CH=CH-CH(OSiX₃)-CH₂CH₂-OSiX₃] | 80 | 0-0.2(m, 18H), 0.88(s, 27H), 1.4-1.7(m, 4H), 2.36(s, 3H), 3.4-3.8(m, 2H), 4.1-4.5(m, 1H), 5.1-5.5(m, 1H), 5.8-7.8(m, 4H) |
| 339 | [structure: cyclopentenone with MeS, OH, (CH₂)n-COOMe, OSiX₃] | 36 | 0.09(s, 6H), 0.89(s, 9H), 1.1-2.5(m, 10H), 2.37(s, 3H), 3.68(s, 3H), 4.8-5.2(m, 1H), 6.5-7.1(m, 2H) |
| 340 | [structure: cyclopentenone with MeS, OH, CH=CH-C₆H₄-NMe₂, OSiX₃] | 53 | 0.09(s, 6H), 0.89(s, 9H), 2.34(s, 3H), 2.99(s, 6H), 5.0-5.4(m, 1H), 6.0-7.7(m, 8H) |
| 341 | [structure: cyclopentenone with PhS, OH, CH=CH-CH(OSiX₃)-CH₂CH₂-OSiX₃] | 58 | 0-0.2(m, 18H), 0.89(s, 18H), 0.92(s, 9H), 1.2-1.8(m, 4H), 3.4-3.8(m, 2H), 4.1-4.5(m, 1H), 5.2-5.6(m, 1H), 6.0-7.5(m, 10H) |
| 342 | [structure: cyclopentenone with cyclohexyl-S, OH, CH=CH-CH(OSiX₃)-CH₂CH₂-OSiX₃] | 70 | 0-0.3(m, 18H), 0.88(s, 18H), 0.90(s, 9H), 1.1-1.8(m, 14H), 2.2-2.6(m, 1H), 3.5-3.8(m, 2H), 4.1-4.5(m, 1H), 5.1-5.5(m, 1H), 5.9-7.6(m, 4H) |
| 343 | [structure: cyclopentenone with pyrimidinyl-S, OH, CH=CH-CH(OSiX₃)-CH₂CH₂-OSiX₃] | 66 | 0-0.2(m, 18H), 0.88(s, 18H), 0.89(s, 9H), 1.2-1.8(m, 4H), 2.47(s, 3H), 3.4-3.8(m, 2H), 4.1-4.4(m, 1H), 5.2-5.6(m, 1H), 5.9-8.4(m, 6H) |

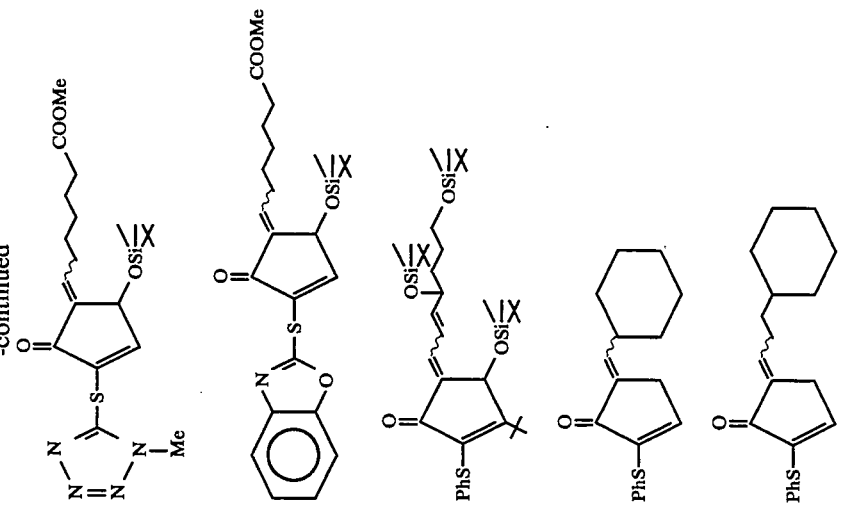
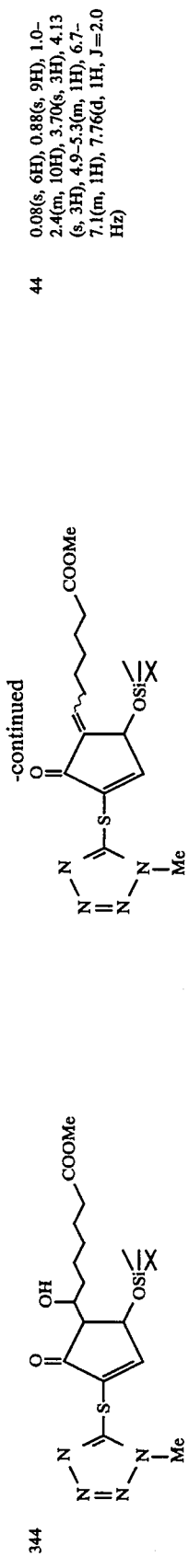
| | |
|---|---|
| 344 | 44 | 0.08(s, 6H), 0.88(s, 9H), 1.0–2.4(m, 10H), 3.70(s, 3H), 4.13(s, 3H), 4.9–5.30(m, 1H), 6.7–7.1(m, 1H), 7.76(d, 1H, J=2.0 Hz) |
| 345 | 59 | 0.04(s, 6H), 0.87(s, 9H), 1.1–2.4(m, 10H), 3.68(s, 3H), 4.9–5.4(m, 1H), 6.8–8.1(m, 6H) |
| 346 | 88 | 0–0.2(m, 18H), 0.89(s, 6H), 0.94(s, 12H), 1.4–1.8(m, 4H), 1.51(s, 9H), 3.4–3.8(m, 2H), 4.0–4.5(m, 1H), 5.34(s, 1H), 5.8–7.7(m, 8H) |
| 347 | 57 | 1.1–2.0(m, 10H), 2.2–2.5(m, 1H), 3.0–3.2(m, 2H), 6.6–6.9(m, 2H), 7.2–7.6(m, 5H) |
| 348 | 37 | 1.1–1.8(m, 13H), 2.0–2.4(m, 2H), 3.0–3.2(m, 2H), 6.6–6.9(m, 2H), 7.2–7.6(m, 5H) |

TABLE 19

| Ex. No. | Starting compd. (2-Substituted-2-cyclopentenones) | 2-Substituted-2-cyclopentenones | Yield (%) | NMR (δ, CDCl₃) |
|---|---|---|---|---|
| 349 | (structure) | (structure) | 67 | 0.7–1.1(m, 3H), 1.1–2.6(m, 32H), 3.0–3.3(m, 1H), 3.67(s, 3H), 3.7–3.9(m, 1H), 3.9–4.3 (m, 1H), 5.5–4.7(m, 2H), 6.82 (d, 1H, J=2.8Hz) |
| 350 | (structure) | (structure) | 58 | 0.7–1.0(m, 3H), 1.1–2.4(m, 21H), 3.1–3.3(m, 1H), 3.69(s, 3H), 3.7–3.9(m, 1H), 3.9–4.3 (m, 1H), 5.5–5.8(m, 2H), 6.78 (d, 1H, J=2.4Hz), 7.2–8.1(m, 4H) |
| 351 | (structure) | (structure) | 54 | 0.7–1.0(m, 3H), 1.1–2.4(m, 21H), 3.1–3.4(m, 1H), 3.69(s, 3H), 3.7–4.3(m, 2H), 4.12(s, 3H), 5.4–5.7(m, 2H), 6.82(d, 1H, J=2.7Hz) |
| 352 | (structure) | (structure) | 41 | 0.7–1.1(m 6H), 1.1–2.7(m, 18H), 3.1–3.3(m, 1H), 3.68(s, 3H), 3.7–4.0(m, 1H), 4.0–4.3 (m, 1H), 5.4–5.8(m, 2H), 5.88 (d, 1H, J=16.0Hz), 6.7–7.2(m, 2H), 7.2–7.8(m, 4H) |
| 353 | (structure) | (structure) | 71 | 1.1–2.9(m, 15H), 3.4–3.7(m, 2H), 3.67(s, 3H), 3.8–4.2(m, 2H), 4.2–4.7(m, 2H), 5.5–5.8 (m, 2H), 6.7–7.1(m, 5H), 7.1–7.5(m, 2H) |

TABLE 19-continued

| | | |
|---|---|---|
| 354 | 39 | 1.1–2.1(m, 11H), 2.1–3.0(m, 7H), 3.2–3.5(m, 1H), 3.68(s, 3H), 3.7–4.3(m, 3H), 4.6–4.9(m, 1H), 5.4–5.8(m, 2H), 6.0–6.5(m, 2H), 7.08(d, 1H, J = 3.0 Hz), 7.2–7.4(m, 1H) |
| 355 | 57 | 0.7–1.1(m, 6H) 1.1–2.8(m, 27H), 2.35(s, 3H), 3.0–3.3(m, 1H), 3.66(s, 3H), 3.6–3.9(m, 1H), 3.9–4.2(m, 1H), 5.2–5.9(m, 2H) |
| 356 | 56 | 0.7–1.0(m, 3H), 1.1–2.7(m, 23H), 2.9–3.4(m, 6H), 3.69(s, 3H), 3.4–4.2(m, 4H), 4.5–4.9(m, 1H), 5.3–5.9(m, 2H) |
| 357 | 63 | 0.7–1.0(m, 3H), 1.1–3.0(m, 23H), 3.0–3.3(m, 1H), 3.4–3.6(m, 1H), 3.68(s, 3H), 3.8–4.1(m, 1H), 4.7–4.9(m, 1H), 5.3–5.9(m, 2H), 7.2–7.7(m, 5H) |
| 358 | 59 | 0.7–1.1(m, 6H) 1.1–2.9(m, 24H), 3.1–3.3(m, 1H), 3.6–4.1(m, 5H) 5.3–5.9(m, 2H), 5.86(d, 1H, J=15.8Hz), 6.90(dt, 1H, J=15.8, 7.1Hz), 7.2–7.7(m, 4H) |

TABLE 19-continued

| # | Structure (left) | # | Structure (right) | Yield | NMR |
|---|---|---|---|---|---|
| 359 | | | | 67 | 0.7–1.1(m, 6H), 1.1–2.9(m, 38H), 3.1–3.3(m, 1H), 3.67(s, 3H), 3.6–4.2(m, 2H), 5.3–5.9 (m, 2H) |
| 360 | | | | 47 | 0.7–1.1(m, 6H), 1.1–3.0(m, 27H), 3.1–3.3(m, 1H), 3.67(s, 3H), 3.68(s, 3H), 3.6–3.9(m, 1H), 3.9–4.2(m, 1H), 5.5–5.7 (m, 2H), 7.0–7.3(m, 2H) |
| 361 | | | | 52 | 1.1–2.3(m, 11H), 2.00(s, 3H), 2.34(s, 3H), 2.5–2.8(m, 1H), 3.5–3.8(m, 2H), 3.8–4.2(m, 3H), 5.5–6.4(m, 3H), 6.7–7.1 (m, 4H), 7.1–7.4(m, 2H) |
| 362 | | | | 27 | 1.1–2.2(m, 6H), 2.03(s, 3H), 2.35(s, 3H), 2.6–2.9(m, 1H), 3.5–3.8(m, 2H), 4.0–4.2(m, 2H), 4.6–4.8(m, 1H), 5.5–6.0 (m, 1H), 6.0–6.5(m, 2H), 6.95 (d, 1H, J=2.5Hz), 7.1–7.5(m, 5H) |
| 363 | | | | 40 | 1.0–3.0(m, 19H), 2.11(s, 9H), 3.0–3.3(m, 1H), 2.11(s, 3H), 3.8–4.0(m, 1H), 4.1–4.5(m, 2H), 5.0–5.4(m, 1H), 5.4–6.0 (m, 3H), 7.25(d, 1H, J=7.0Hz) |

TABLE 19-continued

| | | | |
|---|---|---|---|
| 364 | (structure) | 49 | 1.1–2.5(m, 13H), 2.02(s, 3H), 2.5–2.8(m, 1H), 3.5–3.8(m, 2H), 3.8–4.2(m, 3H), 5.5–6.3 (m, 3H), 6.7–7.4(m, 8H) |
| 365 | (structure) | 61 | 1.0–2.0(m, 11H), 2.0–3.1(m, 7H), 3.67(s, 3H), 3.78(s, 3H), 3.6–4.0(m, 1H), 5.4–5.9(m, 3H), 6.83(d, 1H, J=2.6Hz) |
| 366 | (structure) | 38 | 1.24(d, 1H, J=5.9Hz), 1.1–2.3 (m, 14H), 2.35(s, 3H), 2.5–3.0 (m, 1H), 3.4–3.7(m, 2H), 3.8–4.2(m, 3H), 4.4–5.0(m, 1H), 5.3–6.0(m, 3H), 6.7–7.1(m, 4H), 7.1–7.4(m, 2H) |
| 367 | (structure) | 32 | 1.24(d, 1H, J=6.0Hz), 1.3–1.7 (m, 4H), 2.35(s, 3H), 2.7–3.1 (m, 1H), 3.4–3.7(m, 2H), 4.0–4.2(m, 1H), 4.4–4.9(m, 1H), 5.4–4.9(m, 3H), 6.95(d, 1H, J=3.3Hz), 7.1–7.5(m, 5H) |
| 368 | (structure) | 47 | 1.0–3.1(m, 30H), 3.68(s, 3H), 3.8–4.1(m, 1H), 4.6–5.1(m, 1H), 5.4–6.1(m, 3H), 6.95(d, 1H, J=2.8Hz), 7.1–7.5(m, 5H) |

TABLE 19-continued

| | | | | |
|---|---|---|---|---|
| 369 | (structure with OSiX₃, OCOOⁱPr, OPh, N-Me thiazoline-S) | (structure with OH, OCOOⁱPr, OPh, N-Me thiazoline-S) | 40 | 1.25(d, 1H, J=6.1Hz), 1.2-2.3 (m, 14H), 2.5-3.0(m, 1H), 3.4-3.7(m, 2H), 3.75(s, 3H), 3.8-4.2(m, 3H), 4.5-5.0(m, 1H), 5.4-6.1(m, 3H), 6.7-7.4(m, 8H) |
| 370 | (structure with COOMe, OSiX₃, cyclohexyl-S) | (structure with COOMe, OH, cyclohexyl-S) | 64 | 0.7-1.0(m, 3H), 1.2-2.5(m, 30H), 3.67(s, 3H), 3.9-4.1(m, 2H), 5.4-5.8(m, 2H), 6.5-6.8 (m, 2H) |
| 371 | (structure with COOMe, OSiX₃, pyridyl-S) | (structure with COOMe, OH, pyridyl-S) | 77 | 0.7-1.1(m, 3H), 1.1-2.6(m, 19H), 3.69(s, 3H), 3.8-4.1(m, 2H), 5.3-5.8(m, 2H), 6.5-6.8 (m, 2H) |
| 372 | (structure with COOMe, OSiX₃, N-Me tetrazolyl-S) | (structure with COOMe, OH, N-Me tetrazolyl-S) | 73 | 0.7-1.1(m, 3H), 1.1-2.5(m, 19H), 3.68(s, 3H), 2.9-4.1(m, 2H), 4.1(s, 3H), 5.4-5.8(m, 2H), 6.5-7.0(m, 2H) |
| 373 | (structure with COOMe, OSiX₃, benzoxazolyl-S) | (structure with COOMe, OH, benzoxazolyl-S) | 69 | 0.7-1.1(m, 6H), 1.1-2.0(m, 12H), 2.0-2.5(m, 4H), 3.69(s, 3H), 3.7-4.4(m, 2H), 5.1-6.0 (m, 3H), 6.5-7.2(m, 3H), 7.2-7.8(m, 4H) |

TABLE 19-continued

| | | | | |
|---|---|---|---|---|
| 374 | [structure with OSi, OPh, cyclopentenone-S-N-methylimidazole] | [structure with OH, OPh, cyclopentenone-S-N-methylimidazole] | 76 | 1.1–2.2(m, 12H), 3.4–3.8(m, 3H), 3.70(s, 3H), 3.8–4.2(m, 2H), 4.1–4.5(m, 1H), 6.0–6.8(m, 2H), 6.8–7.5(m, 9H) |
| 375 | [structure with COOMe, cyclopentyl, OSi, cyclopentenone-S-furan] | [structure with COOMe, cyclopentyl, OH, cyclopentenone-S-furan] | 53 | 1.0–2.0(m, 12H), 2.0–3.0(m, 4H), 3.68(s, 3H), 3.8–4.3(m, 3H), 4.6–4.9(m, 1H), 5.3–5.8(m, 2H), 6.0–6.5(m, 2H), 6.6–7.1(m, 2H), 7.2–7.4(m, 1H) |
| 376 | [structure with OSi, cyclohexyl, cyclopentenone-S-N-methylimidazole] | [structure with OH, cyclohexyl, cyclopentenone-S-N-methylimidazole] | 39 | 1.0–2.2(m, 17H), 3.4–3.8(m, 3H), 3.69(s, 3H), 3.8–4.2(m, 2H), 4.2–4.6(m, 1H), 6.0–6.8(m, 2H), 6.8–7.4(m, 4H) |
| 377 | [structure with COOMe, OSi, MeS-cyclopentenone] | [structure with COOMe, OH, MeS-cyclopentenone] | 83 | 0.7–1.1(m, 6H), 1.1–2.8(m, 25H), 2.35(s, 3H), 3.64(s, 3H), 3.9–4.2(m, 2H), 5.2–5.9(m, 2H), 6.6–6.8(m, 1H) |
| 378 | [structure with COOMe, OSi, EtS-cyclopentenone] | [structure with COOMe, OH, EtS-cyclopentenone] | 72 | 0.7–1.1(m, 6H), 1.1–2.9(m, 30H), 3.68(s, 3H), 3.7–4.2(m, 2H), 5.3–5.9(m, 2H), 6.6–6.9(m, 1H) |

TABLE 19-continued

| | | | |
|---|---|---|---|
| 379 | (structure) | 63 | 0.7-1.1(m, 6H), 1.1-3.0(m, 32H), 3.68(s, 3H), 3.7-4.2(m, 2H), 5.3-5.9(m, 2H), 6.6-6.9 (m, 1H) |
| 380 | (structure) | 59 | 0.7-1.0(m, 6H), 1.37(s, 9H) 1.0-3.0(m, 24H), 3.67(s, 3H), 3.7-4.2(m, 2H), 5.3-5.8(m, 2H), 6.6-6.9(m, 1H) |
| 381 | (structure) | 48 | 0.7-1.0(m, 3H), 1.1-3.0(m, 32H), 3.68(s, 6H), 3.7-4.2(m, 2H), 5.3-5.9(m, 2H), 6.5-6.9 (m, 1H) |
| 382 | (structure) | 43 | 0.7-1.0(m, 3H), 1.1-3.0(m, 22H), 3.68(s, 3H), 3.7-4.2(m, 2H), 5.3-5.9(m, 2H), 6.5-6.9 (m, 1H), 7.0-7.5(m, 5H) |

TABLE 19-continued

| | | | |
|---|---|---|---|
| 383 | (structure) | (structure) | 53 | 0.7–1.0(m, 3H), 1.1–2.9(m, 24H), 2.33(s, 3H), 3.69(s, 3H), 2.7–4.2(m, 2H), 5.3–5.9(m, 2H), 6.5–6.9(m, 1H), 6.9–7.5(m, 4H) |
| 384 | (structure) | (structure) | 56 | 0.7–1.0(m, 3H), 1.1–3.0(m, 22H), 3.68(s, 3H), 3.7–4.2(m, 2H), 3.97(s, 3H), 5.4–5.9(m, 2H), 6.5–6.9(m, 1H), 7.0–8.1(m, 5H) |
| 385 | (structure) | (structure) | 56 | 0.7–1.0(m, 3H), 1.0–3.1(m, 28H), 3.68(s, 3H), 3.7–4.2(m, 2H), 5.3–5.9(m, 2H), 6.5–6.9(m, 1H), 7.0–7.5(m, 5H) |
| 386 | (structure) | (structure) | 57 | 0.7–1.1(m, 6H), 1.1–2.8(m, 22H), 3.6–4.1(m, 6H), 5.3–5.9(m, 2H), 5.88(d, 1H, J=16Hz), 6.6–7.1(m, 2H), 7.2–7.7(m, 4H) |
| 387 | (structure) | (structure) | 68 | 0.7–1.1(m, 6H), 1.1–2.9(m, 36H), 3.68(s, 3H), 3.7–4.2(m, 2H), 5.3–5.9(m, 2H), 6.6–6.9(m, 1H) |

TABLE 19-continued

| | | NMR |
|---|---|---|
| 388 | (structure: cyclopentenone with S-pyridyl, butyl, OSiX chain, COOMe) | |
| 55 | (structure: cyclopentenone with S-pyridyl, butyl, OH chain, COOMe) | 0.7–1.1(m, 6H), 1.0–3.0(m, 25H), 3.68(s, 3H), 3.7–4.2(m, 2H), 5.3–5.9(m, 2H), 6.6–6.9(m, 1H), 7.2–8.1(m, 4H) |
| 389 | (structure: cyclopentenone with S-(N-Me-imidazolyl), butyl, OSiX chain, COOMe) | |
| 63 | (structure: cyclopentenone with S-(N-Me-imidazolyl), butyl, OH chain, COOMe) | 0.7–1.1(m, 6H), 1.0–3.0(m, 25H), 3.67(s, 3H), 3.69(s, 3H), 3.6–4.2(m, 2H), 5.3–5.8(m, 2H), 6.6–6.9(m, 1H), 7.0–7.3(m, 2H) |
| 390 | (structure: cyclopentenone with S-(Me-pyrimidyl), butyl, OSiX chain, COOMe) | |
| 58 | (structure: cyclopentenone with S-(Me-pyrimidyl), butyl, OH chain, COOMe) | 0.7–1.1(m, 6H), 1.1–3.0(m, 25H), 2.47(s, 3H), 3.69(s, 3H), 3.6–4.2(m, 2H), 5.3–5.9(m, 2H), 6.6–7.1(m, 2H), 8.30(d, 1H, J=5.0Hz) |
| 391 | (structure: cyclopentenone with S-furfuryl, butyl, cyclopentyl/ynyl chain, OSiX, COOMe) | |
| 47 | (structure: cyclopentenone with S-furfuryl, butyl, cyclopentyl/ynyl chain, OH, COOMe) | 0.7–1.0(m, 3H), 1.0–3.1(m, 22H), 3.69(s, 3H), 3.7–4.3(m, 4H), 5.3–5.9(m, 2H), 6.1–6.5(m, 1H), 6.5–6.8(m, 1H), 7.3–7.6(m, 1H) |

TABLE 19-continued

| # | Structure (OSi) | Structure (OH) | Yield | NMR |
|---|---|---|---|---|
| 392 | MeS-enone with OSiX chain, COOMe | MeS-enone with OH chain, COOMe | 76 | 0.7–1.0(m, 3H), 1.1–2.3(m, 22H), 2.34(s, 3H), 3.0–3.4(m, 1H), 3.69(s, 3H), 3.8–4.1(m, 1H), 5.5–5.8(m, 2H), 7.18(d, 1H, J=2.5Hz) |
| 393 | S-CH2CH(OH)CH2OH enone with OSiX, COOMe | S-CH2CH(OH)CH2OH enone with OH, COOMe | 92 | 0.7–1.0(m, 3H), 1.1–2.8(m, 22H), 2.8–3.3(m, 3H), 3.67(s, 3H), 3.4–4.2(m, 4H), 4.81(brs, 1H), 5.3–5.7(m, 2H), 7.16(d, 1H, J=2.8Hz) |
| 394 | PhS-enone with OSiX, COOMe | PhS-enone with OH, COOMe | 69 | 0.7–1.0(m, 3H), 1.1–2.3(m, 2H), 3.0–3.3(m, 1H), 3.70(s, 3H), 3.8–4.1(m, 1H), 5.5–5.8(m, 2H), 7.1–7.4(m, 6H) |
| 395 | Cyclohexyl-S-enone with OSiX, COOMe | Cyclohexyl-S-enone with OH, COOMe | 71 | 0.7–1.0(m, 3H), 1.1–2.5(m, 33H), 3.0–3.3(m, 1H), 3.68(s, 3H), 3.9–4.1(m, 1H), 5.5–5.8(m, 2H), 7.17(d, 1H, J=2.0Hz) |
| 396 | N-Me imidazole-S-enone with OSiX, COOMe | N-Me imidazole-S-enone with OH, COOMe | 58 | 0.7–1.0(m, 3H), 1.1–2.2(m, 22H), 3.0–3.4(m, 1H), 3.68(s, 3H), 3.71(s, 3H), 3.9–4.2(m, 1H), 5.4–5.8(m, 2H), 6.7–7.2(m, 3H) |

| | | | |
|---|---|---|---|
| 397 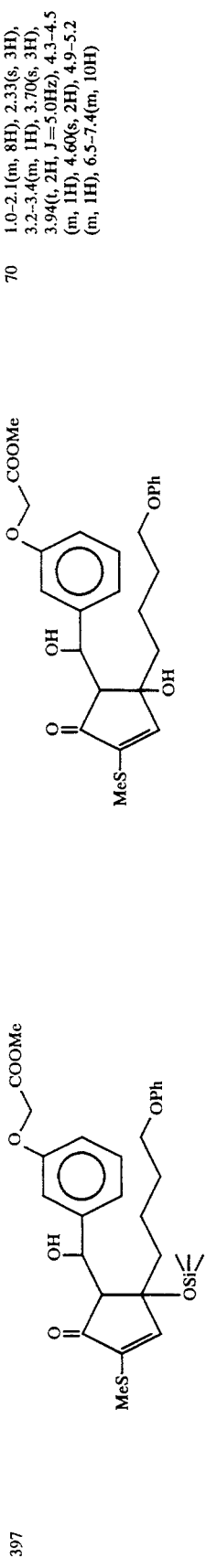 | 70 | 1.0–2.1(m, 8H), 2.33(s, 3H), 3.2–3.4(m, 1H), 3.70(s, 3H), 3.94(t, 2H, J=5.0Hz), 4.3–4.5 (m, 1H), 4.60(s, 2H), 4.9–5.2 (m, 1H), 6.5–7.4(m, 10H) | |
| 398 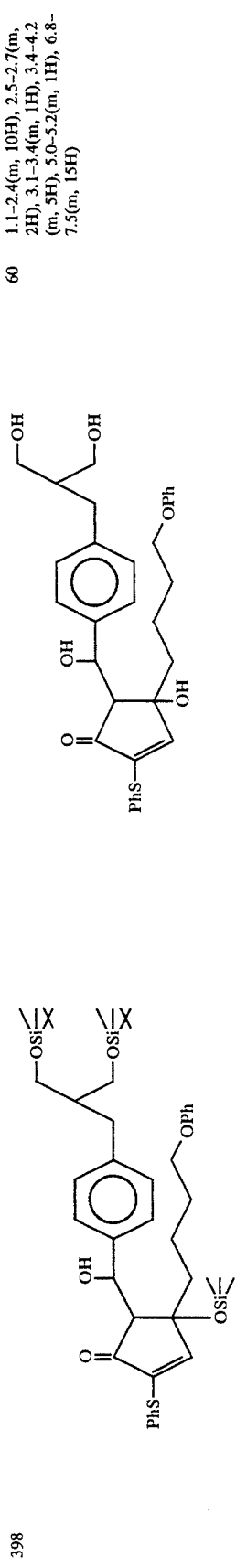 | 60 | 1.1–2.4(m, 10H), 2.5–2.7(m, 2H), 3.1–3.4(m, 1H), 3.4–4.2 (m, 5H), 5.0–5.2(m, 1H), 6.8–7.5(m, 15H) | |
| 399 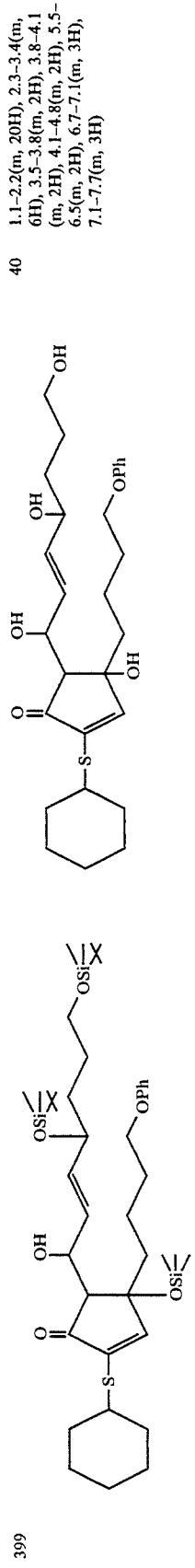 | 40 | 1.1–2.2(m, 20H), 2.3–3.4(m, 6H), 3.5–3.8(m, 2H), 3.8–4.1 (m, 2H), 4.1–4.8(m, 2H), 5.5–6.5(m, 2H), 6.7–7.1(m, 3H), 7.1–7.7(m, 3H) | |
| 400 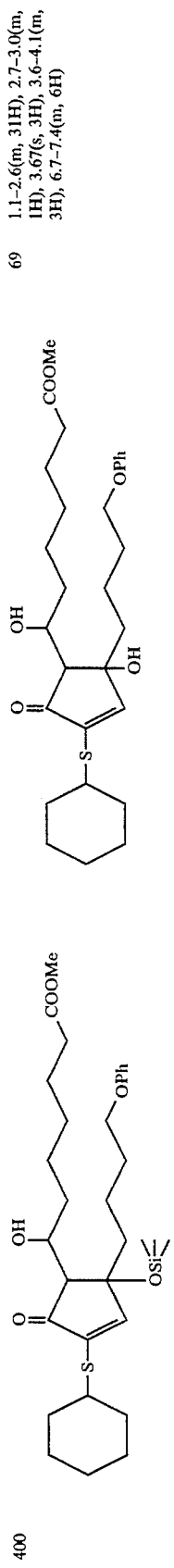 | 69 | 1.1–2.6(m, 31H), 2.7–3.0(m, 1H), 3.67(s, 3H), 3.6–4.1(m, 3H), 6.7–7.4(m, 6H) | |

| | |
|---|---|
| 48 | 1.2–2.9(m, 13H), 3.0–3.3(m, 1H), 3.5–3.7(m, 4H), 3.77(s, 6H), 5.0–5.2(m, 2H), 6.4–7.0 (m, 4H), 7.2–8.1(m, 8H) |
| 65 | 1.0–2.1(m, 10H), 2.5–2.8(m, 1H), 3.0–4.3(m, 8H), 4.4–4.75 (m, 1H), 5.5–6.35(m, 2H), 6.5–7.6(m, 8H) |
| 83 | 1.2–2.3(m, 12H), 2.3–2.7(m, 5H), 2.8–3.0(m, 1H), 3.68(s, 3H), 3.77(s, 3H), 3.8–4.2(m, 2H), 4.6–5.0(m, 1H), 6.8–7.5 (m, 6H) |
| 98 | 1.06(s, 3H), 1.16(s, 3H), 1.3–2.4(m, 13H), 2.62(d, 1H, J=3.6 Hz), 3.65(s, 3H), 3.8–4.1(m, 2H), 4.9–5.1(m, 1H), 6.66(s, 1H), 6.7–7.5(m, 7H) |

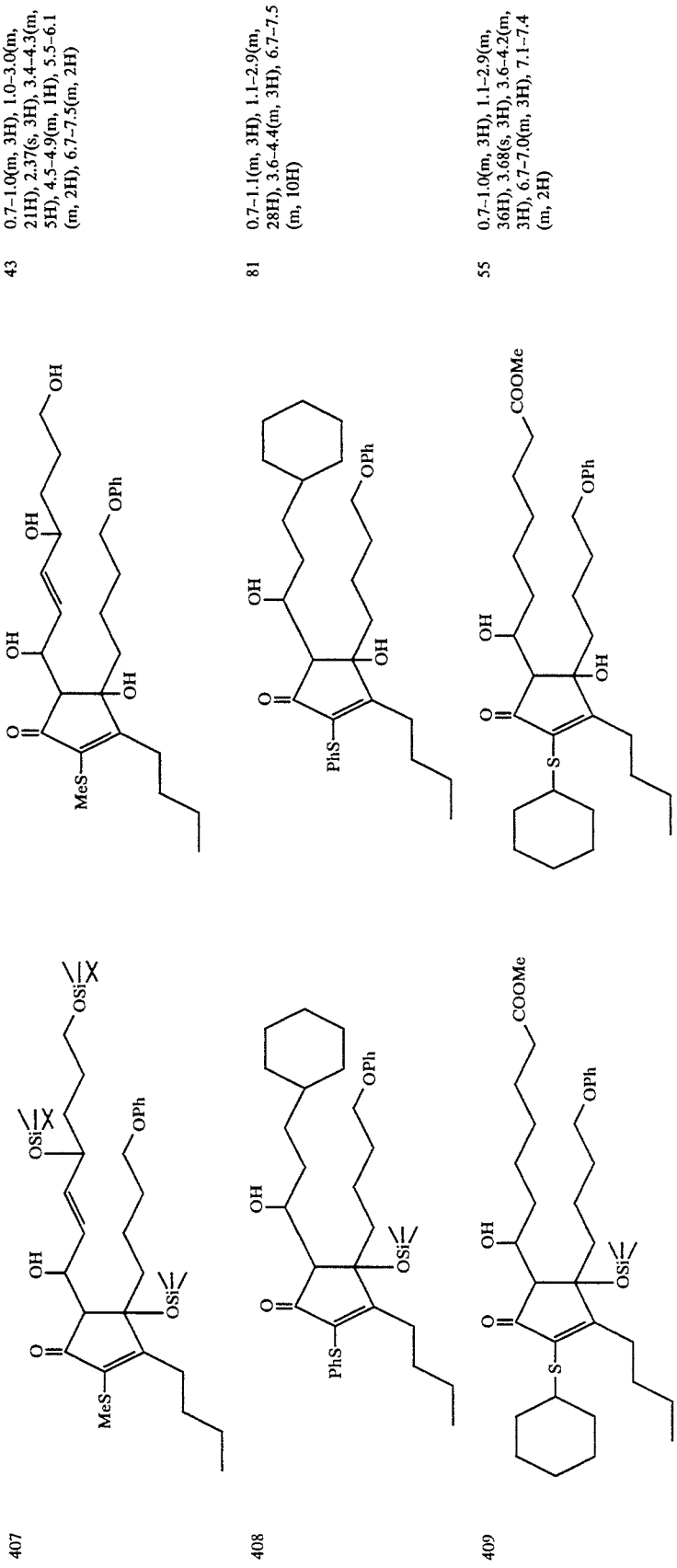

| | | |
|---|---|---|
| 410 | 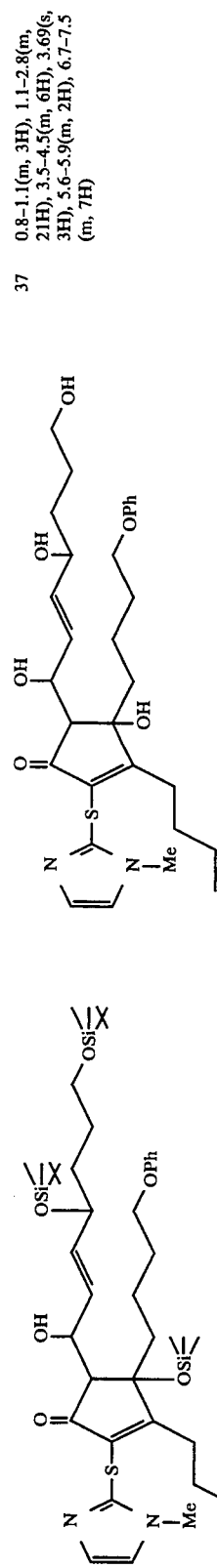 | 37 | 0.8-1.1(m, 3H), 1.1-2.8(m, 21H), 3.5-4.5(m, 6H), 3.69(s, 3H), 5.6-5.9(m, 2H), 6.7-7.5 (m, 7H) |
| 411 | 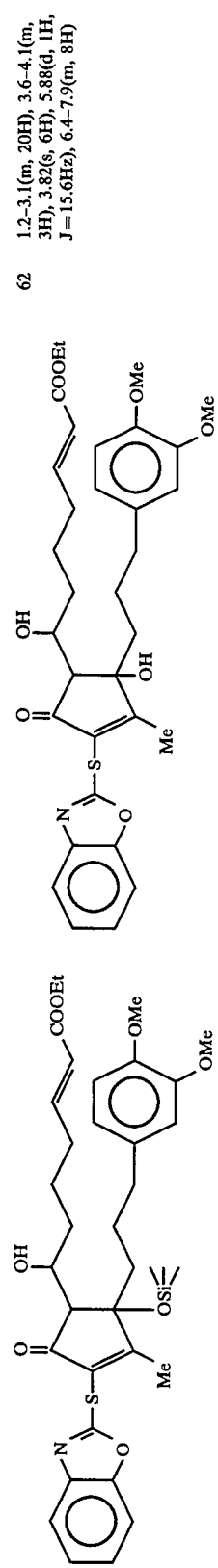 | 62 | 1.2-3.1(m, 20H), 3.6-4.1(m, 3H), 3.82(s, 6H), 5.88(d, 1H, J=15.6Hz), 6.4-7.9(m, 8H) |
| 412 | 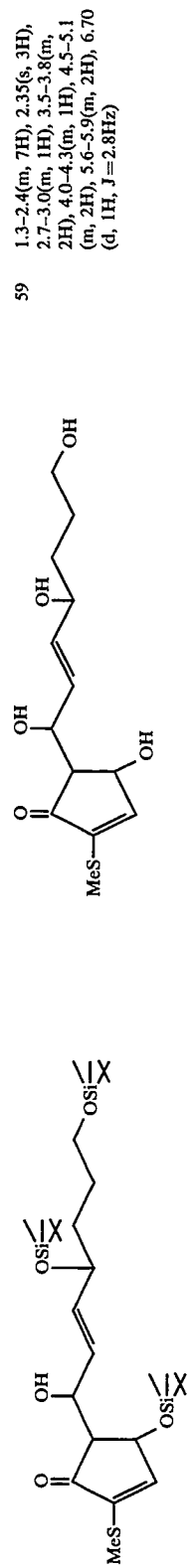 | 59 | 1.3-2.4(m, 7H), 2.35(s, 3H), 2.7-3.0(m, 1H), 3.5-3.8(m, 2H), 4.0-4.3(m, 1H), 4.5-5.1 (m, 2H), 5.6-5.9(m, 2H), 6.70 (d, 1H, J=2.8Hz) |
| 413 | 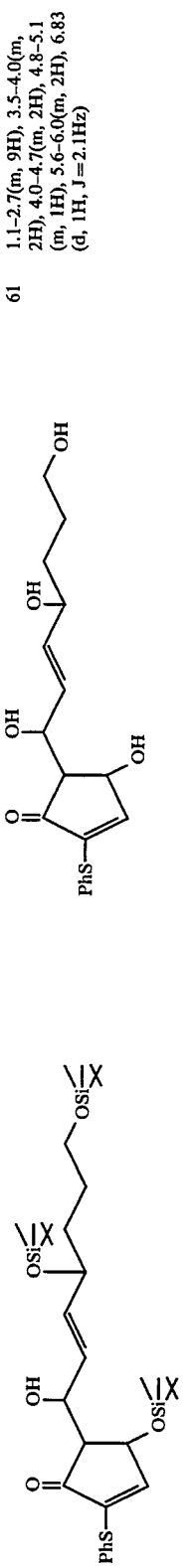 | 61 | 1.1-2.7(m, 9H), 3.5-4.0(m, 2H), 4.0-4.7(m, 2H), 4.8-5.1 (m, 1H), 5.6-6.0(m, 2H), 6.83 (d, 1H, J=2.1Hz) |
| 414 | 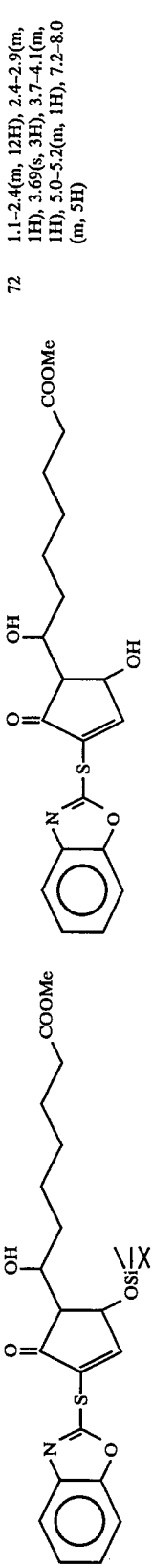 | 72 | 1.1-2.4(m, 12H), 2.4-2.9(m, 1H), 3.69(s, 3H), 3.7-4.1(m, 1H), 5.0-5.2(m, 1H), 7.2-8.0 (m, 5H) |

| | | | |
|---|---|---|---|
| 415 | (structure with MeS, OAc, OSi, OPh groups) | 44 | 1.1-2.2(m, 13H), 2.04(s, 3H), 2.35(s, 3H), 2.6-2.8(m, 1H), 3.5-3.8(m, 2H), 3.8-4.1(m, 2H), 4.1-4.5(m, 1H), 5.5-6.0(m, 1H), 6.0-6.5(m, 2H), 6.66(s, 1H), 6.7-7.1(m, 3H), 7.1-7.4(m, 2H) |
| 416 | (structure with PhS, OAc, OSi, OPh groups) | 37 | 1.1-2.3(m, 13H), 2.03(s, 3H), 2.6-2.9(m, 1H), 3.5-3.8(m, 2H), 3.8-4.2(m, 3H), 5.6-5.9(m, 2H), 5.9-6.3(m, 1H), 6.6-7.1(m, 4H), 7.1-7.4(m, 7H) |
| 417 | (structure with cyclohexyl-S, OAc, OSi, OPh groups) | 45 | 1.1-2.5(m, 24H), 2.05(s, 3H), 2.6-2.9(m, 1H), 3.5-3.8(m, 2H), 3.7-4.2(m, 3H), 5.6-5.9(m, 2H), 5.9-6.3(m, 1H), 6.6-7.1(m, 4H), 7.1-7.4(m, 2H) |
| 418 | (structure with N-methylimidazole-S, OAc, OSi, OPh groups) | 39 | 1.1-2.3(m, 13H), 2.03(s, 3H), 2.6-2.9(m, 1H), 3.5-3.8(m, 2H), 3.69(s, 3H), 3.7-4.3(m, 3H), 5.6-5.9(m, 2H), 5.9-6.3(m, 1H), 6.6-7.5(m, 8H) |

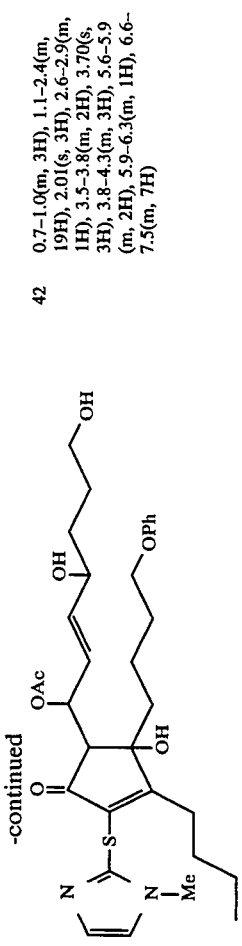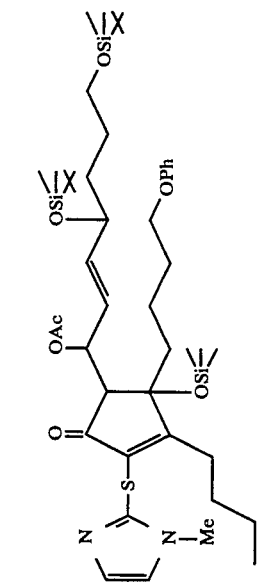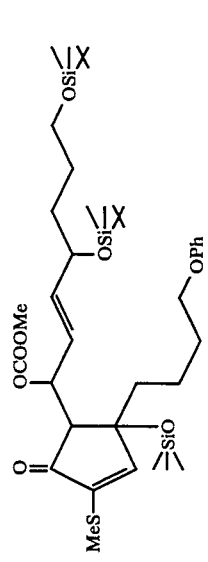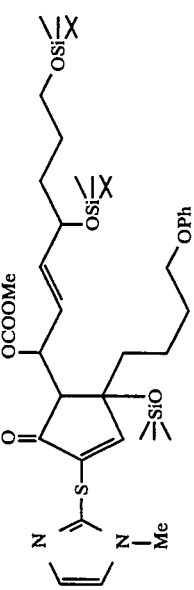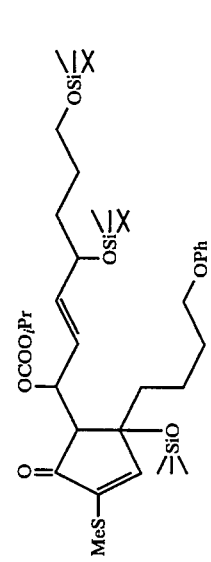
| No. | NMR |
|---|---|
| 42 | 0.7-1.0(m, 3H), 1.1-2.4(m, 19H), 2.01(s, 3H), 2.6-2.9(m, 1H), 3.5-3.8(m, 2H), 3.70(s, 3H), 3.8-4.3(m, 3H), 5.6-5.9(m, 2H), 5.9-6.3(m, 1H), 6.6-7.5(m, 7H) |
| 55 | 1.0-2.1(m, 13H), 2.34(s, 3H), 2.5-3.0(m, 1H), 3.5-3.7(m, 2H), 3.77(s, 3H), 3.8-4.2(m, 3H), 5.3-6.1(m, 3H), 6.6-7.1(m, 4H), 7.1-7.4(m, 2H) |
| 43 | 1.0-2.2(m, 13H), 2.5-3.0(m, 2H), 3.5-3.7(m, 2H), 3.69(s, 3H), 3.76(s, 3H), 3.8-4.3(m, 3H), 5.3-6.2(m, 3H), 6.7-8.5(m, 8H) |
| 20 | 1.26(d, 6H, J=6.2Hz), 1.2-2.2(m, 13H), 2.32(s, 3H), 2.7-2.9(m, 1H), 3.5-3.8(m, 2H), 3.8-4.1(m, 2H), 4.1-4.5(m, 1H), 4.6-5.0(m, 1H), 5.4-6.3(m, 3H), 6.5-7.1(m, 4H), 7.1-7.4(m, 2H) |
| 53 | 1.25(d, 6H, J=5.9Hz), 1.1-2.3(m, 13H), 2.5-3.0(m, 1H), 3.4-3.7(m, 2H), 3.8-4.2(m, 3H), 4.5-5.0(m, 1H), 5.4-6.0(m, 3H), 6.7-7.1(m, 4H), 7.1-7.4(m, 7H) |
419
420
421
422
423

-continued

| # | NMR | Yield |
|---|---|---|
| 424 | 1.24(d, 6H, J=6.4Hz), 1.1–2.4 (m, 23H), 2.5–3.0(m, 1H), 3.4–3.7(m, 2H), 3.8–4.2(m, 3H), 4.5–5.0(m, 1H), 5.3–6.0(m, 3H), 6.7–7.1(m, 4H), 7.1–7.4 (m, 2H) | 39 |
| 425 | 1.26(d, 6H, J=6.3Hz), 1.0–2.4 (m, 24H), 2.5–3.0(m, 1H), 3.4–3.7(m, 2H), 3.8–4.2(m, 3H), 4.5–5.0(m, 4H), 5.3–6.0(m, 3H), 6.7–7.1(m, 4H), 7.1–7.4 (m, 2H) | 49 |
| 426 | 0.7–1.0(m, 3H), 1.27(d, 6H, J=6.0Hz), 1.0–2.3(m, 19H), 2.5–3.0(m, 1H), 3.5–3.8(m, 2H), 3.75(s, 3H), 3.78(s, 3H), 3.8–4.3(m, 3H), 4.5–5.1(m, 1H), 5.3–6.1(m, 3H), 6.8–7.5(m, 7H) | 41 |
| 427 | 1.1–2.0(m, 17H), 2.1–2.4(m, 1H), 2.35(s, 3H), 3.92(t, 2H, J=6.2Hz), 6.6–7.1(m, 5H), 7.1–7.4(m, 2H) | 62 |
| 428 | 0.7–1.0(m, 6H), 1.1–2.1(m, 15H), 2.2–2.6(m, 2H), 2.35(s, 3H), 6.15(d, 1H, J=3.5Hz), 6.64(d, 1H, J=3.5Hz), 6.88(s, 1H), 7.32(s, 1H) | 41 |

| | |
|---|---|
| 38 | 0.7–1.3(m, 13H), 2.28(s, 6H), 1H), 6.6–7.0(m, 2H) 1.2–2.1(m, 2.2–2.5(m, |
| 59 | 1.0–2.1(m, 29H), 2.1–2.5(m, 5H), 3.68(s, 3H), 4.7–5.0(m, 1H), 5.4–5.8(m, 2H), 6.6–7.1 (m, 2H) |
| 68 | 1.1–2.0(m, 17H), 2.1–2.5(m, 1H), 3.92(t, 2H, J=6.2Hz), 6.5–7.1(m, 5H), 7.1–7.5(m, 7H) |
| 75 | 1.2–2.0(m, 9H), 2.69(d, 2H, J=6.9Hz), 3.4–3.8(m, 4H), 3.94(t, 2H, J=6.4Hz), 6.5–7.5 (m, 14H), 7.8–8.1(m, 2H) |
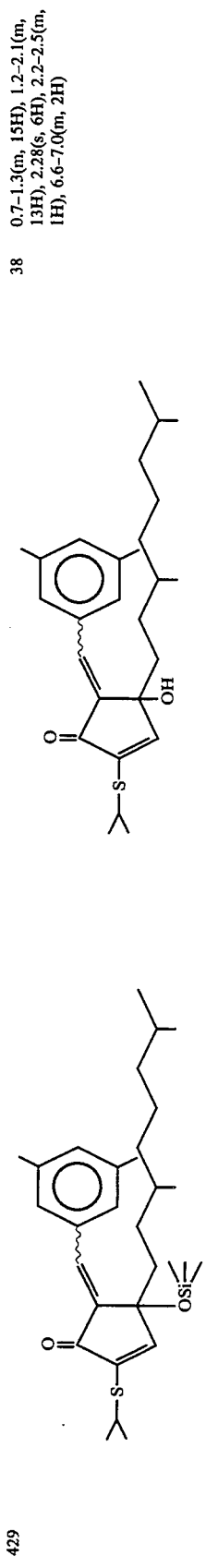
429
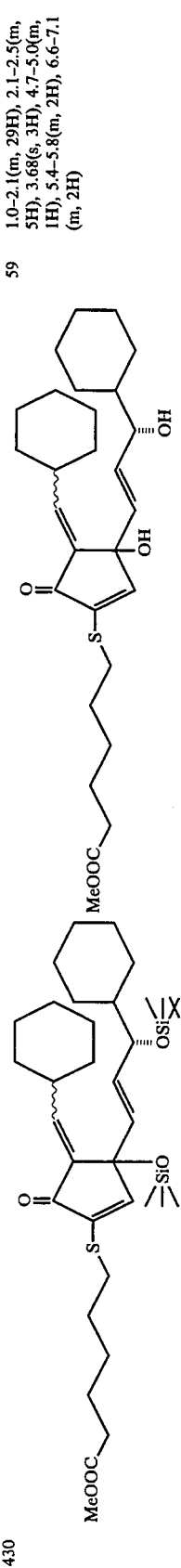
430
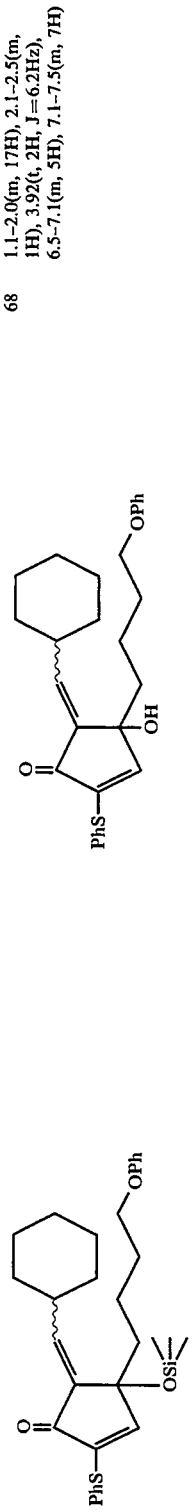
431
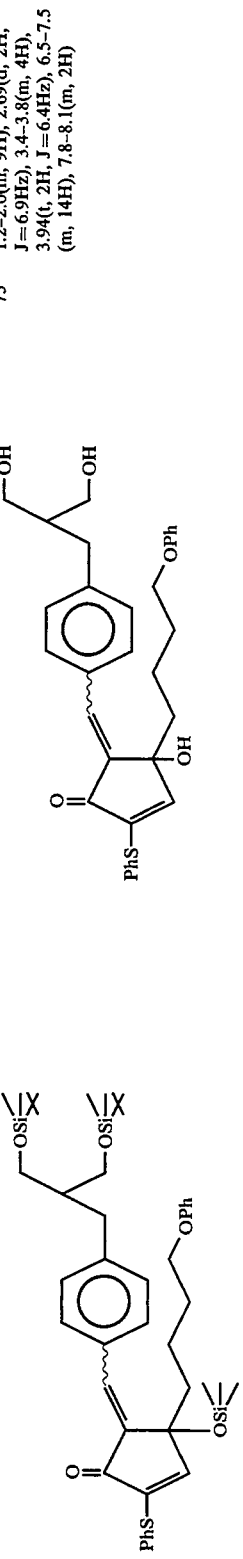
432

| | | | |
|---|---|---|---|
| 433 | 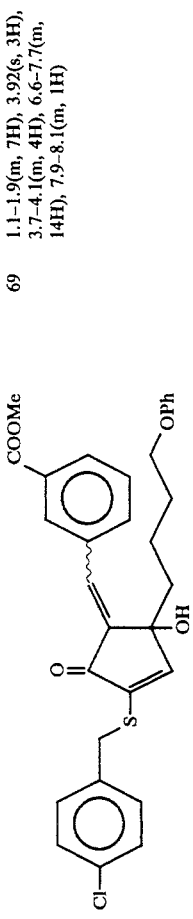 | 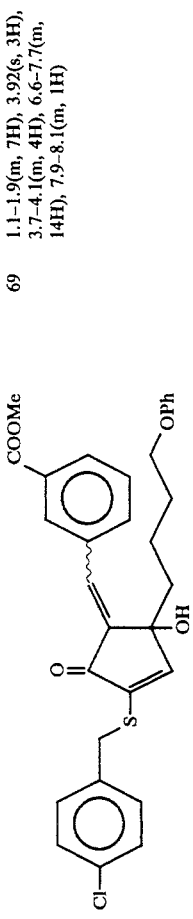 | 69 | 1.1–1.9(m, 7H), 3.92(s, 3H), 3.7–4.1(m, 4H), 6.6–7.7(m, 14H), 7.9–8.1(m, 1H) |
| 434 | 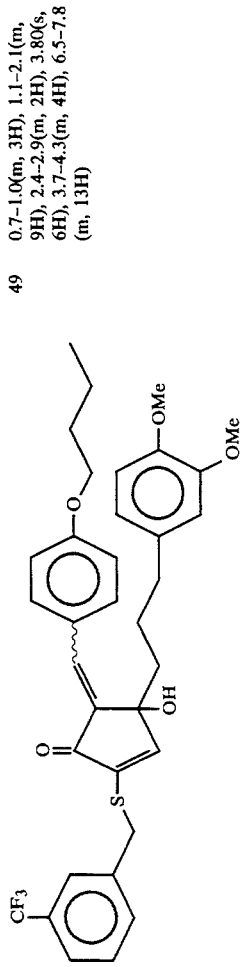 | 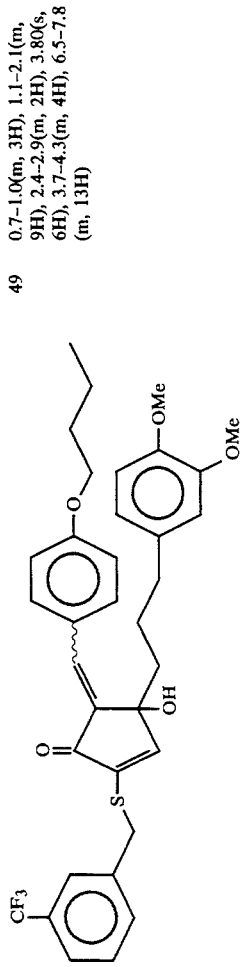 | 49 | 0.7–1.0(m, 3H), 1.1–2.1(m, 9H), 2.4–2.9(m, 2H), 3.80(s, 6H), 3.7–4.3(m, 4H), 6.5–7.8 (m, 13H) |
| 435 | 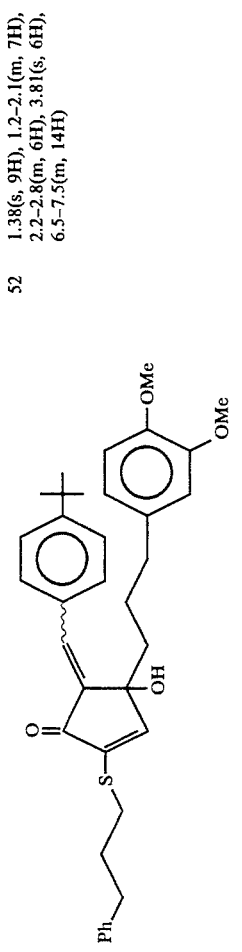 | 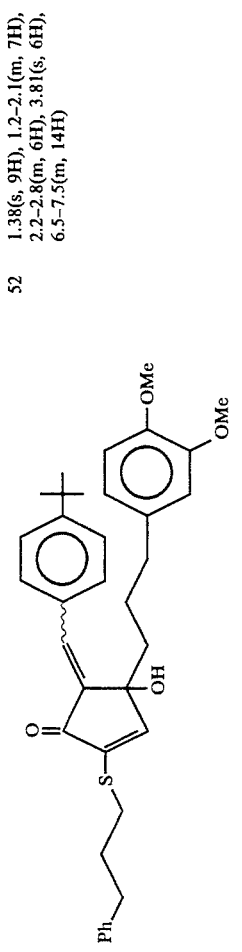 | 52 | 1.38(s, 9H), 1.2–2.1(m, 7H), 2.2–2.8(m, 6H), 3.81(s, 6H), 6.5–7.5(m, 14H) |
| 436 | 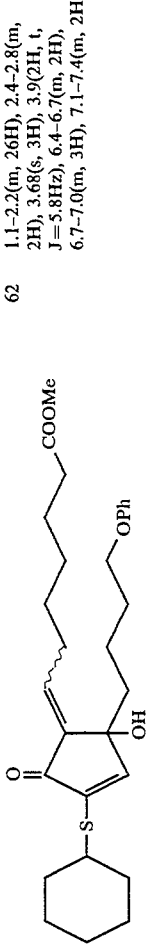 | 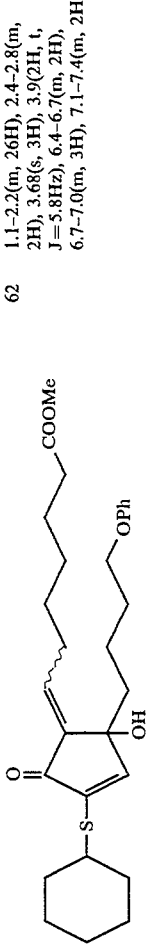 | 62 | 1.1–2.2(m, 26H), 2.4–2.8(m, 2H), 3.68(s, 3H), 3.9(2H, t, J=5.8Hz), 6.4–6.7(m, 2H), 6.7–7.0(m, 3H), 7.1–7.4(m, 2H) |
| 437 | 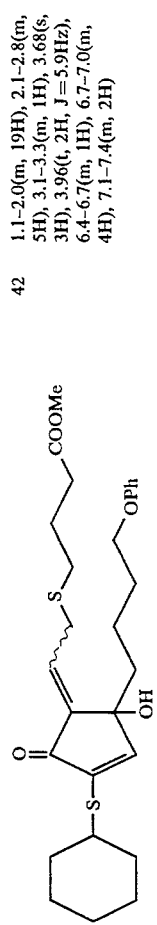 | 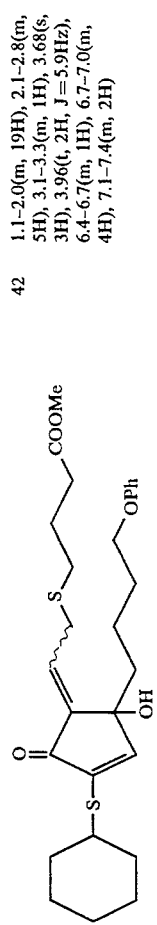 | 42 | 1.1–2.0(m, 19H), 2.1–2.8(m, 5H), 3.1–3.3(m, 1H), 3.68(s, 3H), 3.96(t, 2H, J=5.9Hz), 6.4–6.7(m, 1H), 6.7–7.0(m, 4H), 7.1–7.4(m, 2H) |

| # | Structure | Yield | NMR |
|---|---|---|---|
| 438 / (product 69) | (silyl ether with COOMe, OPh, cyclohexyl-S) → (OH with COOMe, OPh, cyclohexyl-S) | 69 | 1.1–2.0(m, 19H), 2.2–2.6(m, 3H), 3.4–4.0(m, 4H), 3.76(s, 3H), 4.10(s, 2H), 6.4–6.7(m, 1H), 6.7–7.1(m, 4H), 7.1–7.4(m, 2H) |
| 439 / (product 70) | (silyl ether with cyclohexyl-COOMe, OPh, cyclohexyl-S) → (OH analogue) | 70 | 1.1–2.1(m, 28H), 2.2–2.7(m, 4H), 3.69(s, 3H), 3.94(t, J=6.0Hz), 6.4–6.7(m, 2H), 6.7–7.1(m, 4H), 7.1–7.4(m, 2H) |
| 440 / (product 69) | (silyl ether with aryl-OCH2COOMe, OPh, cyclohexyl-S) → (OH analogue) | 69 | 1.1–2.0(m, 17H), 2.2–2.5(m, 1H), 3.6–4.2(m, 2H), 3.79(s, 3H), 4.70(s, 2H), 6.6–7.6(m, 10H), 7.7–8.1(m, 1H) |
| 441 / (product 78) | (silyl ether with long alkyl chain, cyclohexyl-S) → (OH analogue) | 78 | 0.7–1.0(m, 6H), 1.1–2.1(m, 39H), 2.1–2.6(m, 3H), 6.4–6.8(m, 2H) |
| 442 / (product 83) | (silyl ether with cyclohexylidene, dimethoxyphenyl, cyclohexyl-S) → (OH analogue) | 83 | 1.2–2.0(m, 21H), 2.1–2.5(m, 5H), 3.81(s, 6H), 6.3–7.4(m, 6H) |

| | | |
|---|---|---|
| 443 | 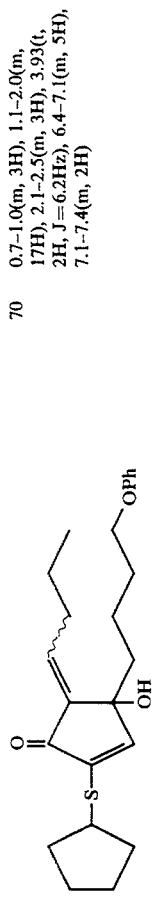 | 70 | 0.7-1.0(m, 3H), 1.1-2.0(m, 17H), 2.1-2.5(m, 3H), 3.93(t, 2H, J=6.2Hz), 6.4-7.1(m, 5H), 7.1-7.4(m, 2H) |
| 444 | 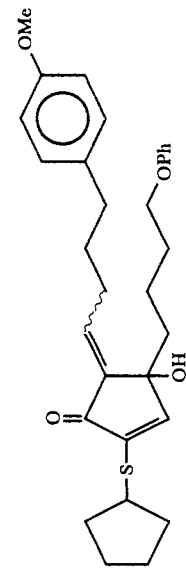 | 69 | 1.1-2.0(m, 17H), 2.1-2.6(m, 5H), 3.76(s, 3H), 3.92(t, 2H, J=6.1Hz), 6.3-7.5(m, 11H) |
| 445 | 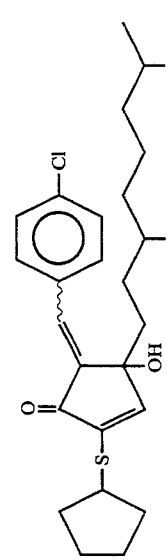 | 71 | 0.83(d, 9H, J=5.0Hz), 0.9-2.1 (m, 21H), 2.1-2.5(m, 1H), 6.6-7.5(m, 5H), 8.0-8.1(m, 1H) |
| 446 | 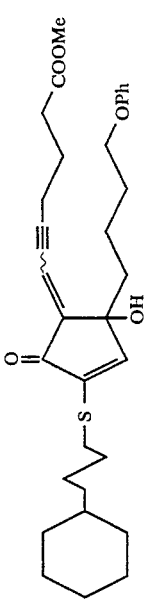 | 63 | 1.2-2.5(m, 30H), 3.68(s, 3H), 3.8-4.1(m, 2H), 6.12(t, 1H, J=1.8Hz), 6.71(s, 1H), 6.8-7.1(m, 3H), 7.1-7.4(m, 2H) |
| 447 | 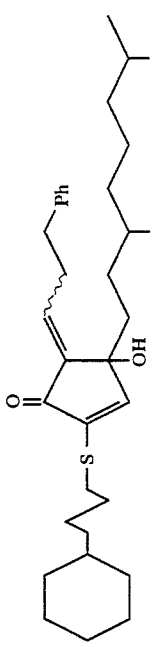 | 58 | 0.86(d, 9H, J=4.8Hz), 0.9-2.1 (m, 28H), 2.1-2.6(m, 6H), 6.5-6.7(m, 1H), 6.8-7.5(m, 6H) |
-continued
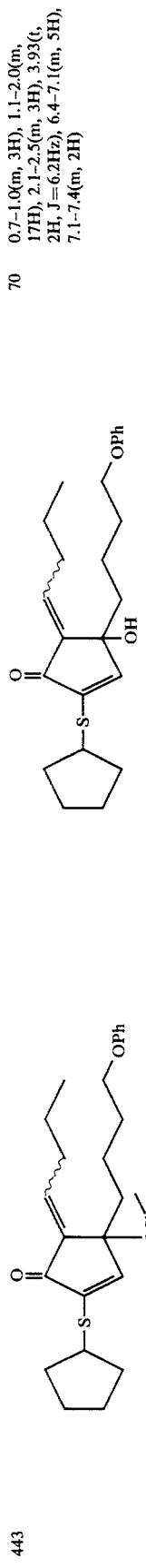
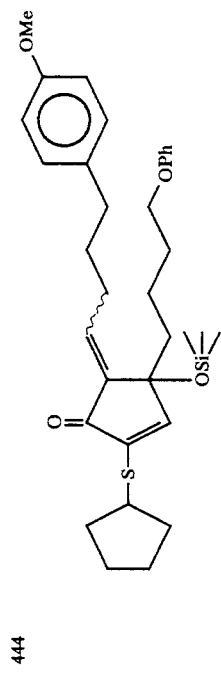
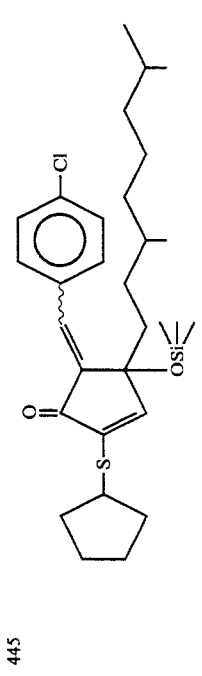
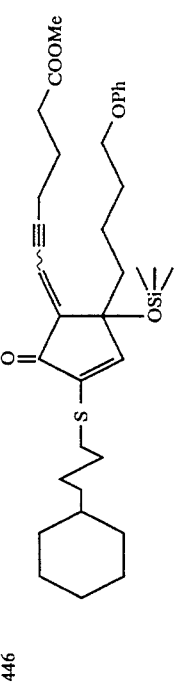
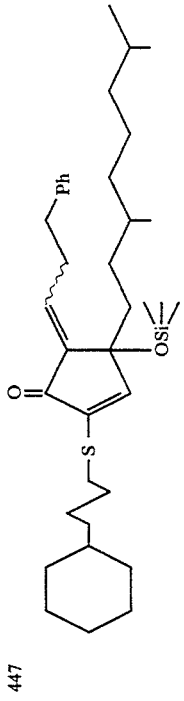

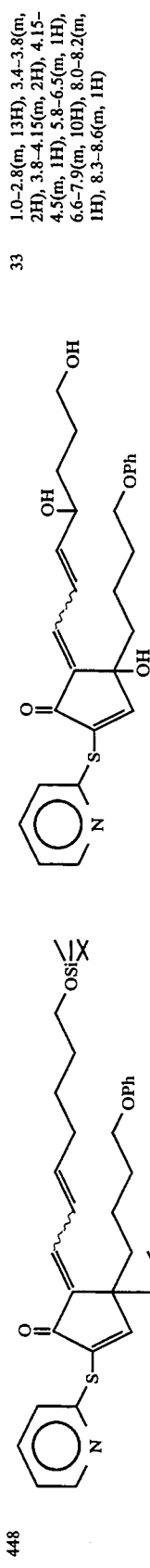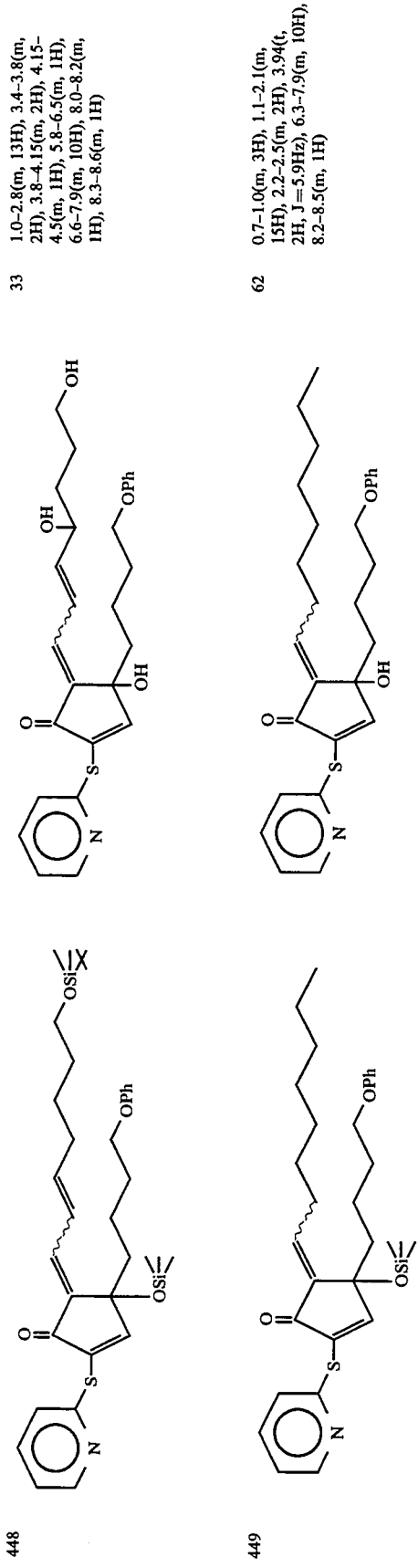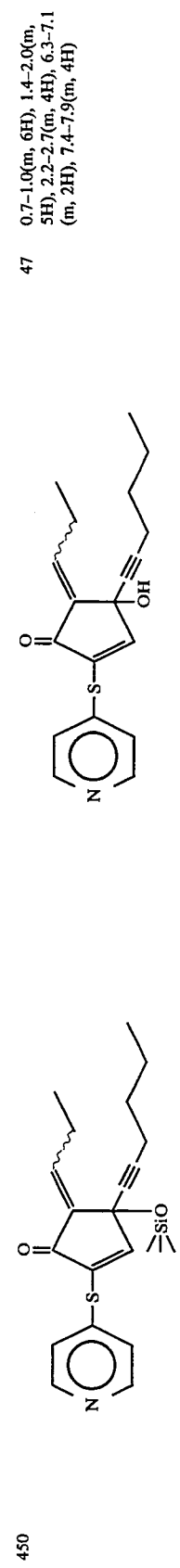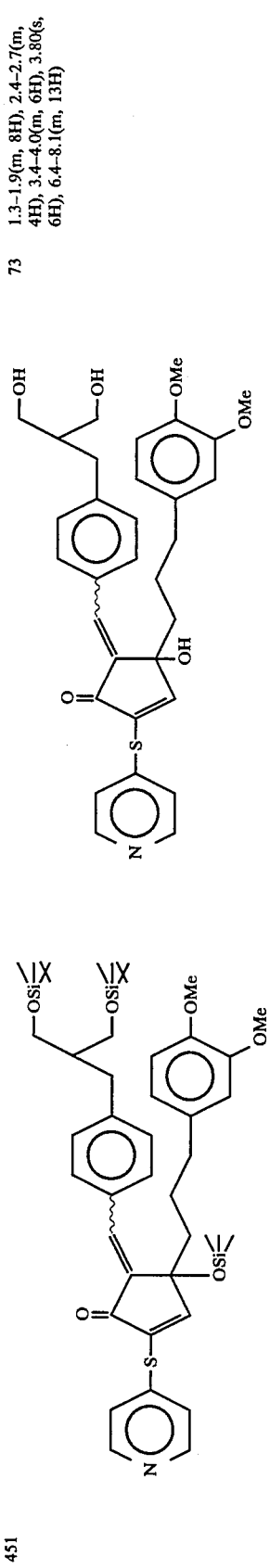
| | | |
|---|---|---|
| 33 | 1.0-2.8(m, 13H), 3.4-3.8(m, 2H), 3.8-4.15(m, 2H), 4.15-4.5(m, 1H), 5.8-6.5(m, 1H), 6.6-7.9(m, 10H), 8.0-8.2(m, 1H), 8.3-8.6(m, 1H) | |
| 62 | 0.7-1.0(m, 3H), 1.1-2.1(m, 15H), 2.2-2.5(m, 2H), 3.94(t, 2H, J=5.9Hz), 6.3-7.9(m, 10H), 8.2-8.5(m, 1H) | |
| 47 | 0.7-1.0(m, 6H), 1.4-2.0(m, 5H), 2.2-2.7(m, 4H), 6.3-7.1(m, 2H), 7.4-7.9(m, 4H) | |
| 73 | 1.3-1.9(m, 8H), 2.4-2.7(m, 4H), 3.4-4.0(m, 6H), 3.80(s, 6H), 6.4-8.1(m, 13H) | |
448
449
450
451

| | | | |
|---|---|---|---|
| 452 | 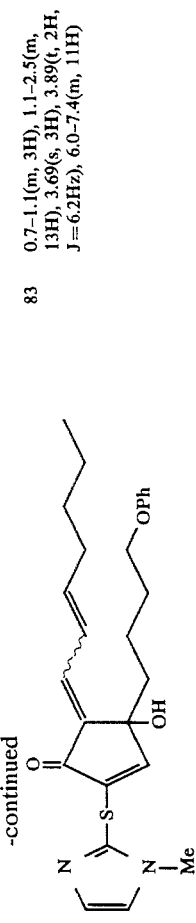 | 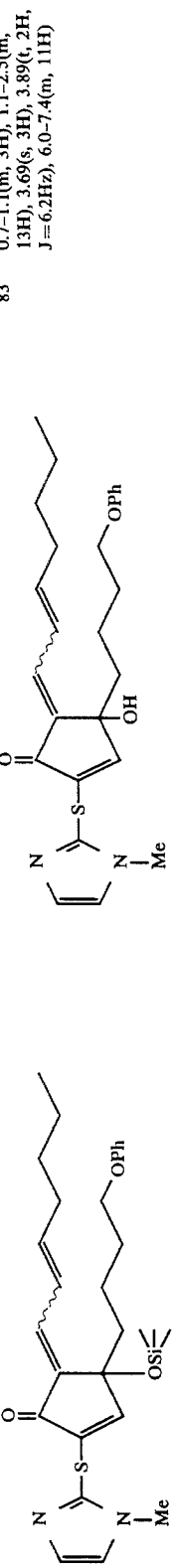 | 83 | 0.7-1.1(m, 3H), 1.1-2.5(m, 13H), 3.69(s, 3H), 3.89(t, 2H, J=6.2Hz), 6.0-7.4(m, 11H) |
| 453 | 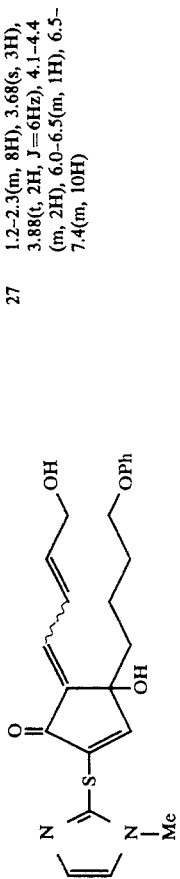 | 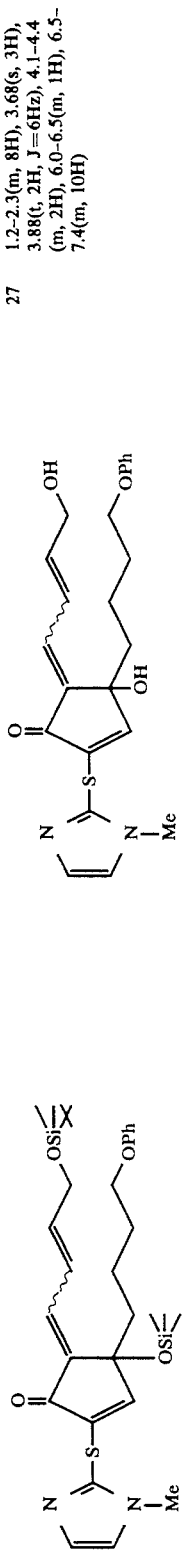 | 27 | 1.2-2.3(m, 8H), 3.68(s, 3H), 3.88(t, 2H, J=6Hz), 4.1-4.4 (m, 2H), 6.0-6.5(m, 1H), 6.5-7.4(m, 10H) |
| 454 | 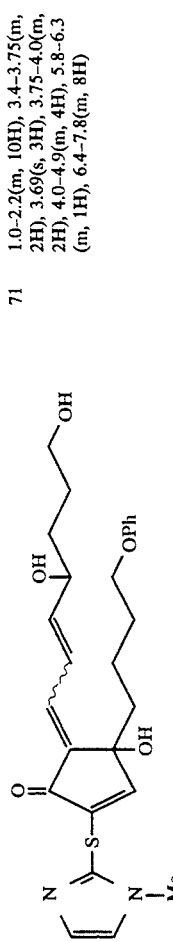 | 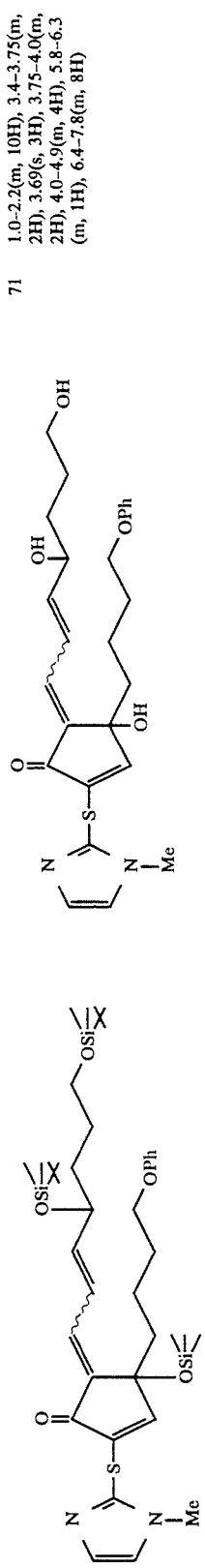 | 71 | 1.0-2.2(m, 10H), 2.2-3.0(m, 2H), 3.69(s, 3H), 3.75-4.0(m, 2H), 4.0-4.9(m, 4H), 5.8-6.3 (m, 1H), 6.4-7.8(m, 8H) |
| 455 | 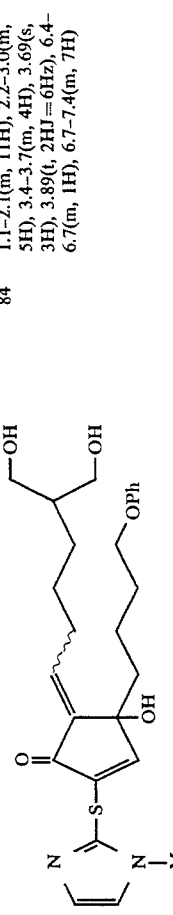 | 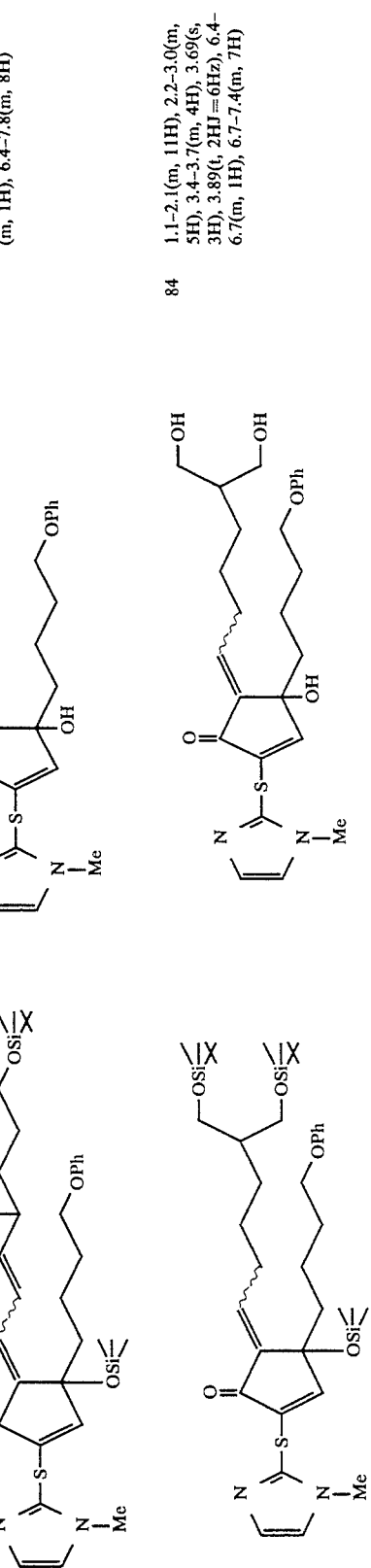 | 84 | 1.1-2.1(m, 11H), 2.2-3.0(m, 5H), 3.4-3.7(m, 4H), 3.69(s, 3H), 3.89(t, 2H,J=6Hz), 6.4-6.7(m, 1H), 6.7-7.4(m, 7H) |
| 456 | 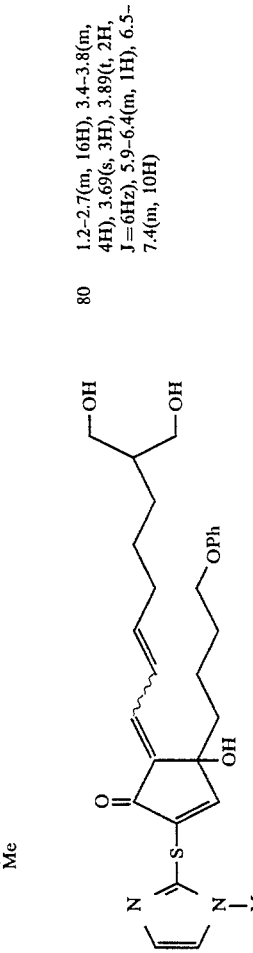 | 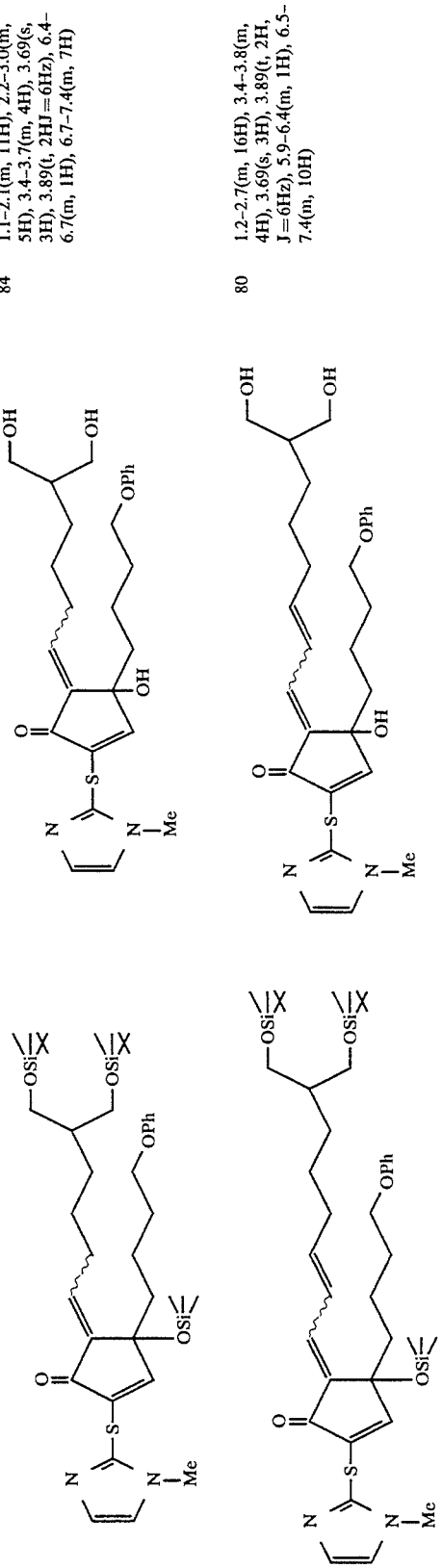 | 80 | 1.2-2.7(m, 16H), 3.4-3.8(m, 4H), 3.69(s, 3H), 3.89(t, 2H, J=6Hz), 5.9-6.4(m, 1H), 6.5-7.4(m, 10H) |

| | | |
|---|---|---|
| 457 | 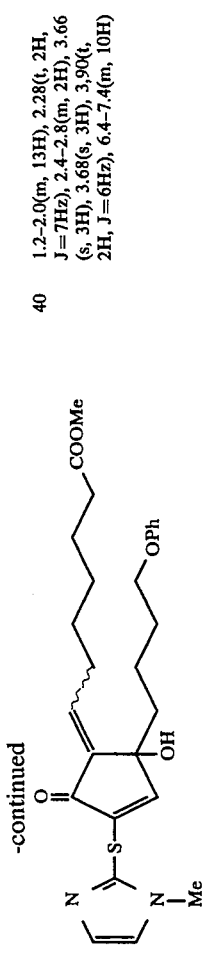 | 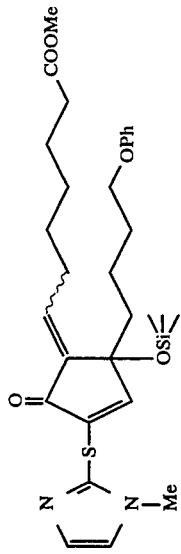 40 1.2-2.0(m, 13H), 2.28(t, 2H, J=7Hz), 2.4-2.8(m, 2H), 3.66 (s, 3H), 3.68(s, 3H), 3.90(t, 2H, J=6Hz), 6.4-7.4(m, 10H) |
| 458 | 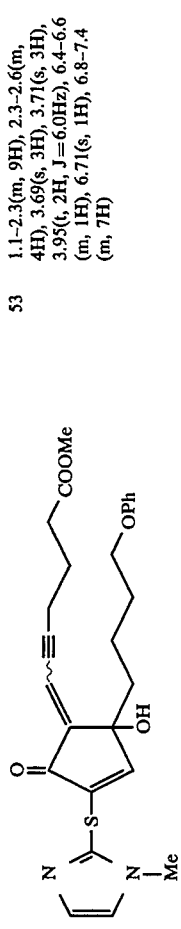 | 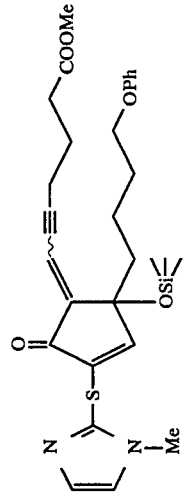 53 1.1-2.3(m, 9H), 2.3-2.6(m, 4H), 3.69(s, 3H), 3.71(s, 3H), 3.95(t, 2H, J=6.0Hz), 6.4-6.6 (m, 1H), 6.71(s, 1H), 6.8-7.4 (m, 7H) |
| 459 | 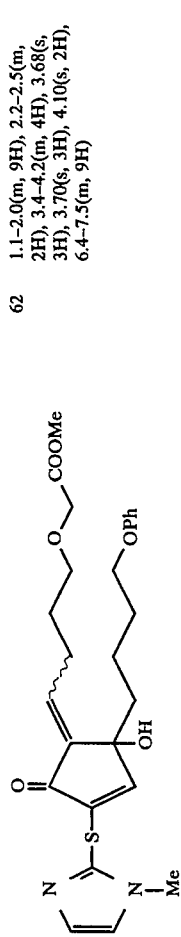 | 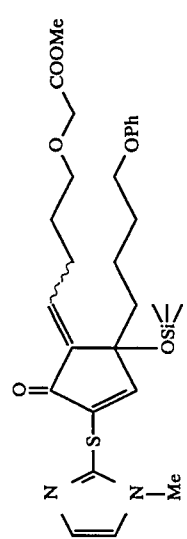 62 1.1-2.0(m, 9H), 2.2-2.5(m, 2H), 3.4-4.2(m, 4H), 3.68(s, 3H), 3.70(s, 3H), 4.10(s, 2H), 6.4-7.5(m, 9H) |
| 460 | | 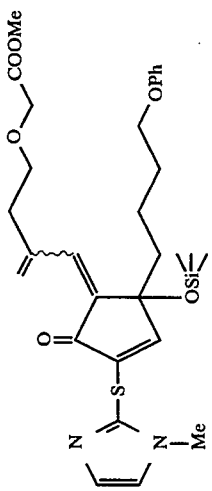 63 1.0-2.2(m, 7H), 2.3-3.1(m, 2H), 3.3-3.7(m, 2H), 3.70(s, 3H), 3.71(s, 3H), 3.88(t, 2H, J=6.2Hz), 4.02(s, 2H), 5.46 (brs, 1H), 5.76(brs(1H), 6.6-7.4(m, 9H) |
| 461 | 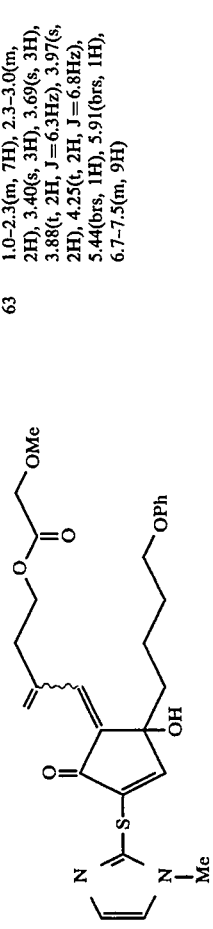 | 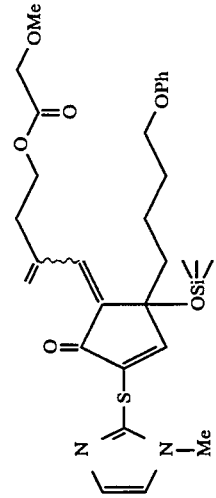 63 1.0-2.3(m, 7H), 2.3-3.0(m, 2H), 3.40(s, 3H), 3.69(s, 3H), 3.88(t, 2H, J=6.3Hz), 3.97(s, 2H), 4.25(t, 2H, J=6.8Hz), 5.44(brs, 1H), 5.91(brs, 1H), 6.7-7.5(m, 9H) |

| | | |
|---|---|---|
| 462 | 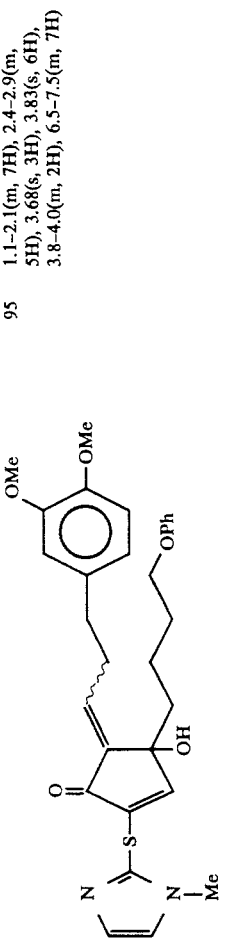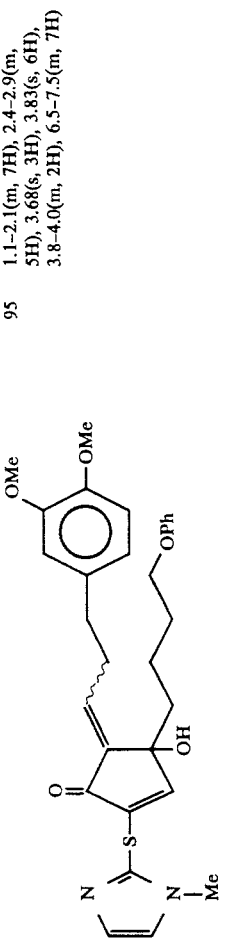 | 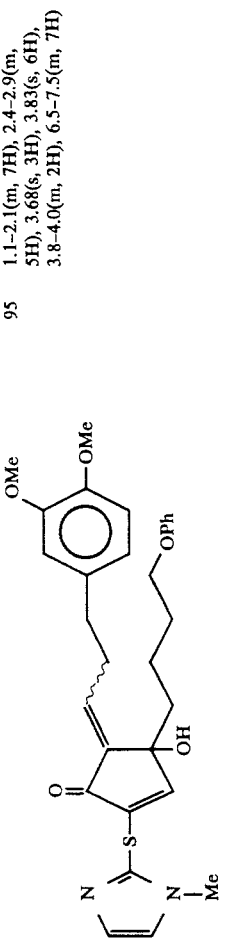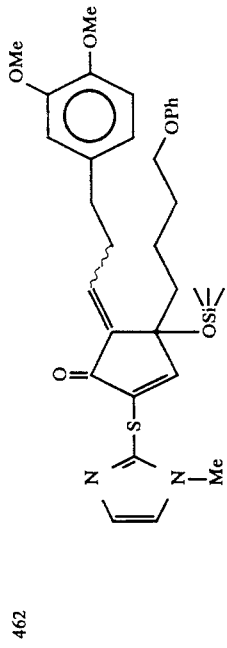 95 | 1.1–2.1(m, 7H), 2.4–2.9(m, 5H), 3.68(s, 3H), 3.83(s, 6H), 3.8–4.0(m, 2H), 6.5–7.5(m, 7H) |
| 463 | 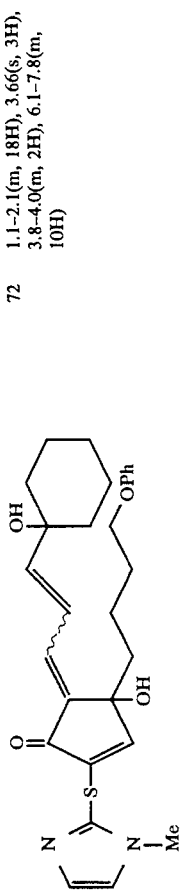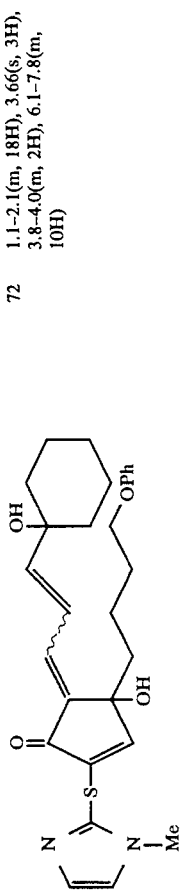 | 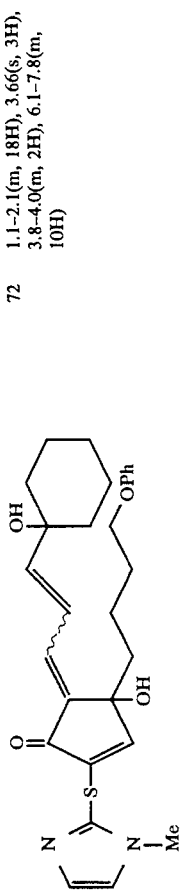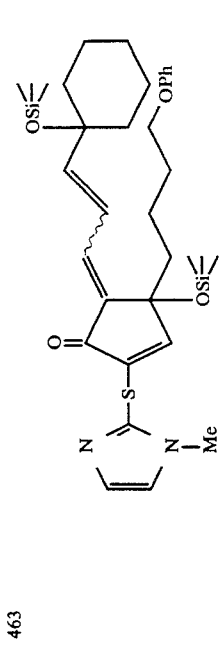 72 | 1.1–2.1(m, 18H), 3.66(s, 3H), 3.8–4.0(m, 2H), 6.1–7.8(m, 10H) |
| 464 | 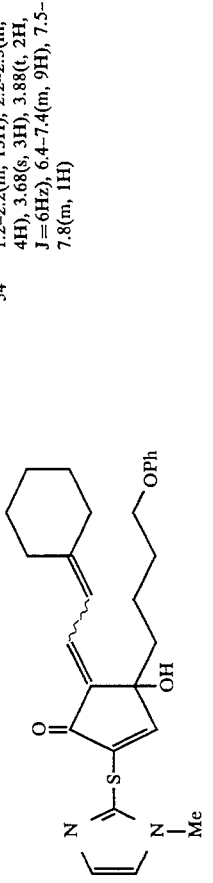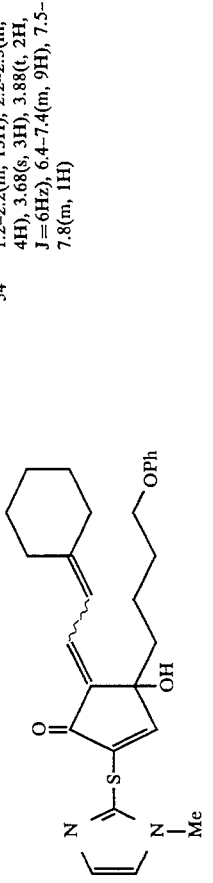 | 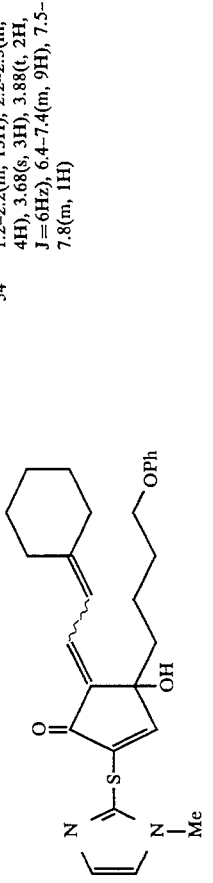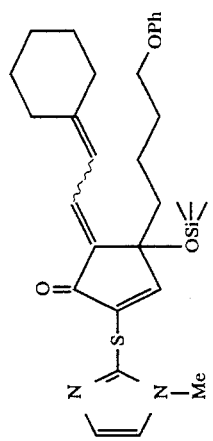 54 | 1.2–2.2(m, 13H), 2.2–2.5(m, 4H), 3.68(s, 3H), 3.88(t, 2H, J=6Hz), 6.4–7.4(m, 9H), 7.5–7.8(m, 1H) |
| 465 | 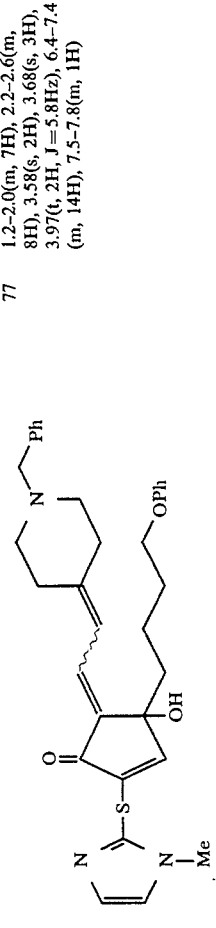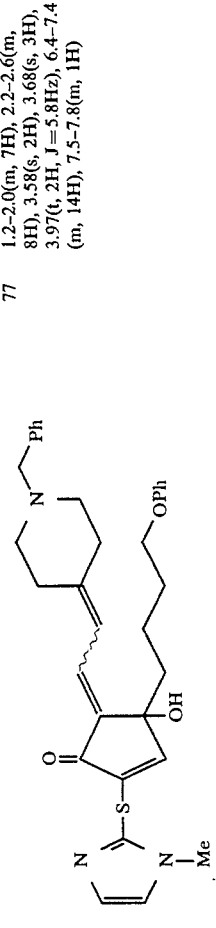 | 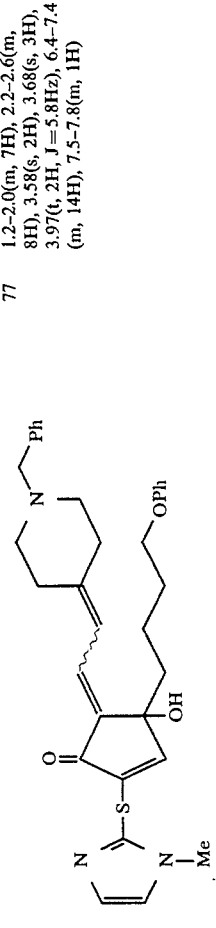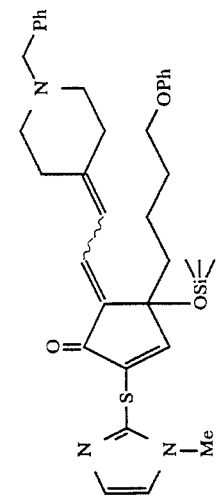 77 | 1.2–2.0(m, 7H), 2.2–2.6(m, 8H), 3.58(s, 2H), 3.68(s, 3H), 3.97(t, 2H, J=5.8Hz), 6.4–7.4 (m, 14H), 7.5–7.8(m, 1H) |

| | | | |
|---|---|---|---|
| 466 | 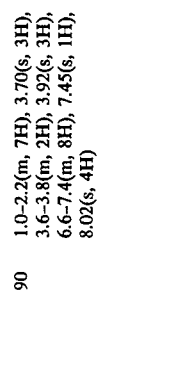 |  | 90 | 1.0–2.2(m, 7H), 3.70(s, 3H), 3.6–3.8(m, 2H), 3.92(s, 3H), 6.6–7.4(m, 8H), 7.45(s, 1H), 8.02(s, 4H) |
| 467 | 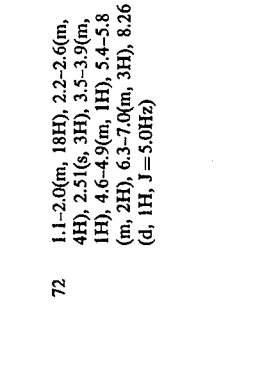 | 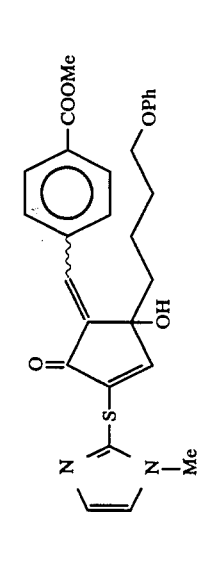 | 84 | 1.0–2.2(m, 10H), 2.4–2.7(m, 2H), 3.4–4.0(m, 6H), 3.73(s, 3H), 6.6–7.4(m, 9H), 7.29(d, 2H, J=8.3Hz), 7.80(d, 2H, J=8.3 Hz) |
| 468 | 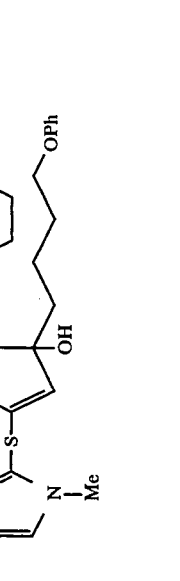 | 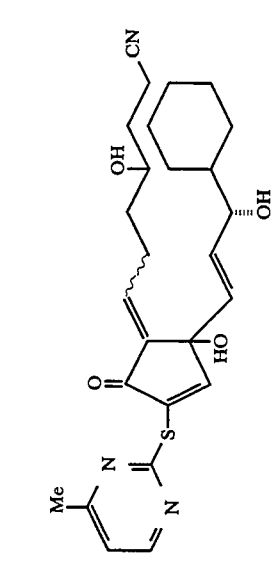 | 68 | 0.7–1.0(m, 3H), 1.2–2.0(m, 17H), 2.1–2.5(m, 4H), 3.68(s, 3H), 3.69(s, 3H), 5.8–8.0(m, 6H) |
| 469 | | | 72 | 1.1–2.0(m, 18H), 2.2–2.6(m, 4H), 2.51(s, 3H), 3.5–3.9(m, 1H), 4.6–4.9(m, 1H), 5.4–5.8(m, 2H), 6.3–7.0(m, 3H), 8.26(d, 1H, J=5.0Hz) |

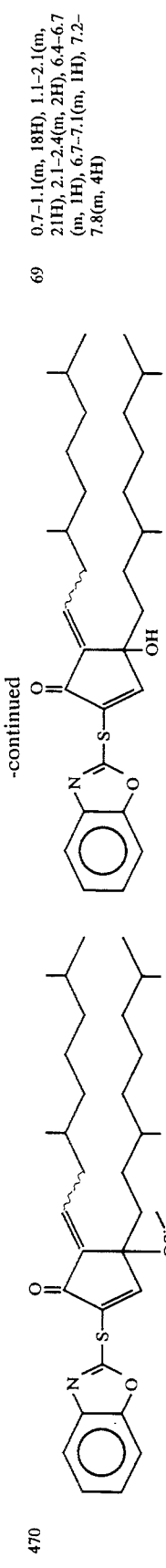
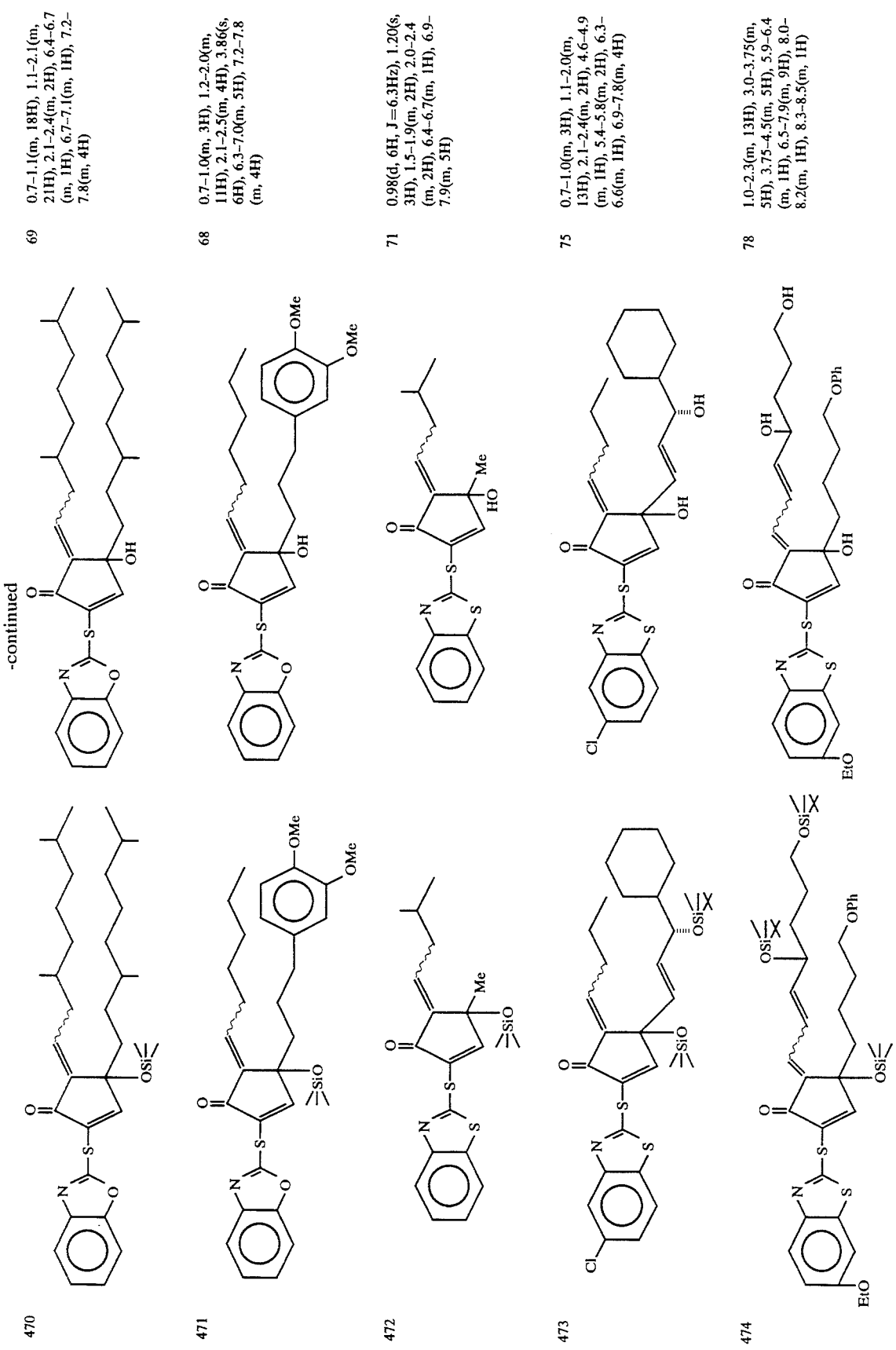

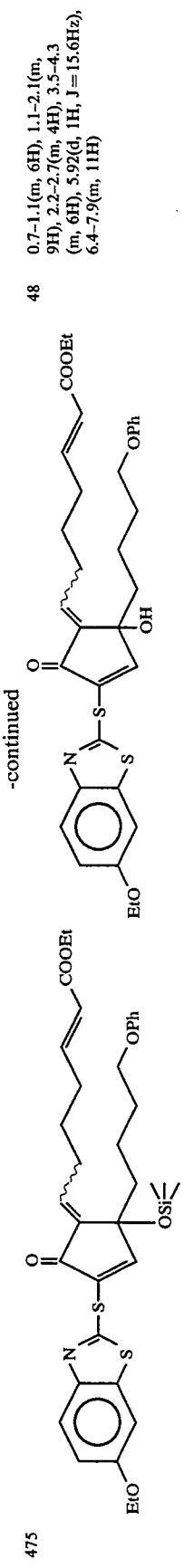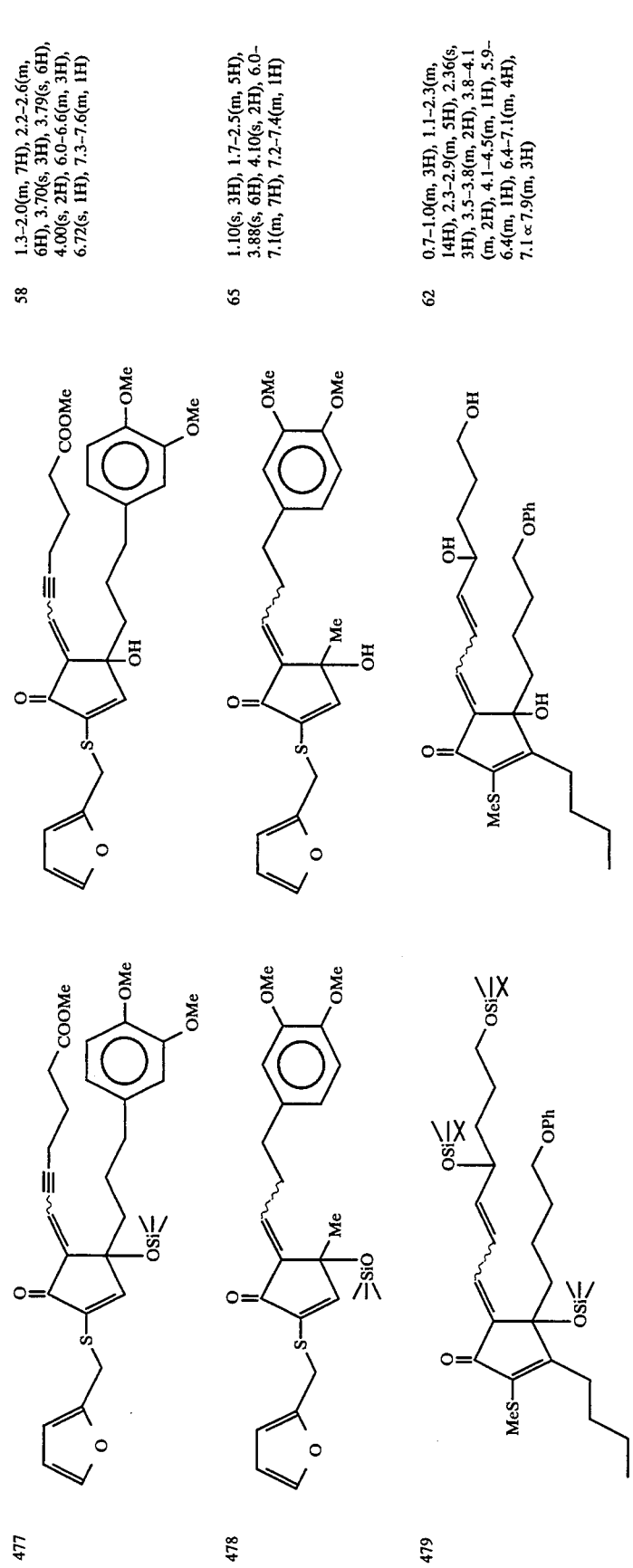

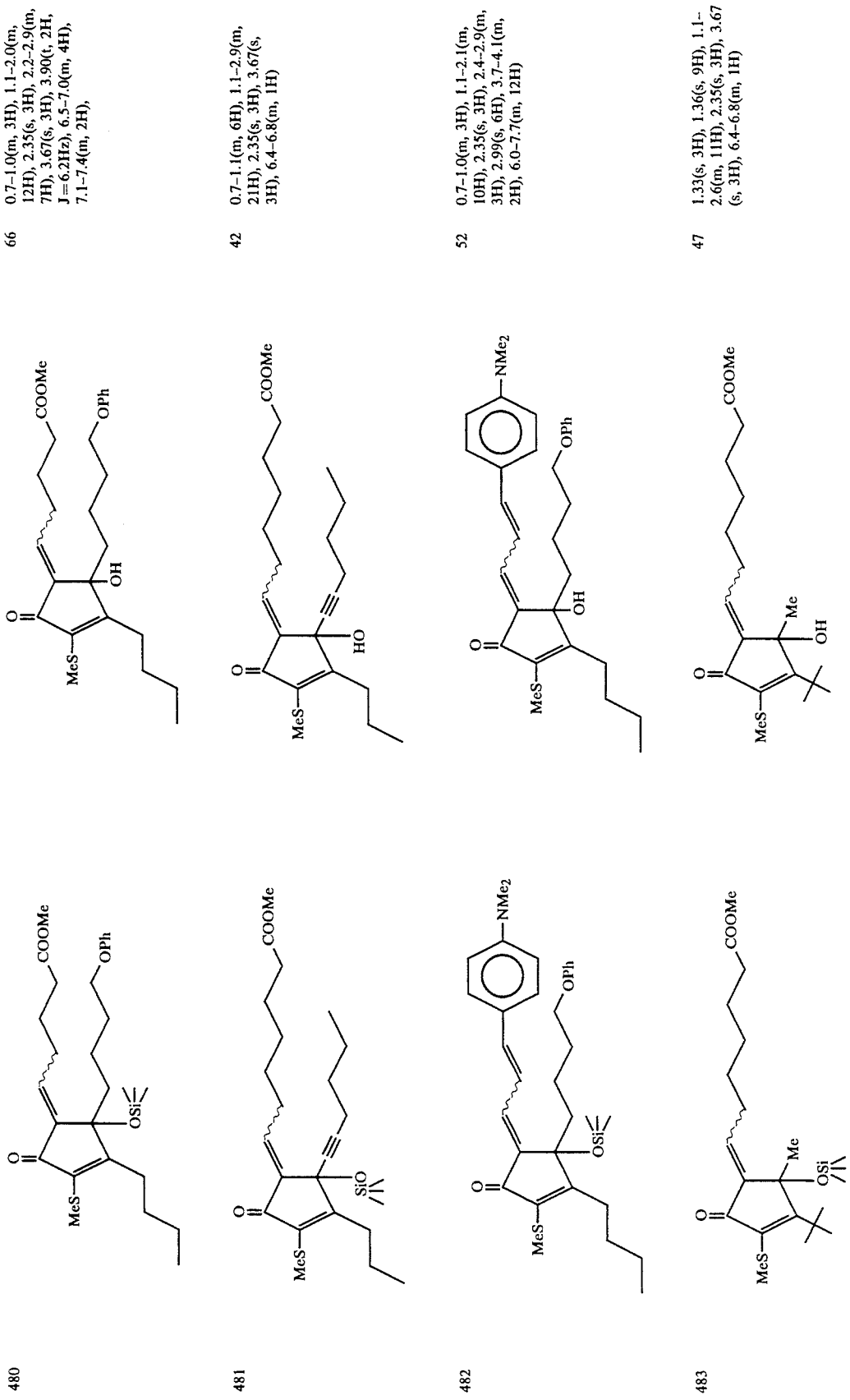

| | | |
|---|---|---|
| 484 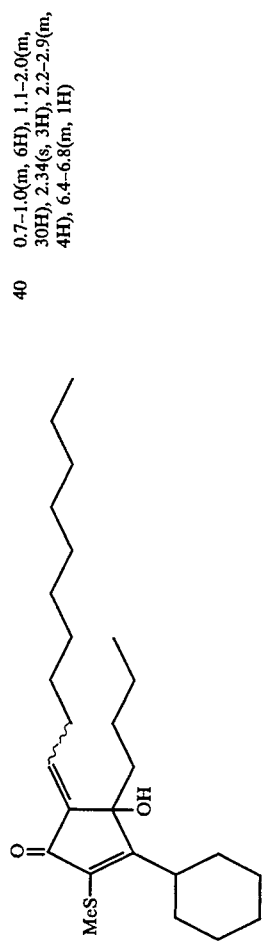 | 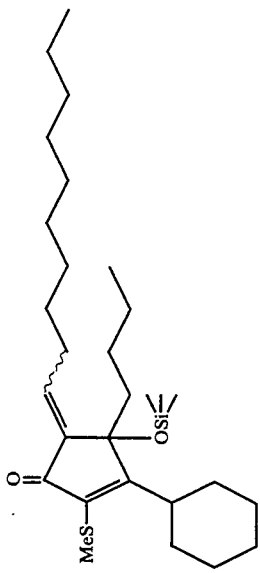 | 40 | 0.7–1.0(m, 6H), 1.1–2.0(m, 30H), 2.34(s, 3H), 2.2–2.9(m, 4H), 6.4–6.8(m, 1H) |
| 485 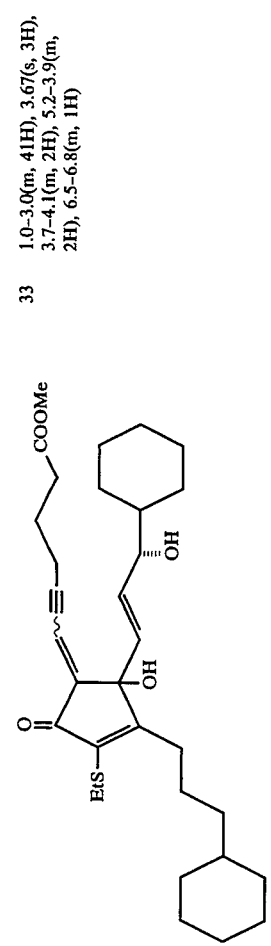 | 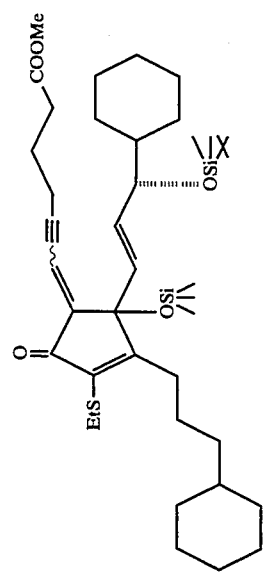 | 33 | 1.0–3.0(m, 41H), 3.67(s, 3H), 3.7–4.1(m, 2H), 5.2–3.9(m, 2H), 6.5–6.8(m, 1H) |
| 486 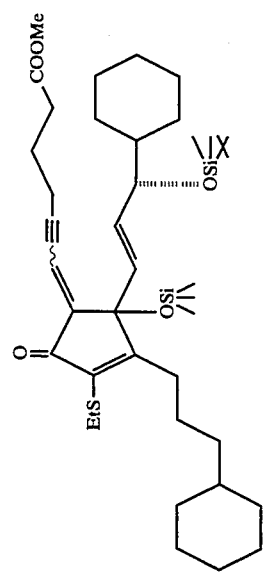 | | 50 | 0.7–1.0(m, 3H), 1.1–2.0(m, 10H), 1.34(s, 9H), 2.4–2.8(m, 3H), 3.90(t, 2H, J=6.0Hz), 6.5–7.8(m, 1H) |

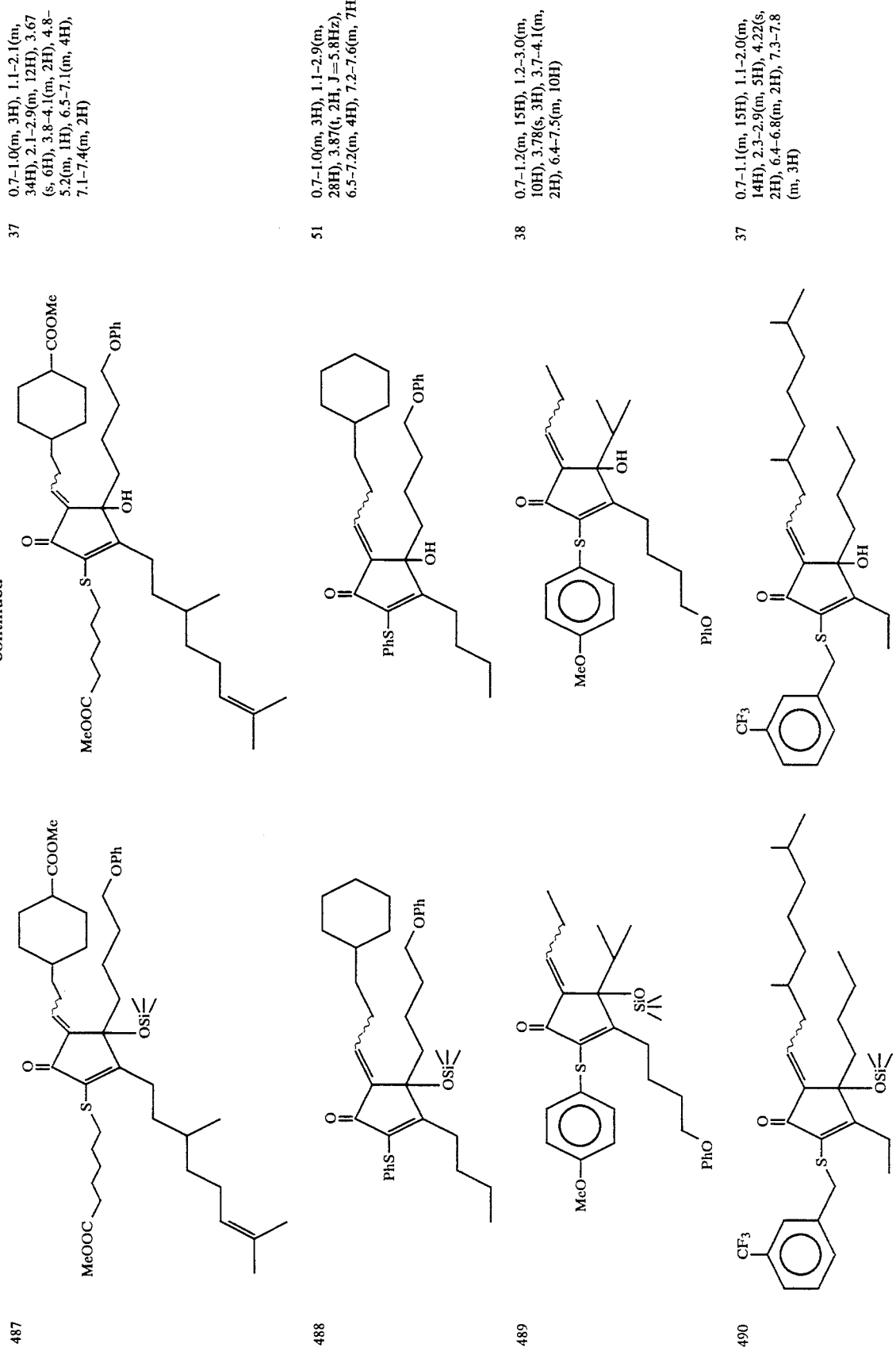

| | | |
|---|---|---|
| 491 | 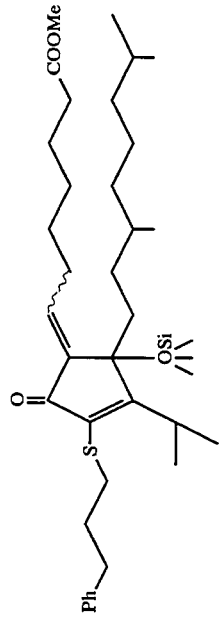 | 51 | 0.7–1.2(m, 15H), 1.2–3.0(m, 30H), 3.67(s, 3H), 6.4–6.8(m, 1H), 7.0–7.4(m, 5H) |
| 492 | 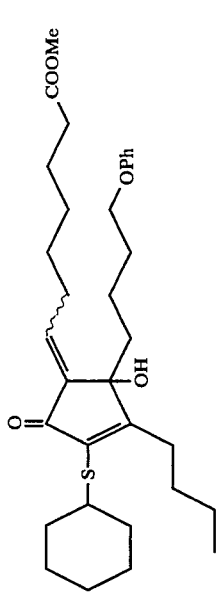 | 56 | 0.7–1.0(m, 3H), 1.1–2.9(m, 34H), 3.68(s, 3H), 3.90(t, 2H, J=6.0Hz), 6.4–7.5(m, 7H) |
| 493 | 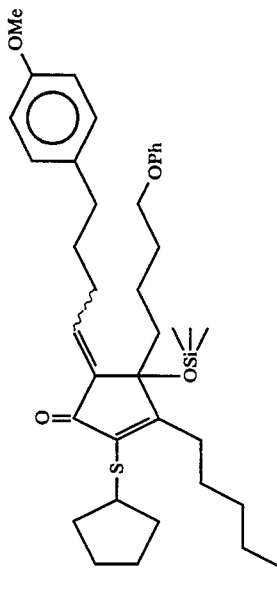 | 41 | 1.1–2.1(m, 22H), 2.1–2.9(m, 10H), 3.75(s, 3H), 3.8–4.1(m, 2H), 6.5–7.6(m, 15H) |
| 494 | 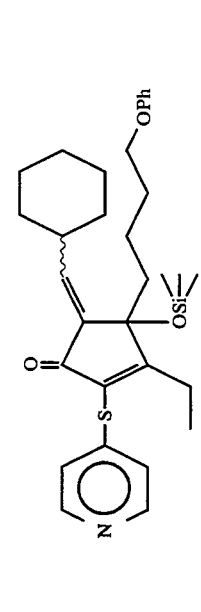 | 41 | 0.7–1.0(m, 3H), 1.1–2.0(m, 17H), 2.1–2.7(m, 3H), 3.94(t, 2H, J=6.3Hz), 6.7–7.1(m, 4H), 7.1–8.0(m, 6H) |

| No. | Product | Yield (%) | NMR |
|---|---|---|---|
| 495 / 69 | (structure with OSi groups, OPh, thiocarbamate) | 69 | 0.7–1.1(m, 3H), 1.1–3.1(m, 19H), 3.4–3.7(m, 2H), 3.78(s, 3H), 3.7–4.4(m, 3H), 5.8–6.2(m, 1H), 6.4–6.7(m, 1H), 6.7–7.1(m, 5H), 7.1–7.7(m, 3H) |
| 496 / 52 | (cyclopentenone with benzoxazole-S, COOEt, dimethoxyphenyl) | 52 | 1.2–3.0(m, 16H), 2.43(s, 3H), 3.84(s, 6H), 3.7–4.0(m, 2H), 5.7–6.2(m, 2H), 6.4–7.1(m, 4H), 7.2–7.8(m, 4H) |
| 497 / 39 | (cyclopentenone MeS, COOMe) | 39 | 1.2–2.5(m, 11H), 2.35(s, 3H), 3.68(s, 3H), 4.8–5.3(m, 1H), 6.5–7.1(m, 2H) |
| 498 / 35 | (cyclopentenone MeS, OH chain) | 35 | 1.5–1.8(m, 7H), 2.39(s, 3H), 3.3–3.7(m, 2H), 4.0–4.5(m, 1H), 5.1–5.4(m, 1H), 6.0–7.9(m, 4H) |
| 499 / 62 | (cyclopentenone MeS, NMe₂-styryl) | 62 | 1.9–2.1(m, 1H), 2.35(s, 3H), 3.01(s, 6H), 5.0–5.4(m, 1H), 6.6–7.7(m, 8H) |

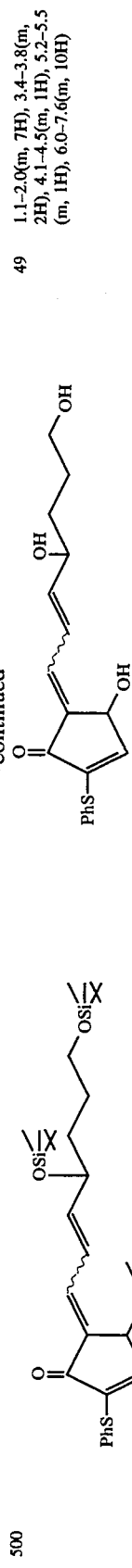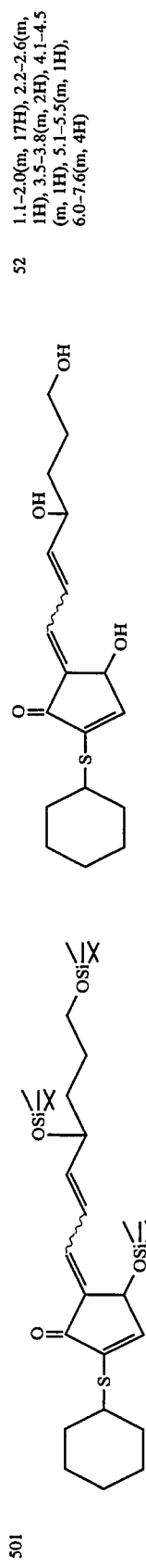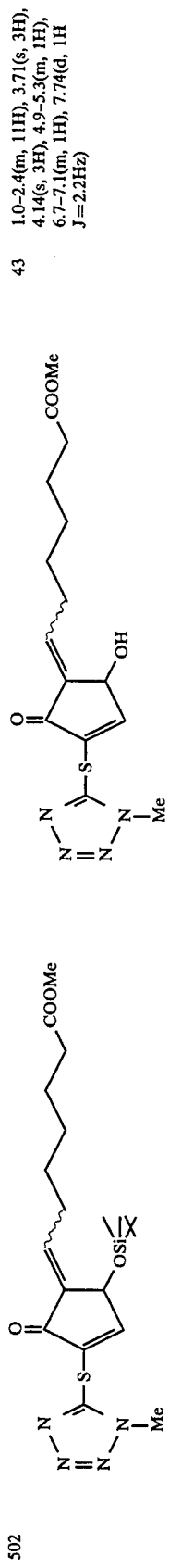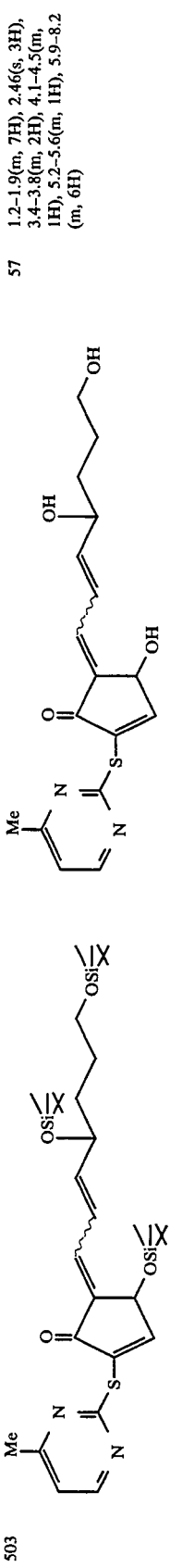

| | | |
|---|---|---|
| 506 | 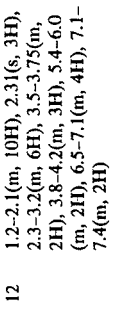 | 12 | 1.2-2.1(m, 10H), 2.31(s, 3H), 2.3-3.2(m, 6H), 3.5-3.75(m, 2H), 3.8-4.2(m, 3H), 5.4-6.0(m, 2H), 6.5-7.1(m, 4H), 7.1-7.4(m, 2H) |
Above table is misaligned; correct rendering below:
| No. | Starting material | Product | Yield | NMR |
|---|---|---|---|---|
| 506 | 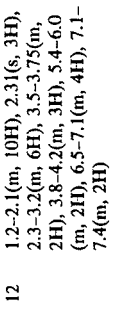 | 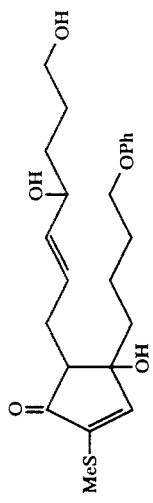 | 12 | 1.2-2.1(m, 10H), 2.31(s, 3H), 2.3-3.2(m, 6H), 3.5-3.75(m, 2H), 3.8-4.2(m, 3H), 5.4-6.0(m, 2H), 6.5-7.1(m, 4H), 7.1-7.4(m, 2H) |
| 507 | 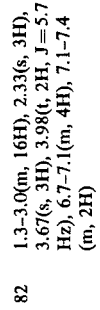 | 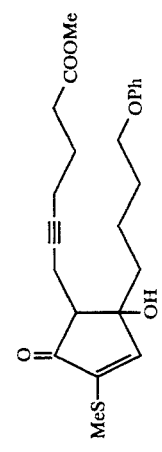 | 82 | 1.3-3.0(m, 16H), 2.33(s, 3H), 3.67(s, 3H), 3.98(t, 2H, J=5.7 Hz), 6.7-7.1(m, 4H), 7.1-7.4(m, 2H) |
| 508 | 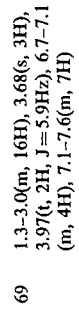 | 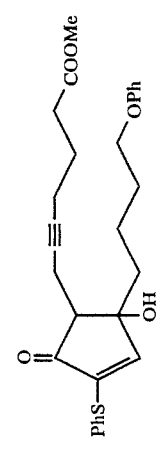 | 69 | 1.3-3.0(m, 16H), 3.68(s, 3H), 3.97(t, 2H, J=5.9Hz), 6.7-7.1(m, 4H), 7.1-7.6(m, 7H) |
| 509 | 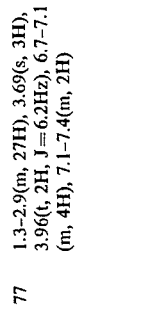 | 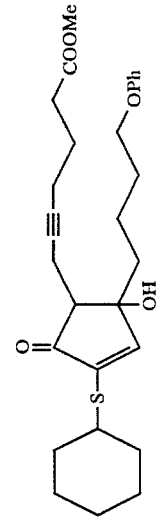 | 77 | 1.3-2.9(m, 27H), 3.69(s, 3H), 3.96(t, 2H, J=6.2Hz), 6.7-7.1(m, 4H), 7.1-7.4(m, 2H) |
| 510 | 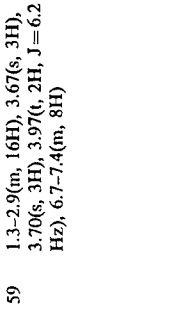 | 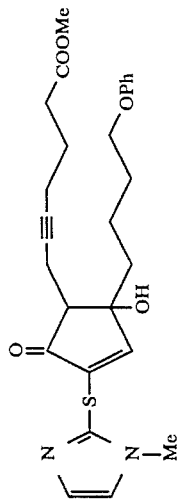 | 59 | 1.3-2.9(m, 16H), 3.67(s, 3H), 3.70(s, 3H), 3.97(t, 2H, J=6.2 Hz), 6.7-7.4(m, 8H) |

| | | |
|---|---|---|
| 511 | 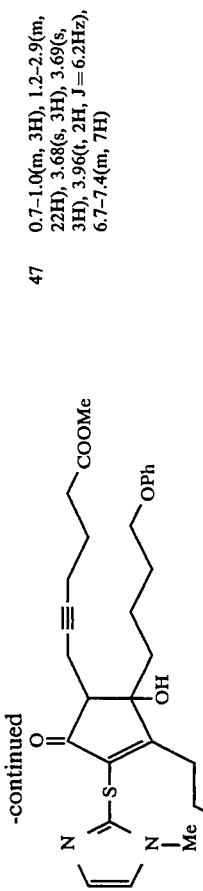 | |
| | 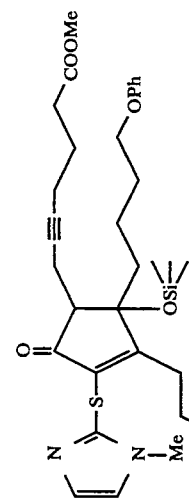 | 47 0.7–1.0(m, 3H), 1.2–2.9(m, 22H), 3.68(s, 3H), 3.69(s, 3H), 3.96(t, 2H, J=6.2Hz), 6.7–7.4(m, 7H) |

TABLE 20

| Ex. No. | Starting compd. (2-Substituted-2-cyclopentenones) | 2-Substituted-2-cyclopentenones | Yield (%) | NMR (δ, CDCl₃) |
|---|---|---|---|---|
| 512 | (structure with OSi groups, SPh, cyclohexyl-S) | (structure with OH groups, SPh, cyclohexyl-S) | 84 | 1.1–2.3(19H, m), 2.3–2.8(4H, m), 3.0–3.4(1H, m), 3.5–3.8 (2H, m), 3.8–4.1(2H, m), 4.1–4.5(1H, m), 5.9–6.4(1H, m), 6.4–7.05(4H, m), 7.05–7.9 (4H, m) |
| 513 | (structure with COOMe, OPh, MeS, OSi) | (structure with COOMe, OPh, MeS, OH) | 12 | 1.1–2.2(21H, m), 2.2–2.8(3H, m), 3.0–3.4(1H, m), 3.5–3.8 (2H, m), 3.8–4.1(2H, m), 4.2–4.5(1H, m), 5.80(1H, t, J = 7.9 Hz), 6.0–6.5(1H, m), 6.6–7.1 (4H, m), 7.1–7.7(3H, m), 7.88 (1H, dd, J = 9.0, 4.5Hz) |
| 514 | (structure with COOMe, OPh, MeS) | (structure with COOMe, OPh, MeS) | 75 | 1.1–3.0(7H, m), 2.36(3H, s), 3.6–4.2(2H, m), 3.82(3H, s), 4.72(2H, s), 6.6–7.6(10H, m), 7.6–8.1(1H, m) |
| 514 | | (structure) | 6 | 1.5–2.9(4H, m), 2.29(3H, s), 3.79(3H, s), 3.8–4.2(2H, m), 4.62(2H, s), 5.75–6.10(1H, m), 6.6–7.7(11H, m) |
| 514 | (structure with OH, OPh, MeS, propyl) | (structure with OH, OPh, MeS, propyl) | 53 | 0.7–1.0(m, 3H), 1.1–2.2(m, 10H), 2.3–2.9(m, 6H), 2.35(s, 3H), 3.5–3.8(m, 2H), 3.8–4.1 (m, 2H), 4.2–4.5(m, 1H), 5.80 (t, 1H, J = 8.0Hz), 6.0–6.5(m, 1H), 6.6–7.1(m, 3H), 7.1–7.9 (m, 4H) |
| 515 | (structure with OH, OPh, PhS, propyl) | (structure with OH, OPh, PhS, propyl) | 49 | 0.7–1.0(m, 3H), 1.1–2.8(m, 16H), 3.5–3.8(m, 2H), 3.8–4.1 (m, 2H), 4.2–4.5(m, 1H), 5.82 (t, 1H, J = 8.0Hz), 6.0–6.5(m, 1H), 6.6–8.1(m, 12H) |

TABLE 20-continued

| Ex. No. | Starting compd. (2-Substituted-2-cyclopentenones) | 2-Substituted-2-cyclopentenones | Yield (%) | NMR (δ, CDCl₃) |
|---|---|---|---|---|
| 516 | (structure with OH, OH, OPh, COOMe-like chain, S-cyclohexyl cyclopentenone) | (structure with OH, OH, OPh, OMe, S-cyclohexyl) | 38 | 1.1–2.1(22H, m), 2.1–2.5(1H, m), 3.05(3H, s), 3.55–3.8(2H, m), 3.93(2H, t, J=6.0Hz), 4.1–4.5(1H, m), 6.17(1H, dd, J=15.0, 6.2Hz), 6.46(1H, d, J=11.0Hz), 6.53(1H, s), 6.7–7.0(3H, m), 7.1–7.4(2H, m), 7.72(1H, dd, J=15.3, 11.2Hz) |
| 517 | Same as above | (structure with OH, OH, OPh, OEt, S-cyclohexyl) | 29 | 1.10(3H, t, J=7.0Hz), 1.1–2.1(22H, m), 2.1–2.5(1H, m), 3.21(2H, q, J=7.0Hz), 3.5–3.8(2H, m), 3.95(2H, t, J=6.1Hz), 4.1–4.5(1H, m), 6.20(1H, dd, J=15.2, 6.0Hz), 6.55(1H, s), 6.7–7.1(3H, m), 7.1–7.5(2H, m), 7.73(1H, dd, J=15.3, 11.0Hz) |
| 518 | (structure with OH, OH, OPh, S-cyclohexyl) | (structure with OAc, OAc, OPh, OH, S-cyclohexyl) | 44 | 1.1–2.1(21H, m), 2.01(3H, s), 2.13(5H, m), 6.0–6.5(1H, m), 6.69(1H, s), 6.7–7.2(4H, m), 7.2–7.5(3H, m) |
| 519 | (structure with COOMe, OSi, S-cyclohexyl) | (structure with OAc, OAc, OPh, OAc, S-cyclohexyl) | 14 | 1.1–2.1(20H, m), 2.01(3H, s), 2.04(3H, s), 2.13(3H, s), 2.1–2.5(1H, m), 3.6–4.5(5H, m), 6.0–6.5(1H, m), 6.64(1H, s), 6.7–7.2(4H, m), 7.2–7.5(3H, m) |
| 520 | (structure with COOMe, OPh, OH, S-cyclohexyl) | (structure with COOH, OPh, OSi, S-cyclohexyl) | 62 | 0.05(6H, s), 0.89(9H, s), 0.86(3H, brt, J=5.6Hz), 1.1–2.5(30H, m), 3.9–4.2(2H, m), 5.2–5.9(2H, m), 6.6–6.8(2H, m) |
|  |  | (structure with COOH, OPh, OH, S-cyclohexyl) | 79 | 1.1–2.5(27H, m), 2.5–3.0(2H, m), 3.94(2H, t, J=6Hz), 6.4–7.1(5H, m), 7.1–7.4(2H, m) |

TABLE 20-continued

| Ex. No. | Starting compd. (2-Substituted-2-cyclopentenones) | 2-Substituted-2-cyclopentenones | Yield (%) | NMR (δ, CDCl₃) |
|---|---|---|---|---|
| 521 | | | 39 | 0.86(3H, brt, J=5.6Hz), 1.1-2.5(30H, m), 3.9-4.2(2H, m), 5.2-6.2(4H, m), 6.6-6.9(2H, m) |
| 522 | | | 53 | 0.86(3H, brt, J=5.6Hz), 1.0-3.1(44H, m), 3.9-4.2(2H, m), 5.2-6.2(4H, m), 6.6-6.9(2H, m) |
| 523 | | | 62 | 0.89(3H, brt), 1.1-2.6(30H, m), 3.67(3H, s), 4.0-4.3(2H, m), 5.3-6.0(2H, m), 6.72(1H, t, J=7Hz), 7.7-7.8(1H, m) |
| 524 | | | 28 | 1.1-3.0(24H, m), 3.5-3.8(2H, m), 3.92(2H, t, J=6.0Hz), 4.1-4.4(1H, m), 6.0-6.5(1H, m), 6.6-7.1(5H, m), 7.1-7.5(2H, m), 7.7(1H, s) |
| 525 | | | 61 | 0.7-1.0(m, 3H), 1.1-2.4(m, 28H), 3.0-3.3(m, 1H), 3.66(s, 3H), 4.0-4.5(m, 2H), 5.3-6.0 (m, 2H), 6.82(t, J=7Hz, 1H), 8.06(d, J=3Hz, 1H) |
| 526 | | | 13 | 1.2-2.5(23H, m), 3.0-3.3(1H, m), 3.5-3.8(2H, m), 3.93(2H, t, J=5.9Hz), 4.1-4.4(1H, m), 6.1-6.4(1H, m), 6.65-7.05(4H, m), 7.05-7.4(2H, m), 7.99(1H, s) |
| 527 | | | 68 | 1.1-3.0(28H, m), 3.25(2H, m), 3.9(2H, t, J=6Hz), 4.5(2H, m), 6.4-7.1(4H, m), 7.1-7.4(3H, m) |

TABLE 20-continued

| Ex. No. | Starting compd. (2-Substituted-2-cyclopentenones) | 2-Substituted-2-cyclopentenones | Yield (%) | NMR (δ, CDCl₃) |
|---|---|---|---|---|
| 528 | (structure) | (structure) | 51 | 1.1–2.9(27H, m), 3.0–5.3(14H, m), 6.4–7.1(4H, m), 7.1–7.4 (3H, m) |
| 529 | (structure) | (structure) | 39 | 1.1–2.9(27H, m), 3.0–5.3(12H, m), 6.4–7.1(4H, m), 7.1–7.4 (3H, m) |

TABLE 21

| Compound to be tested | IC$_{50}$ (μg/ml) |
|---|---|
| (cyclohexyl-S-cyclopentenone with OH, OH, OPh side chains) | 0.78 |
| (MeS-cyclopentenone with benzyl-OPh, OCH$_2$CO$_2$Me) | 0.83 |
| (EtO-benzothiazolyl-S-cyclopentenone with OH, OH, OPh side chains) | 0.02 |
| (N-methylimidazolyl-S-cyclopentenone with OH, OH, OPh side chains) | 0.15 |
| (N-methylimidazolyl-S-cyclopentenone with butyl, OH, OPh side chains) | 2.30 |
| (MeS-cyclopentenone with OH, OH side chain, H,H) | 0.10 |
| (MeS-cyclopentenone with OH, OH, OPh side chains, H) | 1.90 |
| (N-methylimidazolyl-S-cyclopentenone with OH, OH, OH, OPh side chains) | 0.32 |

TABLE 22

| 2-Substituted-2-cyclopentenones | Ca μg/dish | P μg/dish | ALP OD$_{415}$/dish |
|---|---|---|---|
| Control (No compds.) | 45.61 ± 6.19 | 30.68 ± 3.33 | 0.27 ± 0.04 |

TABLE 22-continued

| 2-Substituted-2-cyclopentenones | | Ca μg/dish | P μg/dish | ALP OD$_{415}$/dish |
|---|---|---|---|---|
| 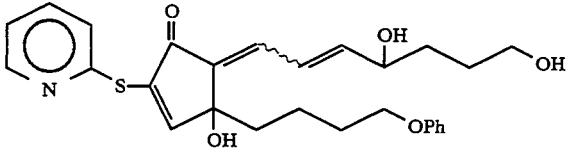 | $10^{-6}$ M<br>$10^{-7}$ M | 70.42 ± 7.82<br>56.85 ± 3.58 | 42.28 ± 6.99<br>33.20 ± 2.26 | 0.36 ± 0.12<br>0.29 ± 0.04 |
| 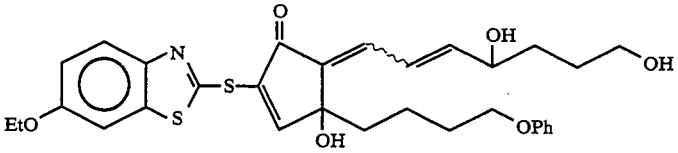 | $10^{-6}$ M<br>$10^{-7}$ M | 81.88 ± 8.47<br>61.19 ± 1.89 | 41.45 ± 7.21<br>40.52 ± 4.45 | 0.10 ± 0.01<br>0.34 ± 0.06 |
| 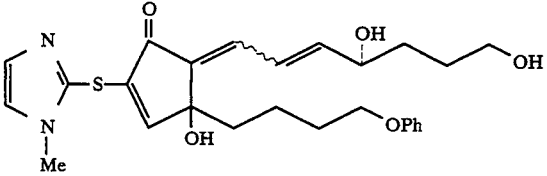 | $10^{-6}$ M<br>$10^{-7}$ M | 79.83 ± 0.58<br>61.95 ± 3.42 | 46.43 ± 1.41<br>38.43 ± 1.97 | 0.48 ± 0.04<br>0.33 ± 0.06 |

TABLE 23

| 2-Substituted-2-cyclopentenones | | Ca μg/dish | P μg/dish | ALP OD$_{415}$/dish |
|---|---|---|---|---|
| Control (No compd.) | | 11.83 ± 3.18 | 11.50 ± 1.73 | 0.58 ± 0.03 |
| 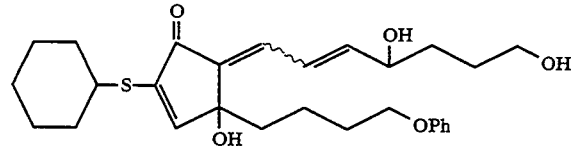 | $10^{-6}$ M<br>$10^{-7}$ M | 33.50 ± 3.91<br>19.67 ± 1.61 | 24.83 ± 2.47<br>16.67 ± 0.76 | 0.64 ± 0.05<br>0.53 ± 0.05 |
| 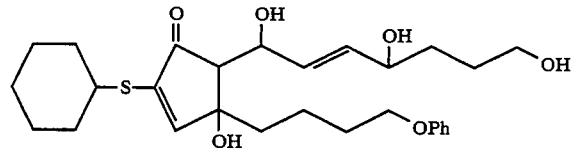 | $10^{-7}$ M<br>$10^{-8}$ M | 13.83 ± 1.15<br>20.17 ± 3.18 | 11.67 ± 3.18<br>16.50 ± 1.73 | 0.55 ± 0.04<br>0.36 ± 0.06 |

TABLE 24

| 2-Substituted-2-cyclopentenones | | Ca μg/dish | P μg/dish | ALP OD$_{415}$/dish |
|---|---|---|---|---|
| Control (No compds.) | | 4.33 ± 0.58 | 4.33 ± 0.58 | 0.72 ± 0.01 |
| 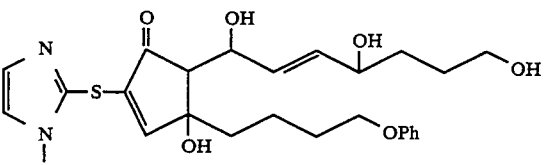 | $10^{-6}$ M<br>$10^{-7}$ M | 26.17 ± 3.25<br>1.17 ± 0.29 | 19.33 ± 2.02<br>4.50 ± 0.50 | 0.76 ± 0.08<br>0.81 ± 0.01 |

TABLE 25

| 2-Substituted-2-cyclopentenones | Ca μg/dish | P μg/dish | ALP OD$_{415}$/dish |
|---|---|---|---|
| Control (No compds.) | 31.26 ± 3.00 | 18.64 ± 3.16 | 0.77 ± 0.20 |

TABLE 25-continued

| 2-Substituted-2-cyclopentenones | | Ca μg/dish | P μg/dish | ALP OD$_{415}$/dish |
|---|---|---|---|---|
| 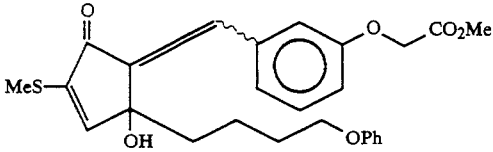 | $10^{-7}$ M $10^{-8}$ M | 36.18 ± 14.29 49.16 ± 26.04 | 21.72 ± 8.88 25.43 ± 9.23 | 0.52 ± 0.10 0.64 ± 0.04 |

TABLE 26

| 2-Substituted-2-cyclopentenones | | Ca μg/dish | P μg/dish | ALP OD$_{415}$/dish |
|---|---|---|---|---|
| Control (No compd.) | | 3.00 ± 1.73 | 5.33 ± 1.15 | 0.60 ± 0.02 |
| 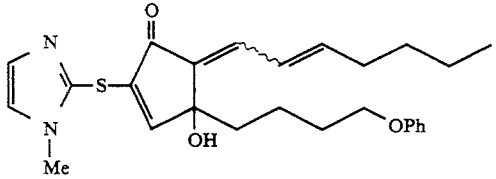 | $10^{-7}$ M $10^{-6}$ M | 13.33 ± 1.53 96.67 ± 0.58 | 12.67 ± 1.15 52.67 ± 0.58 | 0.57 ± 0.04 0.08 ± 0.00 |
| 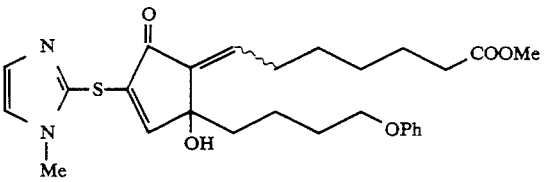 | $10^{-7}$ M $10^{-6}$ M | 3.67 ± 1.15 43.67 ± 0.58 | 6.33 ± 0.58 29.67 ± 0.58 | 0.63 ± 0.02 0.60 ± 0.03 |
| 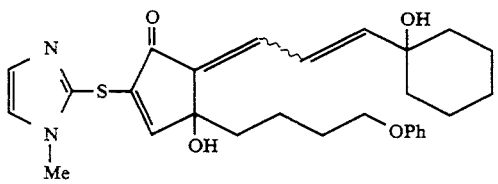 | $10^{-7}$ M $10^{-6}$ M | 14.00 ± 1.00 85.67 ± 14.05 | 12.67 ± 1.15 49.00 ± 7.00 | 0.58 ± 0.03 0.11 ± 0.02 |
| 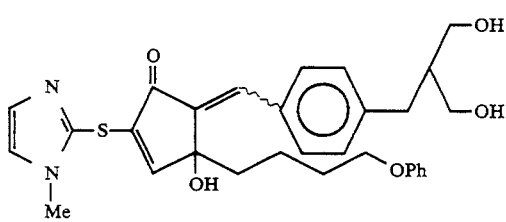 | $10^{-7}$ M $10^{-6}$ M | 11.00 ± 1.73 116.00 ± 14.4 | 11.67 ± 1.15 61.33 ± 5.51 | 0.66 ± 0.03 0.08 ± 0.01 |
| 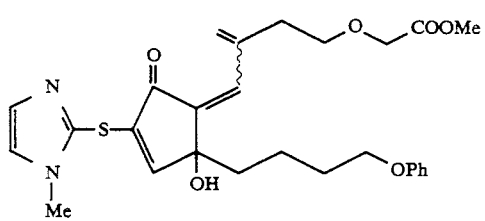 | $10^{-7}$ M $10^{-6}$ M | 1.33 ± 0.56 8.67 ± 1.15 | 5.00 ± 0.00 9.67 ± 0.58 | 0.62 ± 0.02 0.61 ± 0.02 |

TABLE 27

| 2-Substituted-2-cyclopentenones | Ca μg/dish | P μg/dish | ALP OD$_{415}$/dish |
|---|---|---|---|
| Control (No compd.) | 1.88 ± 0.31 | 4.73 ± 0.37 | 0.18 ± 0.06 |

TABLE 27-continued

| 2-Substituted-2-cyclopentenones | | Ca µg/dish | P µg/dish | ALP OD$_{415}$/dish |
|---|---|---|---|---|
| *(structure: cyclopentenone with N-methylimidazole-thio, butyl, OH, and side chains with OH, OPh)* | $10^{-7}$ M $10^{-8}$ M | 4.85 ± 0.84 2.46 ± 0.22 | 6.68 ± 0.34 4.62 ± 0.04 | 0.12 ± 0.01 0.17 ± 0.01 |
| *(structure: PhS-cyclopentenone with OH and hydroxy side chain)* | $10^{-7}$ M $10^{-8}$ M | 2.43 ± 0.19 4.07 ± 1.20 | 4.68 ± 0.27 6.20 ± 0.61 | 0.16 ± 0.04 0.15 ± 0.02 |
| *(structure: cyclopentenone with HO-CH$_2$-CH(OH)-CH$_2$-S substituent, CO$_2$Me side chain, OH)* | $10^{-7}$ M $10^{-8}$ M | 3.73 ± 0.39 2.81 ± 0.17 | 5.65 ± 0.14 5.19 ± 0.77 | 0.12 ± 0.08 0.19 ± 0.02 |

TABLE 28

| 2-Substituted-2-cyclopentenones | | Ca µg/dish | P µg/dish | ALP OD$_{415}$/dish |
|---|---|---|---|---|
| Control (No compd.) | | 23.00 ± 1.00 | 15.67 ± 0.58 | 0.80 ± 0.01 |
| *(structure: MeS-cyclopentenone with OH and hydroxy side chain)* | $10^{-6}$ M $10^{-5}$ M | 23.00 ± 3.46 57.33 ± 2.08 | 16.33 ± 2.08 35.00 ± 1.0 | 0.81 ± 0.06 0.53 ± 0.04 |
| *(structure: MeS-cyclopentenone with OH, OPh and hydroxy side chains)* | $10^{-6}$ M $10^{-5}$ M | 10.67 ± 1.53 30.67 ± 2.31 | 9.33 ± 1.15 20.33 ± 1.15 | 0.84 ± 0.03 0.56 ± 0.04 |

TABLE 29

| 2-Substituted-2-cyclopentenones | | Ca µg/dish | P µg/dish | ALP OD$_{415}$/dish |
|---|---|---|---|---|
| Control (No compd.) | | 22.67 ± 3.06 | 15.67 ± 1.53 | 0.80 ± 0.02 |
| *(structure: MeS-cyclopentenone with CO$_2$Me, OH, OPh side chains)* | $10^{-5}$ M $10^{-6}$ M | 58.67 ± 1.53 24.33 ± 1.53 | 35.33 ± 0.58 17.67 ± 0.58 | 0.98 ± 0.08 0.90 ± 0.05 |
| *(structure: MeS-cyclopentenone with OH, OPh, and hydroxy side chain)* | $10^{-5}$ M $10^{-6}$ M | 50.67 ± 1.15 19.67 ± 2.52 | 31.00 ± 1.00 15.00 ± 1.73 | 0.79 ± 0.02 0.76 ± 0.04 |

TABLE 30

| 2-Substituted-2-cyclopentenones | | Ca μg/dish | P μg/dish | ALP OD$_{415}$/dish |
|---|---|---|---|---|
| Control (No compd.) | | 17.81 ± 0.50 | 12.41 ± 1.50 | 0.35 ± 0.02 |
| 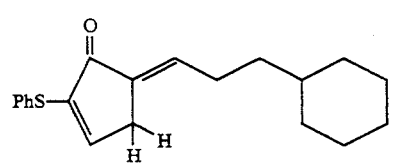 | $10^{-7}$ M | 23.94 ± 5.80 | 12.33 ± 2.80 | 0.36 ± 0.04 |
| | $10^{-8}$ M | 18.13 ± 2.6 | 8.98 ± 1.89 | 0.30 ± 0.01 |

TABLE 31

| 2-Substituted-2-cyclopentenones | | Ca μg/dish | P μg/dish | ALP OD$_{415}$/dish |
|---|---|---|---|---|
| Control (No compd.) | | 3.00 ± 1.00 | 5.67 ± 0.58 | 1.23 ± 0.02 |
| 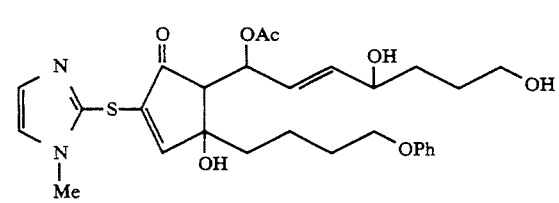 | $10^{-6}$ M | 51.67 ± 8.08 | 35.33 ± 5.03 | 1.28 ± 0.03 |
| | $10^{-5}$ M | 137.00 ± 4.58 | 70.67 ± 2.52 | 0.15 ± 0.00 |
| 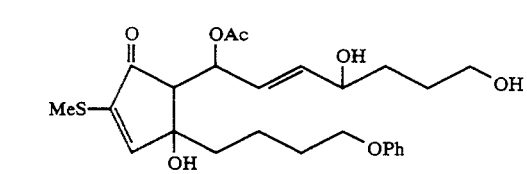 | $10^{-6}$ M | 24.08 ± 2.00 | 18.00 ± 1.00 | 1.10 ± 0.06 |
| | $10^{-5}$ M | 104.00 ± 5.29 | 55.67 ± 3.79 | 0.17 ± 0.01 |
| 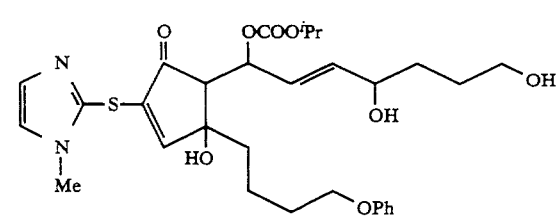 | $10^{-6}$ M | 54.67 ± 2.08 | 35.00 ± 2.00 | 1.24 ± 0.03 |
| | $10^{-5}$ M | 136.67 ± 5.03 | 70.00 ± 3.61 | 0.165 ± 0.01 |
| 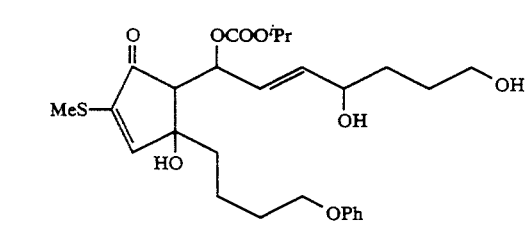 | $10^{-6}$ M | 25.00 ± 1.73 | 19.67 ± 1.15 | 1.22 ± 0.06 |
| | $10^{-5}$ M | 109.67 ± 15.3 | 57.33 ± 7.57 | 0.18 ± 0.01 |

TABLE 32

| 2-Substituted-2-cyclopentenones | | Ca μg/dish | P μg/dish | ALP OD$_{415}$/dish |
|---|---|---|---|---|
| Control (No compd.) | | 2.33 ± 1.15 | 5.00 ± 0.00 | 1.17 ± 0.03 |
| 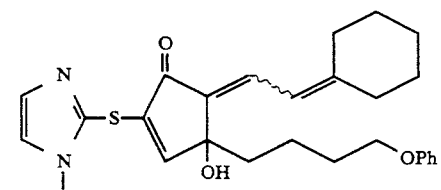 | $10^{-7}$ M | 3.33 ± 0.58 | 5.67 ± 0.58 | 1.19 ± 0.06 |
| | $10^{-6}$ M | 15.33 ± 1.53 | 13.33 ± 1.15 | 1.09 ± 0.05 |

TABLE 32-continued

| 2-Substituted-2-cyclopentenones | | Ca μg/dish | P μg/dish | ALP OD$_{415}$/dish |
|---|---|---|---|---|
| 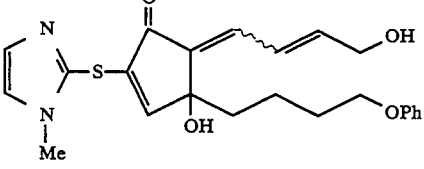 | $10^{-7}$ M $10^{-6}$ M | 2.33 ± 0.58 37.33 ± 2.08 | 4.33 ± 0.58 25.00 ± 2.00 | 1.20 ± 0.03 1.18 ± 0.06 |
| 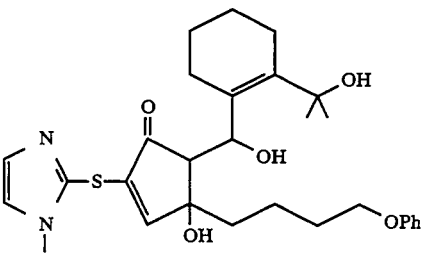 | $10^{-6}$ M $10^{-5}$ M | 2.00 ± 0.00 50.67 ± 3.21 | 5.00 ± 1.00 32.00 ± 1.00 | 1.20 ± 0.05 0.87 ± 0.06 |
| 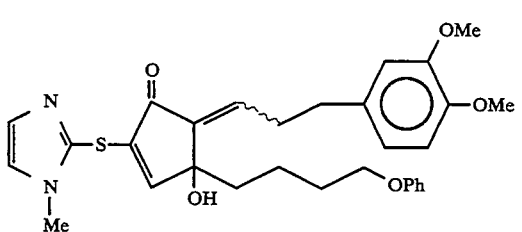 | $10^{-7}$ M $10^{-6}$ M | 2.00 ± 0.00 30.33 ± 0.58 | 4.33 ± 0.58 23.33 ± 0.58 | 1.08 ± 0.03 1.37 ± 0.04 |
| 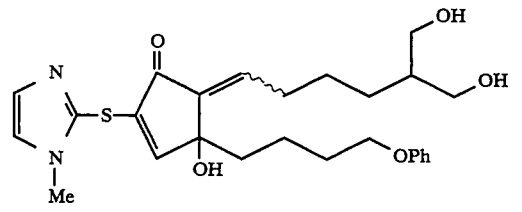 | $10^{-7}$ M $10^{-6}$ M | 4.33 ± 0.58 48.00 ± 1.73 | 5.00 ± 1.00 31.00 ± 1.00 | 1.21 ± 0.08 1.32 ± 0.02 |
| 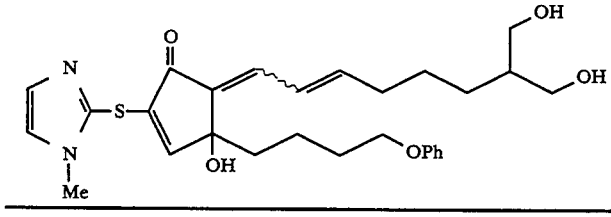 | $10^{-7}$ M $10^{-6}$ M | 4.67 ± 1.53 66.67 ± 0.58 | 4.33 ± 0.58 42.00 ± 0.00 | 1.08 ± 0.03 1.11 ± 0.06 |

We claim:

1. A 2-substituted-2-cyclopentenone compound represented by the following formula (I):

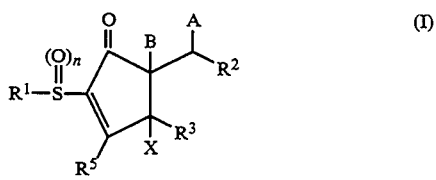

wherein R$^1$ stands for a substituted or unsubstituted monocyclic or bicyclic heterocyclic group having 1 to 9 carbon atoms and having at least one element selected from the group consisting of nitrogen, oxygen and sulfur, or any combined group thereof; said substituent being selected from the group consisting of (i) a halogen atom; (ii) an oxo group; (iii) a cyano group; (iv) a nitro group; (v) —COOR$^{61}$, wherein R$^{61}$ stands for a hydrogen atom; one equivalent of a cation; a residue of a saccharide; or an aliphatic hydrocarbon group having 1 to 10 carbon atoms which may be substituted with a halogen atom, an oxo group, a hydroxyl group, a tri(C$_1$-C$_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms; (vi) —OR$^{71}$, wherein R$^{71}$ stands for a hydrogen atom; an acyl group having 2 to 7 carbon atoms; an alkoxycarbonyl group having 2 to 5 carbon atoms; a tri(C$_1$-C$_7$) hydrocarbon silyl group; a group capable of forming an acetal bond together with the oxygen atom bonded to the R$^{71}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group; an acyloxy group having 7 to 7 carbon atoms, an alkoxycarbonylxoy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, a hydroxyl group, a nitro group, a tri($C_1$–$C_7$)hydrocarbon silyloxy group, an alkoxy group having 1 to 4 carbon atoms, an acyloxy group having 2 to 7 carbon atoms, an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms; (vii) —$CONR^{81}R^{810}$, wherein $R^{81}$ and $R^{810}$, which may be the same or different from each other, stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$)hydrocarbon silyloxy group, an acyloxy group having 2 to 7 carbon atoms, an alkoxycarbvonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri-($C_1$–$C_7$) hydrocarbon silyloxy group, an acyloxy group having 2 to 7 carbon atoms, an alkoxycarbonylxoy group having 2 to 5carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein $R^{81}$ and $R^{810}$ are combined with each other to form a five- or six-membered ring; (vii) —$NR^{91}R^{910}$, wherein $R^{91}$ and $R^{910}$, which may be the same of different from each other, stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxy group, a nitro group, a tri($C_1$–$C_7$)hydrocarbon silyloxy group, an acyloxy group having 2 to 7 carbon atoms, an alkoxycarbonylkoxy group having 2 to 5 carbon atoms, an alkoxy group having 1 to 4 carbon atoms or an alkyl group having 1 to 4 carbon atoms; or a group wherein $R^{91}$ and $R^{910}$ are combined with each other to form a five- or six-membered ring; (ix) an aliphatic hydrocarbon group having 1 to 10 carbon atoms; (x) an alicyclic hydrocarbon group having 4 to 10 carbon atoms; (xi) an aromatic hydrocarbon group having 6 to 10 carbon atoms; and (xii) a heterocyclic group having 1 to 9 carbon atoms;

$R^2$ stands for a substituted or unsubstituted (i) aliphatic hydrocarbon group having 1 to 10 carbon atoms, (ii) alicyclic hydrocarbon group having 4 to 10 carbon atoms, (iii) aromatic hydrocarbon group having 6 to 10 carbon atoms or (iv) heterocyclic group having 1 to 9 carbon atoms; wherein the substituent for $R^2$ is defined in the same way as the substituent for $R^1$, provided that the substituent —$COOR^{61}$ in the definition of $R^1$ is —$COOR^{62}$ where $R^{62}$ is defined in the same way as $R^{61}$ except that $R^{62}$ further stands for an aliphatic hydrocarbon having 1 to 10 carbon atoms substituted with a nitro group, (b) the substituent —$OR^{71}$ in the definition or $R^1$ is $OR^{72}$ where $R^{72}$ is defined in the same way as $R^{71}$ except that $R^{72}$ does not represent an aromatic hydrocarbon group having 6 to 10 carbon atoms which is substituted with an alkoxy group having 1 to 4 carbon atoms or an acyloxy group having 2 to 7 carbon atoms, (c) the substituent —$CONR^{81}R^{810}$ in the definition of $R^1$ is —$CONR^{82}R^{820}$ where $R^{82}$ and $R^{820}$ are defined in the same way as $R^{81}$ and $R^{810}$, respectively, (d) the substituent —$NR^{91}R^{910}$ in the definition of $R^1$ is —$NR^{92}R^{920}$ independently further stand for an aromatic hydrocarbon group having 6 to 10 carbon atoms which is substituted with an acyl group having 2 to 7 carbon atoms, a carboxyl group, or an alkoxycarbonyl group having 2 to 5 carbon atoms, and (e) $R^2$ further may stand for —$SR^{76}$, wherein $R^{76}$ stands for an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group, an acyloxy group having 2 to 7 carbon atoms, an alkoxycarbonylxoy group having 2 to 5 carbon atoms, an alkoxy group having 1 to 4 carbon atoms, an alkylcarbonyl group having 2 to 5 carbon atoms or an aromatic hydrocarbon group having 6 to 10 carbon atoms; an aromatic hydrocarbon having 6 to 10 carbon atoms which may be substituted with a halogen atom, a hydroxyl group, a tri($C_1$–$C_7$)hydrocarbon silyloxy group, a nitro group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; p1 $R^3$ stands for a hydrogen atom or a substituted or unsubstituted (i) aliphatic hydrocarbon group having 1 to 10 carbon atoms, (ii) alicyclic hydrocarbon group having 4 to 10 carbon atoms or (iii) aromatic hydrocarbon group having 6 to 10 carbon atoms; wherein the substituent for $R^3$ is defined in the same way as the substituent for $R^1$, provide that (a) the substituent —$COOR^{61}$ in the definition of $R^1$ is —$COOR^{63}$ where $R^{63}$ is defined in the same way as $R^{61}$ except that $R^{63}$ further stands for an aliphatic hydrocarbon group having 1 to 10 carbon atoms substituted with a nitro group, (b) the substituent —$OR^{71}$ in the definition of $R^1$ is —$OR^{73}$ where $R^{73}$ is defined in the same way as $R^{71}$, (c) the substituent —$CONR^{81}R^{810}$ in the definition of $R^1$ is —$CONR^{83}R^{830}$ where $R^{83}$ and $R^{830}$ are defined in the same way as $R^{81}$ and $R^{810}$, respectively, and (d) the substituent —$NR^{91}R^{910}$ is —$NR^{93}R^{930}$ where $R^{93}$ and $R^{930}$ are defined in the same way as $R^{91}$ and $R^{910}$, respectively, except that $R^{93}$ and $R^{930}$ independently further stand for an aromatic hydrocarbon group having 6 to 10 carbon atoms which is substituted with an acyl group having 2 to 7 carbon atoms, a carboxyl group, or an alkoxycarbonyl group having 2 to 5 carbon atoms;

X stands for a hydrogen atom or —OR$^4$, wherein R$^4$ stands for a hydrogen atom, an alkyl group having 1 to 4 carbon atoms, an acyl group having 2 to 7 carbon atoms, an alkoxycarbonyl group having 2 to 5 carbon atoms, a tri(C$_1$-C$_7$) hydrocarbon silyl group or a group capable of forming an acetal bond together with the oxygen atom attached to the R$^4$, provided that X is absent when R$^3$ is bonded to the carbon atom bonding thereto through a double bond;

R$^5$ stands for a hydrogen atom, or a substituted or unsubstituted (i) aliphatic hydrocarbon group having 1 to 10 carbon atoms or (ii) an alicyclic hydrocarbon group having 4 to 10 carbon atoms; wherein the substituent for R$^5$ is defined in the same way as the substituent for R$^1$, provided that (a) the substituent —COOR$^{61}$ in the definition of R$^1$ is —COOR$^{65}$ where R$^{65}$ is defined in the same way as R$^{61}$ except that R$^{65}$ further stands for an aliphatic hydrocarbon group having 1 to 10 carbon atoms substituted with a nitro group, (b) the substituent —OR$^{71}$ in the definition of R$^1$ is —OR$^{75}$ where R$^{75}$ is defined in the same way as R$^{71}$, (c) the substituent —CONR$^{81}$R$^{810}$ in the definition of R$^1$ is —CONR$^{85}$R$^{850}$ where R$^{85}$ and R$^{850}$ are defined in the same way as R$^{81}$ and R$^{810}$, respectively, and (d) the substituent —NR$^{91}$R$^{910}$ in the definition of R$^1$ is —NR$^{95}$R$^{950}$ where R$^{95}$ and R$^{950}$ are defined in the same way as R$^{91}$ and R$^{910}$, respectively, except that R$^{95}$ and R$^{950}$ independently further stand for an aromatic hydrocarbon group having 6 to 10 carbon atoms which is substituted with an acyl group having 2 to 7 carbon atoms, a carboxyl group, or an alkoxycarbonyl group having 2 to 5 carbon atoms;

B stands for a hydrogen atom where A stands for a hydrogen atom, a hydroxyl group, an acyloxy group having 2 to 7 carbon atoms, an alkoxycarbonyloxy group having 2 to 5 carbon atoms, a sulfonyloxy group having 1 to 7 carbon atoms or

or A and B are combined with each other to form a bond;

m and n, which may be the same or different from each other, stand for 0, 1 or 2.

2. A 2-substituted-2-cyclopentenone compound according to claim 1, which is represented by the following formula (I$_4$-A):

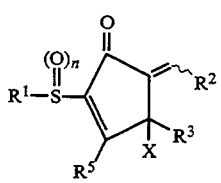

wherein R$^1$, R$^2$, R$^3$, R$^5$, X and n are as defined in claim 1 and ∼ represents that the substituent attached to the double bond is in an E-configuration or a Z-configuration or a mixture thereof in any proportion.

3. A 2-substituted-2-cyclopentenone compound according to claim 1, which is represented by the following formula (I$_4$-B):

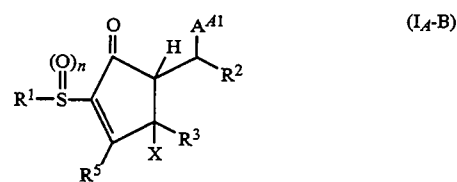

wherein A$^{41}$ stands for a hydrogen atom, a hydroxyl group, an acyloxy group having 2 to 7 carbon atoms, an alkoxycarbonyloxy group having 2 to 5 carbon atoms, a sulfonyloxy group having 1 to 7 carbon atoms or

; and R$^1$, R$^2$, R$^3$, R$^5$, X, m and n are as defined in claim 1.

4. A 2-substituted-2-cyclopentenone compound according to claim 1 or 2, which is represented by the following formula (I$_4$-A-2):

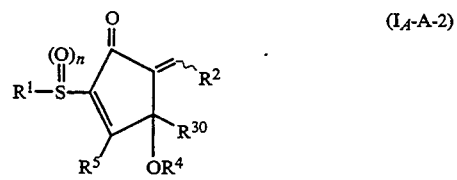

wherein R$^1$, R$^2$, R$^4$, R$^5$, and n are as defined in claim 1; and ∼ represents that the substituent attached to the double bond is in an E-configuration or a Z-configuration or a mixture thereof in any proportion; and R$_{30}$ stands for a hydrogen atom or a substituted or unsubstituted (i) aliphatic hydrocarbon group having 1 to 10 carbon atoms, (ii) alicyclic hydrocarbon group having 4 to 10 carbon atoms or (iii) aromatic hydrocarbon group having 6 to 10 carbon atoms.

5. A 2-substituted-2-cyclopentenone compound according to claim 1 or 2, which is represented by the following formula (I$_4$-A-3):

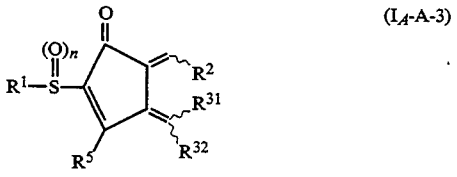

wherein R$^1$, R$^2$, R$^5$, and n are as defined in claim 1 and ∼represents that the substituent attached to the double bond is in an E-configuration or a Z-configuration or a mixture thereof in any proportion; and R$^{31}$ and R$^{32}$ which may be the same of different from each other stand for a hydrogen atom or a substituted or unsubstituted (i) aliphatic hydrocarbon group having 1 to 9 carbon atoms (ii) alicyclic hydrocarbon group having 4 to 10 carbon atoms or (iii) aromatic hydrocarbon group having 6 to 10 carbon atoms, or a group wherein the R$^{31}$ and R$^{32}$ are combined with each other to form an alicyclic hydrocarbon group having a four to ten-membered ring.

6. A 2-substituted-2-cyclopentenone compound according to claim 1 or 3, which is represented by the following formula ($I_4$-B-2):

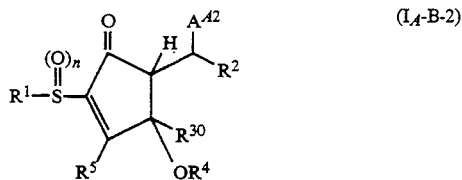

wherein $R^1$, $R^2$, $R^4$, $R^5$ and n are as defined in claim 1; $R^{30}$ stands for a hydrogen atom or a substituted or unsubstituted (i) aliphatic hydrocarbon group having 1 to 10 carbon atoms, (ii) alicyclic hydrocarbon group having 4 to 10 carbon atoms or (iii) aromatic hydrocarbon group having 6 to 10 carbon atoms; and $A^{42}$ stands for a hydrogen atom, a hydroxyl group, an acyloxy group having 2 to 7 carbon atoms or an alkoxycarbonyloxy group having 2 to 5 carbon atoms.

7. A 2-substituted-2-cyclopentenone compound according to claim 1, 2 or 4, which is represented by the following formula ($I_{4O}$-A-2):

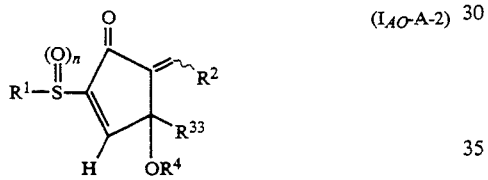

wherein $R^1$, $R^2$, $R^4$, and n are as defined in claim 1 and ⁓ represents that the substituent attached to the double bond is in an E-configuration or a Z-configuration or a mixture thereof in any proportion; and $R^{33}$ stands for a substituted or unsubstituted (i) aliphatic hydrocarbon group having 1 to 10 carbon atoms, (ii) alicyclic hydrocarbon group having 4 to 10 carbon atoms or (iii) aromatic hydrocarbon group having 6 to 10 carbon atoms.

8. A 2-substituted-2-cyclopentenone compound according to claim 1, 2 or 5 which is represented by the following formula ($I_{4O}$-A-3):

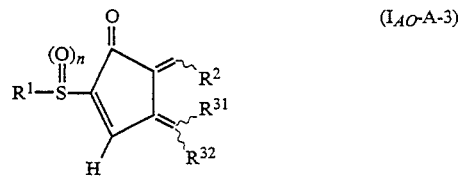

wherein $R^1$, $R^2$, and n are as defined in claim 1; and $R^{31}$ and $R^{32}$ which may be the same of different from each other stand for a hydrogen atom or a substituted or unsubstituted (i) aliphatic hydrocarbon group having 1 to 9 carbon atoms or (ii) alicyclic hydrocarbon group having 4 to 10 carbon atoms or a group wherein the $R^{31}$ and $R^{32}$ are combined with each other to form an alicyclic hydrocarbon group having a four to ten-membered ring.

and ⁓ represents that the substituent attached to the double bond is in the E-configuration or a Z-configuration or a mixture thereof in an proportion.

9. A 2-substituted-2-cyclopentenone compound according to claim 1, 3 or 6 which is represented by the following formula

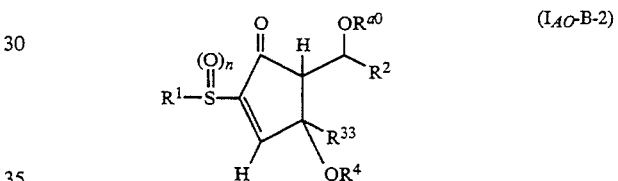

wherein $R^1$, $R^2$, $R^4$ and n are as defined in claim 1, $R^{33}$ stands for a substituted or unsubstituted (i) aliphatic hydrocarbon group having 1 to 10 carbon atoms, (ii) alicyclic hydrocarbon group having 4 to 10 carbon atoms or (iii) aromatic hydrocarbon group having 6 to 10 carbon atoms; and $R^{aO}$ stands for a hydrogen atom, an acyl group having 2 to 7 carbon atoms or an alkoxycarbonyl group having 2 to 5 carbon atoms.

* * * * *